US008168380B2

(12) United States Patent
Chan

(10) Patent No.: US 8,168,380 B2
(45) Date of Patent: *May 1, 2012

(54) METHODS AND PRODUCTS FOR ANALYZING POLYMERS

(75) Inventor: Eugene Y. Chan, Brookline, MA (US)

(73) Assignee: Life Technologies Corporation, Carlsbad, CA (US)

( * ) Notice: Subject to any disclaimer, the term of this patent is extended or adjusted under 35 U.S.C. 154(b) by 1678 days.

This patent is subject to a terminal disclaimer.

(21) Appl. No.: 09/852,968

(22) Filed: May 10, 2001

(65) Prior Publication Data

US 2002/0119455 A1    Aug. 29, 2002

Related U.S. Application Data

(60) Division of application No. 09/134,411, filed on Aug. 13, 1998, now Pat. No. 6,355,420, which is a continuation of application No. PCT/US98/03024, filed on Feb. 11, 1998.

(60) Provisional application No. 60/064,687, filed on Nov. 5, 1997, provisional application No. 60/037,921, filed on Feb. 12, 1997.

(51) Int. Cl.
G01N 21/64 (2006.01)
C12Q 1/68 (2006.01)
(52) U.S. Cl. .......................... 435/6; 536/23.1
(58) Field of Classification Search .................. None
See application file for complete search history.

(56) References Cited

U.S. PATENT DOCUMENTS

| 3,303,085 A | 2/1967 | Price et al. |
| 3,662,178 A | 5/1972 | Caputi et al. |
| 3,713,921 A | 1/1973 | Fleischer et al. |
| 3,802,972 A | 4/1974 | Fleischer et al. |
| 3,852,134 A | 12/1974 | Bean |
| 3,996,345 A | 12/1976 | Ullman et al. |
| 4,332,332 A | 6/1982 | Ingemann |
| 4,351,760 A | 9/1982 | Khanna et al. |
| 4,424,054 A | 1/1984 | Conn et al. |
| 4,654,267 A | 3/1987 | Ugelstad et al. |
| 4,683,195 A | 7/1987 | Mullis et al. |
| 4,683,202 A | 7/1987 | Mullis |
| 4,711,955 A | 12/1987 | Ward et al. |
| 4,739,044 A | 4/1988 | Stabinsky |
| 4,757,141 A | 7/1988 | Fung et al. |
| 4,764,460 A | 8/1988 | Furuichi et al. |
| 4,793,705 A | 12/1988 | Shera |
| 4,800,159 A | 1/1989 | Mullis et al. |
| 4,956,219 A | 9/1990 | Legras et al. |
| 4,962,020 A | 10/1990 | Tabor et al. |
| 4,962,037 A | 10/1990 | Jett et al. |
| 4,965,188 A | 10/1990 | Mullis et al. |
| 4,971,903 A | 11/1990 | Hyman |
| 4,979,824 A | 12/1990 | Mathies et al. |
| 4,994,373 A | 2/1991 | Stavrianopoulos et al. |
| 4,997,928 A | 3/1991 | Hobbs et al. |
| 5,001,050 A | 3/1991 | Blanco et al. |
| 5,047,519 A | 9/1991 | Hobbs, Jr. et al. |
| 5,079,169 A | 1/1992 | Chu et al. |
| 5,079,352 A | 1/1992 | Gelfand et al. |
| 5,091,310 A | 2/1992 | Innis |
| 5,091,652 A | 2/1992 | Mathies et al. |
| 5,119,463 A * | 6/1992 | Vurek et al. .................. 385/129 |
| 5,143,854 A | 9/1992 | Pirrung et al. |
| 5,151,507 A | 9/1992 | Hobbs, Jr. et al. |
| 5,171,534 A | 12/1992 | Smith et al. |
| 5,188,934 A | 2/1993 | Menchen et al. |
| 5,198,543 A | 3/1993 | Blanco et al. |
| 5,200,313 A | 4/1993 | Carrico |
| 5,230,781 A | 7/1993 | Middendorf et al. |
| 5,241,060 A | 8/1993 | Engelhardt et al. |
| 5,270,214 A | 12/1993 | Sessler et al. |
| 5,274,240 A | 12/1993 | Mathies et al. |
| 5,302,509 A | 4/1994 | Cheeseman |
| 5,324,401 A * | 6/1994 | Yeung et al. .................. 204/452 |
| 5,356,776 A | 10/1994 | Kambara et al. |
| 5,360,523 A | 11/1994 | Middendorf et al. |
| 5,362,653 A | 11/1994 | Carr et al. |
| 5,366,603 A | 11/1994 | Middendorf et al. |
| 5,403,707 A | 4/1995 | Atwood et al. |
| 5,403,708 A | 4/1995 | Brennan et al. |
| 5,405,747 A | 4/1995 | Jett et al. |
| 5,405,776 A | 4/1995 | Kotewicz et al. |
| 5,424,841 A | 6/1995 | Van Gelder et al. |
| 5,436,130 A | 7/1995 | Mathies et al. |
| 5,442,045 A | 8/1995 | Haugland et al. |
| 5,449,917 A | 9/1995 | Clements |
| 5,459,325 A | 10/1995 | Hueton et al. |
| 5,462,467 A | 10/1995 | Macaulay et al. |
| 5,470,707 A | 11/1995 | Sasaki et al. |
| 5,470,710 A | 11/1995 | Weiss et al. |
| 5,473,060 A | 12/1995 | Gryaznov et al. |
| 5,492,806 A | 2/1996 | Drmanac et al. |
| 5,494,030 A | 2/1996 | Swartz et al. |
| 5,498,523 A | 3/1996 | Tabor et al. |
| 5,510,270 A | 4/1996 | Fodor et al. |
| 5,512,462 A | 4/1996 | Cheng |
| 5,528,046 A | 6/1996 | Ishikawa |
| 5,534,125 A | 7/1996 | Middendorf et al. |
| 5,538,848 A | 7/1996 | Livak et al. |
| 5,538,898 A | 7/1996 | Wickramasinghe et al. |
| 5,547,835 A | 8/1996 | Köster |
| 5,547,839 A | 8/1996 | Dower et al. |
| 5,558,991 A | 9/1996 | Trainor |
| 5,564,959 A | 10/1996 | Spindt et al. |

(Continued)

FOREIGN PATENT DOCUMENTS

EP          109147       5/1984

(Continued)

OTHER PUBLICATIONS

Huang, XC et al. "DNA Sequencing using capillary array electrophoresis", Anal Chem 1992, vol. 64, p. 2149-2154.*

(Continued)

*Primary Examiner* — Stephanie K Mummert

(57) ABSTRACT

Methods and products for analyzing polymers are provided. The methods include methods for determining various other structural properties of the polymers.

6 Claims, 10 Drawing Sheets

U.S. PATENT DOCUMENTS

| | | | |
|---|---|---|---|
| 5,571,388 A | 11/1996 | Patonay et al. |
| 5,576,204 A | 11/1996 | Blanco et al. |
| 5,578,443 A | 11/1996 | Santamaria et al. |
| 5,599,675 A | 2/1997 | Brenner |
| 5,599,695 A | 2/1997 | Pease et al. |
| 5,601,982 A | 2/1997 | Sargent et al. |
| 5,605,662 A | 2/1997 | Heller et al. |
| 5,620,854 A | 4/1997 | Holzrichter et al. |
| 5,631,134 A | 5/1997 | Cantor |
| 5,635,728 A | 6/1997 | Cantu et al. |
| 5,639,874 A | 6/1997 | Middendorf et al. |
| 5,646,264 A | 7/1997 | Glazer et al. |
| 5,654,419 A | 8/1997 | Mathies et al. |
| 5,661,028 A | 8/1997 | Foote |
| 5,674,743 A | 10/1997 | Ulmer |
| 5,677,196 A | 10/1997 | Herron et al. |
| 5,688,648 A | 11/1997 | Mathies et al. |
| 5,695,934 A | 12/1997 | Brenner |
| 5,703,222 A | 12/1997 | Grossman et al. |
| 5,706,805 A | 1/1998 | Swartz et al. |
| 5,707,797 A | 1/1998 | Windle |
| 5,707,804 A | 1/1998 | Mathies et al. |
| 5,720,928 A | 2/1998 | Schwartz |
| 5,723,298 A | 3/1998 | Oommen et al. |
| 5,723,332 A | 3/1998 | Chernajovsky |
| 5,725,839 A | 3/1998 | Hsia |
| 5,741,893 A | 4/1998 | Hsia |
| 5,755,943 A | 5/1998 | Middendorf et al. |
| 5,776,674 A | 7/1998 | Ulmer |
| 5,776,677 A | 7/1998 | Tsui et al. |
| 5,789,167 A | 8/1998 | Konrad |
| 5,795,782 A * | 8/1998 | Church et al. ............... 436/2 |
| 5,800,995 A | 9/1998 | Patonay et al. |
| 5,800,996 A | 9/1998 | Lee et al. |
| 5,804,561 A | 9/1998 | Hsia |
| 5,807,831 A | 9/1998 | Hsia |
| 5,814,524 A | 9/1998 | Walt et al. |
| 5,817,632 A | 10/1998 | Hsia |
| 5,824,781 A | 10/1998 | Hsia |
| 5,830,659 A | 11/1998 | Stewart |
| 5,831,070 A | 11/1998 | Pease et al. |
| 5,833,601 A | 11/1998 | Swartz et al. |
| 5,840,701 A | 11/1998 | Hsai |
| 5,843,767 A | 12/1998 | Beattie |
| 5,846,727 A | 12/1998 | Soper et al. |
| 5,858,671 A | 1/1999 | Jones |
| 5,863,727 A | 1/1999 | Lee et al. |
| 5,866,336 A | 2/1999 | Nazarenko et al. |
| 5,869,255 A | 2/1999 | Mathies et al. |
| 5,888,792 A | 3/1999 | Bandman et al. |
| 5,906,723 A | 5/1999 | Mathies et al. |
| 5,922,591 A | 7/1999 | Anderson et al. |
| 5,928,869 A | 7/1999 | Nadeau et al. |
| 5,932,442 A | 8/1999 | Lal et al. |
| 5,945,312 A | 8/1999 | Goodman et al. |
| 5,961,923 A | 10/1999 | Nova et al. |
| 5,972,603 A | 10/1999 | Bedford et al. |
| 5,976,802 A | 11/1999 | Ansorge et al. |
| 6,004,446 A | 12/1999 | Middendorf et al. |
| 6,004,744 A | 12/1999 | Goelet et al. |
| 6,008,379 A | 12/1999 | Benson et al. |
| 6,015,714 A | 1/2000 | Baldarelli et al. |
| 6,020,481 A | 2/2000 | Benson et al. |
| 6,027,709 A | 2/2000 | Little et al. |
| 6,027,890 A | 2/2000 | Ness et al. |
| 6,048,690 A | 4/2000 | Heller et al. |
| 6,051,719 A | 4/2000 | Benson et al. |
| 6,054,316 A | 4/2000 | Baker et al. |
| 6,083,695 A | 7/2000 | Hardin et al. |
| 6,086,737 A | 7/2000 | Patonay et al. |
| 6,087,095 A | 7/2000 | Rosenthal et al. |
| 6,130,101 A | 10/2000 | Mao et al. |
| 6,136,543 A | 10/2000 | Anazawa et al. |
| 6,141,096 A | 10/2000 | Stern et al. |
| 6,143,151 A | 11/2000 | Middendorf et al. |
| 6,143,496 A | 11/2000 | Brown et al. |
| 6,162,931 A | 12/2000 | Gee et al. |
| 6,200,748 B1 | 3/2001 | Smith et al. |
| 6,207,229 B1 | 3/2001 | Bawendi et al. |
| 6,207,421 B1 | 3/2001 | Middendorf et al. |
| 6,210,891 B1 | 4/2001 | Nyren et al. |
| 6,210,896 B1 | 4/2001 | Chan |
| 6,221,392 B1 | 4/2001 | Khankari et al. |
| 6,232,075 B1 | 5/2001 | Williams |
| 6,245,506 B1 | 6/2001 | Laugharn, Jr. et al. |
| 6,255,083 B1 | 7/2001 | Williams |
| 6,255,475 B1 | 7/2001 | Kwiatkowski |
| 6,258,568 B1 | 7/2001 | Nyren |
| 6,263,286 B1 | 7/2001 | Gilmanshin et al. |
| 6,291,164 B1 | 9/2001 | Blakesley |
| 6,294,136 B1 | 9/2001 | Schwartz |
| 6,309,836 B1 | 10/2001 | Kwiatkowski |
| 6,322,901 B1 | 11/2001 | Bawendi et al. |
| 6,355,420 B1 | 3/2002 | Chan |
| 6,362,002 B1 | 3/2002 | Denison et al. |
| 6,399,334 B1 | 6/2002 | Li et al. |
| 6,403,311 B1 | 6/2002 | Chan |
| 6,423,551 B1 | 7/2002 | Weiss et al. |
| 6,448,065 B2 | 9/2002 | Laugharn, Jr. et al. |
| 6,458,758 B1 | 10/2002 | Hsia |
| 6,485,944 B1 | 11/2002 | Church et al. |
| 6,524,829 B1 | 2/2003 | Seeger |
| 6,593,148 B1 | 7/2003 | Narayanan |
| 6,639,088 B2 | 10/2003 | Kwiatkowski |
| 6,696,022 B1 | 2/2004 | Chan et al. |
| 6,762,059 B2 | 7/2004 | Chan et al. |
| 6,772,070 B2 | 8/2004 | Gilmanshin et al. |
| 6,780,591 B2 | 8/2004 | Williams et al. |
| 6,790,671 B1 | 9/2004 | Austin et al. |
| 6,818,395 B1 | 11/2004 | Quake et al. |
| 6,908,736 B1 | 6/2005 | Densham |
| 6,911,345 B2 | 6/2005 | Quake et al. |
| 6,927,065 B2 | 8/2005 | Chan et al. |
| 6,982,146 B1 | 1/2006 | Schneider et al. |
| 7,008,766 B1 | 3/2006 | Densham |
| 7,037,687 B2 | 5/2006 | Williams et al. |
| 7,105,300 B2 | 9/2006 | Parce et al. |
| 7,169,560 B2 | 1/2007 | Lapidus et al. |
| 7,179,906 B2 | 2/2007 | Benson et al. |
| 7,270,951 B1 | 9/2007 | Stemple et al. |
| 7,276,720 B2 | 10/2007 | Ulmer |
| 7,279,563 B2 | 10/2007 | Kwiatkowski |
| 7,282,337 B1 | 10/2007 | Harris |
| 7,297,518 B2 | 11/2007 | Quake et al. |
| 7,329,496 B2 | 2/2008 | Dower et al. |
| 7,462,449 B2 | 12/2008 | Quake et al. |
| 7,482,120 B2 | 1/2009 | Buzby |
| 7,491,498 B2 | 2/2009 | Lapidus et al. |
| 7,501,245 B2 | 3/2009 | Quake et al. |
| 7,593,109 B2 | 9/2009 | Ulmer |
| 7,635,562 B2 | 12/2009 | Harris et al. |
| 7,645,596 B2 | 1/2010 | Williams et al. |
| 7,666,593 B2 | 2/2010 | Lapidus |
| 7,678,894 B2 | 3/2010 | Siddiqi |
| 7,767,400 B2 | 8/2010 | Harris |
| 7,767,805 B2 | 8/2010 | Buzby |
| 7,790,391 B2 | 9/2010 | Harris et al. |
| 2002/0110818 A1 | 8/2002 | Chan |
| 2002/0119455 A1 | 8/2002 | Chan |
| 2002/0150938 A1 | 10/2002 | Kneipp et al. |
| 2002/0187508 A1 | 12/2002 | Wong |
| 2002/0197639 A1 | 12/2002 | Shia et al. |
| 2003/0059822 A1 | 3/2003 | Chan et al. |
| 2003/0138809 A1 | 7/2003 | Williams et al. |
| 2003/0215864 A1 | 11/2003 | Gilmanshin et al. |
| 2003/0235854 A1 | 12/2003 | Chan |
| 2004/0009612 A1 | 1/2004 | Zhao et al. |
| 2004/0053399 A1 | 3/2004 | Gilmanshin |
| 2004/0166025 A1 | 8/2004 | Chan et al. |
| 2004/0214211 A1 | 10/2004 | Gilmanshin et al. |
| 2004/0235014 A1 | 11/2004 | Nadel et al. |
| 2005/0042649 A1 | 2/2005 | Balasubramanian et al. |
| 2005/0042665 A1 | 2/2005 | Gilmanshin |
| 2005/0112595 A1 | 5/2005 | Zhao et al. |
| 2005/0112606 A1 | 5/2005 | Fuchs et al. |
| 2005/0112620 A1 | 5/2005 | Chan |
| 2005/0112671 A1 | 5/2005 | Maletta et al. |

| | | | |
|---|---|---|---|
| 2005/0123944 A1 | 6/2005 | Neely et al. |
| 2005/0123974 A1 | 6/2005 | Gilmanshin et al. |
| 2005/0142595 A1 | 6/2005 | Maletta et al. |
| 2005/0147992 A1 | 7/2005 | Quake |
| 2005/0153354 A1 | 7/2005 | Gilmanshin et al. |
| 2005/0196790 A1 | 9/2005 | Rooke et al. |
| 2005/0221408 A1 | 10/2005 | Nalefski et al. |
| 2005/0239085 A1 | 10/2005 | Buzby |
| 2005/0260609 A1 | 11/2005 | Lapidus |
| 2006/0019267 A1 | 1/2006 | Quake |
| 2006/0024711 A1 | 2/2006 | Lapidus et al. |
| 2006/0046258 A1 | 3/2006 | Lapidus |
| 2006/0078915 A1 | 4/2006 | Fuchs et al. |
| 2006/0263790 A1 | 11/2006 | Harris |
| 2007/0099212 A1 | 5/2007 | Harris |
| 2007/0111350 A1 | 5/2007 | Weiss et al. |
| 2008/0032307 A1 | 2/2008 | Buzby |
| 2008/0096216 A1 | 4/2008 | Quake |
| 2008/0213770 A1 | 9/2008 | Williams |
| 2008/0233575 A1 | 9/2008 | Harris et al. |
| 2008/0261833 A1 | 10/2008 | Stemmer et al. |
| 2009/0053705 A1 | 2/2009 | Harris |
| 2009/0075252 A1 | 3/2009 | Harris |
| 2009/0253141 A1 | 10/2009 | Quake |
| 2010/0143932 A1 | 6/2010 | Lapidus |
| 2010/0173363 A1 | 7/2010 | Buzby |
| 2010/0203524 A1 | 8/2010 | Efcavitch et al. |

FOREIGN PATENT DOCUMENTS

| | | |
|---|---|---|
| EP | 0 141 409 A1 | 5/1985 |
| EP | 141409 | 5/1985 |
| EP | 272007 | 3/1992 |
| EP | 665293 | 8/1995 |
| EP | 745686 | 12/1996 |
| EP | 258017 | 6/1997 |
| EP | 640146 | 10/1997 |
| EP | 0 834 576 A3 | 6/1999 |
| EP | 1105529 | 11/2005 |
| EP | 1141409 B2 | 3/2006 |
| WO | WO-89/09283 | 10/1989 |
| WO | WO 89/09283 | 10/1989 |
| WO | WO 90/07576 | 7/1990 |
| WO | WO-90/11369 | 10/1990 |
| WO | WO-90/13666 | 11/1990 |
| WO | WO 91/01087 | 2/1991 |
| WO | WO-91/04507 | 4/1991 |
| WO | WO-91/06678 | 5/1991 |
| WO | WO 91/13075 | 9/1991 |
| WO | WO-93/21340 | 10/1993 |
| WO | WO-93/23564 | 11/1993 |
| WO | WO 95/06138 | 3/1995 |
| WO | WO-96/27025 | 9/1996 |
| WO | WO 96/29593 A1 | 9/1996 |
| WO | WO 96/30508 A1 | 10/1996 |
| WO | WO-96/36737 | 11/1996 |
| WO | WO-97/00987 | 1/1997 |
| WO | WO-97/07245 | 2/1997 |
| WO | WO-97/39064 | 10/1997 |
| WO | WO-97/39150 | 10/1997 |
| WO | WO 98/10097 A2 | 3/1998 |
| WO | WO-98/13520 | 4/1998 |
| WO | WO 98/13520 | 4/1998 |
| WO | WO 98/13523 | 4/1998 |
| WO | WO-98/13523 | 4/1998 |
| WO | WO 98/22615 | 5/1998 |
| WO | WO 98/27440 | 6/1998 |
| WO | PCT/US98/0302 | 7/1998 |
| WO | WO-98/28440 | 7/1998 |
| WO | WO 98/30486 | 7/1998 |
| WO | WO 98/031834 | 7/1998 |
| WO | WO 98/35012 | 8/1998 |
| WO | WO 98/35012 A2 | 8/1998 |
| WO | WO 98/40496 | 9/1998 |
| WO | WO 98/044152 | 10/1998 |
| WO | WO 99/05315 | 2/1999 |
| WO | WO 99/05315 A2 | 2/1999 |
| WO | WO-99/10366 | 3/1999 |
| WO | WO-99/15517 | 4/1999 |
| WO | WO 99/019341 | 4/1999 |
| WO | WO-99/57321 | 4/1999 |
| WO | WO 99/24583 A1 | 5/1999 |
| WO | WO-99/42611 | 8/1999 |
| WO | WO-99/55857 | 11/1999 |
| WO | WO-99/57321 | 11/1999 |
| WO | WO-00/04364 | 1/2000 |
| WO | WO 00/06587 A1 | 2/2000 |
| WO | WO 00/09757 A1 | 2/2000 |
| WO | WO 00/60072 A1 | 10/2000 |
| WO | WO-00/60114 | 10/2000 |
| WO | WO 00/60114 A2 | 10/2000 |
| WO | WO-01/25480 | 4/2001 |
| WO | WO-2006/055521 | 5/2006 |

OTHER PUBLICATIONS

Mergny, J-L et al. "Fluorescence energy transfer as a probe for nucleic acid structures and sequences", Nucleic Acids Research, 1994, vol. 22, No. 6, p. 920-928.*

Mank et al. (Journal of Chromatography A, 1995, vol. 708, p. 309-321).*

Chan, Eugene, Mutation Research, 2005, 573, p. 13-40.*

Sauer et al. (Journal of Biotechnology, 2001, 86, p. 181-201).*

Rhee et al. (Trends. in Biotechnology, 2006, vol. 24, No. 12, p. 580-586).*

Braslaysky et al. (PNAS, 2003, vol. 100, No. 7, p. 3690-3694).*

Rigler et al. (Journal of Biotechnology, 1995, vol. 41, p. 177-186).*

Nie et al. (1995, Anal. Chem., 67(17), p. 2849-2857).*

Higuchi et al. (Nature Biotechnology, 1993, vol. 11, p. 1026-1030).*

Yin et al. (Science, 1995, 270, 1653-1657).*

Aikens, R., "Chapter 21: Properties of Low-Light-Level Slow-Scan Detectors", Fluorescent and Luminescent Probes for Biological Activity, 1992, pp. 277-286.

Akerman, B. et al, "Electrophoretic Orientation of DNA detected by Linear Dichroism Spectroscopy", *J. Chem. Soc. D. Chem. Commun.*, 1985, pp. 422-423.

Alexander, P. et al., "The Reaction of Oxidizing Agents with Wool—5. The Oxidation Products of the Disulphide Bond and the Formation of a Sulphonamide in the Peptide Chain", *Biochem.*, 1951, pp. 129-138, vol. 49.

Allen, M.J. et al., "Scanning Tunneling Microscope Images of Adenine and Thymine at Atomic Resolution", *Scanning Microscopy*, 1991, pp. 625-630, vol. 5, No. 3, Scanning Microscopy International, Chicago.

Alper, J., "From the Bioweapons Trenches, New Tools for Battling Microbes", *Biotechnology Industry Organization Meeting, Science*, Jun. 11, 1999, pp. 1754-1755, vol. 284, No. 5421, The American Association for the Advancement of Science.

Ambrose, W.P. et al., "Application of Single Molecule Detection to DNA Sequencing and Sizing", *Ber. Bunsenges. Phys. Chem.*, 1993, pp. 1535-1542, vol. 97, No. 12, VCH Verlagsgesellschaft mbH.

Andersson-Engels, S. et al., "Multicolor fluorescence imaging system for tissue diagnostics", *SPIE Bioimaging and Two-Dimensional Spectroscopy*, 1990, pp. 179-189, vol. 1205.

Aurup, H. et al., "Oligonucleotide duplexes containing 2'-amino-2'-deoxycytidines: thermal stability and chemical reactivity", *Nucleic Acids Research*, 1994, pp. 20-24, vol. 22, No. 1.

Arts, E.G.J.M. et al., "Fusion of artificial membranes with mammalian spermatozoa specific involvement of the equatorial segment after acrosome reaction", *Eur. J. Biochem.*, 1993, pp. 1001-1009, vol. 217.

Bains, W., "Hybridization Methods for DNA Sequencing", *Genomics*, 1991, pp. 294-301, vol. 11, Academic Press, Inc.

Balzarini, J. et al., "Thymidylate synthetase-deficient mouse FM3A mammary carcinoma cell line as a tool for studying the thymidine salvage pathway and the incorporation of thymidine analogues into host cell DNA", *Biochem. J.*, 1984, pp. 245-252, vol. 217.

Barbin, A. et al., "Lack of Miscoding Properties of 7-(2-Oxoethyl)guanine, the Major Vinyl Chloride—DNA Adduct", *Cancer Research*, Jun. 1985, pp. 2440-2444, vol. 45.

Bathori, G. et al., "Th-AM-K8 DNA can be translocated across planar bilayer membranes containing Mitochondrial Porin", Mitochondrial Channels, Abstract, p. A348.

Bello, M.S. et al., "Electroosmosis of polymer in fused silica capillaries", *Electrophoresis*, 1994, pp. 623-626, vol. 15, VCH Verlagsgesellschaft mbH.

Bezrukov, S.M. et al., "Counting polymers moving through a single ion channel", *Nature*, Jul. 28, 1994, pp. 279-281, vol. 370.

Bezrukov, S.M. et al., "The charge state of an ion channel controls neutral polymer entry into its pore", *Eur. Biophys. J.*, 1997, pp. 471-476, vol. 26, Springer-Verlag.

Bick, M.D. et al., "Total Substitution of Bromodeoxyuridine for Thymidine in the DNA of a Bromodeoxyuridine-Dependent Cell Line", *Proc. Natl. Acad. Sci USA*, May 1974, pp. 2082-2086, vol. 71, No. 5.

Bignold, L.P., "A novel polycarbonate (Nuclepore) membrane demonstrates chemotaxis, unaffected by chemokinesis, of polymorphonuclear leukocytes in the Boyden chamber", *Journal of Immunological Methods*, 1987, pp. 275-280, vol. 105.

Bloom, L.B. et al., "Dynamics of Loading the β Sliding Clamp of DNA Polymerase III onto DNA", *Journal of Biological Chemistry*, Nov. 29, 1996, pp. 30699-30708, vol. 271, No. 48, The American Society of Biochemistry and Molecule Biology, Inc.

Bock, G. et al., "Photometric Analysis of Antifading Reagents for Immunofluorescence with Laser and Conventional Illumination Sources", *The Journal of Historhemistry and Cytochemistry*, 1985, pp. 699-705, vol. 33, No. 7, The Histochemical Society, Inc.

Bohmer, R.M., "Chapter 18. Cell Division Analysis Using Bromodeoxyuridine-Induced Suppression of Hoechst 33258 Fluorescence", *Methods in Cell Biology*, 1990, pp. 173-184, Academic Press, Inc.

Bukrinskaya, A.G. et al., "Synthesis of Protein in Paramyxovirus-Infected Cells of Susceptible and Resistant Lines at the Early Stage of Infection", *D.I. Ivanovskii Institute of Virology, Academy of Medical Sciences of the USSR, Moscow* (Translated from Biokhimiya), May-Jun. 1970, pp. 516-523, vol. 35, No. 3, Consultants Bureau, a division of the Plenum Publishing Corporation, NY.

Bustamante, C., "Direct Observation and Manipulation of Single DNA Molecules Using Fluorescence Microscopy", *Annu. Rev. Biophys. Biophys. Chem.*, 1991, pp. 415-446, vol. 20, Annual Reviews, Inc.

Buurman, E.P. et al., "Fluorescence Lifetime Using a Confocal Laser Scanning Microscope", *Scanning*, 1992, pp. 155-159, vol. 14, FAMS, Inc.

Cantor, C.R. et al, "Meeting Report—Report on the Sequencing by Hybridization Workshop", *Genomics*, 1992, pp. 1378-1383, vol. 13, Academic Press, Inc.

Castro, A. et al., "Single-Molecule Electrophoresis", *Analytical Chemistry*, Sep. 15, 1995, pp. 3181-3186, vol. 67, No. 18.

Chang, H.T. et al., "Dynamic control to improve the separation performance in capillary electrophoresis", *Electrophoresis*, 1995, pp. 2069-2073, vol. 16, VCH Verlagsgesellschall mbH.

Chen, D. et al., "Single-Molecule Detection in Capillary Electrophoresis: Molecular Shot Noise as a Fundamental Limit to Chemical Analysis", *Anal. Chem.*, Feb. 15, 1996, pp. 690-696, vol. 68, No. 4.

Chu, G. et al., "Separation of Large DNA Molecules by Contour-Clamped Homogeneous Electric Fields", *Science*, Dec. 1986, pp. 1582-1585, vol. 234.

Church, G.M. et al., "Multiplex DNA Sequencing", *Science*, Apr. 8, 1988, pp. 185-191, vol. 240.

Clark, I.D. et al., "A Study of Sensitized Lanthanide Luminescence in an Engineered Calcium-Binding Protein", *Analytical Biochemistry*, 1993, pp. 1-6, vol. 210.

Clegg, R.M., "Fluorescence Resonance Energy Transfer and Nucleic Acids", *Methods in Enzymology*, 1992, pp. 353-385, vol. 211, Academic Press, Inc.

Clegg, R.M. et al., "Observing the helical geometry of double-stranded DNA in solution by fluorescence resonance energy transfer", *Proc. Natl. Acad Sci. USA*, Apr. 1993, pp. 2994-2998, vol. 90.

Clegg, R.M., "Fluorescence resonance energy transfer", *Current Opinion in Biotechnology*, 1995, pp. 103-110, vol. 6, Current Biology LTD.

Crain, P.E., "Mass spectrometric techniques in nucleic acid research", *Mass Spectrometry Reviews*, 1990, pp. 505-554, vol. 9, John Wiley & Sons, Inc.

Crissman, H.A. et al., "Chapter 20. Detection of Bromodeoxyuridine-Labeled Cells by Differential Fluorescence Analysis of DNA Fluorochromes", *Methods in Cell Biology*, 1990, pp. 199-206, vol. 33, Academic Press, Inc.

Davis, L.M. et al., "Rapid DNA Sequencing Based Upon Single Molecule Detection", *Genet. Anal. Tech. Appl.*, 1991, pp. 1-7, vol. 8, No. 1, Elsevier Science Publishing Co., Inc.

Davis, L.M. et al., "Rapid DNA Sequencing Based on Single-Molecule Detection", *Los Alamos Science*, 1992, pp. 280-286, vol. 20.

Dejong, P.J. et al., "Human chromosome-specific partial digest libraries in k and cosmid vectors (A2333)", Abstract, *Cytogenet. Cell Genet.*, p. 985, vol. 51.

Ding, D.W. et al., "The Dichroism of DNA Electric Fields", *Biopolymers*, 1972, pp. 2109-2124, vol. 11.

Drmanac, R. et al., "Sequencing of Magabase Plus DNA by Hybridization: Theory of the Method", *Genomics*, 1989, pp. 114-128, vol. 4, Academic Press, Inc.

Eigen, M. et al., "Sorting single molecules: Application to diagnostics and evolutionary biotechnology", *Proc. Natl. Acad. Sci. USA*, Jun. 1994, pp. 5740-5747, vol. 91.

El-Deiry, W.S. et al., "WAFI, a Potential Mediator of p53 Tumor Suppression", *Cell*, Nov. 19, 1993, pp. 817-825, vol. 75, Cell Press.

Faerber, P. et al., "Synthese von 5'-Mono-, 5'-Di- und 5'-Triphosphaten der Nucleoside 2.4-Dithio-uridin, 2.4-Dithioribothymedin, 2-Thio-thymidin und 2.4-Dithio-thymidin", *Chem. Ber.*, 1971, pp. 456-460, vol. 104.

Fairclough, R.H. et al., "The Use of Singlet-Singlet Energy Transfer to Study Macromolecular Assemblies", *Methods in Enzym.*, 1978, pp. 347-379.

Fan, F.R.F. et al., "Electrochemical Detection of Single Molecules", *Science*, Feb. 10, 1995, pp. 871-874, vol. 267.

Fawcett, J.J. et al., "Chapter 19: Large-Scale Chromosome Sorting", *Methods in Cell Biology*, 1994, pp. 319-330, vol. 42, Academic Press, Inc.

Feinberg, A.P. et al., "A Technique for Radiolabeling DNA Restriction Endonuclease Fragments to High Specific Activity", *Anal. Biochem.*, 1983, pp. 6-13, vol. 132, Academic Press, Inc.

Feinberg, A.P. et al., "A Technique for Radiolabeling DNA Restriction Endonuclease Fragments to High Specific Activity", (Addendum), *Anal. Biochem.*, 1983, pp. 266-267, vol. 132, No. 1, Academic Press, Inc.

Ferreiro, M. et al., "Molecular-Level Processing of Conjugated Polymers. 1. Layer-by-Layer Manipulation of Conjugated Polyions", *Macromolecules*, 1995, pp. 7107-7114, vol. 28, American Chemical Society.

Franklin, A.L. et al., "A New Technique for Retarding Fading of Fluorescence: DPX-BME", *Stain Technology*, 1985, pp. 125-135, vol. 60, No. 3, The Williams & Wilkins Co.

Frey, M.W. et al., "The Nucleotide Analog 2-aminopurine as a Spectroscopic Probe of Nucleotide Incorporation by the Klenow Fragment of *Escherichia coli* Polymerase I and Bacteriophase T4 DNA Polymerase", *Biochemistry*, 1995, pp. 9185-9192, vol. 34, No. 28.

Fu, T.J. et al., "Dynamics of DNA-tracking by two sliding-clamp proteins", *The EMBO Journal*, 1996, pp. 4414-4422, vol. 15, No. 16, Oxford University.

Gadella, T.W.J. et al., "Fluorescence lifetime imaging microscopy (FLIM): Spatial resolution of microstructures on the nanosecond time scale", *Biophysical Chemistry*, 1993, pp. 221-239, vol. 48, Elsevier Science Publishers B.V. Amsterdam.

Gaines, H. et al., "A new method for measuring lymphoproliferation at the single-cell level in whole blood cultures by flow cytometry", *Journal of Immunological Methods*, 1996, pp. 63-72, vol. 195, Elsevier Science B.V.

Garland, P.B. et al., "Phosphorescence of Protein-Bound Eosin and Erythrosin—A possible probe for measurements of slow rational MOI", *Biochem. J.*, 1979, pp. 561-572, vol. 183.

Gawrisch, K. et al., "Interaction of Peptide Fragment 828-848 of the Envelope Glycoprotein of Human Immunodeficiencey Virus Type I with Lipid Bilayers", *Biochemistry*, 1993, pp. 3112-3118, vol. 32, No. 12, American Chemical Society.

Gebeychu, G. et al., "Novel biotinylated nucleotide-analogs for labeling and colorimetric detection of DNA" *Nucleic Acid Research*, 1987, pp. 4531-4535, vol. 15, No. 11, Press Limited, Oxford, England.

Gibson, T.J. et al., "Lorist2, a cosmid with transcriptional terminators insulating vector genes from interference by promoters within the insert: effect on DNA yield and cloned insert frequency", *Gene.*, 1987, pp. 275-281, vol. 53, No. 2-3, Elsevier Science Publishers B.V.

Gibson, T.J. et al., "Lorist6, a cosmid vector with BamHI, NotI, ScaI and HindIII cloning sites and altered neomycin phosphotranaferase gene expression", *Gene.*, 1987, pp. 283-286, vol. 53, No. 2-3, Elsevier Science Publishers B.V.

Gill, D., "Inhibition of fading in fluorescence microscopy of fixed cells", *Experientia*, Mar. 15, 1979, pp. 400-401, vol. 35, No. 3.

Gillam, I.C. et al., "$N^4$-(6-Aminohexyl)cytidine and—deoxycytidine Nucleotides can be Used to Label DNA", *Anal. Biochemistry*, 1986, pp. 199-207, vol. 157, No. 2.

Giloh, H. et al., "Fluorescence Microscopy: Reduced Photobleaching of Rhodamine and Fluorescein Protein Conjugates by *n*-Proply Gallate", *Science*, Sep. 24, 1982, pp. 1252-1255, vol. 217.

Glazer, A.N. et al., "Energy-transfer fluorescent reagents for DNA analyses", *Curr. Opin. Biotechnol.*, Feb. 1997, pp. 94-102, vol. 8, No. 1.

Glickman, B.W., "2-Aminopurine Mutagenesis in *Escherichia coli*", *Basic Life Sciences*, 1985, pp. 353-379, vol. 31.

Goodwin, P.M. et al., "Spatial Dependence of the Optical Collection Efficiency in Flow Cytometry", *Cytometry*, 1995, pp. 133-144, vol. 21, Wiley-Liss, Inc.

Gratton, E. et al., "A Continuously Variable Frequency Cross-Correlation Phase Fluorometer with Picosecond Resolution", *Biophys. J.*, Dec. 1983, pp. 315-324, vol. 44, Biophysical Society.

Griep, M.A., "Fluorescence Recovery Assay: A Continuous Assay for Processive DNA Polymerases Applied Specifically to DNA Polymerase III Holoenzyme", *Analytical Biochemistry*, 1995, pp. 180-189, vol. 232, Academic Press, Inc.

Gueron, M. et al., "Excited States of Nucleotides and Singlet Energy Transfer in Polynucleotides", *The Journal of Chemical Physics*, Nov. 15, 1967, pp. 4077-4091, vol. 47, No. 10.

Gurrieri, S. et al., "Imaging of Kinked Configurations of DNA Molecules Undergoing Orthogonal Field Alternating Gel Electrophoresis by Fluorescence Microscopy", *Biochemistry*, 1990, pp. 3396-3401, vol. 29, American Chemical Society.

Haab, B.B. et al., "Single Molecule Fluorescence Burst Detection of DNA Fragments Separated by Capillary Electrophoresis", *Analytical Chemistry*, Sep. 15, 1995, pp. 3253-3260, vol. 67, No. 18.

Hamada, S. et al., "DAPI Staining Improved for Quantitative Cytofluorometry", *Histochemistry*, 1983, pp. 219-226, vol. 79, Springer-Verlag.

Harding, J.D. et al., "Single-molecule detection as an approach to rapid DNA sequencing", *Trends in Biotechnology*, Jan.-Feb. 1992, pp. 55-57, vol. 10, Elsevier Science Publishers Ltd. (UK).

Harris, C.M. et al., "On the dielectrically observable consequences of the diffusional motions of lipids and proteins in membranes. 2. Experiments with microbial cells, protoplastics and membrane vesicles", *Eur. Biophys. J.*, 1985, pp. 11-24, vol. 11-24, Springer-Verlag.

Haugland, R.F., "Handbook of Fluorescent Probes and Research Chemicals—Sixth Edition", *Molecular Probes*, 1996, pp. 143-200.

Herendeen, D.R. et al., "DNA Polymerase III: Running Rings around the Fork", *Cell*, Jan. 12, 1996, pp. 5-8, vol. 84, Cell Press.

Herman, B. et al., "Fluorescence Lifetime Imaging in Cell Biology", *SPIE*, pp. 88-97, vol. 2678.

Hogan, M. et al., "Transient electric dichrosim of rod-like DNA molecules", *Proc. Natl. Acad Sci. USA*, Jan. 1978, pp. 195-199, vol. 75, No. 1.

Holzwarth, A.R., "Time-Resolved Fluorescence Spectroscopy", *Methods in Enzymology*, 1995, pp. 334-362, vol. 246, Academic Press, Inc.

Holzwarth, G. et al., "The Acceleration of Liner DNA During Pulsed-Field Gel Electrophoresis", *Biopolymers.*, Jun. 1989, pp. 1043-1058, vol. 28, No. 6.

Houseal, T.W. et al., "Real-time imaging of single DNA molecules with fluorescence microscopy", *Biophys. J.*, Sep. 1989, pp. 507-516, vol. 56, Biophysical Society.

Huff, J.C. et al., "Enhancement of Specific Immunofluorescent Findings with Use of a Para-Phenylenediamine Mounting Buffer", *Journal of Investigative Dermatology*, 1982, pp. 449-450, vol. 78, No. 5, The Williams & Wilkins co.

Hung, S.C. et al., "Cyanine Dyes with High Absorption Cross Section as Donor Chromophores in Energy Transfer Primers", *Anal. Biochem.*, Dec. 1, 1996, pp. 15-27, vol. 243, Academic Press, Inc.

Ikehara, M. et al., "Polynucleotides. VII. Synthesis of Ribopolynucleotides Containing 8-Substituted Purine Nucleotides by Polynucleotide Phosphorylase", *Biochemistry*, Feb. 1969, pp. 736-743, vol. 8, No. 2.

Jett, J.H. et al., "High-Speed DNA Sequencing: An Approach Based Upon Fluorescence Detection of Single Molecules", *Journal of Biomolecular Structure & Dynamics*, 1989, pp. 301-309, vol. 7, No. 2, Adenine Press.

Johnson, G.D. et al., "A Simple Method of Reducing the Fading of Immunofluorescence During Microscopy", *Journal of Immunological Methods*, 1981, pp. 349-350, vol. 43, Elsevier/North-Holland Biomedical Press.

Johnson, G.D. et al., "Fading of Immunofluorescence during Microscopy: a Study of the Phenomenon and its Remedy", *Journal of Immunological Methods*, 1982, pp. 231-242, vol. 55, Elsevier Biomedical Press.

Ju, J. et al., "Cassette labeling for facile construction of energy transfer fluorescent primers", *Nucleic Acids Research*, 1996, pp. 1144-1148, vol. 24, No. 6, Oxford University Press.

Ju, J. et al., "Energy transfer primers: A new fluorescence labeling paradigm for DNA sequencing and analysis", *Nature Medicine*, Feb. 1996, pp. 246-249, vol. 2, No. 2.

Jumppanen, J.H. et al., "Influence of electrolyte composition on the effective electric field strength in capillary zone electrophoresis", *Electrophoresis*, Aug. 1995, pp. 1441-1444, vol. 16, No. 8, VCH Verlagsgesellschaft mbH.

Kasianowicz, J.J. et al., "Characterization of individual polynucleotide molecules using a membrane channel", *Proc. Natl. Acad. Sci. USA*, Nov. 1996, pp. 13770-13773, vol. 93.

Kasianowicz, J.J., "Polymer Transport in the Alpha-Hemolysin Ion Channel 6", Abstract, p. 111.

Kato, H. et al., "Nondisjunction of chromosomes in a synchronized cell population initiated by reversal of colcemid inhibition", *Expl. Cell Res.*, 1970, pp. 459-464, vol. 60.

Keough, T. et al., "Antisense DNA oligonucleotides. II: The use of matrix-assisted laser desorption/ionization mass spectrometry for the sequence verification of methylphosphonate oligodeoxyribonucleotides", *Rapid Commun. Mass Spectrum.*, Mar. 1993, pp. 195-200, vol. 7, No. 3.

Kinjo, M. et al., "Ultrasensitive hybridization analysis using fluorescence correlation spectroscopy", *Nucleic Acid Research*, 1995, pp. 1795-1799, vol. 23, No. 10, Oxford University Press.

Kirk, W.R. et al., "Lanthanide-Dependent Perturbations of Luminescence in Indolylethylenediaminetetraacetic Acid-Lanthanide Chelate", *J. Phys. Chem.*, 1993, pp. 10326-10340, vol. 97, No. 40, American Chemical Society.

KIVA Genetics Web Page, Printout.

Klenchin, V.A. et al., "Electrically induced DNA uptake by cells is a fast process involving DNA electrophoresis", *Biophys. J.*, Oct. 1991, pp. 804-811, vol. 60, Biophysical Society.

Korchemnaya, E.K. et al., "Electrophoresis in Nonaquenous and Mixed Solvents", *J. Anal. Chem. USSR* (English Translation), 1978, pp. 635-639, vol. 33, Plenum Publishing Corp.

Lakowicz, J.R. et al., "Lifetime-selective fluorescence imaging using an rf phase-sensitive camera", *Rev. Sci Instru.*, 1991, pp. 3653-3660, vol. 62.

Lang, R.A. et al., "Synthetic Procedures in Nucleic Acid Chemistry", 1968, p. 228, vol. I, John Wiley & Sons, New York.

Langer, P.R. et al., "Enzymatic synthesis of biotin-labeled polynucleotides: Novel nucleic acid affinity probes", *Proc. Natl. Acad Sci. USA*, Nov. 1981, pp. 6633-6637, vol. 78, No. 11.

Lee, K.B. et al., "A New Approach to Assay Endo-Type Carbohydrases: Bifluorescent-Labeled Substrates for Glycoamidases and Ceramide Glycanases", *Analytical Biochemistry*, 1995, pp. 31-36, vol. 230, Academic Press, Inc.

Lee, L.G. et al., "DNA sequencing with dye-labeled terminators and T7 DNA polymerase: effect of dyes and dNTPs on incorporation of dye-terminators and probability analysis of termination fragments", *Nucleic Acid Research*, 1992, pp. 2471-2483, vol. 20, No. 10, Oxford University Press.

Lee, N. et al., "Diffusion of a Polymer Chain through a Thin Membrane", *J. Phys. II France*, Feb. 1996, pp. 195-204, vol. 6, Les Editions de Physique.

Lee, S.P. et al., "A Fluorometric Assay for DNA Cleavage Reactions Characterized with *Bam*HI Restriction Endonuclease", *Analytical Biochemistry*, 1994, pp. 377-383, vol. 220, Academic Press, Inc.

Lee, S.P. et al., "Characterization of Endonucleolytic Activity of HIV-1 Integrase Using a Fluorogenic Substrate", *Analytical Biochemistry*, 1995, pp. 295-301, vol. 227, Academic Press, Inc.

Lee, Y.H. et al., "Laser-Induced Fluorescence Detection of a Single Molecule in a Capillary", *Analytical Chemistry*, Dec. 1, 1994, pp. 4142-4149, vol. 66, No. 23, American Chemical Society.

Lewotsky, K., "Hyperspectral Imaging: evolution of imaging spectrometry", *SPIE OE/Rep.*, Nov. 1994, pp. 1-3.

Little, D.P. et al., "Rapid Sequencing of Oligonucleotides by High-Resolution Mass Spectrometry", *J. Am. Chem. Soc.*, 1994, pp. 4893-4897, vol. 116, No. 11.

Lockhart, D.J. et al., "Expression monitoring by hybridization to high-density oligonucleotide arrays", *Nature Biotechnology*, Dec. 1996, pp. 1675-1680, vol. 14.

Loros, J.J. et al., "Molecular Cloning of Genes Under Control of the Circadian Clock in *Neurospora*", *Science*, 1989, pp. 385-388, vol. 243.

Mal'Tsev, V.G. et al., "Optimization of the Chromatographic Analysis of Amino Acids", Institute of High-Molecular-Weight Compounds, Academy of Sciences of the USSR, Leningrad, Translated from Zhurnal Analiticheskoi Khimii, Apr. 1978, pp. 798-807, vol. 33, No. 4.

Marcus, P.I. et al., "Viral Inhibition in the Metaphase-Arrest Cell", *Proc. Natl. Acad. Sci. USA*, 1963, pp. 1156-1164, v.ol. 50.

Marra, M. et al., End Sequence Determination from Large Insert Clones Using Energy Transfer Fluorescent Primers, *Genome Research*, 1996, pp. 1118-1122, vol. 6, No. 11, Cold Spring Harbor Laboratory Press.

Martin, I. et al., "Correlation between Fusogenieity of Synthetic Modified Peptides Corresponding to the $NH_2$-Terminal Extremity of Simian Immunodeficiency Virus gp32 and Their Mode of Insertion into the Lipid Bilayer: an Infrared Spectroscopy Study", *J. Virol.*, Feb. 1994, pp. 1139-1148, vol. 68, No. 2, American Society for Microbiology.

Matayoshi, E.D. et al., "Novel Fluorogenic Substrates for Assaying Retroviral Proteases by Resonance Energy Transfer", *Science*, Feb. 1990, pp. 954-958, vol. 247.

Matsumoto, S. et al., "Light Microscopic Structure of DNA in Solution Studied by the 4',6-Diamidino-2-phenylindole Staining Method", *J. Mol. Biol.*, 1981, pp. 501-516, vol. 152, Academic Press, Inc. (London) Ltd.

Maurizi, M.R. et al., "Distances between Active Site Probes in Glutamine Synthetase from *Escherichia coli*: Fluorescence Energy Transfer in Free and in Stacked Dodecamers", *Biochemistry*, 1986, pp. 141-151, vol. 25, No. 1.

Mautner, H.G., "The Synthesis and Properties of Some Selenopurines and Selenopyrimidines", *J. Am. Chem. Soc.*, Oct. 20, 1956, pp. 5292-5294, vol. 78.

Maxam, A.M. et al., "A new method for sequencing DNA", *Proc. Natl. Acad. Sci. USA*, Feb. 1977, pp. 560-564, vol. 74, No. 2.

Maymon, P.W. et al., "Optical system design alternatives for the Moderate-Resolution Imaging Spectrometer-Tilt (MODIS-T) for the Earth Observing System (EoS)", SPIE, 1988, pp. 10-22, vol. 924.

Meffert, R. et al., "UV-induced cross-linking of proteins to plasmid pBR322 containing 8-azidoadenine 2'-deoxyribonucleotides", *FEB06443*, Nov. 1988, pp. 190-194, vol. 239, No. 2, Elsevier Science Publishers B.V. (Biomedical Division), Federation of European Biochemical Society.

Meng, X. et al., "Optical mapping of lambda bacteriophage clones using restriction endonucleases", *Nature Genetics*, Apr. 1995, pp. 432-438, vol. 9.

Meng, X. et al., "Inhibition of Restriction Endonuclease Activity by DNA Binding Fluorochromes", *Dynamics*, 1996, pp. 945-951, vol. 13, No. 6, Adenine Press.

Mertz, J. et al., "Single-molecule detection by two-photon-excited fluorescence", *Optics Letters*, Dec. 15, 1995, pp. 2532-2534, vol. 20, No. 24, Optical Society of America.

Meinkoth, J. et al., "Nick Translation", *Methods in Enzymology*, 1987, pp. 91-93, vol. 152, Academic Press, Inc.

Menter, J.M. et al., "Kinetics of Fluorescence Fading of Acridine Orange-heparin Complexes in Solution", *Photochemistry and Photobiology*, 1978, pp. 629-633, vol. 27, Pergamon Press (Great Britain).

Metzger, R.A., Article from *Wired*, Nov. 1998, p. 4.

Miki, M. et al., "Structure of actin observed by fluorescence resonance energy transfer spectroscopy", *J. Muscle Res. Cell Motil.*, 1992, pp. 132-145, vol. 13, Chapman & Hall.

Miki, M. et al., "Kinetics of Structural Changes of Reconstituted Skeletal Muscle Thin Filaments Observed by Fluorescence Resonance Energy Transfer", *The Journal of Biological Chemistry*, Apr. 5, 1993, pp. 7101-7106, vol. 268, No. 10, The American Society for Biochemistry and Molecular Biology, Inc.

Moore, D.P. et al., "The Orientation, Relaxation and Reptation of DNA in Orthogonal Field, Alternatively-Pulsed Gel Electrophoresis (OFAGE): A Linear Dichroism Study", *Biophysical J.*, 1986, p. 130a, vol. 49.

Morikawa, K. et al., "Visualization of Individual DNA Molecules in Solution by Light Microscopy: DAPI Staining Method", *J. Biochem.*, 1981, pp. 693-696, vol. 89, No. 2.

Morozov, V.N. et al., "New polyacrylamide gel-based methods of sample preparation for optical microscopy: immobilization of DNA molecules for optical mapping", *Journal of Microscopy*, Sep. 1996, pp. 205-214, vol. 183, Pt. 3, The Royal Microscopical Society.

Nakashima, M. et al., "448-Detector Optical Recording System: Development and Application to *Aplysia* Gill-Withdrawal Reflex", *IEEE Transactions on Biomedical Engineering*, Jan. 1992, pp. 26-36, vol. 39, No. 1.

Naktinis, V. et al., "A Molecular Switch in a Replication Machine Defined by an Internal Competition for Protein Rings", *Cell*, Jan. 12, 1996, pp. 137-145, vol. 84, Cell Press.

Nie, S. et al., "Probing Individual Molecules with Confocal Fluorescence Microscopy", *Science*, Nov. 11, 1994, pp. 1018-1021, vol. 266.

Nguyen, D.C. et al., "Detection of Single Molecules of Phycoerythrin in Hydrodynamically Focused Flows by Laser-Induced Fluorescence", *Anal. Chem.*, Sep. 1, 1987, pp. 2158-2161, vol. 59, No. 17.

Oida, T. et al., "Fluorescence lifetime imaging microscopy (flimscopy). Methodology development and application to studies of endosome fusion in single cells", *Biophys. J.*, Mar. 1993, pp. 676-685, vol. 64, Biophysical Society.

Onrust, R. et al., "DNA Polymerase III Accessory Proteins. II. Characterization of δ and δ'", *The Journal of Biological Chemistry*, Jun. 5, 1993, pp. 11766-11772, vol. 268, No. 16, The American Society for Biochemistry and Molecular Biology, Inc.

Pap, E.H.W. et al., "Quantitation of the Interaction of Protein Kinase C with Diacylglycerol and Phosphoinositides by Time-Resolved Detection of Resonance Energy Transfer", *Biochemistry*, 1993, pp. 13310-13317, vol. 32, No. 48.

Parsegian, V.A. et al., "Watching Small Molecules Move: Interrogating Ionic Channels Using Neutral Solutes", *Bioscience Reports*, 1995, pp. 503-514, vol. 15, No. 6, Plenum Publishing Corp.

Paz-Elizur, T. et al., "β, a UV-inducible Smaller Form of the β Subunit Sliding Clamp of DNA Polymerase III of *Escherichia coli*. I. Gene Expression and Regulation", *The Journal of Biological Chemistry*, Feb. 2, 1996, pp. 2482-2490, vol. 271, No. 5, The American Society for Biochemistry and Molecular Biology, Inc.

Peck, K. et al., "Single-molecule fluorescence detection: Autocorrelation criterion and experimental realization with phycoerythrin", *Proc. Natl. Acad Sci. USA*, Jun. 1989, pp. 4087-4091, vol. 86.

Periasamy, A. et al., "Computerized Fluorescence Microscopic Vision in the Biomedical Sciences", *Journal of Computer-Assisted Microscopy*, 1994, pp. 1-26, vol. 6, No. 1, Plenum Publishing Corp.

Picciolo, G.L. et al., "Reduction of Fading of Fluorescent Reaction Product for Microphotometric Quantitation", *Advances in Applied Microbiology*, 1984, pp. 197-234, vol. 30, Academic Press, Inc.

Pillai, V.N. R., "Photoremovable Protecting Groups in Organic Synthesis", *Synthesis*, Jan. 1980, pp. 1-26, Georg. Thieme Publishers.

Platt, J.L. et al., "Retardation of fading and enhancement of intensity of immunofluorescence by p-phenylenediamine", *J. of Histochemistry and Cytochemistry*, 1983, pp. 840-842, vol. 31, No. 6.

Poot, M. et al., "Chapter 19. Cell Cycle Analysis Using Continuous Bromodeoxyuridine Labeling and Hoechst 33258-Ethidium Bromide Bivariate Flow Cytometry", *Methods in Cell Biology*, 1990, pp. 185-198, vol. 33, Academic Press, Inc.

Priore, D.R.C. et al., "Comparisons Between Oriented Film and Solution Tertiary Structure of Various Nucleic Acids", *Biopolymers*, 1979, pp. 1809-1820, vol. 18, John Wiley & Sons, Inc.

Purmal, A.A. et al., "5-Hydroxypyrimidine deoxynucleoside triphosphates are more efficiently incorporated into DNA by exonuclease-free Klenow fragment than 8-oxopurine deoxynucleoside triphosphates", *Nucleic Acids Research*, 1994, pp. 3930-3935, vol. 22, No. 19, Oxford University Press.

Qu, D. et al., "A role for melanin-concentrating hormone in the central regulation of feeding behaviour", *Nature*, Mar. 21, 1996, pp. 243-247, vol. 380.

Rahn, R.O. et al., "The UV-induced Triplet State in DNA", *Proc. Natl. Acad Sci. USA*, 1965, pp. 893-896, vol. 53.

Rampino, N. J. et al., "Apparatus for Gel Electrophoresis with Continuous Monitoring of Individual DNA Molecules by Video Epifluorescence Microscopy", *Analytical Biochemistry*, 1991, pp. 278-283, vol. 194, Academic Press, Inc.

Rao, P.N., "Mitotic Synchrony in Mammalian Cells Treated with Nitrous Oxide at High Pressure", *Science*, 1968, pp. 774-776, vol. 160.

Rigby, P.W.J. et al., "Labeling Deoxyribonucleic Acid to High Specific Activity in Vitro by Nick Translation with DNA Polymerase I", *J. Mol. Biol.*, 1977, pp. 237-251, vol. 113.

Reddick, R.C. et al., "New form of scanning optical microscopy", *Physical Review B*, Jan. 1, 1989, pp. 767-770, vol. 39, No. 1.

Rodgers, M.A.J. et al., "Instrumentation for Fluorescence Microscopy with Picosecond Time Resolution", *Photochemistry and Photobiology*, 1985, pp. 613-616, vol. 42, No. 5, Pergamon Press Ltd.

Ronaghi, M. et al., "Real-Time DNA Sequencing Using Detection of Pyrophosphate Release", *Analytical Biochemistry*, 1996, pp. 84-89, vol. 242, Academic Press, Inc.

Ross, P.D. et al., "Electrophoresis of DNA. III. The Effect of Several Univalent Electrolytes on the Mobility of DNA", *Biopolymers*, 1964, pp. 231-236, vol. 2.

Roychoudhury, R. et al., "Influence of nucleotide sequence adjacent to duplex DNA termini on 3' terminal labeling by terminal transferase", *Nucleic Acids Research*, Apr. 1979, pp. 1323-1333, vol. 6, No. 4, Information Retrieval Limited, London, England.

Saha, A.K. et al., "Time-Resolved Fluorescence of a New Europium Chelate Complex: Demonstration of Highly Sensitive Detection of Protein and DNA Samples", *J. Am. Chem. Soc.*, 1993, pp. 11032-11033, vol. 115, No. 23, American Chemical Society.

Sahota, R.S. et al., "Nonaqueous Capillary Electrophoresis", *Anal. Chem.*, Apr. 1, 1994, pp. 1141-1146, vol. 66, No. 7.

Saiki, R.K. et al., "Primer-Directed Enzymatic Amplification of DNA with a Thermostable DNA Polymerase", *Science*, Jan. 29, 1988, pp. 487-491, vol. 239.

Sanger, F. et al., "DNA sequencing with chain-terminating inhibitors", *Proc. Natl. Acad Sci. USA*, Dec. 1977, pp. 5463-5467, vol. 74, No. 12.

Sase, I. et al., "Real Time Imaging of Single Fluorophores on Moving Actin with an Epifluorescence Microscope", *Biophysical Journal*, Aug. 1995, pp. 323-328, vol. 69.

Schellman, J. et al., "Optical Spectroscopy of Oriented Molecules", *Chem. Rev.*, 1987, pp. 1359-1399, vol. 87, American Chemical Society.

Schott, J.R., "Remote Sensing of the Earth: A Synoptic View. Space-based and aerial images can provide information about Earth resources, agricultural conditions, weather patterns and a host of other phenomena that would be impossible to observe from the ground.", *Physics Today*, Sep. 1989, pp. 72-79, American Institute of Physics.

Schwartz, D.C. et al., "Conformational dynamics of individual DNA molecules during gel electrophoresis", *Nature*, Apr. 6, 1989, pp. 520-522, vol. 338.

Selvin, P.R. et al., "Luminescence Resonance Energy Transfer", *J. Am. Chem. Soc.*, 1994, pp. 6029-6030, vol. 116, American Chemical Society.

Shera, E.B. et al., "Detection of single fluorescent molecules", *Chemical Physics Letters*, Nov. 23, 1990, pp. 553-557, vol. 174, No. 6, Elsevier Science Publishers B.V. (North-Holland).

Shikmus, M.L. et al., "Synthesis and Characterization of Biotin-Labeled Nucleotide Analogs", *DNA*, 1986, pp. 247-255, vol. 5, No. 3, Mary Ann Liebert, Inc. Publishers.

Skaliter, R. et al., "β, a UV-inducible Shorter Form of the β Subunit of DNA Polymerase III of *Escherichia coli*. II. Overproduction, Purification, and Activity as a Polymerase Processivity Clamp", *The Journal of Biological Chemistry*, Feb. 2, 1996, pp. 2491-2496, vol. 271, No. 5, The American Society for Biochemistry and Molecular Biology, Inc.

Smirnov, I.P. et al., "Sequencing Oligonucleotides by Exonuclease Digestion and Delayed Extraction Matrix-Assisted Laser Desorption Ionization Time-of-Flight Mass Spectrometry", *Analytical Biochemistry*, 1996, pp. 19-25, vol. 238, Academic Press, Inc.

Smith, D.P. et al., "Isolation and structure of an arrestin gene from *Drosophila*", *Proc. Natl. Acad. Sci. USA*, Feb. 1990, pp. 1003-1007, vol. 87

Smith, L.M. et al., "Fluorescence detection in automated DNA sequence analysis", *Nature*, Jun. 12, 1986, pp. 674-679, vol. 321.

Smith, S.B. et al., "Observation of Individual DNA Molecules Undergoing Gel Electrophoresis", *Science*, Jan. 13, 1989, pp. 203-206, vol. 243.

Spatz, W.B. et al., "Reduced Fading of Fast Blue Fluorescence in the Brain of the Guinea-Pig by Treatment with Sodium-Nitroprusside", *Neuroscience Letters*, 1983, pp. 1-4, vol. 38, Elsevier Scientific Publishers Ireland Ltd.

Soper, S.A. et al., "Sanger DNA-Sequencing Reactions Performed in a Solid-Phase Nanoreactor Directly Coupled to Capillary Gel Electrophoresis", *Analytical Chemistry*, Oct. 1, 1998, pp. 4036-4043, vol. 70, No. 19, American Chemical Society.

Soper, S.A. et al., "Nanoliter-scale sample preparaion methods directly coupled to polymethylmethacrylate-based microchips and gel-filled capillaries for the analysis of oligonucleotides", *Journal of Chromatography A*, 1999, pp. 107-120, vol. 853, Elsevier Science B.V.

Steinberg, I.Z., "Long-Range Nonradiative Transfer of Electronic Excitation Energy in Proteins and Polypeptides", *Annu. Rev. Biochem.*, 1971, p. 83-114, vol. 40.

Stewart, J.R. et al., "Chinese Hamster Cell Monolayer Cultures. II. X-Ray Sensitivity and Sensitization by 5-Bromodeoxycytidine in the Exponential and Plateau Periods of Growth", *Experimental Cell Research*, 1968, pp. 293-299, vol. 49.

Stryer, L., "Fluoescence Energy Transfer as a Spectroscopic Ruler", *Ann. Rev. Biochem.*, 1978, pp. 819-846, vol. 47, Annual Review, Inc.

Stubblefield, E., "Chapter 2. Synchronization Methods for Mammalian Cell Cultures", *Methods in Cell Physiology*, 1968, pp. 25-43, vol. 3, Academic Press, Inc.

Sturm, J. et al., "Direct Observation of DNA Chain Orientation and Relaxation by Electric Birefringence: Implications for the Mechanism of Separation during Pulsed-Field Gel Electrophoresis", *Physical Review Letters*, Mar. 27, 1989, pp. 1484-1487, vol. 62, No. 13, The American Physical Society.

Sung, W. et al., "Polymer Translocation through a Pore in a Membrane", *Physical Review Letters*, Jul. 22, 1996, pp. 783-786, vol. 77, No. 4, The American Physical Society.

Taliani, M. et al., "A Continuous Assay of Hepatitis C Virus Protease Based on Resonance Energy Transfer Depsipeptide Substrates", *Analytical Biochemistry*, 1996, pp. 60-67, vol. 240, Academic Press, Inc.

Taylor, D.L. et al., "Chapter 13. Basic Fluorescence Microscopy", *Methods in Cell Biology*, 1989, pp. 207-237, vol. 29, Academic Press, Inc.

Taylor, D.L. et al., "Detection of Actin Assembly by Fluorescence Energy Transfer", *The Journal of Cell Biology*, May 1981, pp. 362-367, vol. 89, The Rockefeller University Press.

Ter Beest, M.B.A. et al., "Interaction of myeline basic protein with artificial membranes Parameters governing binding, aggregation and dissociation", *Eur. J. Biochem.*, 1993, pp. 689-696, vol. 211.

Uchiyama, H. et al., "Detection of Undegraded Oligonucleotides in vivo by Fluorescence Resonance Energy Transfer. Nuclease Activities in Living Sea Urchin Eggs", *The Journal of Biological Chemistry*, Jan. 5, 1996, pp. 380-384, vol. 271, No. 1, The American Society for Biochemistry and Molecular Biology, Inc.

Ueda, T. et al., "Nucleosides and Nucleotides. X. Synthesis of 4-Thiouracil Nucleosides and Nucleotides by the Solvolysis of Cytidine and Its Phosphates with Hydrogen Sulfide", *Chem. Pharm. Bull.*, 1974, pp. 2377-2382, vol. 22, No. 10.

Valnes, K. et al., "Retardation of Immunofluorescence Fading during Microscopy", *The Journal of Histochemistry and Cytochemistry*, 1985, pp. 755-761, vol. 33, No. 8, The Histochemical Society, Inc.

Van Hulst, N. F. et al., "Near-field optical microscope using a silicon-nitride probe", *Appl. Phys. Letter*, Feb. 1, 1993, pp. 461-463, vol. 62, No. 5, American Institute of Physics.

Vaughn, W. et al;. "Oxygen quenching of pyrenebutyric acid fluorescence in water. A dynamic probe of the microenvironment", *Biochemistry*, 1970, pp. 464-473, vol. 9, No. 3.

Waggoner, A., "Covalent Labeling of Proteins and Nucleic Acids with Fluorophores", *Methods Enzymol.*, 1995, pp. 362-373, vol. 246, Academic Press, Inc.

Wang, X. et al., "Discovery of adrenomedullin in rat ischemic cortex and evidence for its role in exacerbating focal brain ischemic damage", *Proc. Natl. Acad Sci. USA*, Dec. 1995, pp. 11480-11484, vol. 92.

Wang, X.F. et al., "Time-Resolved Fluorescence Microscopy Using Multichannel Photon Counting", *Applied Spectroscopy*, 1990, pp. 25-30, vol. 44, No. 1, Society for Applied Spectroscopy.

Wang, Y. et al., "Rapid Sizing of Short Tandem Repeat Alleles Using Capillary Array Electrophoresis and Energy-Transfer Fluorescent Primers", *Anal. Chem.*, Apr. 1, 1995, pp. 1197-1203, vol. 67, No. 7.

Wang, Y. et al., "High-resolution capillary array electrophoretic sizing of multiplexed short tandem repeat loci using energy-transfer fluorescent primers", *Electrophoresis*, 1996, pp. 1485-1490, vol. 17, VCH Verlagsgesellschaft mbH.

Ward, D.C. et al., "Fluorescence Studies of Nucleotides and Polynucleotides. I. Formycin, 2-Aminopurine Riboside, 2,6-Diaminopurine Riboside and Their Derivatives", *The Journal of Biological Chemistry*, Mar. 10, 1969, pp. 1228-1237, vol. 244, No. 5.

Wiemann, S. et al., "Primer Design for Automated DNA Sequencing Utilizing T7 DNA Polymerase and Internal Labeling with Fluorescein-15-dATP", *BioTechniques*, Apr. 1995, pp. 688-697, vol. 18, No. 4.

Wilkinson, J.Q. et al., "Identification of mRNAs with enhanced expression in ripening strawberry fruit using polymerase chain reaction differential display", *Plant Molecular Biology*, 1995, pp. 1097-1108, vol. 27, Kluwer Academic Publishers, Belgium.

Wittwer, C.T. et al., "Continuous Fluorescence Monitoring of Rapid Cycle DNA Amplification", *BioTechniques*, Jan. 1997, pp. 130-138, vol. 22, No. 1.

Woolley, A.T. et al., "Ultra-High-Speed DNA Sequencing Using Capillary Electrophoresis Chips", *Anal. Chem.*, Oct. 15, 1995, pp. 3676-3680, vol. 67, No. 20, American Chemical Society.

Woronicz, J.D. et al., "Requirement for the orphan steroid receptor Nur77 in apoptosis of T-cell hybridomas", *Nature*, Jan. 20, 1994, pp. 277-281, vol. 367.

Wu, H.M. et al., "Solution structural studies of the A and Z forms of DNA", *Proc. Natl. Acad Sci. USA*, Nov. 1981, pp. 6808-6811, vol. 78, No. 11.

Wu, J.Y. et al., "Chapter 30. Fast Multisite Optical Measurement of Membrane Potential", Department of Physiology, Yale University School of Medicine, New Haven, CT USA, pp. 389-404.

Wu, P. et al., "Resonance Energy Transfer: Methods and Applications", *Anal. Chem.*, 1994, pp. 1-13, vol. 218, Academic Press, Inc.

Wunderlich, F. et al., "Antimitotic agents and macronuclear division of ciliates. II. Endogenous recovery from colchicine and colcemid-a new method of synchronization in Tatrahymena pyriformis GL", *Expl. Cell Res.*, 1969, pp. 142-144, vol. 57.

Yamaoka, K. et al., "Electric Dichroism Studies of Macromolecules in Solutions. II. Measurements of Linear Dichroism and Birefringence of Deoxyribonucleic Acid in Orienting Electric Fields", *Macromolecules*, Jan.-Feb. 1973, pp. 66-76, vol. 6, No. 1.

Yamaoka, K. et al., "Electric Dichroism Study of a Sonicated DNA and Its Complex with an Acridine Dye in Aqueous Solutions: Field-Strength Dependence and Linear Dichroic Spectra", *Macromolecules*, 1981, pp. 595-601, vol. 14, American Chemical Society.

Vane, G. et al., "Comparison of laboratory calibrations of the Airborne Visible/Infrared Imaging Spectrometer (AVIRIS) at the beginning and end of the first flight season", *Proc. SPIE-Recent Adv. Sensors, Radiometry Data Proc. Remote Sens.*, 1988, pp. 168-178, vol. 924.

Zweig, A., "Photochemical Generation of Stable Fluorescent Compounds (Photofluorescence)", *Pure and Applied Chemistry*, 1973, pp. 389-410, vol. 33.

Nie, S. et al., "Optical Detection of Single Molecules", *Annu. Rev. Biophys. Biomol. Struct.*, 1997, pp. 567-596, vol. 26, Annual Reviews, Inc.

Castro et al., Single-Molecule Electrophoresis: Applications to Biomolecular Detection. SPIE. 1995; 2396:79-85.

Ekstrøm et al., Two-point fluorescence detection and automated fraction collection applied to constant denaturant capillary electrophoresis. Biotechniques. Sep. 2000;29(3):582-4, 586-9.

Otobe et al., Behavior of DNA fibers stretched by precise meniscus motion control. Nucleic Acids Res. Nov. 15, 2001;29(22):E109, 6 pages.

Sauer et al., Single molecule DNA sequencing in submicrometer channels: state of the art and future prospects. J Biotechnol. Apr. 13, 2001;86(3):181-201.

Shortreed et al., High-throughput single-molecule DNA screening based on electrophoresis. Anal Chem. Jul. 1, 2000;72(13):2879-85.

Amended Complaint filed Oct. 22, 2010 against Pacific Biosciences of California Inc., Life Technologies Corporation, Illumina, Inc., by Helicos Biosciences Corporation, and supporting Exhibits 1-19.

Answer and Counterclaims of Pacific Biosciences of California Inc., filed Nov. 8, 2010 to Amended Complaint filed Oct. 22, 2010 against Pacific Biosciences of California Inc., Life Technologies Corporation, Illumina, Inc., by Helicos Biosciences Corporation.

Reply of Helicos Biosciences Corp. filed Dec. 2, 2010 to Answer of Pacific Biosciences of California Inc., filed Nov. 8, 2010 to Amended Complaint filed Oct. 22, 2010 against Pacific Biosciences of California Inc., Life Technologies Corporation, Illumina, Inc., by Helicos Biosciences Corporation.

Allen, D., et al. Biochemistry "Resonance Energy Transfer Measurements between Substrate Binding Sites within the Large (Klenow) Fragment of *Escherichia coli* DNA Polymerase I" published (1989) 28: 9586-9593.

Funatsu, T., et al. FEBS Letters "Single molecular assay of individual ATP turnover by a myosin-GFP fusion protein expressed in vitro" (1997) 407: 235-238.

Furey, W. Scott, et al. "Use of Fluorescence Resonance Energy Transfer to Investigate the Conformation of DNA Substrates Bound to the Klenow Fragment"; (1998) 37: 2979-2990.

Ha, T., et al. Proc. Natl. Acad. Sci. USA "Single-molecule fluorescence spectroscopy of enzyme conformational dynamics and cleavage mechanism" (1999) 96: 893-898.

Funatsu, T., et al. Letters to Nature "Imaging of single fluorescent molecules and individual ATP turnovers by single myosin molecules in aqueous solution" (1995) 374 (6): 555-559.

Tyagi, Suresh Biochemistry "Proximity between Nucleotide/Dinucleotide and Metal Ion Binding Sites in DNA-Dependent RNA Polymerase from *Escherichia coli*" (1992) 31(28): 6447-6453.

Weiss, Shimon Science "Fluorescence Spectroscopy of Single Biomolecules" (1999) 283(5408): 1676-1683.

Wu, F., et al. ,J. of Biological Chemistry "Fluorescence Resonance Energy Transfer Studies on the Proximity Relationship between the Intrinsic Metal Ion and Substrate Binding Sites of *Escherichia coli* RNA Polymerase" (1987) 262(27):13147-13154.

ABI PRISM Dye Primer Cycle Sequencing Core Kit (1997) 61 pgs.

Alexandrova et al., Nucleic Acids Res (1998) 26(3):778-786.

Allen et al., Hepatology (1998) 27(6):1670-1677.
Allen et al., Hereditas (1998) 129(2):161-167.
Allen et al., Biochemistry (1989) 28(11): 4601-4607.
Allen et al., Biochemistry (1989) 28(25): 9586-9593.
Allmer, Doctoral Theses, Royal Institute of Technology, Stockholm, Sweden (1988), pp. 1-35.
Ambrose et al., Phys Rev Lett (1994) 72(1):160-163.
American Heritage Dictionary 1374-75 (2$^{nd}$ College Ed. 1982).
Antosiewicz et al., J Mol Biol (1994) 238(3):415-436.
Arkin, et al., Proc. Natl. Acad. Sci. (1992) 89:7811-7815.
Armstrong et al., Eur. J. Biochem. (1976) 70:33-38.
Arnold, F., Nature BioTechnology (1991) 9:151-156.
Arzumanov et al., J of Biol Chem (1996) 271(40):24389-24394.
Astatke et al., Proc. Natl. Acad. Sci. (1998) 95:3402-3407.
Ausubel, F.M. et al., eds., "Chapter 3. Enzymatic Manipulation of DNA and RNA," in: *Short Protocols in Molecular Biology*, 3$^{rd}$ Ed., p. 3-1 to 3-50 (1995).
Ausubel, F.M. et al., eds., "Chapter 7. DNA Sequencing," in: *Short Protocols in Molecular Biology*, 3$^{rd}$ Ed., p. 7-1 to 7-69 (1995).
Axelrod, Daniel, *Fluorescence Microscopy of Living Cells in Culture Part B. Quantitative Fluorescence Microscopy—Imaging and Spectroscopy*, in Methods in Cell Biology, (1989) 246-270 (D. Lansing Taylor and Yu-Li Wang eds.,.
Barker et al, Journal Biol. Chem. (1972) 247(22):7135-7147.
Baez, S., J. Appl. Physiol. (1966) 21:299-301.
Beabealashvilli, et al., Biochimica et Biophysica Acta, 868:136-44 (1986).
Beattie, Wanda G. et al. (1995) Mol. Biotech. 4(3):213-225.
Beaucage et al, Tetrahedron (1992) 48(12):2223-2311.
Berg, Howard C., Random Walks in Biology, expanded edition (1983).
Bergstrom et al., J. Am. Chem. Soc. (1989) 111:374-375.
Betzig, E., Optics Letters (1995) 20(3): 237-239.
Betzig et al. Biophys. J. (1986) 49: 269-279.
Betzig et al., Science, 257:189-95 (1992).
Betzig, R.J. et al., "Near-field fluorescence imaging of cytoskeletal actin," *BioImaging* 1:129- 135.
Betzig et al., Science (1993) 262: 1422-1425, Sep. 9, 2011.
Bouizar, Zhor et al., Eur. J. Biochem. (1986) 155(1):141-147.
Brandis et al., Biochemistry (1996) 35:2189-2200.
Brinkley, Michael, Bioconjugate Chem. (1992) 3:2-13.
Browning, Jeffrey et al., J. Immunol. (1989) 143(6):1859-1867.
Bruchez et al., Science (1998) 281: 2013-2016.
Burgess et al., 210$^{th}$ ACS Nat'l Mtg. (1995): Abstract #005.
Cai et al., New J. Chem. (1993) 17:325-329.
Cadwell, et al., PCR Methods and Applications (1992) 2:28-33.
Calogero, Sabina et al., FEMS Microbiology Letters (1992) 97(1-2): 41-44.
Campbell, A. K. et al., Biochem. J. (1983) 216: 185-194.
Canard and Sarfati, Gene (1994) 148:1-6.
Caren, Robert et al., Nature (1994) 12:517-520.
Cashel, M., Analytical Biochem (1974) 57(1):100-107.
Caspar, Jonathan V. et al., J. Phys. Chem. (1983) 87(6):952-957.
Castro et al., "Single-Molecule Electrophoresis," *Anal. Chem.* 67:3181-3186 (1995).
Chan et al., Science (1998) 281: 2016-2018.
Chang et al., Topics in Applied Physics (1982) 50: 179-205.
Chatterji et al., Methods in Enzymology (1996) 274:456-479.
Chen et al., Anal. Chem. (1996) 68:690-696.
Chidgeavadze et al., Biochimica et Biophysica Acta, (1986) 868:145-52.
Chrisey, Linda A. et al., Nucleic Acid Research (1996) 24(15):3031-3039.
Churchich, Eur. J. Biochem. (1995) 231:736-741.
Clegg et al., Braz J Med Biol Res (1993) 26(4):405-416.
Cull, Millard G. et al., Proc. Natl. Acad. Sci. USA (1992) 89:1865-1869.
Cwirla, Steven E. et al., Proc. Natl. Acad. Sci. USA (1990) 87:6378-6382.
Dapprich, J. & Nicklaus, N., Bioimaging (1998) 6:25-32.
Davis et al., Mem Inst Oswaldo Cruz (1992) 87:235-239.
Decher, G. et al., Thin Solid Films (1992) 210-211(Part 2):831-835.
Delagrave, Simon et al., Protein Engineering (1993) 6(3):327-331.

Delagrave, Simon et al., Bio/Technology (1993) 11:1548-1552.
Dickson, R.M. et al., Science (1996) 274:966-969.
Dos Remedios, Cristobal G. et al., Journal of Structural Biology (1995) 115: 175-185.
Doublie et al., Nature (1998) 391: 251-258.
Drosopoulos et al., J Molecular Med (1998) 76(9):604-612.
Dunn, R.C. et al., J. Phys. Chem. (1994) 98:3094-3098.
Eigen, M. et al., Proc. Natl. Acad. Sci. USA (1994) 91:5740-5747.
Enderlein, J. et al., Bioimaging (1998) 6:3-13.
Engelke et al., Anal Biochem (1990) 191(2):396-400.
Ewing and Green, Genome Res (1998) 8(3):175-194.
Fahy, et al., PCR Methods and Applications (1991) 1:25-33.
Fasman, G., Practical Handbook of Biochemistry and Molecular Biology, CRC Press, Boca Raton, FL (1989) pp. 385-394.
Foquet et al., SPIE (1998) 3258: 141-147.
Forster, T., Annalen der Physik (1948) 437(1-2): 55-75.
Fu, Dong-Jing. et al., Nucleic Acids Research (1997) 25(3):677-679.
Funatsu et al., Nature (1995) 374(6522): 555-559.
Furey et al., Biochemistry, (1998) 37:2979-2990.
Garcia-Parajo, M.F., et al., Bioimaging (1998) 6:43-53.
Gelfand, D.H. et al., "Chapter 16. Thermostable DNA Polymerases," in: *PCR Protocols: A Guide to Methods and Applications*, Innis, M.A. et al., eds., p. 129-141 (1990).
Gelles, J. et al., Nature (1988) 331:450-453.
Giusti, et al., PCR Methods and Applications (1993) 2:223-227.
Givens, Richard S. et al., J. Am. Chem. Soc. (1997) 119:8369-8370.
Glazer and Mathies, Current Opinion in Biotechnology (1997) 8:94-102.
Goldman, Ellen R. et al., Bio/Technology (1992) 10:1557-1561.
Goodwin et al., Nucl. Acids Res. (1993) 21(4): 803-806.
Goodwin et al., Nucleosides, Nucleotides and Nucleic Acids (1997) 16(5&6):543-550.
Gram, Hermann et al., Proc. Natl. Acad. Sci. USA (1992) 89:3576-3580.
Gruber, et al., Proc. Natl. Acad. Sci. USA (1975) 72:3966-3969.
Guatelli, et al., Proc. Natl. Acad. Sci. USA (1990) 87:1874-1878.
Guo, Zhen et al., Nucleic Acids Research (1994) 22(24):5456-5465.
Guttler, F. et al., Chem. Phys. Lett. (1994) 217(4):393-397.
Gyllensten, et al., Genome Research (1991) 1:91-98.
Ha, T. et al., Proc. Natl. Acad. Sci. USA (1996) 93:6264-6268.
Haralambidis, J. et al., Nucl. Acids Res. (1987) 15:4857-4876.
Harris et al., ACS Nat'l Mtg. (1997) Abstract #122.
Hart, Hiram E. et al., Molecular Immunology (1979) 16(4):265-267.
Hermes, Jeffrey D. et al., Proc. Natl. Acad. Sci. USA (1990) 87:696-700.
Higgins, D.A. et al., J. Am. Chem. Soc. (1996) 118:4049-4058.
Hiratsuka, Biochimica et Biophysica Acta, 742:496-508 (1983).
Hirschfeld, T., Appl. Opt. (1976) 15(12):2965-2966.
Hobbs, J. Org. Chem. (1989) 54:3420-3422.
Huang et al., Nucleic Acids Res (1992) 20:4567-4573.
Huang S. G. et al., Biochemistry (1995) 34:349-360.
Hull, R. et al., "Parvoviridae," in: *Virology: Directory and Dictionary of Animal, Bacterial and Plant Viruses*, p. 158, Macmillan Publishers, Ltd. (1989).
Ihalainen et al., BioTechniques (1994) 16:938-943.
Inoué, Shinya, Video Microscopy 393-421 (Plenum Press 1986).
Ishijima et al., Cell (1998) 92: 161-171.
Ishikawa, M. et al., Jpn. J. Appl. Phys. (1994) 33:1571-1576.
Iwane, A. et al., FEBS Letters (1997) 407(2):235-238.
Jabukowski, H., Proc Nat'l Acad Sci (1986) 83: 2378-2382.
Jameson et al., Methods in Enzymology (1997) 278:363-390.
Jeng et al., J. Supramolecular Structure (1975) 3:448-68.
Jeong, Lak S. et al., J. Med. Chem. (1993) 36:2627-2638.
Johnson, K.A., Methods Enzymol. (1986) 134:677-705.
Joos, B. et al., Analytical Biochem. (1997) 247(1):96-101.
Joshi, Saroj et al., J. Biol. Chem. (1990) 265(24):14518-14525.
Ju et al., Anal. Biochem., (1995) 231:131-140.
Jung, Stephanie M. et al., Biochimica et Biophysica Acta (1983) 761(2):152-162.
Jung, G. et al., "Confocal microscopy of single molecules of the green fluorescent protein," *Bioimaging* 6:54-61 (1998).
Kasianowicz et al., Proc. Natl. Acad. Sci. (1996) 93:13770-13773.
Keller et al., Applied Spectroscopy, 50(7):12A-32A (1996).

Kiefer et al., Nature (1998) 391:304-307.
Kim, Hea O. et al., J. Med. Chem. (1993) 36(1):30-37.
Klenow, Fragment of DNA Polymerase I, *Stratagene Catalog*, p. 158 (1997/1998).
Kolodziej, P.A., Young, Methods of Enzymology (1991) 194:508-519.
Krohn et al., Analytical Biochem (1995) 225(1): 188-190.
Kumar, Amarendra et al., Biochemistry (1997) 36(45):13954-13962.
Kung et al., Biochemistry (1989) 28(16): 6678-6686.
Kuroda et al., J of Biol Chem (1997) 272(34): 21240-21243.
Lagerholm, B.C. et al., Biophys. J. (1998) 74:1215-1228.
Lakowicz, Joseph R., Principles of Fluorescence Spectroscopy 1-18, 257-301 (Plenum Press 1983).
Lamture, Jagannath B. et al., Nucleic Acids Research (1994) 22(11):2121-2125.
Lawyer et al., J of Biol. Chem. (1989) 264(11):6427-6437.
Lee, Y. et al., Anal. Chem. (1994) 66:4142-4149.
Lee, L.G. et al., Nucl. Acids Res. (1997) 25:2816-2822.
Lewin, B., "Chapter 6. Isolating the gene," in: *Genes V*, p. 127-159, Oxford University Press (1994).
Li and Moclure, J. Biol. Chem. (1998) 273(36):23558-23566.
Lin, T.C. et al., Proc. Natl. Acad. Sci. (1987) 84:7000-7004.
Livak et al., PCR Methods Appl. (1995) 4(6):357-362.
Loh et al., Science, (1989) Reports 243:217-220.
Lundberg, Kelly S. et al., Gene (1991) 108:1-6.
Machara, N. P. et al., Bioimaging (1998) 6:33-42.
Madura et al., Reviews in Computational Chemistry (1995) 91:57-95.
Marshall, P.N., Histochemical Journal (1975) 7:299-303.
Martinez, Carlos I. et al., Bioorganic & Medicinal Chemistry Letters (1997) 7(23):3013-3016.
Masafumi Oshiro, Methods in Cell Biology (1998) (Greenfield Sluder & David E. Wolf eds.) 56(Ch. 3):46-62.
Matayoshi, Edmund D. et al, Science (1990) 247:954-958.
Mathies et al., Analytical Chemistry (1990) 62(17):1786-1791.
Mathis, Gerard, Clin. Chem. (1995) 41(9):1391-1397.
Mc Cafferty, John et al., Nature (1990) 348:552-554.
Meisel, Andreas et al., Nature (1992) 355:467-469.
Meixner, A.J. et al., "Super-resolution imaging and detection of fluorescence from single molecules by scanning near-field optical microscopy," *Opt. Eng.* 34(8):2324-2332 (1995).
Mertz, J. et al., "Single-molecule detection by two-photon-excited fluorescence," *Opt. Lett.* 20(24):2532-2534 (1995).
Metzker et al., Nucleic Acids Research, 22(20):4259-67 (1994).
Moerner, W.E. et al., "Optical Detection and Spectroscopy of Single Molecules in a Solid," *Phys. Rev. Lett.* 62(21):2535-2538 (1989).
Moore et al., Proc. Natl. Acad. Sci. (1982) 79: 7166-7170.
Nguyen, D.C. et al., "Detection of Single Molecules of Phycoerythrin in Hydrodynamically Focused Flows by Laser-Induced Fluorescence," *Anal. Chem.* 59:2158-2161 (1987).
Nilsson et al., Biotechniques (1997) 22:744-751.
Oliphant, Arnold R. et al., Gene (1986) 44(2-3):177-183.
Park, Linda S. et al., J. Biol. Chem. (1986) 261(1):205-210.
Patel et al., Biochemistry (1991) 30:511-525.
Pease, Ann C. et al., Proc. Natl. Acad. Sci. USA (1994) 91(11):5022-5026.
Peck et al., Proc. Natl. Acad. Sci. USA (1989) 86(11):4087-4091.
Pelletier et al., Science (1994) 264: 1891-1903.
Perkins et al., Science (1997) 276(5321): 2016-2021.
Rao, et al., *Mikrochim. Acta*, vol. 128 (1998) , 127-143.
Rienitz, Axel et al., Nucleic Acids Research (1985) 13(15):5685-5695.
Revich et al., "Utilization of 1, $N^6$-Etheno-2'-deoxyadenosine 5'-triphosphate during DNA synthesis on natural templates, catalyzed by DNA polymerase I of *Escherichia coli*" Carcinogenesis, (1986) 7(9):1569-1576, Feb. 9, 2011.
Rigler, R. et al., "Fluorescence correlation spectroscopy with high count rate and low background: analysis of translational diffusion," *Eur. Biophys. J.* (1993) 22:169-175.
Sakthivel et al., Chem. Int. Ed., (1998) 37(20):2872-75.
Sase, I. et al., "Real Time Imaging of Single Fluorophores on Moving Actin with an Epifluorescence Microscope," *Biophys. J.* (1995) 69:323-328.
Sauer et al., "Diode laser based detection of single molecules in solutions," *Chem. Phys. Lett.* (1996) 254:223-228.
Sauer et al., Bioimaging (1998) 6:14-24.
Schecker, et al., Proc. SPIE-Int. Soc. Opt Eng. (1995) 2386:4-12.
Schwartz, David C. et al., Cell (1984) 37:67-75.
Scott, Jamie K. et al., Science (1990) 249:386-390.
Selvin, Paul R., Methods in Enzymology (1995) 246:300-334.
Service, Robert F., Science (1998) 282(5391):1020-1021.
Shao et al., J. Am. Chem. Soc. (1995) 117(14): 3893-3899.
Shera, E.B. et al., "Detection of single fluorescent molecules," *Phys. Lett.* (1990)174(6):553-557.
Singer, M. et al., "Chapter 2. Replication, Maintenance, and Modification of the Genome," in: *Genes and Genomes, A Changing Perspective*, p. 73-128, University Science Books (1991).
Singer, M. et al., "Chapter 6. The Means: Constructing, Cloning, and Selecting Recombinant DNA," in: *Genes and Genomes, A Changing Perspective*, (1991) p. 321-367, University Science Books.
Soderling, T. R., Biochem. Biophys. Acta, (1996) 1297:131-138.
Soper, S.A., et al., "Photon Burst Detection of Single Near-Infrared Fluorescent Molecules," *Anal. Chem.* (1993) 65:740-747.
Steitz, T.A., "A mechanism for all polymerases," *Nature* (1998) 391:231-232.
Stout, A.L. et al., "Evanescent field excitation of fluorescence by epi-illumination microscopy," *Appl. Opt.*(1989) 28:5237-5242.
Stryer et al., "Energy Transfer: A Spectroscopic Ruler," Biochemistry, (1967) 58:719-726.
Stryer, Lubert, Ann. Rev. Biochem. (1978) 47:819-846.
Szöllösi, J. et al., "Application of Fluorescence Resonance Energy Transfer in the Clinical Laboratory: Routine and Research," *Cytometry* (1998) 34:159-179.
Tan et al., Biochem. (1991) 30:2651-2655.
Thompson et al., Biophys. J., (1983) 43:103-14.
Trautman, J.K. et al., "Near-field spectroscopy of single molecules at room temperature," Nature (1994) 369:40-42, Feb. 9, 2011.
Tsang, Shui Y. et al., Biochem. J. (1996) 317:13-16.
Tyagi and Wu, J Biol Chem (1987) 262:10684-10688.
Tyagi, Biochem (1992) 31:6447-6453.
Tyagi, Sanjay, Nature Biotechnology (1996) 14:947-948.
Tyagi, Sanjay et al., Nature Biotechnology (1998) 16:49-53.
USB Molecular Biology Reagents/Protocol 1992, United States Biochemical Corporation, (1991) 135-137,150-153.
Vale, R.D. et al., "Direct observation of single kinesin molecules moving along microtubules," Nature (1996) 380:451-453.
Valenzuela et al., J of Biol Chem (1998) 273(46):30583-30590.
van Oijen, a.M. et al., "3-Dimensional super-resolution by spectrally selective imaging," Chem. Phys. Lett. (1998) 292:183-187.
Voet et al., Biochem, John Wiley & Sons, First Edition (1990) 329-352.
Voet, D. et al., "Chapter 15. Introduction to Metabolism," in: Biochemistry, p. 394-422, John Wiley & Sons (1990).
Voet, D. et al., "Chapter 26. Nucleotide Metabolism," in: Biochemistry, (1990) p. 740-767, John Wiley & Sons.
Walt, D.R., "Fiber optic imaging sensors," Acc. of Chem. Res. (1998) 31:267-278.
Weisenhorn et al., (1990) 58: 1251-1258.
Welsh, J, Cell Science (1993) Supp 17:235-239.
Wennmalm et al., Proc. Natl. Acad. Sci. (1997) 94: 10641-10646.
Wetmur, J. G., Crit. Rev. Biochem. Mol. Biol. (1991) 26(3-4):227-259.
Wisdom, B., Methods in Mol. Biol. (1994) 32: 433-440.
Wu et al., Arch. Biochem. Biophys. (1986) 246(2): 564-571.
Wu et al., J. of Biol. Chem. (1987) 262(27): 13147-13154.
Wu, P. G. et al., Analytical Biochemistry (1994) 218(1):1-13.
Wu et al., FEBS Letters (1998) 440:111-115.
Xia, Jie et al., Bioorganic & Medicinal Chemistry Letters (1997) 7(10):1243-1248.
Xie, et al., Science (1994) 265:361-364.
Xu, X. et al., Science (1997) 275:1106-1109.
Yarbrough et al., J. Biol. Chem. (1980) 255(20):9907-11.
Zarling, David A. et al., Journal of Immunology (1980) 124(2):913-920.
Zhu et al., Nucleic Acids Research (1994) 22(16): 3418-3422.

Zhuang et al., Hum Mut (1996) 7(2):89-99.
Ashworth, D.C. et al. "Section II. Systems and programs. Transducer mechanisms for optical . . ." Computer Methods and Programs in Biomedicine (1989) 30:21-31.
Chang, H.T., et al. "Dynamic control to improve the separation performance in capillary electrophoresis" Electrophoresis (1995) 16:2069-2073.

Hamada, et al., "DAPI Staining Improved for Quantitative Cytofluorometry", Histochemistry (1983) 79:219-226.
Schwartz, et al., "Conformational Dynamics of Individual DNA Molecules During Gel Electrophoresis", Letters to Nature (1989) 338:520-522.

* cited by examiner

METHODS AND PRODUCTS FOR ANALYZING POLYMERS

RELATED APPLICATION

This application is a divisional of prior application Ser. No. 09/134,411, filed on Aug. 13, 1998, entitled Methods and Products for Analyzing Polymers, and now issued as U.S. Pat. No. 6,355,420 on Mar. 12, 2002, which is a continuation of PCT/US98/03024, filed on Feb. 11,1998, which claims priority to U.S. Provisionals 60/064,687, filed on Nov. 5, 1997 and 60/037,921, filed on Feb. 12, 1997.

BACKGROUND

The study of molecular and cellular biology is focused on the macroscopic structure of cells. We now know that cells have a complex microstructure that determine the functionality of the cell. Much of the diversity associated with cellular structure and function is due to the ability of a cell to assemble various building blocks into diverse chemical compounds. The cell accomplishes this task by assembling polymers from a limited set of building blocks referred to as monomers. The key to the diverse functionality of polymers is based in the primary sequence of the monomers within the polymer and is integral to understanding the basis for cellular function, such as why a cell differentiates in a particular manner or how a cell will respond to treatment with a particular drug.

The ability to identify the structure of polymers by identifying their sequence of monomers is integral to the understanding of each active component and the role that component plays within a cell. By determining the sequences of polymers it is possible to generate expression maps, to determine what proteins are expressed, to understand where mutations occur in a disease state, and to determine whether a polysaccharide has better function or loses function when a particular monomer is absent or mutated.

Expression maps relate to determining mRNA expression patterns. The need to identify differentially expressed mRNAs is critical in the understanding of genetic programming, both temporally and spatially. Different genes are turned on and off during the temporal course of an organisms' life development, comprising embryonic, growth, and aging stages. In addition to developmental changes, there are also temporal changes in response to varying stimuli such as injury, drugs, foreign bodies, and stress. The ability to chart expression changes for specific sets of cells in time either in response to stimuli or in growth allows the generation of what are called temporal expression maps. On the other hand, there are also body expression maps, which include knowledge of differentially expressed genes for different tissues and cell types. Expression maps are different not only between species and between individuals, but also between diseased and disease-free states. Examination of differential gene expression has yielded key discoveries of genes in widely varying disciplines, such as signal transduction (Smith et al., 1990), circadian rhythms (Loros et al., 1989), fruit ripening (Wilinson et al., 1995), hunger (Qu et al., 1996), cell cycle control (el-Deiry et al., 1993), apoptosis (Woronicz et al., 1994), and ischemic injury (Wang et al., 1995), among many others. Since generation of expression maps involve the sequencing and identification of cDNA or mRNA, more rapid sequencing necessarily means more rapid generation of multiple expression maps.

Currently, only 1% of the human genome and an even smaller amount of other genomes have been sequenced. In addition, only one very incomplete human body expression map using expressed sequence tags has been achieved (Adams et al., 1995). Current protocols for genomic sequencing are slow and involve laborious steps such as cloning, generation of genomic libraries, colony picking, and sequencing. The time to create even one partial genomic library is on the order of several months. Even after the establishment of libraries, there are time lags in the preparation of DNA for sequencing and the running of actual sequencing steps. Given the multiplicative effect of these unfavorable facts, it is evident that the sequencing of even one genome requires an enormous investment of money, time, and effort.

In general DNA sequencing is currently performed using one of two methods. The first and more popular method is the dideoxy chain termination method described by Sanger et al. (1977). This method involves the enzymatic synthesis of DNA molecules terminating in dideoxynucleotides. By using the four ddNTPs, a population of molecules terminating at each position of the target DNA can be synthesized. Subsequent analysis yields information on the length of the DNA molecules and the base at which each molecule terminates (either A, C, G, or T). With this information, the DNA sequence can be determined. The second method is Maxam and Gilbert sequencing (Maxam and Gilbert, 1977), which uses chemical degradation to generate a population of molecules degraded at certain positions of the target DNA. With knowledge of the cleavage specificities of the chemical reactions and the lengths of the fragments, the DNA sequence is generated. Both methods rely on polyacrylamide gel electrophoresis and photographic visualization of the radioactive DNA fragments. Each process takes about 1-3 days. The Sanger sequencing reactions can only generate 300-800 bases in one run.

Methods to improve the output of sequence information using the Sanger method also have been proposed. These Sanger-based methods include multiplex sequencing, capillary gel electrophoresis, and automated gel electrophoresis. Recently, there has also been increasing interest in developing Sanger independent methods as well. Sanger independent methods use a completely different methodology to realize the base information. This category contains the most novel techniques, which include scanning electron microscopy (STM), mass spectrometry, enzymatic luminometric inorganic pyrophosphate detection assay (ELIDA) sequencing, exonuclease sequencing, and sequencing by hybridization. A brief summary of these methods is set forth below.

Currently, automated gel electrophoresis is the most widely used method of large-scale sequencing. Automation requires reading of fluorescently labeled Sanger fragments in real time with a charge coupled device (CCD) detector. The four different dideoxy chain termination reactions are run with different labeled primers. The reaction mixtures are combined and co-electrophoresed down a slab of polyacrylamide. Using laser excitation at the end of the gel, the separated DNA fragments are resolved and the sequence determined by computer. Many automated machines are available commercially, each employing different detection methods and labeling schemes. The most efficient of these is the Applied Biosystems Model 377XL, which generates a maximum actual rate of 115,200 bases per day.

In the method of capillary gel-electrophoresis, reaction samples are analyzed by small diameter, gel-filled capillaries. The small diameter of the capillaries (50 µm) allows for efficient dissipation of heat generated during electrophoresis. Thus, high field strengths can be used without excessive Joule heating (400 V/m), lowering the separation time to about 20 minutes per reaction run. Not only are the bases separated more rapidly, there is also increased resolution over conventional gel electrophoresis. Furthermore, many capillaries are analyzed in parallel (Wooley and Mathies, 1995), allowing amplification of base information generated (actual rate is equal to 200,000 bases/day). The main drawback is that there is not continuous loading of the capillaries since a new gel-filled capillary tube must be prepared for each reaction. Capillary gel electrophoresis machines have recently been commercialized.

Multiplex sequencing is a method which more efficiently uses electrophoretic gels (Church and Kieffer-Higgins, 1988). Sanger reaction samples are first tagged with unique oligomers and then up to 20 different samples are run on one lane of the electrophoretic gel. The samples are then blotted onto a membrane. The membrane is then sequentially probed with oligomers that correspond to the tags on the Sanger reaction samples. The membrane is washed and reprobed successively until the sequences of all 20 samples are determined. Even though there is a substantial reduction in the number of gels run, the washing and hybridizing steps are as equally laborious as running electrophoretic gels. The actual sequencing rate is comparable to that of automated gel electrophoresis.

Sequencing by mass spectrometry was first introduced in the late 80's. Recent developments in the field have allowed for better sequence determination (Crain, 1990; Little et al., 1994; Keough et al., 1993; Smimov et al., 1996). Mass spectrometry sequencing first entails creating a population of nested DNA molecules that differ in length by one base. Subsequent analysis of the fragments is performed by mass spectrometry. In one example, an exonuclease is used to partially digest a 33-mer (Smimov, 1996). A population of molecules with similar 5' ends and varying points of 3' termination is generated. The reaction mixture is then analyzed. The mass spectrometer is sensitive enough to distinguish mass differences between successive fragments, allowing sequence information to be generated.

Mass spectrometry sequencing is highly accurate, inexpensive, and rapid compared to conventional methods. The major limitation, however, is that the read length is on the order of tens of bases. Even the best method, matrix-assisted laser desorption ionization time-of-flight (MALDI-TOF) mass spectroscopy (Smimov et al., 1996), can only achieve maximum read lengths of 80-90 base pairs. Much longer read lengths are physically impossible due to fragmentation of longer DNA at guanidines during the analysis step. Mass spectrometry sequencing is thus limited to verifying short primer sequences and has no practical application in large-scale sequencing.

The Scanning tunneling microscope (STM) sequencing (Ferrell, 1997) method was conceived at the time the STM was commercially available. The initial promise of being able to read base-pair information directly from the electron micrographs no longer holds true. DNA molecules must be placed on conducting surfaces, which are usually highly ordered pyrolytic graphite (HOPG) or gold. These lack the binding sites to hold DNA strongly enough to resist removal by the physical and electronic forces exerted by the tunneling tip. With difficulty, DNA molecules can be electrostatically adhered to the surfaces. Even with successful immobilization of the DNA, it is difficult to distinguish base information because of the extremely high resolutions needed. With current technology, purines can be distinguished from pyrimidines, but the individual purines and pyrimidines cannot be identified. The ability to achieve this feat requires electron microscopy to be able to distinguish between aldehyde and amine groups on the purines and the presence or absence of methyl groups on the pyrimidines.

Enzymatic luminometric inorganic pyrophosphate detection assay (ELIDA) sequencing uses the detection of pyrophosphate release from DNA polymerization to determine the addition of successive bases. The pyrophosphate released by the DNA polymerization reaction is converted to ATP by ATP sulfurylase and the ATP production is monitored continuously by firefly luciferase. To determine base specificity, the method uses successive washes of ATP, CTP, GTP, and TTP. If a wash for ATP generates pyrophosphate, one or more adenines are incorporated. The number of incorporated bases is directly proportional to the amount of pyrophosphate generated. Enhancement of generated sequence information can be accomplished with parallel analysis of many ELIDA reactions simultaneously.

The main disadvantage is the short read length. Ronaghi et al. (1996) have only achieved a maximum read length of 15 bases because of the multiple washings needed. Since there are four washes per base read, this means that a total of 400 washes mush be performed for a read length of a hundred bases. If there is even 1% loss of starting material for each wash, after 400 washes there would be 1.8% of the starting material remaining, which is insufficient for detection.

Exonuclease sequencing involves a fluorescently labeled, single-stranded DNA molecule which is suspended in a flowing stream and sequentially cleaved by an exonuclease. Individual fluorescent bases are then released and passed through a single molecule detection system. The temporal sequence of labeled nucleotide detection corresponds to the sequence of the DNA (Ambrose et al., 1993; Davis et al., 1992; Jett et al., 1989). Using a processive exonuclease, it theoretically is possible to sequence 10,000 bp or larger fragments at a rate of 10 bases per second.

In practice, exonuclease sequencing has encountered many difficulties in each of the steps. The labeling step requires that all four bases in the DNA be tagged with different fluorophores. Sterically, this is extremely unfavorable. Ambrose et al., 1993 has achieved complete labeling of two bases on a 7 kb strand of M13 DNA. Furthermore, difficult optical trapping is needed to suspend DNA molecules in a flowing stream. The step is time intensive and requires considerable expertise. Lastly, single molecules of fluorophore need to be detected with high efficiency. Even a 1% error is significant. Improvements in detection from 65% to 95% efficiency have been achieved. The efficiency of detection has been pushed to the limit and it would be difficult to achieve further improvements.

In the sequencing by hybridization method, a target DNA is sequentially probed with a set of oligomers consisting of all the possible oligomer sequences. The sequence of the target DNA is generated with knowledge of the hybridization patterns between the oligomers and the target (Bains, 1991; Cantor et al., 1992; Drmanac et al., 1994). There are two possible methods of probing target DNA. The "Probe Up" method includes immobilizing the target DNA on a substrate and probing successively with a set of oligomers. "Probe Down" on the other hand requires that a set of oligomers be immobilized on a substrate and hybridized with the target DNA. With the advent of the "DNA chip," which applies microchip synthesis techniques to DNA probes, arrays of thousands of different DNA probes can be generated on a 1 $cm^2$ area, making Probe Down methods more practical. Probe Up methods would require, for an 8-mer, 65,536 successive probes and washings, which would take an enormous amount of time. On the other hand, Probe Down hybridization generates data in a few seconds. With perfect hybridization, 65,536 octamer probes would determine a maximum of 170 bases. With 65,536 "mixed" 11-mers, 700 bases can be generated.

In practice, Probe Up methods have been used to generate sequences of about 100 base pairs. Imperfect hybridization has led to difficulties in generating adequate sequence. Error in hybridization is amplified many times. A 1% error rate reduces the maximum length that can be sequenced by at least 10%. Thus if 1% of 65,536 oligonucleotides gave false positive hybridization signals when hybridizing to a 200-mer DNA target, 75% of the scored "hybridizations" would be false (Bains, 1997). Sequence determination would be impossible in such an instance. The conclusion is that hybridization must be extremely effective in order to generate reasonable data. Furthermore, sequencing by hybridization also encounters problems when there are repeats in sequences that are one base less than the length of the probe. When such sequences are present, multiple possible sequences are compatible with the hybridization data.

The most common limitation of most of these techniques is a short read length. In practice a short read length means that additional genetic sequence information needs to be sequenced before the linear order of a target DNA can be deciphered. The short fragments have to be bridged together with additional overlapping fragments. Theoretically, with a 500 base read length, a minimum of $9 \times 10^9$ bases need to be sequenced before the linear sequence of all $3 \times 10^9$ bases of the human genome are properly ordered. In reality, the number of bases needed to generate a believable genome is approximately $2 \times 10^{10}$ bases. Comparisons of the different techniques show that only the impractical exonuclease sequencing has the theoretical capability of long read lengths. The other methods have short theoretical read lengths and even shorter realistic read lengths. To reduce the number of bases that need to be sequenced, it is clear that the read length must be improved.

Protein sequencing generally involves chemically induced sequential removal and identification of the terminal amino acid residue, e.g., by Edman degradation. See Stryer, L., *Biochemistry*, W. H. Freeman and Co., San Francisco (1981) pp. 24-27. Edman degradation requires that the polypeptide have a free amino group which is reacted with an isothiocyanate. The isothiocyanate is typically phenyl isothiocyanate. The adduct intramolecularly reacts with the nearest backbone amide group of the polymer thereby forming a five membered ring. This adduct rearranges and the terminal amino acid residue is then cleaved using strong acid. The released phenylthiohydantoin (PTH) of the amino acid is identified and the shortened polymer can undergo repeated cycles of degradation and analysis.

Further, several new methods have been described for carboxy terminal sequencing of polypeptides. See Inglis, A. S., Anal. Biochem. 195:183-96 (1991). Carboxy terminal sequencing methods mimic Edman degradation but involve sequential degradation from the opposite end of the polymer. See Inglis, A. S., Anal. Biochem. 195:183-96 (1991). Like Edman degradation, the carboxy-terminal sequencing methods involve chemically induced sequential removal and identification of the terminal amino acid residue.

More recently, polypeptide sequencing has been described by preparing a nested set (sequence defining set) of polymer fragments followed by mass analysis. See Chait, B. T. et al., Science 257:1885-94 (1992). Sequence is determined by comparing the relative mass difference between fragments with the known masses of the amino acid residues. Though formation of a nested (sequence defining) set of polymer fragments is a requirement of DNA sequencing, this method differs substantially from the conventional protein sequencing method consisting of sequential removal and identification of each residue. Although this method has potential in practice it has encountered several problems and has not been demonstrated to be an effective method.

Each of the known methods for sequencing polymers has drawbacks. For instance most of the methods are slow and labor intensive. The gel based DNA sequencing methods require approximately 1 to 3 days to identify the sequence of 300-800 units of a polymer. Methods such as mass spectroscopy and ELIDA sequencing can only be performed on very short polymers.

An enormous need exists for de noveau polymer sequence determination. The rate of sequencing has limited the capability to generate multiple body and temporal expression maps which would undoubtedly aid the rapid determination of complex genetic function. A need also exists for improved methods for analyzing polymers in order to speed up the rate at which diagnosis of diseases and preparation of new medicines is carried out.

SUMMARY OF THE INVENTION

The invention relates to new methods and products for analyzing polymers and in particular new methods and products useful for determining the sequence of polymers. The invention has surprising advantages over prior art methods used to sequence polymers. Prior to the present invention no method or combination of methods has come close to achieving the rate of sequencing which the instant invention is capable of achieving. Using the methods of the invention the entire human genome can be sequenced several orders of magnitude faster than could be accomplished using conventional technology. In addition to sequencing the entire genome, the methods and products of the invention can be used to create comprehensive and multiple expression maps for developmental and disease processes. The ability to sequence an individual's genome and to generate multiple expression maps will greatly enhance the ability to determine the genetic basis of any phenotypic trait or disease process.

The method for analyzing polymers according to the invention is based on the ability to examine each unit of a polymer individually. By examining each unit individually the type of unit and the position of the unit on the backbone of the polymer can be identified. This can be accomplished by positioning a unit at a station and examining a change which occurs when that unit is proximate to the station. The change can arise as a result of an interaction that occurs between the unit and the station or a partner and is specific for the particular unit. For instance if the polymer is a nucleic acid molecule and a T is positioned in proximity to a station a change which is specific for a T occurs. If on the other hand, a G is positioned in proximity to a station then a change which is specific for a G will occur. The specific change which occurs depends on the station used and the type of polymer being studied. For instance the change may be an electromagnetic signal which arises as a result of the interaction.

The methods of the invention broadly encompass two types of methods for analyzing polymers by identifying a unit (or in some cases a group of units) within a polymer. The first type of method involves the analysis of at least a single polymer. An individual unit of the single polymer in one aspect is caused to interact with an agent such that a change, e.g., energy transfer or quenching occurs and produces a signal. The signal is indicative of the identity of the unit. In another aspect an individual unit is exposed to a station resulting in a detectable physical change to the unit or station. The change in the unit or station produces a signal which can be detected and is characteristic of that particular unit. The second type of method involves the analysis of a plurality of polymers. A unit of each of the plurality of polymers is positioned at a station where an interaction can occur. The interaction is one which produces a polymer dependent impulse that specifically identifies the unit. The polymer dependent impulse may arise from, for example, energy transfer, quenching, changes in conductance, mechanical changes, resistance changes, or any other physical change.

The proposed method for analyzing polymers is particularly useful for determining the sequence of units within a DNA molecule and can eliminate the need for generating genomic libraries, cloning, and colony picking, all of which constitute lengthy pre-sequencing steps that are major limitations in current genomic-scale sequencing protocols. The methods disclosed herein provide much longer read lengths than achieved by the prior art and a million-fold faster sequence reading. The proposed read length is on the order of several hundred thousand nucleotides. This translates into significantly less need for overlapping and redundant sequences, lowering the real amount of DNA that needs to be sequenced before genome reconstruction is possible.

Methods for preparing polymers for analysis are also claimed herein. The combination of the long read length and the novel preparation methods results in a much more streamlined and efficient process. Lastly, the actual time taken to read a given number of units of a polymer is a million-fold more rapid than current methods because of the tremendous parallel amplification supplied by a novel apparatus also claimed herein, which is referred to as a nanochannel plate or a microchannel plate. The combination of all these factors translates into a method of polymer analysis including sequencing that will provide enormous advances in the field of molecular and cell biology.

The ability to sequence polymers such as genomic DNA by the methods described in the instant invention will have tremendous implications in the biomedical sciences. The recovery of genetic data at such a rapid pace will advance the Human Genome Project. The methods and products of the invention will allow the capability to prepare multiple expression maps for each individual, allowing complete human genetic programs to be deciphered. The ability to compare pools of individual genetic data at one time will allow, for the first time, the ability to discover not only single gene diseases with ease, but also complex multigene disorders as rapidly as the DNA itself is sequenced.

In one aspect the invention is a method for analyzing a polymer of linked units. The method involves the steps of exposing a plurality of individual units of a polymer to an agent selected from the group consisting of electromagnetic radiation, a quenching source and a fluorescence excitation source, individual units interacting with the agent to produce a detectable signal, and detecting sequentially the signals resulting from said interaction to analyze the polymer. In one embodiment the signal is electromagnetic radiation. In another embodiment the agent is electromagnetic radiation. According to an embodiment of the invention individual units of the polymer are labeled with a fluorophore.

The plurality of individual units of the polymer may be sequentially exposed to electromagnetic radiation by bringing the plurality of individual units in proximity to a light emissive compound and exposing the light emissive compound to electromagnetic radiation, and wherein the plurality of individual units of the polymer detectably affect emission of electromagnetic radiation from the light emissive compound. In another embodiment the plurality of individual units of the polymer are sequentially exposed to electromagnetic radiation, and wherein the electromagnetic radiation detectably affects emission of electromagnetic radiation from the plurality of individual units of the polymer to produce the detectable signal.

According to another embodiment of the invention the method involves the step of moving the polymer through a nanochannel in a wall material in order to locate the detectable signal. The plurality of individual units of the polymer are sequentially exposed to the agent by moving the polymer through a nanochannel in a wall material and exposing the plurality of individual units of the polymer to the agent at an interaction station at the nanochannel. The agent can be attached to (embedded in, covalently attached to the surface of or coated on the surface of) the wall material. In one embodiment the wall material includes a plurality of nanochannels, an interaction station at each nanochannel, and a plurality of polymers is moved through said nanochannel, only one polymer passes the interaction station at any given time (more than one polymer may be in a single nanochannel at a given time as long as they do not overlap), and signals resulting from the interaction of individual units of the polymers and the agent at the interaction stations are detected simultaneously. Preferably the nanochannel is fixed in the wall material.

The signals which are detected can be stored in a database for further analysis. In one method of analysis these signals can be compared to a pattern of signals from another polymer to determine the relatedness of the two polymers. Alternatively the detected signals can be compared to a known pattern of signals characteristic of a known polymer to determine the relatedness of the polymer being analyzed to the known polymer. The analysis may also involve measuring the length of time elapsed between detection of a first signal from the first unit and a second signal from a second unit. In one embodiment the plurality of individual units are two units, a first unit at a first end of the polymer and a second unit at an opposite second end of the polymer. The time elapsed between the sequential detection of signals may indicate the distance between two units or the length of the polymer.

The polymer may be any type of polymer known in the art. In a preferred embodiment the polymer is selected from the group consisting of a nucleic acid and a protein. In a more preferred embodiment the polymer is a nucleic acid.

The units of the polymer which interact with the agent to produce a signal are labeled. The units may be intrinsically labeled or extrinsically labeled. In one embodiment only a portion of the units of the polymer are labeled. In another embodiment all of the units are labeled. In yet another embodiment at least two units of the polymer are labeled differently so as to produce two different detectable signals. The units of the polymer may be labeled such that each unit or a specified portion of the units is labeled or it may be randomly labeled.

In another embodiment the plurality of individual units of the polymer are exposed to at least two stations positioned in distinct regions of the channel, wherein the interaction between the units of the polymer and the at least two stations produces at least two signals.

In one embodiment the individual unit of the polymer is labeled with radiation and the signal is electromagnetic radiation in the form of fluorescence.

In another embodiment the unit is exposed to the agent at a station. Preferably the station is a non-liquid material.

In yet another embodiment the plurality of individual units of the polymer are exposed to at least two agents and the interaction between the units of the polymer and the at least two agents produces at least two signals. The at least two agents may be positioned in distinct regions of a channel through which the polymer passes. In one embodiment the at least two signals are different signals. In another embodiment the at least two signals are the same signals.

According to another aspect of the invention a method for analyzing a polymer of linked units is provided. The method involves the steps of moving a plurality of individual units of a polymer of linked units with respect to a station and detecting sequentially signals arising from a detectable physical change in the polymer or the station as individual units pass the station to analyze the polymer. This aspect of the invention also encompasses each of the embodiments discussed above.

In one embodiment the station is an interaction station and the individual units are exposed at the interaction station to an agent that interacts with the individual unit to produce a detectable electromagnetic radiation signal characteristic of the interaction. In another embodiment the station is a signal generation station and the characteristic signal produced is a polymer dependent impulse. Preferably the station is a non-liquid material.

In another aspect the invention is a method for analyzing a polymer of linked units by exposing a plurality of individual units of a polymer to a station to produce to produce a non-ion conductance signal resulting from the exposure of the units of the polymer to the station, and wherein the station is attached to a wall material having a surface defining a channel. This aspect of the invention also encompasses each of the embodiments discussed above.

According to another aspect of the invention a method for identifying an individual unit of a polymer is provided. The method involves the steps of transiently exposing the individual unit of the polymer to an agent selected from the group consisting of electromagnetic radiation, a quenching source and a fluorescence excitation source, the identity of the individual unit being unknown, to generate an interaction with a detectable electromagnetic radiation signal characteristic of said individual unit, detecting said signal, and distinguishing said signal from signals generated from adjacent signal generating units of the polymer as an indication of the identity of the individual unit.

The agent can be one or more fluorophores and preferably is at least three fluorophores. When the individual unit is transiently exposed to one or more fluorophores (agent) by positioning the individual unit within energy transfer proximity of the agent, fluorescence energy transfer occurs between the agent and the individual unit. The signal is detected by detecting the fluorescence energy transfer.

In one embodiment the individual unit of the polymer is exposed to the agent by positioning the individual unit at an interaction station comprising a nanochannel in a wall material. Preferably the wall material comprises at least two layers, one of the layers allowing signal generation and the other preventing signal generation and the nanochannel traverses both layers.

According to another aspect the invention is a method for identifying an individual unit of a polymer. The method includes the steps of transiently moving the individual unit of the polymer relative to a station, the identity of the individual unit being unknown, detecting a signal arising from a detectable physical change in the unit or the station, and distinguishing said signal from signals arising from exposure of adjacent signal generating units of the polymer to the station as an indication of the identity of the individual unit. This aspect of the invention also encompasses each of the embodiments discussed above.

In one embodiment the station is an interaction station and the individual units are exposed at the interaction station to an agent that interacts with the individual unit to produce a detectable electromagnetic radiation signal characteristic of the interaction. In another embodiment the station is a signal generation station and the characteristic signal produced is a polymer dependent impulse.

In yet another aspect the invention is a method for determining the proximity of two individual units of a polymer of linked units. The method includes the steps of moving the polymer relative to a station, exposing individual units to the station to produce a characteristic signal arising from a detectable physical change in the unit or the station, detecting characteristic signals generated, and measuring the amount of time elapsed between detecting characteristic signals, the amount of time elapsed being indicative of the proximity of the two individual units.

In one embodiment the station is an interaction station. In another embodiment the interaction station includes an agent and the agent is selected from the group consisting of electromagnetic radiation, a quenching source and a fluorescence excitation source and the characteristic signal is a detectable electromagnetic radiation signal. In another embodiment the interaction station is a nanochannel in a wall material.

In certain other embodiments the station referred to is a signal generation station. In another embodiment the signal generation station includes a physical impulse source which interacts with the polymer to produce a characteristic signal which is a physical impulse. The physical impulse in one embodiment arises from a change in a physical quantity such as resistance or conductance as a result of the exposure of the physical impulse source to the unit of the polymer. In one embodiment the physical impulse arises from changes in capacitance or resistance caused by the movement of the unit between microelectrodes or nanoelectrodes positioned adjacent to the polymer unit. For instance the signal generation station may include microelectrodes or nanoelectrodes positioned on opposite sides of the polymer unit. The changes in resistance or conductance which occur as a result of the movement of the unit past the electrodes will be specific for the particular unit. In another embodiment the physical impulse arises from a release of radioactive signal from the unit. In other embodiments it arises from piezoelectric tip, direct physical contact, and NMR-nuclear spin signal.

The polymer may be any type of polymer known in the art. In a preferred embodiment the polymer is selected from the group consisting of a nucleic acid and a protein. In a more preferred embodiment the polymer is a nucleic acid. The polymers can be labeled, randomly or non randomly. Different labels can be used to label different linked units to produce different signals. In one embodiment the individual units of the polymer are labeled with a fluorophore.

A method for determining the order of two individual units of a polymer of linked units is provided in another aspect of the invention. The method involves the steps of moving the polymer linearly with respect to a station, exposing one of the individual units to the station to produce a signal arising from a detectable physical change in the unit or the station, exposing the other of the individual units to the station to produce a second detectable signal arising from a detectable physical change in the unit or the station, different from the first signal, and determining the order of the signals as an indication of the order of the two individual units.

In one embodiment the station is an interaction station. In another embodiment the interaction station includes an agent and the agent is selected from the group consisting of electromagnetic radiation, a quenching source and a fluorescence excitation source and the characteristic signals produced are detectable electromagnetic radiation signals. In another embodiment the interaction station is a nanochannel in a wall material.

In certain other embodiments the station referred to is a signal generation station. In another embodiment the signal generation station includes a physical impulse source which interacts with the polymer to produce a characteristic signal which is a physical impulse. The physical impulse in one embodiment arises from a change in a physical quantity such as resistance or conductance as a result of the exposure of the physical impulse source to the unit of the polymer. In one embodiment the physical impulse arises from changes in capacitance or resistance caused by the movement of the unit between microelectrodes or nanoelectrodes positioned adjacent to the polymer unit. For instance the signal generation station may include microelectrodes or nanoelectrodes positioned on opposite sides of the polymer unit. The changes in resistance or conductance which occur as a result of the movement of the unit past the electrodes will be specific for the particular unit. In another embodiment the physical impulse arises from a release of radioactive signal from the unit. In other embodiments it arises from piezoelectric tip, direct physical contact, and NMR-nuclear spin signal.

The polymer may be any type of polymer known in the art. In a preferred embodiment the polymer is selected from the group consisting of a nucleic acid and a protein. In a more preferred embodiment the polymer is a nucleic acid. The polymers can be labeled, randomly or non randomly. Different labels can be used to label different linked units to produce different signals. In one embodiment the individual units of the polymer are labeled with a fluorophore. In another embodiment the individual units of the polymer are labeled with radioactivity.

According to yet another aspect of the invention a method for determining the distance between two individual units of a polymer of linked units is provided. The method involves the steps of causing the polymer to pass linearly relative to a station, detecting a characteristic signal generated as each of the two individual units passes by the station, measuring the time elapsed between the signals measured, repeating steps 1, 2 and 3 for a plurality of similar polymers to produce a data set, and determining the distance between the two individual units based upon the information obtained from said plurality of similar polymers by analyzing the data set.

In one embodiment the station is an interaction station. In another embodiment the interaction station includes an agent and the agent is selected from the group consisting of electromagnetic radiation, a quenching source and a fluorescence excitation source. In another embodiment the characteristic signals produced are detectable electromagnetic radiation signals. In another embodiment the interaction station is a nanochannel in a wall material.

In certain other embodiments the station referred to is a signal generation station. In another embodiment the signal generation station includes a physical impulse source which interacts with the polymer to produce a characteristic signal which is a physical impulse. The physical impulse in one embodiment arises from a change in a physical quantity such as resistance or conductance as a result of the exposure of the physical impulse source to the unit of the polymer. In one embodiment the physical impulse arises from changes in capacitance or resistance caused by the movement of the unit between microelectrodes or nanoelectrodes positioned adjacent to the polymer unit. For instance the signal generation station may include microelectrodes or nanoelectrodes positioned on opposite sides of the polymer unit. The changes in resistance or conductance which occur as a result of the movement of the unit past the electrodes will be specific for the particular unit. In another embodiment the two linked units are detected at the signal generation station by measuring light emission at the station. In another embodiment the physical impulse arises from a release of radioactive signal from the unit. In other embodiments it arises from piezoelectric tip, direct physical contact, and NMR-nuclear spin signal.

The polymer may be any type of polymer known in the art. In a preferred embodiment the polymer is selected from the group consisting of a nucleic acid and a protein. In a more preferred embodiment the polymer is a nucleic acid. The polymers can be labeled, randomly or non randomly. Different labels can be used to label different linked units to produce different signals. In one embodiment the individual units of the polymer are labeled with a fluorophore.

According to another embodiment the plurality of similar polymers is a homogeneous population. In another embodiment the plurality of similar polymers is a heterogenous population.

In another embodiment steps (1)-(4) are carried out substantially simultaneously.

According to yet another aspect of the invention a method for detecting resonance energy transfer or quenching between two interactive partners capable of such transfer or quenching is disclosed. The method involves the steps of bringing the two partners in close enough proximity to permit such transfer or quenching, applying an agent to one of said partners, the agent selected from the group consisting of electromagnetic radiation, a quenching source and a fluorescence excitation source, shielding fluorescence resonance energy transfer and quenching occurring from electromagnetic radiation emission and interaction between said partners with a material shield, and detecting the emitted electromagnetic radiation. In a preferred embodiment the material shield is a conductive material shield.

In another aspect the invention is a method for analyzing a polymer of linked units. The method includes the steps of providing a labeled polymer of linked units, detecting signals from unit specific markers of less than all of the linked units, and storing a signature of said signals detected to analyze the polymer. In one embodiment all of the unit specific markers are detected. In another embodiment the polymer is partially and randomly labeled with unit specific markers. In yet another embodiment only a portion of the unit specific markers are detected. All of the units of the polymer are labeled with a unit specific marker in another embodiment.

The labeled polymer of linked units in one embodiment is exposed to an agent selected from the group consisting of electromagnetic radiation, a quenching source and a fluorescence excitation source and the signals are produced by the interaction between a unit specific marker of the polymer and the agent.

In one embodiment the signals are detected linearly. In another embodiment the signature of signals includes at least 10 signals, and preferably 20 signals. The signature of signals includes any information about the polymer. Preferably the signature of signals includes information about the order, distance and number of unit specific markers.

In another embodiment the labeled polymer of linked units is moved with respect to a station and wherein the signals are generated upon exposure of a unit specific marker of the polymer to the station. The station may be an interaction station.

The method in some embodiments is a method for identifying a unit specific marker of the polymer, the identity of the unit specific marker being indicative of the identity of at least one unit of the polymer. The unit specific marker is transiently exposed to a station to produce signals characteristic of said unit specific marker and the signal is distinguished from signals generated from adjacent signal generating unit specific markers of the polymer as an indication of the identity of the unit specific marker. The station may be an interaction station including an agent selected from the group consisting of electromagnetic radiation, a quenching source and a fluorescence excitation source and wherein the signals are detectable electromagnetic radiation signals.

The method in other embodiments is a method for determining the proximity of two unit specific markers of the polymer wherein the proximity of the two unit specific markers is the signature of said signals, the identity of each unit specific marker being indicative of the identity of at least one unit of the polymer. The labeled polymer is moved relative to a station to expose the two unit specific markers to the station to produce a characteristic signal arising from a detectable physical change in the unit specific marker or the station, and the amount of time elapsed between detecting each characteristic signal is measured, the amount of time elapsed being indicative of the proximity of the two unit specific markers.

The method may also be a method for determining the order of two unit specific markers of the polymer, the identity of each unit specific marker being indicative of the identity of at least one unit of the polymer wherein the order of the two unit specific markers is the signature of said signals. The labeled polymer is moved linearly with respect to a station, to expose one of the unit specific markers to the station to produce a signal which is a unit specific marker and to expose the other of the unit specific markers to the station to produce a second detectable which is a unit specific marker, different from the first signal. The order of the signals determined is an indication of the order of the two unit specific markers.

The method in an embodiment is a method for determining the distance between two unit specific markers of the polymer, the identity of each unit specific marker being indicative of the identity of at least one unit of the polymer wherein the distance between two unit specific markers is the signature of said signals. The labeled polymer is moved linearly relative to a station to produce a characteristic signal generated as each of the two unit specific markers passes by the station and the distance between the signals is determined as an indication of the distance between the two unit specific markers.

The method is a method for characterizing a test labeled polymer, wherein a plurality of labeled polymers is exposed to a station to obtain the signature of signals for each of the plurality of labeled polymers in another embodiment. The method involves the steps of comparing the signature of signals of the plurality of polymers, determining the relatedness of the polymers based upon similarities between the signature of signals of the polymers, and characterizing the test polymer based upon the signature of signals of related polymers.

According to yet another embodiment the method is a method for sequencing a polymer of linked units. A signature of signals is obtained from each of a plurality of overlapping polymers, at least a portion of each of the polymers having a sequence of linked units identical to the other of the polymers, and the signature of signals is compared to obtain a sequence of linked units which is identical in the plurality of polymers.

The method in another embodiment is a method for analyzing a set of polymers, each polymer of said set being an individual polymer of linked units and wherein the set of polymers is oriented parallel to one another and a polymer specific feature of said polymers is detected.

Each of the above methods is based on an interaction between a polymer and a station involving in some embodiments energy transfer or quenching between a unit and an agent which results in the generation of a signal and in other embodiments a physical change in the unit or station which results in the generation of a signal. Each of the methods can be performed on many polymers simultaneously or on as few as one polymer at a time.

Methods for analyzing multiple polymers at one time based on an interaction involving polymer dependent impulses between the unit and the station also can be performed. These methods, which are set forth below, are based on an interaction between a unit and a signal generation station which produces any type of polymer dependent impulse which can be detected. The polymer dependent impulse is generated by exposure of a unit of the polymer to a signal generation station but does not require that a physical change in the polymer unit or the station occur. For instance, the polymer dependent impulse may result from energy transfer, quenching, changes in conductance, mechanical changes, resistance changes, or any other physical change.

A method for characterizing a test polymer is another aspect of the invention. A method for characterizing a test polymer is carried out by obtaining polymer dependent impulses for each of a plurality of polymers, comparing the polymer dependent impulses of the plurality of polymers, determining the relatedness of the polymers based upon similarities between the polymer dependent impulses of the polymers, and characterizing the test polymer based upon the polymer dependent impulses of related polymers.

The plurality of polymers may be any type of polymer but preferably is a nucleic acid. In one embodiment the plurality of polymers is a homogenous population. In another embodiment the plurality of polymers is a heterogenous population. The polymers can be labeled, randomly or non randomly. Different labels can be used to label different linked units to produce different polymer dependent impulses.

The polymer dependent impulses provide many different types of structural information about the polymer. For instance the obtained polymer dependent impulses may include an order of polymer dependent impulses or the obtained polymer dependent impulses may include the time of separation between specific signals or the number of specific polymer dependent impulses.

In one important embodiment the polymer dependent impulses are obtained by moving the plurality of polymers linearly past a signal generation station.

According to another aspect the invention is a method for determining the distance between two individual units of a polymer of linked units. The method involves the steps of (1) causing the polymer to pass linearly relative to a station, (2) detecting a polymer dependent impulse generated as each of the two individual units passes by the signal generation station, (3) measuring the time elapsed between the polymer dependent impulses measured, (4) repeating steps 1, 2 and 3 for a plurality of similar polymers to produce a data set, and (5) determining the distance between the two individual units based upon the information obtained from said plurality of similar polymers by analyzing the data set. In one embodiment steps (1)-(4) are carried out substantially simultaneously.

The plurality of polymers may be any type of polymer but preferably is a nucleic acid. In one embodiment the plurality of polymers is a homogenous population. In another embodiment the plurality of polymers is a heterogenous population. The polymers can be labeled, randomly or non randomly. Different labels can be used to label different linked units to produce different polymer dependent impulses.

In one embodiment the polymer dependent impulse measured is an electromagnetic radiation signal generated. In another embodiment the two linked units are detected at the signal generation station by measuring light emission at the station. The signal generation station can be a nanochannel.

According to another aspect the invention is a method for determining the order of two individual units of a polymer of linked units. The method involves the steps of (1) moving the polymer to linearly with respect to a signal generation station, (2) exposing one of the individual units to the station to produce a polymer dependent impulse, (3) exposing the other of the individual units to the station to produce a second polymer dependent impulse, (4) repeating steps 1, 2 and 3 for a plurality of similar polymers to produce a data set, and (5) determining the order of the two individual units based upon the information obtained from said plurality of similar polymers by analyzing the data set. In one embodiment steps (1)-(4) are carried out substantially simultaneously. In one embodiment the signal measured is an electromagnetic radiation signal.

The plurality of polymers may be any type of polymer but preferably is a nucleic acid. In one embodiment the plurality of polymers is a homogenous population. In another embodiment the plurality of polymers is a heterogenous population. The polymers can be labeled, randomly or non randomly. Different labels can be used to label different linked units to produce different polymer dependent impulses.

In one embodiment the polymer dependent impulse measured is an electromagnetic radiation signal generated. In another embodiment the two linked units are detected at the signal generation station by measuring light emission at the station. The signal generation station can be a nanochannel.

In another aspect of the invention a method for sequencing a polymer of linked units is provided. The method involves the steps of obtaining polymer dependent impulses from a plurality of overlapping polymers, at least a portion of the polymers having a sequence of linked units identical to the other of the polymers, and comparing the polymer dependent impulses to obtain a sequence of linked units which is identical in the plurality of polymers.

In one embodiment the polymer dependent impulses are optically detectable. In another embodiment the nucleic acids are labeled with an agent selected from the group consisting of an electromagnetic radiation source, a quenching source, a fluorescence excitation source, and a radiation source.

The plurality of polymers may be any type of polymer but preferably is a nucleic acid. In one embodiment the plurality of polymers is a homogenous population. In another embodiment the plurality of polymers is a heterogenous population. The polymers can be labeled, randomly or non randomly. Different labels can be used to label different linked units to produce different polymer dependent impulses.

A method for labeling nucleic acids is also provided. The method involves the step of contacting a dividing cell with a nucleotide analog, isolating from the cell nucleic acids that have incorporated the nucleotide analog, and modifying the nucleic acid with incorporated nucleotide analog by labeling the incorporated nucleotide analog. In one embodiment the nucleotide analog is a brominated analog.

The dividing cell may optionally be contacted with a nucleotide analog by growth arresting the cell in the cell division cycle, performing the contacting step, and allowing the cell to reenter the cell division cycle. The nucleic acids may then be isolated after the cells have reentered and completed the cell division cycle and before a second cell division cycle is completed.

In another embodiment the incorporated nucleotide analog is labeled with an agent selected from the group consisting of an electromagnetic radiation source, a quenching source and a fluorescence excitation source.

According to another aspect of the invention a method is provided for analyzing a set of polymers, each polymer of said set being an individual polymer of linked units. The method involves the step of orienting the set of polymers parallel to one another, and detecting a polymer specific feature of said polymers. In one embodiment the orientation step is in a solution free of gel. The polymers may be oriented using any method. A preferred method for orienting the polymers is to apply an electric field to the polymers.

The plurality of polymers may be any type of polymer but preferably is a nucleic acid. In one embodiment the plurality of polymers is a homogenous population. In another embodiment the plurality of polymers is a heterogenous population. The polymers can be labeled, randomly or non randomly. Different labels can be used to label different linked units to produce different polymer dependent impulses.

The polymer specific feature is information about a structural feature of a polymer. The polymer specific feature can be an order of linked unity in the polymers.

In one embodiment the detecting step is performed simultaneously for said polymers. In another embodiment the detection step comprises measuring electromagnetic radiation signals. According to a preferred embodiment the detection step comprises causing the polymers to pass linearly relative to a plurality of signal generation stations, and detecting and distinguishing polymer dependent impulses generated as said polymers pass said signal generation stations.

A method for analyzing a set of polymers, each polymer of the set being an individual polymer of linked units is provided in another aspect of the invention. The method involves the steps of orienting the set of polymers in an electric field, simultaneously moving the set of polymers through defined respective channels, and detecting a polymer specific feature as the polymers are moved through the channels. In one embodiment the orientation step is in a solution free of gel. Preferably the channels are nanochannels.

The plurality of polymers may be any type of polymer but preferably is a nucleic acid. In one embodiment the plurality of polymers is a homogenous population. In another embodiment the plurality of polymers is a heterogenous population. The polymers can be labeled, randomly or non randomly. Different labels can be used to label different linked units to produce different polymer dependent impulses.

The polymer specific feature is information about a structural feature of a polymer. The polymer specific feature can be an order of linked unity in the polymers.

In one embodiment the detecting step is performed simultaneously for said polymers. In another embodiment the detection step comprises measuring electromagnetic radiation signals. According to a preferred embodiment the detection step comprises causing the polymers to pass linearly relative to a plurality of signal generation stations, and detecting and distinguishing polymer dependent impulses generated as said polymers pass said signal generation stations.

According to yet another aspect of the invention an article of manufacture is provided. The article of manufacture includes a wall material having a surface defining a channel, an agent wherein the agent is selected from the group consisting of an electromagnetic radiation source, a quenching source, a luminescent film layer and a fluorescence excitation source, attached to the wall material adjacent to the channel, wherein the agent is close enough to the channel and is present in an amount sufficient to detectably interact with a partner compound selected from the group consisting of a light emissive compound, a light accepting compound, radiative compound, and a quencher passing through the channel. Preferably the channel is a support for a polymer.

The agent in one embodiment is an electromagnetic radiation source and the electromagnetic radiation source is a light emissive compound. In another embodiment the channel is selected from the group consisting of is a microchannel and a nanochannel.

According to another embodiment the surface of the wall material defining the channel is free of the light emissive compound. In another embodiment the light emissive compound is attached to an external surface of the wall material. In yet another embodiment the light emissive compound is attached to a linker which is attached to the external surface of the wall material. In still another embodiment the light emissive compound is embedded in the wall material or in a layer of or upon the wall material. The light emissive compound can be concentrated at a region of the external surface of the wall material that surrounds a portion of the channel in another embodiment. The light emissive compound may form a concentric ring in the wall material around a portion of the channel. A masking layer having openings which allow exposure of only localized areas of the light emissive compound may also be part of the article of manufacture.

A second light emissive compound different from the first may be attached to the wall material adjacent to the channel, wherein the light emissive compound is close enough to the channel and is present in an amount effective to detectably interact with a partner light emissive compound passing through the channel.

The wall material may be made up of different layers. In one embodiment the external surface of the wall material adjacent to the light emissive compound is a conducting layer. In another embodiment the wall material comprises two layers, the conducting layer and a nonconducting layer. The wall material may also be composed of at least two layers, a first layer preventing signal generation and a second layer allowing signal generation. Alternatively the wall material adjacent to the light emissive compound is a light impermeable layer. In another embodiment the wall material comprises two layers, the light impermeable layer and a support light permeable layer. The wall material can be a second light impermeable layer on a second side of the light emissive compound, the first and second layers sandwiching the light emissive compound. In a preferred embodiment the light emissive compound is a fluorescent compound.

The channel can have any shape or dimensions. Preferably the channel is a nanochannel which is between 1 Angstrom and 1 mm. In a preferred embodiment the width of the channel is between 1 and 500 Angstroms. Preferably the wall includes multiple channels. Preferably the wall material includes at least 2 and more preferably at least 50 channels.

In one embodiment the wall material is formed of two layers, a first light impermeable layer and a luminescent film layer attached to one another, wherein the channel extends through both layers and is defined by surfaces of both layers. Preferably the channel is a nanochannel. In a preferred embodiment the length of the channel is between 1 Angstrom and 1 mm. The article in some embodiments includes a second light impermeable layer, the luminescent film layer positioned between the first and second light impermeable layers. In a preferred embodiment the surface defining the channel includes a surface of the light impermeable layer which is free of luminescent film layer material.

In another embodiment the agent is a fluorescence excitation source and wherein the fluorescence excitation source is a scintillation layer. The scintillation layer may be selected from the group consisting of NaI(TI), ZnS(Ag), anthracene, stilbene, and plastic phosphors. Preferably the scintillation layer is embedded in the wall material between two radiation impermeable layers, such as lead or Lucite.

In another aspect the invention is an article of manufacture which is a wall material having a surface defining a plurality of channels, and a station attached to a discrete region of the wall material adjacent to at least one of the channels, wherein the station is close enough to the channel and is present in an amount sufficient to cause a signal to arise from a detectable physical change in a polymer of linked units passing through the channel or in the station as the polymer is exposed to the station.

According to another aspect of the invention an article of manufacture is provided. The article is a wall material having a surface defining a channel, and a plurality of stations each attached to a discrete region of the wall material adjacent to the channel, wherein the stations are close enough to the channel and are present in an amount sufficient to cause a signal to arise from a detectable physical change in a polymer of linked units passing through the channel or in the station as the polymer is exposed to the station.

A method for preparing a wall material is another aspect of the invention. The method involves the steps of covalently bonding light emissive compounds or quenching compounds to a plurality of discrete locations of a wall material, each of said discrete locations close enough to a respective interaction station on said wall material, whereby when an individual unit of a polymer, which is interactive with said light emissive compound or quenching compound to produce a signal, is positioned at said interaction station, the light emissive compound or the quenching compound interacts with the individual unit to produce the signal. In one embodiment the method includes the step of applying a layer of conductive material to said wall material.

In another embodiment the light emissive compounds or quenching compounds are covalently bonded at discrete locations close to channels in said wall material, said channels defining interaction stations. The channels preferably are microchannels. In a more preferred embodiment the channels are nanochannels. The light emissive compounds or quenching compounds can be covalently bonded to the wall material in a manner whereby the surfaces of the wall material defining the channel are free of the light emissive compounds and quenching compounds.

The invention also encompasses a method for attaching a chemical substance selectively at a rim of a channel through a wall material that is opaque. The method involves the steps of providing a wall material with photoprotective chemical groups attached at the rim of the channel through the wall material, applying light to the photoprotective chemical groups to dephotoprotect the chemical groups, and attaching the chemical substance to the deprotected chemical groups.

In one embodiment the light is applied to only selected regions of a surface of the wall material defining the rim of the channel. In another embodiment the channel has a first end and a second end, the rim being at the first end, and wherein the light is applied to the second end, the light passing through the channel to contact the photoprotected chemical groups at the rim of said first end. The channels preferably are microchannels. In a more preferred embodiment the channels are nanochannels.

According to another aspect of the invention a method is provided for preparing a wall material having localized areas of light emission on a surface of the wall material. The method involves the steps of providing a wall material having a surface and applying a light emissive compound to the surface to produce at least localized areas of light emission on the surface, wherein the localized areas define a target region for detecting light emission, and wherein the target region is a rim of a channel through the wall material. In one embodiment the method further includes the steps of attaching a photoprotective chemical group to the surface of the wall material, applying light to the photoprotective chemical groups to dephotoprotect the chemical groups prior to attaching the light emissive compound, and attaching the light emissive compound to the dephotoprotected chemical groups.

In one embodiment the light is applied to only selected regions of a surface of the wall material defining the rim of the channel. In a preferred embodiment the photoprotective chemical group is attached to only selected regions of the surface of the wall material defining the rim of the channel. In another embodiment the channel has a first end and a second end, the rim being at the first end, and wherein the light is applied to the second end, the light passing through the channel to contact the photoprotected chemical groups at the rim of said first end. The channels preferably are microchannels. In a more preferred embodiment the channels are nanochannels.

The method can include the further step of positioning a mask having openings over the surface of the wall material such that only localized areas of light emission are exposed through the openings of the mask. In one embodiment the light emissive compound is attached to a portion of the surface of the wall material.

According to another aspect of the invention an apparatus for detecting a signal is provided. The apparatus is a housing with a buffer chamber, a wall defining a portion of the buffer chamber, and having a plurality of openings for aligning polymers, a sensor fixed relative to the housing, the sensor distinguishing the signals emitted at each opening from the signals emitted at the other of the openings to generate opening dependent sensor signals, and a memory for collecting and storing said sensor signals. In a preferred embodiment the sensor is an optical sensor.

In one embodiment the optical sensor senses electromagnetic radiation signals emitted at the plurality of openings. In another embodiment the apparatus includes a microprocessor.

In one embodiment the openings are defined by channels in the wall. Preferably the openings are defined by microchannels in the wall. More preferably the openings are defined by nanochannels in the wall. In one embodiment the plurality of openings is at least two. In a preferred embodiment the plurality is at least 50.

In one embodiment the apparatus includes a second buffer chamber separated from said first buffer chamber, by said wall, and wherein the buffer chambers are in fluid communications with one another via the openings. In another embodiment the apparatus includes a pair of electrodes secured to the housing, one of said pair positioned in the first buffer chamber and the other of the pair positioned in the second buffer chamber.

According to another aspect of the invention an apparatus for detecting a signal is provided. The apparatus includes a housing defining a first buffer chamber and a second buffer chamber, a wall supported by the housing and separating the first and second buffer chambers, a plurality of channels defined by the wall and providing fluid communications between the first and second buffer chambers, and a sensor for distinguishing and collecting channel dependent signals. Preferably the channel is a microchannel. More preferably the channel is a nanochannel. In one embodiment the plurality of channels is at least two. In a preferred embodiment the plurality is at least 50. Preferably the signal is an optical signal.

In one embodiment the wall surrounding the channel includes an agent is selected from the group consisting of electromagnetic radiation, a quenching source and a fluorescence excitation source is attached to the wall. Preferably the agent is electromagnetic radiation and the electromagnetic radiation is a light emissive compound. In one embodiment the light emissive compound is concentrated at the channels in the wall.

According to another embodiment the apparatus includes a means for moving biological entities through the channels.

According to another aspect of the invention an apparatus including a housing with a buffer chamber, a wall material defining a portion of the buffer chamber, the wall including polymer interaction stations, and an optical sensor secured to the housing, the optical sensor constructed and arranged to detect electromagnetic radiation signals emitted at the interaction stations is provided.

In another aspect the invention is a computer system for making characteristic information of a plurality of polymers available in response to a request. The system has a memory for storing, for the plurality of the polymers and in a manner accessible using a unique identifier for the polymer, records including information indicative of sequentially detected signals arising from a detectable physical change in the plurality of individual units of the polymer or a station to which the polymer is exposed and a processor for accessing the records stored in the memory for a selected one of the plurality of the polymers according to a unique identifier associated with the selected polymer.

In one embodiment the signal results from an interaction of a plurality of individual units of the polymer exposed to an agent selected from the group consisting of electromagnetic radiation, a quenching source and a fluorescence excitation source. In another embodiment the computer system also includes a means for comparing the sequentially detected signals of the selected polymer to a known pattern of signals characteristic of a known polymer to determine relatedness of the selected polymer to the known polymer.

Each of the limitations of the invention can encompass various embodiments of the invention. It is, therefore, anticipated that each of the limitations of the invention involving any one element or combinations of elements can be included in each apparatus and each method.

BRIEF DESCRIPTION OF THE DRAWINGS

FIG. 7B shows an enlarged view of a single nanochannel with a single acceptor positioned adjacent to a conducting layer.

FIG. 8A shows an enlarged view of one nanochannel.

FIG. 10A illustrates the amount of change as volumes. FIG. 10B shows the change for one acceptor.

DETAILED DESCRIPTION OF THE INVENTION

Figure 1:
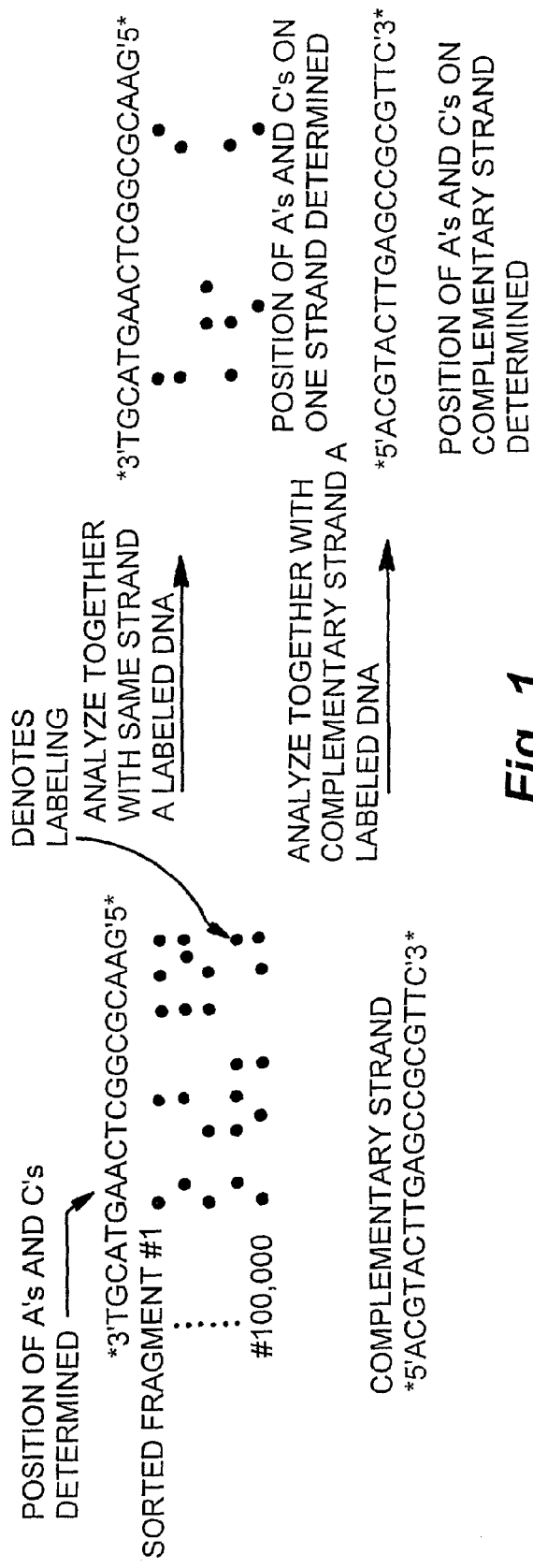
FIG. 1 shows a schematic of a random labeling method.

The invention encompasses methods of analyzing or identifying a polymer or a unit of a polymer, by detecting a signal or polymer dependent impulse that results from an interaction between at least one unit of the polymer and a station or an agent or by a change in the unit or a station when the unit is exposed to the station. By "analyzing" a polymer, it is meant obtaining some information about the structure of the polymer such as its size, the order of its units, its relatedness to other polymers, the identity of its units, or its presence. Since the structure and function of biological molecules are interdependent, the structural information can reveal important information about the function of the polymer.

One method according to the invention is a method for analyzing a polymer of linked units by exposing a plurality of units of the polymer to an agent selected from the group consisting of electromagnetic radiation, a quenching source and a fluorescence excitation source such that each of the individual units interacts with the agent to produce a detectable signal. The signal resulting from the interaction is detected sequentially.

As used herein a unit of a polymer is "exposed" to an agent or a station by positioning or presenting the unit and the agent or station in interactive proximity to one another such that energy transfer or quenching or a physical change in the unit or agent or station can occur between them to produce a detectable signal. By interactive proximity it is meant close enough to permit the interaction or change which yields the detectable signal.

In one embodiment the units of the polymer are exposed sequentially to the agent. By "sequentially exposed" it is meant in general separated from one another in time. In a preferred embodiment, the polymer and the agent are caused to move relative to one another in a "linear" manner such that each unit of the polymer passes within interactive proximity to the agent at an interaction station. When each unit of the polymer interacts with the agent or station, a detectable signal is produced. This detectable signal can be captured (sequentially detected) and recorded by a detection device. The detectable signal produced for each unit can be indicative of the type of unit. As used herein signals are detected "sequentially" when signals from different units of a single polymer are detected spaced apart in time. Not all units need to be detected or need to generate a signal to detect signals "sequentially."

When the units are sequentially exposed to the agent or station the unit and the agent or station move relative to one another. As used herein the phrase "the unit and the agent or station move relative to one another" means that either the unit and the agent or station are both moving or only one of the two is moving and the other remains stationary at least during the period of time of the interaction between the unit and the agent or station. The unit and the agent or station may be moved relative to one another by any mechanism. For instance the agent or station may remain stationary and the polymer may be drawn past the agent or station by an electric current. Other methods for moving the polymer include but are not limited to movement resulting from a magnetic field, a mechanical force, a flowing liquid medium, a pressure system, a gravitational force, and a molecular motor such as e.g., a DNA polymerase or a helicase when the polymer is DNA or e.g., myosin when the polymer is a peptide such as actin. The movement of the polymer may be assisted by the use of a channel, groove or ring to guide the polymer. Alternatively the agent or station may be moved and the polymer may remain stationary. For instance the agent or station may be held within a scanning tip that is guided along the length of the polymer.

In another embodiment signals are detected simultaneously. As used herein signals are "detected simultaneously" by causing a plurality of the labeled units of a polymer to be exposed to an agent or station at once. The plurality of the units can be exposed to an agent or station at one time by using multiple interaction sites. Signals can be detected at each of these sites simultaneously. For instance multiple agents or stations may be localized at specific locations in space which correspond to the units of the polymer. When the polymer is brought within interactive proximity of the multiple agents or stations signals will be generated simultaneously. This may be embodied, for example, in a linear array of agents or stations positioned at substantially equivalent distances which are equal to the distance between the units. The polymer may be positioned with respect to the agent or station such that each unit is in interactive proximity to an agent or station to produce simultaneous signals.

When the signals are detected sequentially multiple polymers also can be analyzed simultaneously. Multiple polymers are analyzed simultaneously by causing more than one polymer to move relative to respective agent or stations at one time. The polymers may be similar or distinct. If the polymers are similar, the same or different units may be detected simultaneously. It is preferred that at least two polymers are analyzed simultaneously. In a more preferred embodiment at least 50 polymers are analyzed simultaneously and in another preferred embodiment at least 100 polymers are analyzed simultaneously.

A "polymer" as used herein is a compound having a linear backbone of individual units which are linked together by linkages. In some cases the backbone of the polymer may be branched. Preferably the backbone is unbranched. The term "backbone" is given its usual meaning in the field of polymer chemistry. The polymers may be heterogeneous in backbone composition thereby containing any possible combination of polymer units linked together such as peptide-nucleic acids (which have amino acids linked to nucleic acids and have enhanced stability). In a preferred embodiment the polymers are homogeneous in backbone composition and are, for example, nucleic acids, polypeptides, polysaccharides, carbohydrates, polyurethanes, polycarbonates, polyureas, polyethyleneimines, polyarylene sulfides, polysiloxanes, polyimides, polyacetates, polyamides, polyesters, or polythioesters. In the most preferred embodiments, the polymer is a nucleic acid or a polypeptide. A "nucleic acid" as used herein is a biopolymer comprised of nucleotides, such as deoxyribose nucleic acid (DNA) or ribose nucleic acid (RNA). A polypeptide as used herein is a biopolymer comprised of linked amino acids.

As used herein with respect to linked units of a polymer, "linked" or "linkage" means two entities are bound to one another by any physicochemical means. Any linkage known to those of ordinary skill in the art, covalent or non-covalent, is embraced. Such linkages are well known to those of ordinary skill in the art. Natural linkages, which are those ordinarily found in nature connecting the individual units of a particular polymer, are most common. Natural linkages include, for instance, amide, ester and thioester linkages. The individual units of a polymer analyzed by the methods of the invention may be linked, however, by synthetic or modified linkages. Polymers where the units are linked by covalent bonds will be most common but also include hydrogen bonded, etc.

The polymer is made up of a plurality of individual units. An "individual unit" as used herein is a building block or monomer which can be linked directly or indirectly to other building blocks or monomers to form a polymer. The polymer preferably is a polymer of at least two different linked units. The at least two different linked units may produce or be labeled to produce different signals, as discussed in greater detail below. The particular type of unit will depend on the type of polymer. For instance DNA is a biopolymer comprised of a deoxyribose phosphate backbone composed of units of purines and pyrimidines such as adenine, cytosine, guanine, thymine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. RNA is a biopolymer comprised of a ribose phosphate backbone composed of units of purines and pyrimidines such as those described for DNA but wherein uracil is substituted for thymidine. DNA units may be linked to the other units of the polymer by their 5' or 3' hydroxyl group thereby forming an ester linkage. RNA units may be linked to the other units of the polymer by their 5', 3' or 2' hydroxyl group thereby forming an ester linkage. Alternatively, DNA or RNA units having a terminal 5', 3' or 2' amino group may be linked to the other units of the polymer by the amino group thereby forming an amide linkage. The individual units of a polypeptide are amino acids, including the 20 naturally occurring amino acids as well as modified amino acids. Amino acids may exist as amides or free acids and are linked to the other units in the backbone of the polymers through their a-amino group thereby forming an amide linkage to the polymer.

A "plurality of individual units" is at least two units linked to one another.

Whenever a nucleic acid is represented by a sequence of letters it will be understood that the nucleotides are in 5'→3' order from left to right and that "A" denotes adenosine, "C" denotes cytidine, "G" denotes guanosine, "T" denotes thymidine, and "U" denotes uracil unless otherwise noted.

The polymers may be native or naturally-occurring polymers which occur in nature or non-naturally occurring polymers which do not exist in nature. The polymers typically include at least a portion of a naturally occurring polymer. The polymers can be isolated or synthesized de novo. For example, the polymers can be isolated from natural sources e.g. purified, as by cleavage and gel separation or may be synthesized e.g.,(i) amplified in vitro by, for example, polymerase chain reaction (PCR); (ii) synthesized by, for example, chemical synthesis; (iii) recombinantly produced by cloning, etc.

The polymer or at least one unit thereof is in a form which is capable of interacting with an agent or station to produce a signal characteristic of that interaction. The unit of a polymer which is capable of undergoing such an interaction is said to be labeled. If a unit of a polymer can undergo that interaction to produce a characteristic signal, then the polymer is said to be intrinsically labeled. It is not necessary that an extrinsic label be added to the polymer. If a non-native molecule, however, must be attached to the individual unit of the polymer to generate the interaction producing the characteristic signal, then the polymer is said to be extrinsically labeled. The "label" may be, for example, light emitting, energy accepting, fluorescent, radioactive, or quenching.

Many naturally occurring units of a polymer are light emitting compounds or quenchers. For instance, nucleotides of native nucleic acid molecules have distinct absorption spectra, e.g., A, G, T, C, and U have absorption maximums at 259 nm, 252 nm, 267 nm, 271 nm, and 258 nm respectively. Modified units which include intrinsic labels may also be incorporated into polymers. A nucleic acid molecule may include, for example, any of the following modified nucleotide units which have the characteristic energy emission patterns of a light emitting compound or a quenching compound: 2,4-dithiouracil, 2,4-Diselenouracil, hypoxanthine, mercaptopurine, 2-aminopurine, and selenopurine.

A unit may also be considered to be intrinsically labeled when a property of the unit other than a light emitting, quenching or radioactive property provides information about the identity of the unit without the addition of an extrinsic label. For instance the shape and charge of the unit provides information about the unit which can result in a specific characteristic signal, such as a change in conductance arising from the blockage of a conductance path by the unit.

If an extrinsic label is selected for use according to the methods of the invention, the type of extrinsic label selected will depend on a variety of factors, including the nature of the analysis being conducted, the type of the agent and the type of polymer. Extrinsic label compounds include but are not limited to light emitting compounds, quenching compounds, radioactive compounds, spin labels, and heavy metal compounds. The label should be stearically compatible and chemically compatible with the units of the polymer being analyzed.

A "light emissive compound" as used herein is a compound that emits light in response to irradiation with light of a particular wavelength. These compounds are capable of absorbing and emitting light through phosphorescence, chemiluminescence, luminescence, polarized fluorescence, scintillators or, more preferably, fluorescence. The particular light emissive compound selected will depend on a variety of factors which are discussed in greater detail below. Light emissive compounds have been described extensively in the literature. For example, Haugland, R. P., *Handbook of Fluorescent Probes and Research Chemicals,* 6th edition, Molecular Probes, Inc., 1996, which is hereby incorporated by reference provides a description of light emitting compounds.

Radioactive compounds are substances which emit alpha, beta, or gamma nuclear radiation. Alpha rays are positively charged particles of mass number 4 and slightly deflected by electrical and magnetic fields. Beta rays are negatively charged electrons and are strongly deflected by electrical and magnetic fields. Gamma rays are photons of electromagnetic radiation and are undeflected by electrical and magnetic fields and are of wavelength of the order to $10^{-8}$ to $10^{-9}$ cm.

Generally, fluorescent dyes are hydrocarbon molecules having a chain of several conjugated double bonds. The absorption and emission wavelengths of a dye are approximately proportional to the number of carbon atoms in the conjugated chain. A preferred fluorescent compound is "Cy-3" (Biological Detection Systems, Pittsburgh, PA). Other preferred fluorescent compounds useful according to the invention include but are not limited to fluorescein isothiocyanate ("FITC"), Texas red, tetramethylrhodamine isothiocyanate ("TRITC"), 4,4-difluoro-4-bora-3a, and 4a-diaza-s-indacene ("BODIPY").

Chemiluminescent compounds are compounds which luminesce due to a chemical reaction. Phosphorescent compounds are compounds which exhibit delayed luminescence as a result of the absorption of radiation. Luminescence is a non-thermal emission of electromagnetic radiation by a material upon excitation. These compounds are well known in the art and are available from a variety of sources.

In one embodiment of the invention the light emissive compound is a donor or an acceptor fluorophore. A fluorophore as used herein is a molecule capable of absorbing light at one wavelength and emitting light at another wavelength. A donor fluorophore is a fluorophore which is capable of transferring its fluorescent energy to an acceptor molecule in close proximity. An acceptor fluorophore is a fluorophore that can accept energy from a donor at close proximity. (An acceptor of a donor fluorophore does not have to be a fluorophore. It may be non-fluorescent.) Fluorophores can be photochemically promoted to an excited state, or higher energy level, by irradiating them with light. Excitation wavelengths are generally in the UV, blue, or green regions of the spectrum. The fluorophores remain in the excited state for a very short period of time before releasing their energy and returning to the ground state. Those fluorophores that dissipate their energy as emitted light are donor fluorophores. The wavelength distribution of the outgoing photons forms the emission spectrum, which peaks at longer wavelengths (lower energies) than the excitation spectrum, but is equally characteristic for a particular fluorophore.

In another embodiment of the invention the unit is labeled with a radioactive compound. The radioactive compound emits nuclear radiation as it passes the agent or station. When the agent is a scintillation layer the nuclear radiation interacts with the scintillation layer and causes fluorescent excitation. A fluorescent signal indicative of the radioactively labeled unit can then be detected.

Extrinsic labels can be added to the polymer by any means known in the art. For example, the labels may be attached directly to the polymer or attached to a linker which is attached to the polymer. For instance, fluorophores have been directly incorporated into nucleic acids by chemical means but have also been introduced into nucleic acids through active amino or thio groups into a nucleic acid. Proudnikov and Mirabekov, *Nucleic Acids Research,* 24: 4535-4532 (1996). Modified units which can easily be chemically derivitized or which include linkers can be incorporated into the polymer to enhance this process. An extensive description of modification procedures which can be performed on the polymer, the linker and/or the extrinsic label in order to prepare a bioconjugate can be found in Hermanson, G. T., *Bioconjugate Techniques,* Academic Press, Inc., San Diego, 1996, which is hereby incorporated by reference.

There are several known methods of direct chemical labeling of DNA (Hermanson, 1996; Roget et al., 1989; Proudnikov and Mirzzbekov, 1996). One of the methods is based on the introduction of aldehyde groups by partial depurination of DNA. Fluorescent labels with an attached hydrazine group are efficiently coupled with the aldehyde groups and the hydrazone bonds are stabilized by reduction with sodium labeling efficiencies around 60%. The reaction of cytosine with bisulfite in the presence of an excess of an amine fluorophore leads to transamination at the $N_4$ position (Hermanson, 1996). Reaction conditions such as pH, amine fluorophore concentration, and incubation time and temperature affect the yield of products formed. At high concentrations of the amine fluorophore (3M), transamination can approach 100% yield (Draper and Gold, 1980).

Light emissive compounds can be attached to polymers or other materials by any mechanism known in the art. For instance, functional groups which are reactive with various light emissive groups include, but are not limited to, (functional group: reactive group of light emissive compound) activated ester:amines or anilines; acyl azide:amines or anilines; acyl halide:amines, anilines, alcohols or phenols; acyl nitrile:alcohols or phenols; aldehyde:amines or anilines; alkyl halide:amines, anilines, alcohols, phenols or thiols; alkyl sulfonate:thiols, alcohols or phenols; anhydride:alcohols, phenols, amines or anilines; aryl halide:thiols; aziridine: thiols or thioethers; carboxylic acid:amines, anilines, alcohols or alkyl halides; diazoalkane:carboxylic acids; epoxide: thiols; haloacetamide:thiols; halotriazine:amines, anilines or phenols; hydrazine:aldehydes or ketones; hydroxyamine:aldehydes or ketones; imido ester:amines or anilines; isocyanate:amines or anilines; and isothiocyanate:amines or anilines.

The agent that interacts with the unit of the polymer is selected from the group consisting of electromagnetic radiation, a quenching source, and a fluorescence excitation source. "Electromagnetic radiation" as used herein is energy produced by electromagnetic waves. Electromagnetic radiation may be in the form of a direct light source or it may be emitted by a light emissive compound such as a donor fluorophore. "Light" as used herein includes electromagnetic energy of any wavelength including visible, infrared and ultraviolet.

As used herein, a quenching source is any entity which alters or is capable of altering a property of a light emitting source. The property which is altered can include intensity fluorescence lifetime, spectra, fluorescence, or phosphorescence.

A fluorescence excitation source as used herein is any entity capable of fluorescing or giving rise to photonic emissions (i.e. electromagnetic radiation, directed electric field, temperature, fluorescence, radiation, scintillation, physical contact, or mechanical disruption.) For instance, when the unit is labeled with a radioactive compound the radioactive emission causes molecular excitation of an agent that is a scintillation layer which results in fluorescence.

When a unit of the polymer is exposed to the agent the interaction between the two produces a signal. The signal provides information about the polymer. For instance if all units of a particular type, e.g., all of the alanines, of a protein polymer are labeled (intrinsic or extrinsic) with a particular light emissive compound then when a signal characteristic of that light emissive compound is detected upon interaction with the agent the signal signifies that an alanine residue is present at that particular location on the polymer. If each type of unit e.g., each type of amino acid is labeled with a different light emissive compound having a distinct light emissive pattern then each amino acid will interact with the agent to produce a distinct signal. By determining what each signal for each unit of the polymer is, the sequence of units can be determined.

The interaction between the unit and the agent can take a variety of forms, but does not require that the unit and the agent physically contact one another. Examples of interactions are as follows. A first type of interaction involves the agent being electromagnetic radiation and the unit of the polymer being a light emissive compound (either intrinsically or extrinsically labeled with a light emissive compound). When the light emissive unit is contacted with electromagnetic radiation (such as by a laser beam of a suitable wavelength or electromagnetic radiation emitted from a donor fluorophore), the electromagnetic radiation causes the light emissive compound to emit electromagnetic radiation of a specific wavelength. The signal is then measured. The signal exhibits a characteristic pattern of light emission and thus indicates that a particular labeled unit of the polymer is present. In this case the unit of the polymer is said to "detectably affect the emission of the electromagnetic radiation from the light emissive compound."

A second type of interaction involves the agent being a fluorescence excitation source and the unit of the polymer being a light emissive or a radioactive compound. When the light emissive unit is contacted with the fluorescence excitation source, the fluorescence excitation source causes the light emissive compound to emit electromagnetic radiation of a specific wavelength. When the radioactive unit is contacted with the fluorescence excitation source, the nuclear radiation emitted from the unit causes the fluorescence excitation source to emit electromagnetic radiation of a specific wavelength. The signal then is measured.

A variation of these types of interaction involves the presence of a third element of the interaction, a proximate compound which is involved in generating the signal. For example, a unit may be labeled with a light emissive compound which is a donor fluorophore and a proximate compound can be an acceptor fluorophore. If the light emissive compound is placed in an excited state and brought proximate to the acceptor fluorophore, then energy transfer will occur between the donor and acceptor, generating a signal which can be detected as a measure of the presence of the unit which is light emissive. The light emissive compound can be placed in the "excited" state by exposing it to light (such as a laser beam) or by exposing it to a fluorescence excitation source.

Another interaction involves a proximate compound which is a quenching source. In this instance, the light emissive unit is caused to emit electromagnetic radiation by exposing it to light. If the light emissive compound is placed in proximity to a quenching source, then the signal from the light emissive unit will be altered.

A set of interactions parallel to those described above can be created wherein, however, the light emissive compound is the proximate compound and the unit is either a quenching source or an acceptor source. In these instances the agent is electromagnetic radiation emitted by the proximate compound, and the signal is generated, characteristic of the interaction between the unit and such radiation, by bringing the unit in interactive proximity with the proximate compound.

The mechanisms by which each of these interactions produces a detectable signal is known in the art. For exemplary purposes the mechanism by which a donor and acceptor fluorophore interact according to the invention to produce a detectable signal including practical limitations which are known to result from this type of interaction and methods of reducing or eliminating such limitations is set forth below.

In a preferred embodiment the signal generated by the interaction between the unit and the agent results from fluorescence resonance energy transfer (FRET) between fluorophores. Either the unit or the proximate compound/agent may be labeled with either the donor or acceptor fluorophore. FRET is the transfer of photonic energy between fluorophores. FRET has promise as a tool in characterizing molecular detail because of its ability to measure distances between two points separated by 10 Å to 100 Å. The angstrom resolution of FRET has been used in many studies of molecular dynamics and biophysical phenomena (for reviews see Clegg, 1995; Clegg, 1992; Selvin, 1995; and Wu and Brand, 1994). The resolving power of FRET arises because energy transfer between donor and acceptor fluorophores is dependent on the inverse sixth power of the distance between the probes. In practice, this resolution is about an order of magnitude better than that of the highest resolution electron microscope.

In order to undergo FRET, the emission spectrum of the donor overlaps with the excitation spectrum of the acceptor. The unit of the polymer is specifically labeled with an acceptor fluorophore. The agent is a donor fluorophore. A laser is tuned to the excitation wavelength of the donor fluorophore. As the polymer is moved through the channel, the donor fluorophore emits its characteristic wavelength. As the acceptor fluorophore moves into interactive proximity with the donor fluorophore, the acceptor fluorophore is excited by the energy from the donor fluorophore. The consequence of this interaction is that the emission of the donor fluorophore is quenched and that of the acceptor fluorophore is enhanced.

In order to generate an optimal efficient FRET signal for detection, two conditions should be satisfied. The first condition is efficient donor emission in the absence of acceptors. The second is efficient generation of a change in either donor or acceptor emissions during FRET.

In a model system, both the donor fluorophore and the acceptor fluorophore can give rise to photonic emissions indefinitely. In such circumstances, during energy transfer, the decrease in the donor emission is equal to the increase in the acceptor emission. In other words, the emission change is identical for both the donor and the acceptor. This is so because for every one donor emission quenching event, there is an equal and opposite acceptor emission event. Cantor and Schimmel, 1980 present an intuitive outline of this model system. Consider a system of two fluorophores, a donor and an acceptor. At a range within Förster distance, very weak coupling occurs. The interaction between the donor and the acceptor is summarized as:

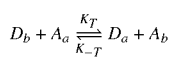

where $D_a$ and $A_a$ are the ground singlet states and $D_b$ and $A_b$ are the first excited singlet states. $k_T$ and $k_{-T}$ are the forward and reverse rates of energy transfer. The above reaction states that for a given donor in the first excited state, it will rapidly lose energy by internal conversion until it reaches its ground state, $D_a$. Since the acceptor absorption energies overlap with the donor emission energies, very weak coupling occurs, allowing resonance energy transfer to take place.

As a result of the resonance energy transfer, both the donor ($D_b$) and the acceptor ($A_b$) are in excited vibrational states. Vibrational relaxation rapidly brings these to their respective ground vibrational levels. Vibrational relaxation is very efficient, with the average lifetime of an excited vibrational state being only about $10^{-15}$ s (Skoog et al., 1992). Internal conversion, on the other hand, for fluorescent molecules is about $10^{-9}$ s. The difference in these rates means that even when $k_T$ is very efficient, the reverse reaction ($k_{-T}$) is unlikely to occur. In this ideal system, there is thus a shift of the relative population of excited donors and acceptors.

The above analysis sets forth a system utilizing a single acceptor and a single donor. The same type of interaction may be performed on a system which utilizes many donors and one acceptor. Whenever the acceptor is in its ground singlet state ($A_a$), energy transfer can occur. This means that for an acceptor with a lifetime of 1 ns, it can be excited $1 \times 10^9$ times per second, a very large rate compared to that of a donor fluorophore under standard illumination (~25,000 excitation events/s). Since the maximum number of excitations that an acceptor can undergo is much greater than that of one donor fluorophore, multiple donors can transfer their energy to one acceptor.

Although acceptor excitation to higher energy levels ($A_x$) and simultaneous donor de-excitation events may be considered to be a potential problem resulting in the interference with signals generated in a system using multiple donors and a single acceptor the following analysis demonstrates that this is not the case. It is improbable that excitation to higher energy levels and simultaneous donor de-excitation events will interfere with signal generation.

Acceptor excitation to higher levels means that there theoretically could be further excitation from the acceptor's first singlet state ($A_b$) to the acceptor's higher singlet states ($A_x$). If this were indeed possible, then the maximum number of excitation events in a given time increases because the effective lifetime is shorter. A shorter effective lifetime arises because the acceptor no longer has to de-excite to undergo energy transfer. Such transitions in the acceptor can only occur if the acceptor absorption energies for a transition were coincident with the donor emission energies, which is generally not the case for most molecules. As a consequence, energy transfer between the donors and the acceptor can only occur when the acceptor is in its ground singlet state.

In cases of simultaneous donor de-excitation, only one of the donors can transfer energy to the acceptor. This means that the other donor is not quenched and emits radiatively. If simultaneous events occurred frequently, then the above scenario for multi-donor quenching would not be as accurate because a fraction of the donors would be able to emit photons. The following probability calculations demonstrate that such events are statistically infrequent, supporting the use of multi-donor quenching.

probability of k simultaneous donor emissions occurring in one ns, where $n = P_{n,k} = (P_k)(_nC_k)$ is the number of fluorophores number of donor emissions that cannot undergo energy transfer =

$$(2-1)P_{n,2}t = (3-1)P_{n,3}t + \ldots + (n-1)P_{n,n}t = \sum_{k=2}^{k=n}(k-1)P_{n,k}t$$

The aim of these calculations is to calculate the number of simultaneous donor de-excitation events for a given amount of time. This number is important because the greater the number of overlapping events, the smaller the percentage of donor energy transfer. For example it is possible to find the probability of two donor emissions (k=2) simultaneously occurring in one nanosecond for four fluorophores (n=4; thus $P_{n,k} = P_{4,2}$). Each emission, in this example, lasts for one nanosecond and are represented as blue circles in the grids. In addition, each fluorophore emits an average of 25,000 photons/second randomly. The variables are defined as n=number of fluorophores, k=number of simultaneous donor emissions, P probability, C=combination, and t=time. The probability for k simultaneous events occurring in one ns for n fluorophores ($P_{n,k}$) is equal to the probability for k simultaneous events ($P_k$) multiplied by the number of possible combinations that k simultaneous events can occur for n fluorophores ($_nC_k$). The total number of simultaneous events is given as the sum of probabilities for all possible values of simultaneous events. This gives the probability in the units of (number of events)/ns. The total number of fluorophores undergoing simultaneous emission is thus the probability for one ns multiplied by the given time (t). It is also necessary to consider the probability of greater than two or more donor emissions ($P_{4,3}$ and $P_{4,4}$) occurring in a given time (t). From this information, the number of donor fluorophores that cannot undergo energy transfer because of simultaneous de-excitation can be derived.

The probability for two simultaneous donor emissions in one nanosecond for four fluorophores is given as:

$$P_{nk} = P_{4,2} = (P_k)(_nC_k) = P_K \frac{n!}{k!(n-k)!} = \left(\frac{25000}{10^9}\right)^2 \left(\frac{4!}{2!2!}\right) = 3.75 \times 10^{-9}$$

The probability that one ns will contain one emission is $25{,}000/10^9$. The probability that two emissions will occur in the same nanosecond is the square $(25{,}000/10^9)^2$. Since there are four different fluorophores, there are 6 different possible combinations that give rise to simultaneous emission (4!2!2!). These values multiplied give $3.75 \times 10^{-9}$ events/ns. This value multiplied by $10^9$ ns yields 3.75 events/s. In this case, there are two emissions/event (k=2) and one of these (k-1) cannot undergo energy transfer so the total number of donor emissions that do not undergo FRET is 3.75 events/s.

The above simple calculation can be applied to a system with a greater number of fluorophores. In this case, one thousand fluorophores are considered (n=1000). In a similar fashion, $P_{1000,2}$ is calculated to be $3.122 \times 10^{-4}$ events/ns. The number of donor emissions that cannot undergo energy transfer is $3.122 \times 10^5$. In some cases, three simultaneous donor emissions can occur. The probability for these events ($P_{1000,3}$) is calculated:

$$= \left(\frac{25000}{10^9}\right)^3 \left(\frac{1000!}{3!997!}\right) = 2.596 \times 10^{-6}$$

The number of donor emissions that cannot occur is $(3-1)$ $(10^9)(2.596 \times 10^{-6})$, or $5.192 \times 10^3$. In a similar fashion, calculations for four simultaneous emissions or greater need to be included in the net number of donor fluorophores that cannot undergo energy transfer. This number is expressed as the following equation:

$$= (2-1)P_{n,2}t = (3-1)P_{n,3}t + \ldots + (n-1)P_{n,n}t = \sum_{k=2}^{k=n}(k-1)P_{n,k}t$$

Solving the above summations yields $3.174 \times 10^5$ donor emissions that do not undergo energy transfer. The donor emission is calculated from the following values: 25 000 photons/s per fluorophore, 1000 fluorophores, and a 1 second time interval. This means that $2.5 \times 10^7$ photons are emitted per second. The conclusion is that 98.7% of donor events can undergo energy transfer.

The conclusion from the above discussion of a multiple donor/single acceptor system is that one acceptor can undergo energy transfer with multiple donors. The limitations that were considered were the ability to excite an acceptor to higher energy levels and also the limitations of simultaneous donor de-excitation. In donor emissions that occur concurrently, only one of the de-excitations would be able to undergo energy transfer with the acceptor. If this occurred often, then the acceptor would not be able to undergo energy transfer with all donor emission events. Probability calculations show that for a one thousand donor/one acceptor system under standard epiillumination conditions, 98.7% of donor emission events can undergo energy transfer with an acceptor. The overall conclusion from these detailed analyses is that a multi-donor system/one acceptor system can indeed exist and that a single acceptor can undergo energy transfer with a large number of donor molecules.

The following description sets forth how conditions can be optimized for the donor and the acceptor fluorophores of the multi-donor/one acceptor system. In order to optimize the system two potential problems which may arise when this system is actually performed should be considered. These are photobleaching and solvent quenching (Rost, 1990; Menter et al., 1978; Giloh and Sedat, 1982; Vaughan and Weber, 1970; Guilbault, 1973; Udenfriend 1962; Pringsheim, 1963). These effects may limit the number of excitation cycles a fluorophore can undergo. Whereas in an ideal system a fluorophore can undergo infinite excitation cycles, in practice, the actual number of cycles is limited to a finite number depending on both the solvent conditions and intensity of the excitation light. The signal produced in a multiple donor/one acceptor system, however, can be optimized under certain experimental conditions.

The theory for optimizing and generating an efficient signal follows. The rationale is that as long as model conditions are simulated as close as possible, signals are generated. Recall that ideal fluorophores can undergo infinite cycles of excitation. If realistic fluorophores behave in a similar fashion, then any number of fluorophores can be detected as long as temporal integration of photonic emissions is sufficient. One method for achieving close to ideal conditions is by immobilizing fluorophores in a solid medium. Embedding fluorophores in solid media can abolish both photobleaching and quenching (Haughland, 1996; Garland and Moore, 1979; Rost, 1991) and that certain types of fluorophores are especially stable (such as ferulic acid in plant cell walls, uranyl glass, and Acriflavine) (Rost, 1991). This will dramatically increase the number of possible excitation cycles. Despite being embedded in a solid medium, donor fluorophores can generate fluorescent signals for several hours (Rost, 1991) and can still undergo FRET with acceptors (Stryer, 1978; Cantor and Schimmel, 1980) and vise versa. Furthermore it is known that the acceptor can undergo resonance energy transfer with donors for several hours in solvent conditions (Wittwer, 1997; Lee et al., 1994; Uchiyama et al., 1996; Livak et al., 1997). The ability for an acceptor to quench a donor that has a stable signal translates into the ability to generate highly efficient signals.

It has been shown that an acceptor can undergo energy transfer with a donor for an extended period of time in solvent conditions (Wittwer, 1997; Lee et al., 1994; Uchiyama et al., 1996; Livak et al., 1997). The evidence arises from experiments done on peptide and nucleic acid cleavage assays. In these assays, a particular substrate is labeled at either end with a donor and an acceptor fluorophore. Since the length of the substrate is within range of the Förster distance of the donor-acceptor pair, the fluorescence of the donor is quenched. Monitoring the donor fluorescence allows a light based assay of cleavage. In this manner, an increase in donor fluorescence is directly proportional to the cleavage activity of the particular enzyme. Assays of this type, commonly called fluorometric cleavage assays, have been used to study a number of systems including HIV proteases (Matayoshi et al., 1990; Toth and Marshall, 1990), neutral proteases (Ng et al., 1989), EcoRV restriction endonucleases (Erskine and Halford, 1994), PaeR7 endonuclease (Ghosh et al., 1994), DNA polymerase I 5'-3' exonuclease activity (Wittwer et al., 1997; Livak, 1997), thermolysin (Yang and Van Wart, 1994), and papain (Garcia-Echeverria and Rich, 1992). The relevance of these experiments is important because they contain evidence that an acceptor can quench a donor for extended periods of time. The controls in fluorometric cleavage assays include the monitoring of uncleaved substrates (in the absence of the cleavage enzymes) for the duration of the experiment. For especially lengthy experiments, these controls need to be monitored for an extended period of time. The lack of increase in donor fluorescence in these controls demonstrates directly that an acceptor can quench a donor for a significant length of time.

The acceptor maintains its ability to transfer energy for an extended period of time because its energy states remain unchanged. Energy transfer occurs when the acceptor absorption energies are coincident with the donor emission energies. The result of energy transfer is a ground singlet state $(A_a)$ to excited singlet state $(A_b)$ conversion. The acceptor loses energy through internal conversion, either fluorescent or non-radiative. The studies cited above demonstrate that despite non-ideal experimental conditions, the acceptors maintain their relative energy levels and hence their ability to undergo energy transfer.

The number of excitation cycles that a fluorophore generally undergoes in a solution is roughly 35,000 cycles (Rost, 1991). The number of fluorophore excitation cycles in solution, however, is limited by the solvent effects discussed above such as oxygen quenching, collisional quenching, and excited state reactions. Solvent conditions can be adjusted so that the number of excitation cycles is optimized (Haughland, 1996). Various chemical methods are used to optimize conditions for detection of acceptor fluorescence. Sodium azide $(NaN_3)$, sodium iodide (NaI), dithiothreitol (DTT), dithioerythritol (DTE), sodium dithionate, n-propyl gallate, ascorbic acid, and polyvinyl alcohol (PVA) all have been found effective with various fluorophores (Böck et al., 1985; Johnson et al., 1982; Picciolo and Kaplan, 1984; Gill, 1979; Giloh and Sedat, 1982; Valnes and Brandtzaeg, 1985). b-mercaptoethanol, sodium nitroprusside, and incorporation of electron donors and molecules with SH groups have also been found to be effective (Franklin and Filion, 1985; Spatz and Grabig, 1983; Hamada and Fujita, 1983). In addition, commercial reagents for reducing solution fluorophore fading are available. SlowFade (Molecular Probes, Oreg.) formulation reduces the fading rate of fluorescein to almost zero. Because it provides a nearly constant emission intensity from fluorescein, the SlowFade reagent is especially useful for quantitative measurements and applications that employ a confocal laser scanning microscope, in which the excitation intensities can be extreme and prolonged. For a system under the proposed optimized conditions, both initial donor emission and the change in donor emission in the presence of acceptors have efficiencies close to that of ideal conditions.

A "detectable signal" as used herein is any type of signal which can be sensed by conventional technology. The signal produced depends on the type of agent or station as well as the unit and the proximate compound if present. In one embodiment the signal is electromagnetic radiation resulting from light emission by a labeled (intrinsic or extrinsic) unit of the polymer or by the proximate compound. In another embodiment the signal is fluorescence resulting from an interaction of a radioactive emission with a scintillation layer. The detected signals may be stored in a database for analysis. One method for analyzing the stored signals is by comparing the stored signals to a pattern of signals from another polymer to determine the relatedness of the two polymers. Another method for analysis of the detected signals is by comparing the detected signals to a known pattern of signals characteristic of a known polymer to determine the relatedness of the polymer being analyzed to the known polymer. Comparison of signals is discussed in more detail below.

More than one detectable signal may be detected. For instance a first individual unit may interact with the agent or station to produce a first detectable signal and a second individual unit may interact with the agent or station to produce a second detectable signal different from the first detectable signal. This enables more than one type of unit to be detected on a single polymer.

The detectable signal is produced at a station. A "station" as used herein is a region where a portion of the polymer to be detected, e.g. the unit, is exposed to, in order to produce a signal or polymer dependent impulse. The station may be composed of any material including a gas. Preferably the station is a non-liquid material. "Non-liquid" has its ordinary meaning in the art. A liquid is a non-solid, non-gaseous material characterized by free movement of its constituent molecules among themselves but without the tendency to separate. In another preferred embodiment the station is a solid material. In one embodiment when the unit interacts with an agent the station is an interaction station. The station may also be a signal generation station, which is discussed in more detail below. As used herein an "interaction station or site" is a region where a unit of the polymer and the agent can be positioned with respect to one another in close enough proximity whereby they can interact. The interaction station for fluorophores, for example, is that region where they are close enough so that they energetically interact to produce a signal.

The interaction station in a preferred embodiment is a region of a nanochannel where a localized agent, such as an acceptor fluorophore, attached to the wall forming the channel, can interact with a polymer passing through the channel. The point where the polymer passes the localized region of agent is the interaction station. As each labeled unit of the polymer passes by the agent a detectable signal is generated. The agent may be localized within the region of the channel in a variety of ways. For instance the agent may be embedded in the material that forms the wall of the channel or the agent may be attached to the surface of the wall material. Alternatively the agent may be a light source which is positioned a distance from the channel but which is capable of transporting light directly to a region of the channel through a waveguide. An apparatus may also be used in which multiple polymers are transported through multiple channels. These and other related embodiments of the invention are discussed in more detail below. The movement of the polymer may be assisted by the use of a groove or ring to guide the polymer.

Other arrangements for creating interaction stations are embraced by the invention. For example, a polymer can be passed through a molecular motor tethered to the surface of a wall or embedded in a wall, thereby bringing units of the polymer sequentially to a specific location, preferably in interactive proximity to a proximate agent, thereby defining an interaction station. A molecular motor is a compound such as polymerase, helicase, or actin which interacts with the polymer and is transported along the length of the polymer past each unit. Likewise, the polymer can be held from movement and a reader can be moved along the polymer, the reader having attached to it the agent. For instance the agent may be held within a scanning tip that is guided along the length of the polymer. Interaction stations then are created as the agent is moved into interactive proximity to each unit of the polymer.

Once the signal is generated it can then be detected. The particular type of detection means will depend on the type of signal generated which of course will depend on the type of interaction which occurs between the unit and the agent. Many interactions involved in the method of the invention will produce an electromagnetic radiation signal. Many methods are known in the art for detecting electromagnetic radiation signals, including two- and three-dimensional imaging systems.

Three-dimensional imaging systems for imaging fluorescence in biological systems has recently been described. Dickson et. al., have described three-dimensional imaging of single molecules in the pores of a gel. Dickson et. al., *Science*, 274:966-969 (1996). Dickson et al. examine the effects of confined environments on Brownian motion of single fluorescent molecules. Single molecules of free fluorescent dye and fluorescent dye bound to protein were trapped in polyacrylamide (PAA) gels. Nile red was incorporated into polyacrylamide gels having pores on the order of 2 nm. The fluorophore gels were excited with an evanescent wave generated by total internal reflection (TIR) to detect movement or immobilization of single molecules within the pores of the gels. The TIR method produces three-dimensional information about the molecules in the pores by using the exponential fall-off in excitation intensity to determine the distance of the fluorophore from the interface. The discrepancy between observed motion and theoretical Brownian motion was studied by both cases. The Brownian motion for free fluorophores was reduced by a factor of $10^4$. The labeled proteins remained completely stationary in space. By direct analogy, the spatial confinement of the nanochannels should limit or eliminate the Brownian motion of the labeled DNA in nanochannel FRET sequencing. This would allow a stable and predictable passage of the DNA through the nanochannels.

An example of a microscopy system useful according to the methods of the invention is provided in Ishijima et al., Cell, 92:161-171 (1998).

Two-dimensional imaging systems are important because they have, among other parameters, low noise, high quantum efficiency, proper pixel-to-image correlation, and efficient processing times. An example of a device useful for detecting signals is a two-dimensional fluorescence imaging system which detects electromagnetic radiation in the fluorescent wavelength range.

There are three categories of fluorescence imaging devices based on the type of fluorescence signal measured, either intensity, lifetime, or spectra. Intensity signals can be captured by a variety of methods including charge coupled device (CCD) camera, streak cameras, and silicon diode arrays. Of these methods, the most common is the CCD camera because of its wide commercial applications. The streak camera offers a superior temporal resolution down to the femtosecond. Silicon diode arrays have superior dynamic range, signal to noise ratios, and temporal resolution (common frame rates at 1000/s), but have larger picture elements (25 µM×500 µM as opposed to 20 µM×20 µM for a CCD). Each of the devices may be used with the methods of the invention but CCD cameras are preferred.

Lifetime and spectral imaging are performed using a combination of instruments including gated image intensifiers, pulsed lasers, and CCD cameras. Time-gated methods, which are lifetime-related techniques, involve temporally discriminating fluorescence signals from background and autofluorescence. Periasamy et. al., which is hereby incorporated by reference provides a review of Time-gated fluorescence microscopy for clinical imaging. Periasamy et. al., *Microscopy and Analysis,* 33-35 (1995). Lifetime imaging uses time-gating or phase-modulation techniques to determine fluorescence lifetime. Spectral imaging determines the emission spectrum at each pixel. Time-gated and lifetime imaging techniques offer many advantages to simple CCD imaging such as better signal-to-noise ratios and greater dye specificity and thus also are preferred devices for the detection method of the invention.

The first type of imaging technique, intensity imaging generally involves the use of a CCD or ICCD camera to independently capture intensity signals. This is a desirable method for detecting signals according to the methods of the invention because of its simplicity. CCD and ICCD cameras can be readily purchased from a number of suppliers (i.e. Photometrics, Hamamatsu, Princeton Instruments).

CCDs are two-dimensional silicon matrices that have many light sensitive elements called pixels that can hold electronic charges generated by photon interaction. Exposure of the CCD to photonic fluorescent emission causes accretion of charge in the individual pixels. After an exposure is complete, entire rows of accumulated charge are transported towards a serial CCD register. In the serial register, individual pixel charge packets are transported to a read-out amplifier that creates a signal proportional to the amount of charge. Each row of the CCD is read in a similar fashion until the image is successfully converted to a two-dimensional series of signals. Charge transfer between the CCD and the serial CCD register is extremely efficient (99.9999% efficient). The output amplifier creates a linear response to the measured analog signals and the image is digitized between 8 and 16 bits.

Upon read-out of the image, there are two options that CCD cameras usually employ to modify images. These are subarray read-out and binning, or charge-grouping. A programmed CCD camera can selectively process pixels in a defined region of interest. The advantage of defining regions of interest is that it allows faster image read-out to occur. The time to process and digitize each pixel is fixed, so that smaller desired regions allow for higher frame rates. Smaller regions are possible from subarray read-out. For instance a 100×100 pixel in a 1024×1024 pixel CCD may be read at a frame rate of 100 frames/s at a pixel read frequency of 1 MHZ. Binning, which is a combination of smaller pixels into one effective larger pixel for faster readout times, on the other hand, allows combination of charge from several pixels. During binning, the CCD operates at reduced resolution for increased dynamic range and a higher frame rate. The dynamic range is the ratio of the largest signal a CCD can detect linearly to the basal readout noise. For example, a 1024×1024 pixel CCD binned 4×4 yields a 256×256 image which has large pixels that are effectively 16 times larger than the unbinned version. The image is also read-out at 16 times the rate. The specific operational mode of the CCD is dictated by the components of the camera and a host computer.

To understand the control of the CCD, there are three components of a typical CCD that need to be discussed, including the camera controller, electronics unit, and camera head. The controller acts as the intermediary processor of input and output between the host computer and the camera. The controller contains logic which causes the camera to act on certain host commands. In addition it also relays digitized pixel data to the computer. Internally, the controller has sequences necessary for coordination of the CCD phases and timing of the analog processing units. The electronics unit convert digital commands into active clocking signals and sequences. Furthermore, the unit contains the A/D converter. Digitizers from 8 to 16 bits are commonly used. The camera head contains the CCD and often a cooling device. Liquid nitrogen or Peltier cooling are common.

With a basic understanding of the operation of a CCD camera, performance is the most important consideration for the camera. Specifically, these parameters are noise, linearity, quantum efficiency, and temporal resolution. There are four components of noise that are important. They are dark current, read noise, shot noise, and lamp noise. Dark current is the leakage current within the CCD. The charge accumulates even in the dark, hence the term. The lower the CCD temperature, the lower the dark current. Thermoelectric coolers or liquid nitrogen can lower the CCD temperature to reduce the dark current. Temperatures of −120° C. can reduce the dark current by several orders of magnitude. Multi-pin phasing (MPP) is a new CCD technology that can reduce dark current by a factor of 100 or more. Read noise is the stochastic electronic charge generated at higher frame rates arising from the output preamplifier. As the collection rate increases, so does the read noise. Read noise can be significantly reduced when the temperature is lowered below −60° C. Shot noise, also commonly called photonic noise, arises because of the quantum nature of light. It is the square root of the photonic signal. At low light levels, the relative shot noise is high and often masks the desired signal. Lamp noise is due to intensity fluctuations in the illuminating source and can be controlled by using stable power supplies. Lamp noise is very often overlooked in quantitative applications of CCD cameras.

Photometric linearity becomes especially important during quantitative fluorescence microscopy. For use in the methods of the invention, concern for linearity is not overly important because in general linear operators are not being applied to the CCD data. Since the charge generation mechanism of a CCD is intrinsically linear, the output signal is precisely proportional to the charge. The electronics between the CCD and the digitizer provide room for deviations. High scientific grade CCDs usually exhibit linearity with less than 0.1% deviation. In most cases, the linearity is difficult to measure because it is more linear than techniques used to test it.

Quantum efficiency is the fraction of photons that reach the CCD that interact to generate electron-hole pairs in the CCD. Quantum efficiencies range from 10% on low-grade CCDs to as high as 80% on back illuminated scientific grade CCDs. There are also spectral variances of the quantum efficiency, with peaks occurring usually in the visible wavelength. Back illuminated CCDs have much greater quantum efficiencies at all spectral positions.

Temporal resolution of a CCD camera becomes important when discussing the possible frame rate of the camera. Exposure times vary for given applications and the exposure time can be adjusted by the number of fluorophores used and the intensity of the excitation light. The limitation to the temporal resolution in a given CCD camera is a function of the analog-to-digital converter operating frequency and also the image size. For example, an A/D converter operating at 1 MHZ can read 100 frames of a 100×100 image in one second. In addition, the higher the dynamic range desired, the slower the read frequency. For example, it is difficult for current CCD cameras digitizing at 14 bits per pixel to operate above 1 MHZ. Use of multiple serial register devices overcomes the temporal limitations imposed by one A/D converter. The speed increase with such a device is proportional to the number of available output channels. A 14 bit 100×100 pixel image acquired by a CCD camera with 4 output registers operating at 1 MHZ can acquire 400 frames per second. The maximum rate limitation that cannot be overcome is dictated by the pixel read-out times, which vary from 20 µs to 500 ns. For a 100×100 pixel image, even the slowest pixel read-out time can allow 500 frames/s. Hence, read-out times are rarely a limitation on the frame rate, but rather it is the A/D converter that is limiting. As evidence of this, frame rates of 2000/s have been possible with a 128×128 array (Ichikawa et al., 1992).

A CCD camera which is particularly useful in the methods of the invention is a large pixel, low noise, and short scan time camera. Large pixel sizes have greater well capacities and allow for greater collection of photons and hence a greater maximal signal-to-noise ratio (SNR). The basis of intensity change discrimination relies on a large SNR, as is to be discussed shortly. Accordingly, low noise aids in improving the SNR. MPP type CCDs with smaller well capacity and lower dynamic range are not well suited. The temporal resolution is high from the short scan time, allowing a high volume data stream that should be storable in real time in the computer RAM or on the hard drive. The quantum efficiency should be reasonable. The linearity of the CCD is not critical, but assumed to be scientific grade (0.1%). The dynamic range is not critical because the donor fluorophores that are images are approximately the same intensity.

An intensified CCDs (ICCDs) camera consists of a photocathode, microchannel plate (MCP), and a phosphor screen in addition to the CCD camera. Fluorescence light impinges on the photocathode, releasing photoelectrons into the MCP. The MCP is a secondary electron multiplier consisting of an array of millions of glass capillaries (channels) fused into the form of a thin disc. When photoelectrons are incident upon the channels, secondary electrons are produced. Passage of the electrons through the channels produces an amplification that is directly controlled as the gain of the instrument. Each channel of the MCP corresponds to a picture element. The output of the MCP is focused onto a phosphor screen where electrons exiting from the MCP strike. The optical image is reproduced on the phosphor screen and is captured by a CCD camera.

In some instances, it is preferred to use a ICCD. The addition of the image intensifier offers high speed gating and high gain. Gating is probably the most important aspect of the ICCD. It is the electronic shutter action produced by controlling the input voltage to the image intensifier. At present, time-resolved imaging methods are possible with nanosecond and sub-nanosecond gating times (Thomas et al., 1992). Gating allows for greater signal detection because of temporal discrimination of background signals. Examples of temporal discrimination and enhancement of signal-to-noise ratios is seen in time-gated fluorescence microscopy and the pulse method of fluorescence lifetime imaging microscopy. The gain of the image intensifier is used to increase the sensitivity of the camera and also serves as a tool in the phase-modulated method of fluorescence lifetime imaging spectroscopy. The electronic gain can be as high as 10,000:1. This allows faint optical signals to be amplified over read noise.

Single photon events can be detected with an ICCD. Single fluorophore imaging, for instance, has been achieved by Sase et al., 1995 using a CCD camera, image intensifier, and an epifluorescence microscope. In "Real Time Imaging of Single Fluorophores on Moving Actin with an Epifluorescence Microscope," Sase et al. demonstrate that single fluorophores can be imaged in real time with a high detection efficiency. Other methods that have achieved solution single molecule sensitivity include fluorescence correlation spectroscopy (Eigen and Rigler, 1994; Kinjo and Rigler, 1995), far-field confocal microscopy (Nie et al., 1994), cryogenic fluorescence spectroscopy (Kartha et al., 1995), single molecule photon burst counting (Haab and Mathies, 1995; Castro and Shera, 1995; Goodwin et al., 1995; Peck et al., 1989; Nguyen and Keller 1987; Lee et al., 1994; Chen and Dovichi, 1996; Shera et al., 1990; Soper et al., 1992), two-photon excited fluorescence (Mertz, 1995), and electrochemical detection (Fan and Bard, 1995).

A numerical SNR value can be calculated based on the desired aspects of a CCD camera. For example, a CCD that satisfies the criteria set out above is an EEV 05-20 CCD (Princeton Instruments, (Princeton, NJ) which has the specifications set forth in Table 1:

TABLE 1

| CCD format | 1152 × 770 | dynamic range, bits | 14 to 17 |
|---|---|---|---|
| pixel size, µm | 22.5 × 22.5 | non-linearity, % | <1 (16 bits) |
| full well capacity, ke- | 500 | dark charge at −120° C., electrons/pixel-hour | <1 |
| readout noise, e- | 4-6, 50 kHz 22,500 kHz | quantum eff., % peak | 40 |

In order to calculate a SNR, an equation that considers the various noise values is needed. In any detection system, there is always a basal level of noise that may hinder detection of signals that are weak and intermittent. Intuitively, the larger the desired signal, the less important the basal level of noise becomes. A larger signal and hence a larger SNR can be attained by increasing either the number of fluorophores or the excitation intensity.

The equation for calculating the SNR is $$SNR = \frac{PE}{\sqrt{(N_{shot}^2 + N_{dark}^2 + N_{read}^2 + N_{lamp}^2)}}$$

$$PE = \frac{I\xi\rho t E N G}{h\upsilon}$$

PE represents the number of photoelectrons emitted from the detector and is related to the efficiency (E) of the detector system. The higher the efficiency (E), the greater the number of photoelectrons emitted for a given number of photons. PE is also related to the number of fluorophores (N), pre-amplifier gain (G), integration time (t), intensity of light (I), molar extinction coefficient of the fluorophore ($\epsilon$), and a fluorescence constant specific for the chosen fluorophore ($\rho$). $N_{shot}$ represents the noise due to random fluctuations of the fluorophore emission and is related to the magnitude of the signal produced. The larger the signal, the larger the shot noise. $N_{dark}$ and $N_{read}$ are dark noise and read noise. $N_{lamp}$ is the noise generated from the illuminating source. It is important to note that $N_{lamp}$ can have large influences in the SNR. An illumination source that has a 1% intensity fluctuation can have a SNR only as large as 100:1. In this case, the lamp noise is minimized by using a stable power supply. For example, commercially available (Uniphase) helium-neon lasers with modified power supplies have intensity fluctuations of less than 0.002% of the total intensity. Furthermore, a tungsten filament lamp can be equipped with a stable power supply so that the output of the bulb fluctuates less than 0.001%. Table 2 lists the values for the variables and provides the reason the particular values were chosen.

One method for generating a large percentage change is to cluster multiple donor fluorophores around the interaction station, e.g., in a concentric ring which the polymer can pass through, ensuring that all donor fluorophores will undergo energy transfer with the acceptor. An appropriate width of such a concentric ring of donor fluorophores can be determined by the rate of emission of the donors and also the Förster distance of the donor-acceptor pair. Typical changes in intensity upon acceptor passage range from 30% to 50%, which correspond to an unequivocal 100% confidence.

Before the CCD camera can process a signal each signal generated must be captured by pixels of the detector system. Each pixel should be capable of capturing a signal from a single interaction station and should have the ability to detect transient changes in the signal. The area of an interaction station, e.g., the localized region of agent on a nanochannel, detected by one pixel is determined by the pixel size on the detector, the magnification of the image, and also the diffraction limit of the wavelengths to be measured. The relationship between the measured area, detector pixel size, and magnification is given by the following equation.

$$a = 2d/M$$

The size of the area to be measured is given by $a^2$ where a is the edge length. The edge length of the detector pixel is given by d. The magnification is given by M. Using convention values of these variables, with d=15 μM and M–60×, the edge length of a measured area turns out to be 500 nm, well within range of the resolving power of a 500 nm wavelength signal. The resolving power for a microscope sample under epiillumination is presented in the following equation (Matsumoto, 1993).

$$R_f = 0.6\lambda/NA$$

TABLE 2

| variable | value | reason |
|---|---|---|
| I | 30 W/cm² | intensity of 2 W laser is given by P/A. A is the beam area. Intensity of laser is 64 W/cm² |
| $\epsilon$ | 91,000 1/M cm | molar extinction coefficient for fluorescein |
| $\rho$ | 3.8 × 10⁻²¹ M cm³ | constant for fluorescence emission of fluorescein |
| t | 0.010 s | integration time for CCD operating at 100 frames/s |
| E | 0.025 | collection efficiency of system including filters, objective, and quantum efficiency of CCD |
| N | 1000 | reasonable number of donor fluorophores/pixel |
| G | 60 | typical pre-amplifier gain; gain for ICCD can be as high as 10,000:1 |
| h | 6.6261 × 10⁻³⁴ J s | Planck's constant |
| ν | 6.1224 × 10¹⁴ × s⁻¹ | c = νλ; λ = 490 nm (excitation of fluorescein) |
| $N_{shot}$ | 632 e⁻¹ | $N_{shot} = PE$ |
| $N_{lamp}$ | 8 e⁻¹ | 0.002% intensity fluctuation |
| $N_{read}$ | 40 e⁻¹ | estimation for EEV 05-20 CCD at high readout speeds |
| $N_{dark}$ | ~0 | value for EEV 05-20 CCD at −120° C. |
| SNR | 631:1 | from the above equation |

A SNR of 631:1 is high. A high SNR ensures efficient detection of both intensity and intensity changes, or in other words, donor emission in the absence and presence of an acceptor. For example, a SNR of 631:1 means that there is a 66% confidence of detecting a 0.158% (1/632×100) change in the signal. There is a 95% confidence in detecting a 0.316% change and a 99.9% confidence for a 0.475% change. The larger the intensity change, the greater chance of detection. A higher baseline SNR in the absence of any intensity changes allows for greater confidence intervals for a given percentage intensity change. In order to maximize the confidence of detection of a signal change, it is important to generate large percentage changes in the presence of acceptors.

$R_f$ is the minimum distance between two bright points that can be resolved. λ is the wavelength of the donor fluorescent emission. NA is the numerical aperture of the microscope objective. The highest numerical aperture is desired because of the inverse relationship between NA and the resolving power. NA is given by the following classic criterion for lens selection (Taylor and Salmon, 1989):

$$NA = n \sin \Theta$$

n is the index of refraction of the immersion medium. It is often desirable to use a higher index medium such as oil. θ is the angle between the optical axis and the greatest marginal ray entering the lens. For quality microscope objectives at high powers, the numerical aperture can be as high as 1.4.

From the above two equations, the resolving power for a 500 nm emission signal and a 1.4 NA lens becomes 218 nm.

The conclusion from the above calculations is that two adjacent pixels on the detection unit can each detect signals from their respective interaction stations without confusion of the origins of the signals. By carefully calculating the magnification and the pixel size cross-interference between pixels can be avoided. For example if the smallest pixel size (d=6 μM) and the largest magnification (M=100×), were used a 120 nm edge length on the detected area is achieved. Since the resolving power of the system remains constant at 218 nm, interference of signals would exist. This can be avoided by performing calculations prior to defining the experimental set up. Hence, by adjusting the magnification and the pixel size on the detection system, an optimal number can be reached where the measured area matches the diffraction limit. This can be determined from a combination of the above two formulas by setting the edge length equal to or greater than the resolving power of the detection system:

$$2d/M \geq 0.61 \lambda/NA$$

the density of the interaction stations can be varied so that only one interaction station corresponds to one pixel of the detector system. For example, if a $4 \times 10^6$ nanochannels/cm² plate is used, 0.01 nanochannels (interaction stations) are found per pixel using a 60× magnification and a 15 μM pixel size. The interaction station density can be adjusted even lower, e.g., an average minimum inter-pore distance of 48 μM is also within the appropriate range.

In addition to intensity imaging both time-gated fluorescence microscopy and fluorescence lifetime imaging may be used to detect signals according to the methods of the invention. Time-gated fluorescence microscopy and fluorescence lifetime imaging are more involved methods that have advantages such as temporal discrimination of fluorescent signals and better signal-to-noise ratios than intensity imaging.

Time-gating is desirable if there is significant background scattering or autofluorescence. Background light scattering is a problem when the scattered wavelengths are equal to the emission wavelengths of the desired fluorophores. Scattering effects can be avoided by using a fluorophore with a large Stokes shift so that the scattered wavelengths are shorter than the detected wavelength. In this case, the scattered light can be eliminated by using optical filters. On the other hand, autofluorescence is a common problem affecting essentially all studies employing fluorescence microscopy. Autofluorescence can arise from solvents, solutes, and the optical components of the microscope system. Autofluorescence decreases the signal-to-noise ratio of detection. This is the case even though there have been many improvements in the various components of the detector systems (Periasamy and Herman, 1994).

Time-gated fluorescence microscopy (TGFM) utilizes differing fluorescence lifetimes to make a distinction between autofluorescence and fluorescence. Lifetimes of fluorescent dyes can be chosen to be longer than that of autofluorescence. Short lived autofluorescence decays to zero in less than 1 μs whereas long lived fluorescence can demonstrate lifetimes from 1 μs to 10 ms (ex. europium chelates, lanthanide chelates). Excitation of the sample is done with a brief intensity pulse, shorter than the lifetime of either the autofluorescence or fluorescence. Exponential decay follows. If measurements are made only after the decay of the fluorescent signal, then the longer lived signals are measured with a greater sensitivity.

An example of an imaging apparatus for TGFM is provided in Periasamy, 1995. A fluorescent microscope (Nikon) with epiillumination capabilities and a continuous wave (CW) laser (Coherent or Spectra-Physics) are shown in the reference, emitting at the desired excitation wavelength. The excitation laser light is chopped by a chopper with a chopper control to create laser pulses with defined pulse widths. The intensity of the light is controlled using a variable neutral density filter (Omega Optics). To delay the time of measurement, a delay pulse generator is used to generate a signal for controlling a high frequency gated image intensifier (Hamamatsu) or a chopper in the emission light path. A CCD camera (Princeton Instruments or Photometrics) is used to collect the signals.

The fluorescence lifetime represents the average amount of time a molecule remains in the excited state prior to its return to ground state. There are two methods for the measurement of fluorescence lifetimes. These are the pulse method and the phase-modulation method (Lakowicz, 1986; McGown, 1989; Gratton and Limkema, 1983). In the pulse method, the sample is excited with a brief pulse of light and the time-dependent fluorescent decay is measured. In the phase-modulation method, the sample is excited with a sinusoidally modulated light. The phase shift and demodulation is used to calculate the lifetime. Until recently, lifetime measurements were only used with cuvette samples. In the past five years, there has been development of methods that combine microscopic two-dimensional resolution and high-resolution lifetime measurements (Rodgers and Firey, 1985; Wang et al., 1990; Morgan et al., 1990; Clegg et al., 1991; Lakowicz and Berndt, 1991; Buurman et al., 1992; van de Ven and Gratton, 1992; Oida et al., 1993). The development of fluorescence lifetime imaging microscopy (FLIM) has allowed the detailed study of location and environment of fluorescent labels in cells and other microscopic samples. In the following, the advantages, theory, and applications of FLIM are discussed.

Fluorescence lifetime measurements have been used for a variety of reasons including specificity, sensitivity, quantitation, and high temporal resolution (Wang et al., 1996). Measurement of lifetimes provide high specificity because fluorescent molecules have distinct lifetimes. In comparison to absorption and emissions, lifetimes provide greater discrimination of molecules. Lifetimes can also be carried out on small amounts of molecules, leading to similar sensitivities as intensity measurements. Quantitation of molecules through lifetimes provide a true measurement because fluorescence lifetime is directly related to the fluorescence quantum yield of the fluorophore. Lastly, lifetimes can be used to detect temporal events that occur on the time scale of biomolecular processes, usually between a picosecond and a microsecond.

There are two methods of determining lifetimes. The pulse method is described first (Lakowicz, 1986). Consider an short pulse of light exciting a population of fluorophores. The fluorescent signal of the excited molecules decays with time in a first order manner, given as the following exponential function:

$$I(t)=Ae^{(-t/\tau)}$$

a is an arbitrary constant, t is the time, and τ is the fluorescent lifetime. Intuitively, the fluorescent lifetime is the time required for the intensity to decay to 1/e of the original value, a decay of 63%. One of the methods to experimentally measure the lifetime is to use a pulse-sampling method (Herman et al., 1996). $D_1$ and $D_2$ are collected on consecutive frames. Frames are analyzed with a lifetime equation and a FIG. 2 and 2-D lifetime array is generated. Following each excitation event, the multichannel plate gated image intensifier (MCP-GII) attached to the CCD camera is turned on for a very brief interval (i.e. 4 ns) at some time interval ($t_1$) after the exciting pulse. The emission is acquired on a CCD that is continually on. The identical process is repeated for a large number of times to capture a sufficient signal on one frame of the CCD. After a sufficient signal at $t_1$ is generated, the CCD is read out and the gate window with respect to the excitation pulse ($t_2$) is shifted and the whole process is repeated. Interpretation of the two frames with a pixel by pixel analysis gives the lifetime of the image at each point.

Wang et al., 1996 describe the apparatus for pulse FLIM as consisting of five main components: 1) pulsed light source; 2) image detection system (gated image intensifier and CCD camera; 3) timing control unit; 4) and fluorescence microscope. The system is identical to the apparatus described for time-gated fluorescence microscopy (TGFM) described above, except for the pulsed light source which is a picosecond pulsed light source (Coherent) consisting of a mode-locked YAG laser, a dye laser with a third harmonic generator, and a cavity dumper. Picosecond pulses having tunable wavelengths from UV to IR. Rates from single shot to 76 MHZ are generated.

The second method of fluorescence lifetime determination is by the phase-modulation method. Instead of using a pulsed light source of excitation, the method uses a light whose intensity is modulated sinusoidally. The emission of the sample, therefore, follows the same sinusoidal variations. The modulated emission is delayed in phase because of the excited lifetime of the fluorescent molecules. The magnitude of the phase shift ($\phi$) is directly related to the lifetime of the fluorophore. Furthermore, there is demodulation of the emission. In other words, the amplitude of the final emission is smaller in amplitude than that of the excitation light. Both the phase angle ($\phi$) and the demodulation factor (m=BA/ba) are measured and used to calculate the phase ($\tau_p$) and modulation lifetimes ($\tau_m$) (Lakowicz, 1986).

$$\tau_p = \frac{\tan\phi}{\omega}$$

$$\tau_m = \frac{\sqrt{[(1-m^2)-1]}}{\omega}$$

In single exponential decay, $\tau_p = \tau_m = \tau$, the actual fluorescence lifetime.

The basic theory behind phase modulation lifetime determination can be applied to a two-dimensional imaging system. The following description is based on from Gadella et al., 1993 and Lakowicz and Szmacinski, 1996, each of which are hereby incorporated by reference. The method uses a gain-modulated image intensifier that generates an image that has an intensity related to the phase shift of the emission signal. With use of several phase-sensitive images collected with various electronic delays or phase shifts, it is possible to calculate the lifetime image of the object. To understand this further, it is necessary to present the equation that describes the time-averaged, phase-sensitive intensity from a certain position r:

$$I(r,\theta-D) = I_o(r)[1 + \tfrac{1}{2} m_D m(r)\cos(\theta(r) - \theta_D)]$$

where r denotes the pixel position, $\theta_D$ is the phase angle of the gain modulation signal, $\theta(r)$ is the phase of the emission, mD is the gain modulation of the detector, m(r) is the modulated amplitude of the emission, $I_o(r)$ is the original intensity of the pixel (which depends on concentration). The equation describes the intensity of a given pixel as a function of two controlled parameters ($\theta_D$ and $m_D$) and three unknowns ($I_o(r)$, $\theta(r)$, $m(r)$). Recall that the lifetime ($\tau$) can be determined if either $\theta(r)$ or m(r) is known. Since there are three unknowns, at least three different images are needed to determine the lifetime of the specimen. By controlling the phase angle of the gain modulation signal ($\theta_D$), a series of phase-sensitive images are generated and hence lifetimes can be determined.

The apparatus for phase-modulation FLIM is described in Lakowicz and Szmacinski, 1996. Excitation is provided by the output of a cavity-dumped laser, which is synchronously pumped by a mode-locked Nd:YAG laser. The excitation light is expanded by a laser beam expander. The gated image intensifier is positioned between the target and the CCD camera. The gain of image intensifier is modulated using output of a frequency synthesizer. A CCD camera captures the phase sensitive images. A computer with FLIM software processes the output to generate a lifetime image.

Other interactions involved in the method will produce a nuclear radiation signal. As a radiolabel on a polymer passes through the defined region of detection, such as the station, nuclear radiation is emitted, some of which will pass through the defined region of radiation detection. A detector of nuclear radiation is placed in proximity of the defined region of radiation detection to capture emitted radiation signals. Many methods of measuring nuclear radiation are known in the art including cloud and bubble chamber devices, constant current ion chambers, pulse counters, gas counters (i.e., Geiger-Müller counters), solid state detectors (surface barrier detectors, lithium-drifted detectors, intrinsic germanium detectors), scintillation counters, Cerenkov detectors, etc.

Other types of signals generated are well known in the art and have many detections means which are known to those of skill in the art. Among these include opposing electrodes, magnetic resonance, and piezoelectric scanning tips. Opposing nanoelectrodes can function by measurement of capacitance changes. Two opposing electrodes create an area of energy storage, which is effectively between the two electrodes. It is known that the capacitance of two opposing electrodes change when different materials are placed between the electrodes. This value is known as a dielectric constant. Changes in the dielectric constant can be measured as a change in the voltage across the two electrodes. In the present example, different nucleotide bases or units of a polymer may give rise to different dielectric constants. The capacitance changes as the dielectric constant of the unit of the polymer per the equation: $C = KC_o$, where K is the dielectric constant and $C_o$ is the capacitance in the absence of any bases. The voltage deflection of the nanoelectrodes is then outputted to a measuring device, recording changes in the signal with time.

A nanosized NMR detection device can be constructed to detect the passage of specific spin-labeled polymer units. The nanosized NMR detection device consists of magnets which can be swept and a means of irradiating the polymer with electromagnetic energy of a constant frequency (This is identical to holding the magnetic field constant while the electromagnetic frequency is swept). When the magnetic field reaches the correct strength, the nuclei absorb energy and resonance occurs. This absorption causes a tiny electric current to flow in an antenna coil surrounding the sample. The signal is amplified and output to a recording device. For known labeled compounds, the time of detection is much faster than current means of NMR detection where a full spectra of the compound in question is required. Known labeled units of polymers have known chemical shifts in particular regions, thereby eliminating the need to perform full spectral sweeps, lowering the time of detection per base to micro or milliseconds.

A nanoscale piezoelectric scanning tip can be used to read the different units of the polymer based on physical contact of the different polymer units with the tip. Depending on the size and shape of the polymer unit, different piezoelectric signals are generated, creating a series of unit dependent changes. Labels on units are physically different than native units and can create a ready means for detection via a piezoelectric scanning tip. Upon contact of a polymer unit with the tip, the piezoelectric crystals change and give rise to a current which is outputted to a detection device. The amplitude and duration of the current created by the interaction of the polymer unit and the tip is characteristic of the polymer unit.

Optical detectable signals are generated, detected and stored in a database the signals can be analyzed to determine structural information about the polymer. The computer may be the same computer used to collect data about the polymers, or may be a separate computer dedicated to data analysis. A suitable computer system to implement the present invention typically includes an output device which displays information to a user, a main unit connected to the output device and an input device which receives input from a user. The main unit generally includes a processor connected to a memory system via an interconnection mechanism. The input device and output device also are connected to the processor and memory system via the interconnection mechanism.

Nanochannels can be prepared by electroless deposition procedures which produce a metal fibril running the complete width of a polycarbonate template membrane. The membrane can also be produced such that both faces of the membrane are covered with thin metal films to produce a nanodisk electrode ensemble, one of the metal films can be removed to expose the surface of the membrane. The metal films can be removed to expose the surface of the membrane. These electrodes can be connected at their bases to a common current collector. This assembly is useful for examining changes in current as polymers flow through changes in conductance can be measured. The preparation of such plates is described in Martin, C. P. R., Science, 266:1961-1965 (1994).

Computer programs for data analysis of the detected signals are readily available from CCD manufacturers. Such programs may be executed using a general purpose computer such as described below. For the methods of the invention, only operations on single pixels need to be performed (point operations). The complexity of the point operations depend on the method of imaging used. Intensity based imaging offers the fastest manipulation of data and because only arithmetic is performed on the individual pixels. Regardless of the imaging technique (intensity, TGFM, or FLIM), the algorithms performed on each pixel in each method are considered low-level when compared to global, whole frame operations that need to be performed in certain more complex imaging situations.

It should be understood that one or more output devices may be connected to the computer system. Example output devices include a cathode ray tube (CRT) display, liquid crystal displays (LCD), printers, communication devices such as a modem, and audio output. It should also be understood that one or more input devices may be connected to the computer system. Example input devices include a keyboard, keypad, track ball, mouse, pen and tablet, communication device, and data input devices such as sensors. It should be understood the invention is not limited to the particular input or output devices used in combination with the computer system or to those described herein.

The computer system may be a general purpose computer system which is programmable using a high level computer programming language, such as AC@. The computer system may also be specially programmed, special purpose hardware. In a general purpose computer system, the processor is typically a commercially available processor, of which the series x86 processors, available from Intel, and similar devices from AMD and Cyrix, the 680X0 series microprocessors available from Motorola, the PowerPC microprocessor from IBM and the Alpha-series processors from Digital Equipment Corporation, are examples. Many other processors are available. Such a microprocessor executes a program called an operating system, of which WindowsNT, UNIX, DOS, VMS and OS8 are examples, which controls the execution of other computer programs and provides scheduling, debugging, input/output control, accounting, compilation, storage assignment, data management and memory management, and communication control and related services. The processor and operating system define a computer platform for which application programs in high-level programming languages are written.

A memory system typically includes a computer readable and writeable nonvolatile recording medium, of which a magnetic disk, a flash memory and tape are examples. The disk may be removable, known as a floppy disk, or permanent, known as a hard drive. A disk has a number of tracks in which signals are stored, typically in binary form, i.e., a form interpreted as a sequence of one and zeros. Such signals may define an application program to be executed by the microprocessor, or information stored on the disk to be processed by the application program. Typically, in operation, the processor causes data to be read from the nonvolatile recording medium into an integrated circuit memory element, which is typically a volatile, random access memory such as a dynamic random access memory (DRAM) or static memory (SRAM). The integrated circuit memory element allows for faster access to the information by the processor than does the disk. The processor generally manipulates the data within the integrated circuit memory and then copies the data to the disk when processing is completed. A variety of mechanisms are known for managing data movement between the disk and the integrated circuit memory element, and the invention is not limited thereto. It should also be understood that the invention is not limited to a particular memory system.

It should be understood the invention is not limited to a particular computer platform, particular processor, or particular high-level programming language. Additionally, the computer system may be a multiprocessor computer system or may include multiple computers connected over a computer network.

The data stored about the polymers may be stored in a database, or in a data file, in the memory system of the computer. The data for each polymer may be stored in the memory system so that it is accessible by the processor independently of the data for other polymers, for example by assigning a unique identifier to each polymer.

The information contained in the data and how it is analyzed depends on the number and type of labeled units that were caused to interact with the agent to generate signals. For instance if every unit of a single polymer, each type of unit (e.g., all the A's of a nucleic acid) having a specific type of label, is labeled then it will be possible to determine from analysis of a single polymer the order of every unit within the polymer. If, however, only one of the four types of units of a polymer such as a nucleic acid is labeled then more data will be required to determine the complete sequence of the nucleic acid. Several labeling schemes and methods for analyzing using the computer system data produced by those schemes are described in more detail below. The labeling strategies are described with respect to nucleic acids for ease of discussion. Each of these strategies, however, is useful for labeling all polymers.

Several different strategies of labeling are possible, involving permutations of different types of nucleotides labeled, different percentage of nucleotides labeled, and single-stranded or double-stranded labeling and diversity labels, such as compound which bind to a polymer having a specific sequence (diversity labels are discussed in more detail below relative to specific embodiments). The simplest labeling scheme involves the labeling of all four nucleotides with different labels. Labeling schemes using three, two, or even one label are also possible.

A four nucleotide labeling scheme can be created where the A's, C's, G's, and T's of a target DNA is labeled with different labels. Such a molecule, upon traversing an interaction station, will generate a linear order of signals which correspond to the linear sequence of nucleotides on the target DNA. The advantage of using a four nucleotide strategy is its ease of data interpretation and the fact that the entire sequence of units can be determined from a single labeled polymer. Adding extrinsic labels to all four bases, however, may cause steric hindrance problems. In order to reduce this problem the intrinsic properties of some or all of the nucleotides may be used to label the nucleotides. As discussed above, nucleotides are intrinsically labeled because each of the purines and pyrimidines have distinct absorption spectra properties. In each of the labeling schemes described herein the nucleotides may be either extrinsically or intrinsically labeled but it is preferred that at least some of the nucleotides are intrinsically labeled when the four nucleotide labeling method is used. It is also preferred that when extrinsic labels are used with the four nucleotide labeling scheme that the labels be small and neutral in charge to reduce steric hindrance.

A three nucleotide labeling scheme in which three of the four nucleotides are labeled may also be performed. When only three of the four nucleotides are labeled analysis of the data generated by the methods of the invention is more complicated than when all four nucleotides are labeled. The data is more complicated because the number and position of the nucleotides of the fourth unlabeled type must be determined separately. One method for determining the number and position of the fourth nucleotide utilizes analysis of two different sets of labeled nucleic acid molecules. For instance, one nucleic acid molecule may be labeled with A, C, and G, and another with C, G, and T. Analysis of the linear order of labeled nucleotides from the two sets yields sequence data. The three nucleotides chosen for each set can have many different possibilities as long as the two sets contain all four labeled nucleotides. For example, the set ACG can be paired with a set of labeled CGT, ACT or AGT.

The sequence including the fourth nucleotide also may be determined by using only a single labeled polymer rather then a set of at least two differently labeled polymers by identifying the position of the fourth nucleotide on the polymer. This can be accomplished by determining the distance between labeled nucleotides on a nucleic acid molecule. For example A, C, and G are labeled and the detectable signals generated indicated that the nucleic acid molecule had a sequence of AGGCAAACG (SEQ. ID. No. 2). If the distances between each of the nucleotides in the nucleic acid molecule are equivalent to the known inter-nucleotide distance for a particular combination of nucleotides except the distance between G and G is twice the normal inter-nucleotide distance then a T is positioned between the two G's and the entire molecule has a sequence of AGTGCAAACG (SEQ. ID. No. 3). The distance between nucleotides can be determined in several ways. Firstly, the polymer and the agent may be moved relative to one another in a linear manner and at a constant rate of speed such that a single unit of the nucleic acid molecule will pass the agent at a single time interval. If two time intervals elapse between detectable signals then the unlabeled nucleotide which is not capable of producing a detectable signal is present within that position. This method of determining the distance between bases is discussed in more detail below in reference to random one base labeling. Alternatively the polymer and the agent may be caused to interact with one another such that each labeled unit interacts simultaneously with an agent to produce simultaneous detectable signals. Each detectable signal generated occurs at the point along the polymer where the unit is positioned. The distance between the detectable signals can be calculated directly to determine whether an unlabeled unit is positioned anywhere along the nucleic acid molecule.

Nucleic acid molecules may also be labeled according to a two nucleotide labeling scheme. Six sets of two nucleotide labeled nucleic acid molecule can be used to resolve the data and interpret the nucleotide sequence. Ambrose et al., 1993 and Harding and Keller, 1992 have demonstrated the synthesis of large fluorescent DNA molecules with two of the nucleotides completely extrinsically labeled. The average size of the molecules were 7 kb. Six different combinations of two nucleotide labeling are possible using the following formula:

$$(_nC_k) = \frac{n!}{k!(n-k)!} = \frac{4}{2!2!} = 6$$

where n nucleotides are taken k at a time. The possible combinations are AC, AG, AT, CG, CT, and GT. Knowledge of the linear order of the labels in each of the sets allows for successful reconstruction of the nucleic acid sequence. Using a 4-mer (5' ACGT 3') as a model sequence, the theory can be demonstrated. The first set, AC, gives the information that there must be a C after the A. This does not give information about the number of nucleotides intervening the A and the C nor does it give information about any G's or T's preceding the A. The second set, AG, shows that there is also a G after the A. Set AT shows there is a T after the A. From these three sets, it is then known that the target DNA is a 4-mer and that one C, one G, and one T follow the A. The subsequent sets give information on the ordering of these three nucleotides following the A. Set CG shows that G follows C. Set CT shows that T follows C. Set GT finishes the arrangement to give the final deciphered sequence of 5' ACGT 3'. In addition to the method using six labeled sets of nucleic acid molecules, the sequence can be established by combing information about the distance between labeled nucleotides generating detectable signals as described above and information obtained from fewer than six sets of two nucleotide labeled nucleic acid molecules.

A fourth labeling scheme, the random one nucleotide labeling scheme also may be used. In this method, distance information which is obtained by either population analysis and/or instantaneous rate of DNA movement is used to determine the number of nucleotides separating two labeled nucleotides. Analysis of four differently labeled target molecules yields the complete sequence.

One method of analysis with these labeling methods includes the use of complementary base information. FIG. 1 demonstrates the labeling strategy in which two differently labeled DNA samples are required. The first sample has two of its non-complementary bases randomly labeled with the same fluorophore. Non-complementary pairs of bases are AC, AG, TC, and TG. The second sample has one of its bases randomly labeled. The base chosen for the second sample can be any of the four bases. In the example given, the two non-complementary bases are chosen to be A and C. As a result, two samples are prepared, one with labeled A's and C's and another with labeled A's. The DNA is genomically digested, end-labeled, purified, and analyzed by nanochannel FRET sequencing. The sequence-specific FRET information arising from each fragment is sorted into one of two complementary strand groups. Sorting allows population analysis to determine the positions of all the desired bases. The figure illustrates the generation of sequence information from the sorted data. The first group of analyzed information yields the positions of all the A's and C's on one strand. The second group analyzed yields knowledge of all the A's and C's on one strand. The same procedure is applied to the complementary stand. Knowledge of the complementary strand's A's and C's is identical to knowledge of the T's and G's on the other stand. The result is sequence reconstruction. To cross-verify the sequence, the process can be repeated for the other pairs of non-complementary bases such as TG, TC and AG.

There are two methods of determining the distance between bases. One requires determining the instantaneous rate of DNA movement, which is readily calculated from the duration of energy transfer or quenching for a particular label. Another involves analyzing a population of target DNA molecules and its corresponding Gaussian distance distributions.

Figure 2:
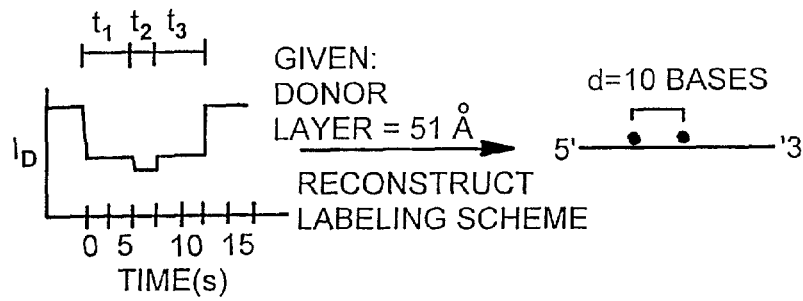
FIG. 2 is a graph of raw data demonstrating changes in energy emission patterns to determine distance information through the instantaneous rate method. The changes in energy patterns result from sequential detectable signals which when plotted produce a curve that from left to right shows two energy intensity decreases, followed by two energy intensity increases. The rate is 6.8 A/s and $t_1$ is the time between the entry of the first and second labels.

The instantaneous rate method, involves a determination of distance separation based on the known instantaneous rate of DNA movement (v) multiplied by the time of separation between signals (t). Instantaneous rate is found by measuring the time that it takes for a labeled nucleotide to pass by the interaction station. Since the length of the concentrated area of agent (d) is known (through calibration and physical measurement of the localized region of the agent, e.g., the thickness of a concentrated donor fluorophore area), the rate is simply v=d/t. As shown in FIG. 2 analysis of raw data demonstrating changes in energy emission patterns resulting from sequential detectable signals when plotted produces a curve which from left to right shows two energy intensity decreases, followed by two energy intensity increases. The plateau from the first energy intensity decrease (denoted $t_1$) is double that of the second plateau ($t_2$). The length of the interaction station is given as 51 Å. From this given information, the number of labeled nucleotides is known. Furthermore, the distance of separation of the two is determined by relating the rate of DNA movement to the time of the donor intensity plateaus. The number of labeled nucleotides is simply denoted by the number of intensity decreases. In FIG. 2, there are two intensity decreases. Accordingly, there must be two detectable labels on the DNA. To determine the distance of base separation, it is necessary to know the instantaneous rate of DNA movement, which is found by knowing the time for one labeled nucleotide to cross the localized region of the agent and the length of the localized region of the agent. The length of the localized region of the agent is given as 51 Å. The time for one labeled nucleotides crossing the localized region of the agent is bounded by the first intensity decrease and the first intensity increase (denoted as the gray shaded region, 7.5 s). The rate of DNA movement is 6.8 Å/s. The base separation is derived from the time separating the labeled nucleotides ($t_1$=5 s) multiplied by the rate (6.8 Å), which is equal to 10 base pairs. As a means of cross-verification, 51 Å–$t_2$v also yields the base separation.

In the population method the entire population of labeled nucleotide is considered. Knowledge of the length of the localized region of the agent and instantaneous rate, as required for the rate method, is not necessary. Use of population analyses statistically eliminates the need for precision measurements on individual nucleic acid molecules.

An example of population analyses using five nucleic acid molecules each traversing a nanochannel is described below. Five molecules representing a population of identical DNA fragments are prepared. In a constant electric field, the time of detection between the first and second labeled nucleotide should be identical for all the DNA molecules. Under experimental conditions, these times differ slightly, leading to a Gaussian distribution of times. The peak of the Gaussian distribution is characteristic of the distance of separation (d) between two labeled nucleotides.

An additional example utilizing a population of one nucleotide randomly labeled nucleic acid molecule (six molecules represent the population) further illustrates the concept of population analysis and the determination of distance information. The nucleic acid is end-labeled to provide a reference point. With enough nucleic acid molecules, the distance between any two A's can be determined. Two molecules, when considered as a sub-population, convey the base separation molecules, distributions of 4 and 6 base separations are created. Extending the same logic to rest of the population, the positions of all the A's on the DNA can be determined. The entire sequence is generated by repeating the process for the other three bases (C, G, and T).

Figure 3:
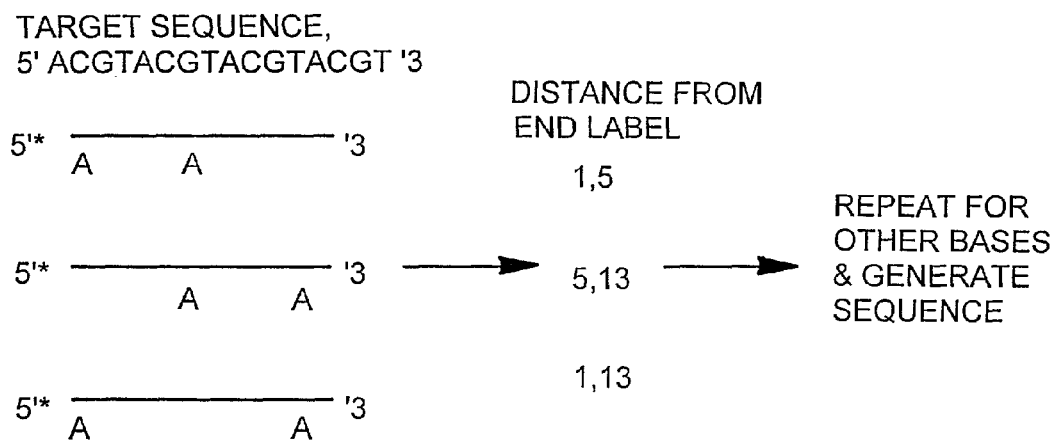
FIG. 3 shows a representative population of random A-labeled fragments for a 16-mer with the sequence 5' ACG-TACGTACGTACGT 3' (SEQ. ID. No. 1) and also depicts how distance information is used to determine base separation between acceptor labeled nucleotides.

In addition to labeling all of one type of unit, it is possible to use a one-nucleotide labeling scheme where not every nucleotide of one type is labeled. An outline of this method is shown in FIG. 3 which shows a representative population of random A-labeled fragments for a 16-mer with the sequence 5' ACGTACGTACGTACGT 3' (SEQ. ID. No. 1). Each individually labeled DNA molecule has half of its A's labeled in addition to 5' and 3' end labels. With a large population of randomly labeled fragments, the distance between every successive A on the target DNA can be found. The end labels serve to identify the distance between the ends of the DNA and the first A. Repeating the same analysis for the other nucleotides generates the sequence of the 16-mer. The advantages of using such a method includes lack of steric effects and ease of labeling. This type of labeling is referred to as random labeling. A polymer which is "randomly labeled" is one in which fewer than all of a particular type of unit are labeled. It is unknown which units of a particular type of a randomly labeled polymer are labeled.

As mentioned briefly above, various combinations of the labeling schemes can be used together. In all of the methods listed above, either ordered linear information from signals or distance information between nucleotides is considered. These two aspects can be combined to give methods that rely on both ordered linear and distance information. For example a random one nucleotide labeling strategy expanded to a random four nucleotide labeling strategy. Random four nucleotide labeling is where a fraction of all four nucleotides is labeled. A population of molecules have a fraction of the four nucleotides labeled. Each of the four nucleotides have a unique label. Analysis of a randomly labeled population results in generation of the sequence data.

The use of double-stranded DNA allows for variations. A single-stranded two-nucleotide labeling scheme can be performed when two of the nucleotides on one strand of DNA are fully replaced by labeled nucleotides. To reduce the steric constraints imposed by two extrinsically labeled nucleotides while preserving the theory behind two-nucleotide labeling, it is possible to label one nucleotide fully on each of the complementary strands to achieve the same end. This method involves using double-stranded DNA in which each strand is labeled with a different label. Six differently labeled duplex DNA sets will produce a data set which is adequate to provide sequence information. Each complementary strand of DNA should have one of the nucleotides labeled. In each of the duplex DNA sets, the equivalent of two different nucleotides (possible combinations are AC, AG, AT, CG, CT, GT) are labeled. When both complementary strands have the adenines labeled, this is equivalent to the combination AT. In duplex two-nucleotide labeling, the advantage is that only one nucleotide on each strand is labeled, allowing longer labeled strands to be synthesized as compared to two-nucleotide labeling on single-stranded DNA. In practice, it has been shown that synthesis of DNA fragments with one nucleotide completely labeled can be achieved with lengths much greater than 10 kb (Ambrose et al., 1993; Harding and Keller, 1992).

One use for the methods of the invention is to determine the sequence of units within a polymer. Identifying the sequence of units of a polymer, such as a nucleic acid, is an important step in understanding the function of the polymer and determining the role of the polymer in a physiological environment such as a cell or tissue. The sequencing methods currently in use are slow and cumbersome. The methods of the invention are much quicker and generate significantly more sequence data in a very short period of time.

Sequencing of a polymer may encompass the sequencing of the entire polymer or portions of the polymer or even the identification of an individual unit on the polymer. One method for identifying an individual unit of a polymer involves the steps of transiently exposing the individual unit of the polymer, the identity of which is unknown, to an agent selected from the group consisting of electromagnetic radiation, a quenching source and a fluorescence excitation source to generate an interaction with a detectable signal characteristic of the individual unit, and detecting and distinguishing the signal from signals generated from adjacent signal generating units of the polymer as an indication of the identity of the individual unit.

The individual unit is "transiently exposed" to the agent in order to produce a detectable signal characteristic of the individual unit. "Transiently exposed" as used herein means that the unit is positioned within interactive proximity of the agent for enough time to produce a signal and then is moved out of interactive proximity. The exact length of time required to produce a signal will depend on the individual unit and the agent involved but generally the amount of time is between one nanosecond and one second.

The signal characteristic of the individual unit is distinguished from signals generated from adjacent signal generating units of the polymer. An "adjacent signal generating unit" is the unit nearest to the individual unit which when exposed to the agent produces a detectable signal. It is not necessarily the unit which is directly linked to the individual unit unless the unit which is directly linked is labeled (intrinsically or extrinsically) and produces a detectable signal.

In the case when the agent is one or more fluorophores the interactive proximity between the agent and the unit is the energy transfer proximity and the signal produced is fluorescence resonance energy transfer. "Energy transfer proximity" as used herein is the distance between the unit and the fluorophore which allows interaction between two complementary sources if one source overlaps with the absorption spectrum of the other source. "Fluorescence resonance energy transfer" as used herein is the transfer of photonic energy between fluorophores with overlapping emission and absorption spectra.

Another method for identifying an individual unit of a polymer involves the steps of transiently moving the individual unit of the polymer relative to a station, the identity of the individual unit being unknown, detecting a signal arising from a detectable physical change in the unit or the station, and distinguishing said signal from signals arising from exposure of adjacent signal generating units of the polymer to the station as an indication of the identity of the individual unit.

Thus in one aspect, the methods of the invention can be used to identify one, some, or all of the units of the polymer. This is achieved by identifying the type of individual unit and its position on the backbone of the polymer by determining whether a signal detected at that particular position on the backbone is characteristic of the presence of a particular labeled unit.

The methods of the invention also are useful for identifying other structural properties of polymers. The structural information obtained by analyzing a polymer according to the methods of the invention may include the identification of characteristic properties of the polymer which (in turn) allows, for example, for the identification of the presence of a polymer in a sample or a determination of the relatedness of polymers, identification of the size of the polymer, identification of the proximity or distance between two or more individual units of a polymer, identification of the order of two or more individual units within a polymer, and/or identification of the general composition of the units of the polymer. Such characteristics are useful for a variety of purposes such as determining the presence or absence of a particular polymer in a sample. For instance when the polymer is a nucleic acid the methods of the invention may be used to determine whether a particular genetic sequence is expressed in a cell or tissue. The presence or absence of a particular sequence can be established by determining whether any polymers within the sample express a characteristic pattern of individual units which is only found in the polymer of interest i.e., by comparing the detected signals to a known pattern of signals characteristic of a known polymer to determine the relatedness of the polymer being analyzed to the known polymer. The entire sequence of the polymer of interest does not need to be determined in order to establish the presence or absence of the polymer in the sample. Similarly the methods may be useful for comparing the signals detected from one polymer to a pattern of signals from another polymer to determine the relatedness of the two polymers.

The proximity of or distance between two individual units of a polymer may be determined according to the methods of the invention. It is important to be able to determine the proximity of or distance between two units for several reasons. Each unit of a polymer has a specific position along the backbone. The sequence of units serves as a blueprint for a known polymer. The distance between two or more units on an unknown polymer can be compared to the blueprint of a known polymer to determine whether they are related. Additionally the ability to determine the distance between two units is important for determining how many units, if any, are between the two units of interest.

In order to determine the proximity of two individual units of a polymer of linked units the polymer is moved relative to a station, where each individual unit is exposed to the station to produce a characteristic signal arising from a detectable physical change in the unit or station. Each of the characteristic signals generated is then detected and the amount of time elapsed between detecting each characteristic signal is measured as described above. The amount of time elapsed is indicative of the proximity of the two individual units. The station may be an interaction station and the unit may be exposed to an agent to produce an electromagnetic signal.

A "signal characteristic of an interaction" as used herein is a signal which is expected to result from the interaction of the station and a specific labeled unit. The specific signal generated will depend on the type of station as well as the type of labeled unit. For instance if the station is an agent which is electromagnetic radiation and the labeled unit is a fluorophore then the interaction between the two will result in the emission of electromagnetic radiation by the fluorophore at a wavelength at which the fluorophore is known to emit. If the station is an agent which is a scintillation layer and the unit is radioactive then the interaction between the two will result in the emission of electromagnetic radiation in the form of fluorescence.

It is possible to determine the order of the units of a polymer using the methods of the invention. In one aspect of the invention the order of two individual units of a polymer can be determined by moving the polymer linearly with respect to a station and exposing two of the individual units to the station to produce first and second detectable signals arising from physical changes in the station or the unit. The order of the signals is an indication of the order of the two individual units.

The general composition of the units of the polymer may also be determined by the methods of the invention. For instance, if the polymer is a nucleic acid the methods of the invention can provide information on the percentage of purines vs. pyrimidines or the percentage of A, C, T, and G in the nucleic acid.

Quantitative information on the size of the sample may also be determined by the methods of the invention. For instance, the size of a polymer can be determined by determining the number of individual units which make up the polymer. The number of units which make up the polymer is determined by measuring the amount of time that is required for the entire polymer to traverse past an agent at an interaction site in a linear manner and dividing that by the average length of time for an individual unit of that particular type of polymer to completely traverse past the site.

In addition to information about a specific unit the methods of the invention may be used to identify greater than one unit at a time in order to provide information about a polymer. In one aspect the method is carried out by providing a labeled polymer of linked units, detecting signals from labeled unit specific markers of less than all of the linked units, and storing a signature of the signals detected to analyze the polymer. In this aspect of the invention each unit of the labeled polymer may be labeled with a unit specific marker or less than all of the units may be labeled with a unit specific marker.

This method is particularly useful for analyzing multiple units of a polymer at one time. This is accomplished by using a unit specific marker which is labeled and which interacts with more than one unit in a sequence specific manner. As used herein a "unit specific marker" is a compound which specifically interacts with one or more units of a polymer and is capable of identifying those units. For instance a unit specific marker for a nucleic acid molecule can be a labeled dimers, trimers, etc. which bind to a specific sequence of bases, such as TG, AG, ATC, etc. By identifying the presence or position of the labeled markers structural information about the polymer can be derived. For instance, the presence of the marker on a polymer can reveal the identity of the polymer. This enables the presence or absence of a polymer in a solution or mixture of polymers to be determined. The order, distance, number etc. of the markers on a polymer can provide information about the sequence or composition of a polymer. Other unit specific markers include but are not limited to sequence specific major and minor groove binders and intercallators, sequence specific DNA and peptide binding proteins, sequence specific peptide-nucleic acids, etc. Many such unit specific markers exist and are well known to those of skill in the art.

This type of analysis can be used in one embodiment to identify DNA fragments by analyzing the hybridization patterns of multiple probes to individual fragments of polymers. The current state-of-the-art methods for hybridization analysis of DNA rely upon DNA chips. The methods of the invention is advantageous for a number of reasons. The number, type, order, and distance between the multiple probes bound to an unknown fragment of DNA can be determined. This information can be used to identify the number of differentially expressed genes unambiguously. Current hybridization approaches can only determine the type of probes bound to a given fragment. Furthermore, the methods of the invention are able to quantitate precisely the actual number of particular expressed genes. Current methods rely on quantitation of fluorescence intensities, which often give rise to errors due to non-linearities in the detection system. Given the great amount of information generated, the methods of the invention do not require a selection of expressed genes or unknown nucleic acids to be assayed. This is in contrast to the requirement of different DNA chips for different genes, sets of expressed genes to be analyzed, and also different organisms. The methods of the invention can identify the unknown expressed genes by computer analysis of the hybridization patterns generated. The data obtained from linear analysis of the DNA probes are then matched with information in a database to determine the identity of the target DNA. The methods can thus analyze information from hybridization reactions, which can then be applied to diagnostics and determination of gene expression patterns.

A "signature" as used herein is a sequence-specific signal arising from a labeled polymer. The signature includes information about the structure of the polymer. For instance, the signature of a polymer may be defined by a series of consecutive units or by specific units spaced a particular distance apart from one another. The signature of the polymer identifies the polymer. Signatures are useful for uniquely identifying fragments by identifying bases at certain positions along the length of a strand of DNA. The probability of knowing any one position is $\frac{1}{4}$. Unambiguous identification of a fragment comes with roughly twenty positions identified ($\frac{1}{4}^{20}$=9.1× $120^{-13}$). For a fragment with 20 detected labels and 10% detection/labeling, the size of the fragment needs to be only 200 base pairs. The proposed read length is on the order of kilobases, which should unambiguously identify any fragment. The identification of fragments allows for grouping by similar sequences, making sequence reconstruction by population analysis possible.

A preferred method of analysis of the invention involves the use of radioactively labeled polymers. The type of radioactive emission influences the type of detection device used. In general, there are three different types of nuclear emission including alpha, beta, and gamma radiation. Alpha emission cause extensive ionization in matter and permit individual counting by ionization chambers and proportional counters, but more interestingly, alpha emission interacting with matter may also cause molecular excitation, which can result in fluorescence. The fluorescence is referred to as scintillation. Beta decay which is weaker than alpha decay can be amplified to generate an adequate signal. Gamma radiation arises from internal conversion of excitation energy. Scintillation counting of gamma rays is efficient and produces a strong signal. Sodium iodide crystals fluoresce with incident gamma radiation.

A "scintillation" layer or material as used herein is any type of material which fluoresces or emits light in response to excitation by nuclear radiation. Scintillation materials are well known in the art. Aromatic hydrocarbons which have resonance structures are excellent scintillators. Anthracene and stilbene fall into the category of such compounds. Inorganic crystals are also known to fluoresce. In order for these compounds to luminesce, the inorganic crystals must have small amounts of impurities, which create energy levels between valence and conduction bands. Excitation and de-excitation can therefore occur. In many cases, the de-excitation can occur through phosphorescent photon emission, leading to a long lifetime of detection. Some common scintillators include NaI (T1), ZnS (Ag), anthracene, stilbene, and plastic phosphors.

Many methods of measuring nuclear radiation are known in the art and include devices such as cloud and bubble chamber devices, constant current ion chambers, pulse counters, gas counters (i.e., Geiger-Müller counters), solid state detectors (surface barrier detectors, lithium-drifted detectors, intrinsic germanium detectors), scintillation counters, Cerenkov detectors, etc.

Analysis of the radiolabeled polymers is identical to other means of generating polymer dependent impulses. For example, a sample with radiolabeled A's can be analyzed by the system to determine relative spacing of A's on a sample DNA. The time between detection of radiation signals is characteristic of the polymer analyzed. Analysis of four populations of labeled DNA (A's, C's, G's, T's) can yield the sequence of the polymer analyzed. The sequence of DNA can also be analyzed with a more complex scheme including analysis of a combination of dual labeled DNA and singly labeled DNA. Analysis of a A and C labeled fragment followed by analysis of a A labeled version of the same fragment yields knowledge of the positions of the A's and C's. The sequence is known if the procedure is repeated for the complementary strand. The system can further be used for analysis of polymer (polypeptide, RNA, carbohydrates, etc.), size, concentration, type, identity, presence, sequence and number.

The methods described above can be performed on a single polymer or on more than one polymer in order to determine structural information about the polymer. The invention also encompasses the practice of the methods described above on multiple polymers. These methods and an apparatus for performing the methods of the invention simultaneously on a plurality of polymers are described in detail below.

Some of the methods described above are based on an interaction involving energy transfer or quenching to produce a detectable signal. The involvement of energy transfer or quenching is described in either one of two limitations in these embodiments of the invention. One limitation is that the agent involved in the interaction is selected from the group consisting of electromagnetic radiation, a quenching source or a fluorescence excitation source. The other limitation is that the detectable signal is an electromagnetic radiation signal. It should be apparent to one of ordinary skill in the art that each of the methods can encompass the other limitation instead of the one described and still encompass the notion of interaction involving energy transfer or quenching. For instance in addition to encompassing the method for analyzing a polymer by exposing the units of the polymer to the agent selected from the group consisting of electromagnetic radiation, a quenching source, and a fluorescence excitation source to produce a detectable signal, the invention in these embodiments also encompasses a method for analyzing a polymer by exposing the units of a polymer to an agent to produce a detectable electromagnetic signal.

In addition to the methods involving energy transfer, quenching or electromagnetic radiation signals, the methods of the invention described above can be performed by detecting signals which arise from a detectable physical change in the unit of the polymer or the station. As used herein a "detectable physical change" in the unit of the polymer or the station is any type of change which occurs in the unit of the polymer or the station as a result of exposing the unit to the station. Once the unit is exposed to the station a detectable signal is created. The station may be for instance, an interaction station or a signal generation station, each of which is discussed in detail herein. The type of change that occurs in the station or the unit to produce the detectable signal depends on the type of station and the type of unit. Several examples of station-unit combinations which undergo a change to produce a detectable signal are discussed herein for exemplary purposes. Those of skill in the art will be able to derive other station-unit combinations that fall within the scope of the invention.

When the interaction between the station and the unit of the polymer is based on energy transfer, either the unit or the station or both may physically change to produce a signal. In one embodiment the station may transfer energy to the unit causing the unit to emit an energy unit specific signal. The physical change which occurs in the unit results from the change in energy state. In another embodiment the unit may transfer energy to the station causing the station to emit a unit-specific signal resulting from the specific energy transfer. In still other embodiments a partner compound may cause the physical change which produces a signal. When the interaction occurs between a radioactive unit and a station the unit physically changes by releasing energy.

Another aspect of the invention encompasses methods for analyzing a plurality of polymers. Each of the polymers is analyzed by sequentially detecting interactions of units of a plurality of polymers at a signal generation station. These methods include but are not limited to a method for characterizing a test polymer, a method for sequencing a polymer, a method for determining the order of units of a polymer, a method for determining the distance between units of a polymer, and analyzing a set of polymers. These methods encompass but are not limited to interactions resulting from energy transfer or quenching.

A method for characterizing a test polymer is performed by obtaining polymer dependent impulses for each of a plurality of polymers, comparing the polymer dependent impulses of the plurality of polymers, determining the relatedness of the polymers based upon similarities between the polymer dependent impulses of the polymers, and characterizing the test polymer based upon the polymer dependent impulses of related polymers.

A "polymer dependent impulse" as used herein is a detectable physical quantity which transmits or conveys information about the structural characteristics of only a single unit of a polymer. The physical quantity may be in any form which is capable of being detected. For instance the physical quantity may be electromagnetic radiation, chemical conductance, electrical conductance, etc. The polymer dependent impulse may arise from energy transfer, quenching, changes in conductance, mechanical changes, resistance changes, or any other physical changes. Although the polymer dependent impulse is specific for a particular unit, a polymer having more than one of a particular labeled unit will have more than one identical polymer dependent impulse. Additionally, each unit of a specific type may give rise to different polymer dependent impulses if they have different labels.

The method used for detecting the polymer dependent impulse depends on the type of physical quantity generated. For instance if the physical quantity is electromagnetic radiation then the polymer dependent impulse is optically detected. An "optically detectable" polymer dependent impulse as used herein is a light based signal in the form of electromagnetic radiation which can be detected by light detecting imaging systems. When the physical quantity is chemical conductance then the polymer dependent impulse is chemically detected. A "chemically detected" polymer dependent impulse is a signal in the form of a change in chemical concentration or charge such as an ion conductance which can be detected by standard means for measuring chemical conductance. If the physical quantity is an electrical signal then the polymer dependent impulse is in the form of a change in resistance or capacitance.

As used herein the "relatedness of polymers" can be determined by identifying a characteristic pattern of a polymer which is unique to that polymer. For instance if the polymer is a nucleic acid then virtually any sequence of 10 contiguous nucleotides within the polymer would be a unique characteristic of that nucleic acid molecule. Any other nucleic acid molecule which displayed an identical sequence of 10 nucleotides would be a related polymer.

A "plurality of polymers" is at least two polymers. Preferably a plurality of polymers is at least 50 polymers and more preferably at least 100 polymers.

The polymer dependent impulses may provide any type of structural information about the polymer. For instance these signals may provide the entire or portions of the entire sequence of the polymer, the order of polymer dependent impulses, or the time of separation between polymer dependent impulses as an indication of the distance between the units.

The polymer dependent impulses are obtained by interaction which occurs between the unit of the polymer and the environment at a signal generation station. A "signal generation station" as used herein is a station that is an area where the unit interacts with the environment to generate a polymer dependent impulse. In some aspects of the invention the polymer dependent impulse results from contact in a defined area with an agent selected from the group consisting of electromagnetic radiation, a quenching source, and a fluorescence excitation source which can interact with the unit to produce a detectable signal. In other aspects the polymer dependent impulse results from contact in a defined area with a chemical environment which is capable of undergoing specific changes in conductance in response to an interaction with a molecule. As a molecule with a specific structure interacts with the chemical environment a change in conductance occurs. The change which is specific for the particular structure may be a temporal change, e.g., the length of time required for the conductance to change may be indicative that the interaction involves a specific structure or a physical change. For instance, the change in intensity of the interaction may be indicative of an interaction with a specific structure. In other aspects the polymer dependent impulse results from changes in capacitance or resistance caused by the movement of the unit between microelectrodes or nanoelectrodes positioned adjacent to the polymer unit. For instance the signal generation station may include microelectrodes or nanoelectrodes positioned on opposite sides of the polymer unit. The changes in resistance or conductance which occur as a result of the movement of the unit past the electrodes will be specific for the particular unit.

A method for determining the distance between two individual units is also encompassed by the invention. In order to determine the distance between two individual units of a polymer of linked units the polymer is caused to pass linearly relative to an signal generation station and a polymer dependent impulse which is generated as each of the two individual units passes by the signal generation station is measured. Each of the steps is then repeated for a plurality of similar polymers. A polymer is said to pass linearly relative to a signal generation station when each unit of the polymer passes sequentially by the signal generation station.

Each of the steps is repeated for a plurality of similar polymers to produce a data set. The distance between the two individual units can then be determined based upon the information obtained from the plurality of similar polymers by analyzing the data set.

The method also includes a method for identifying a quantity of polymers including a label. For instance, it is possible to determine the number of polymers having a specific unit or combination of units in a sample. In a sample of mRNA, for example, the number of a particular mRNA present in the sample can be determined. This is accomplished by identifying a pattern or signature characteristic of the desired mRNA molecule. The sample of RNA can then be analyzed according to the methods of the invention and the number of mRNA molecules having the specific pattern or signature can be determined.

As used herein "similar polymers" are polymers which have at least one overlapping region. Similar polymers may be a homogeneous population of polymers or a heterogenous population of polymers. A "homogeneous population" of polymers as used herein is a group of identical polymers. A "heterogenous population" of similar polymers is a group of similar polymers which are not identical but which include at least one overlapping region of identical units. An overlapping region typically consists of at least 10 contiguous nucleotides. In some cases an overlapping region consists of at least 11, 12, 13, 14, 15, 16, 17, 18, 19, 20, 21, or 22 contiguous nucleotides.

A "plurality of similar polymers" is two or more similar polymers. Preferably a plurality of similar polymers is 50 or more similar polymers. More preferably a plurality of similar polymers is 100 or more similar polymers.

A "data set" as used herein is a set of information defining the polymer dependent impulses generated by similar polymers. The data set is analyzed as discussed above and the method of analysis used depends on the type of labeling scheme used to generate the labeled polymers. Nucleic acid sequencing is a particularly preferred embodiment of the methods of the invention.

Currently, less than 5% of the human genome has been sequenced. This translates into a small fraction of the ideal in human sequence knowledge, which is the sequence of all individuals. For an instance, for the human population, there are $1.4 \times 10^{19}$ (5 billion people$\times 3 \times 10^9$ bases/person). So far, only $2 \times 10^{-9}$ percent of all human genetic information is known. The rate of sequencing of the human genome by all world-wide efforts is roughly $3 \times 10^9/15$ years, or 550,000 bases/day, at a cost of >$1/base. Sequencing by the methods of the invention described herein will constitute an inordinate breakthrough in the rate of sequencing. The predicted time to complete one human genome with one machine is ~15 hours. Several dynamic arrays in parallel will be able to complete the sequence of one human genome in a fraction of an hour.

A method for sequencing a polymer of linked units is also encompassed by the invention. The method is performed by obtaining polymer dependent impulses from each of a plurality of overlapping polymers, at least a portion of each of the polymers having a sequence of linked units identical to the other of the polymers, and comparing the polymer dependent impulses to obtain a sequence of linked units which is identical in the plurality of polymers.

The plurality of overlapping polymers is a set of polymers in which each polymer has at least a portion of its sequence of linked units which is identical to the other polymers. The portion of sequence which is identical is referred to as the overlapping region and which includes at least ten contiguous units.

In another aspect of the invention the order of units of a polymer of linked units can be determined by moving the polymer linearly relative to a signal generation station and measuring a polymer dependent impulse generated as each of two individual units, each giving rise to a characteristic polymer dependent impulse pass by the signal generation station. These steps are repeated for a plurality of similar polymers and the order of at least the two individual units is determined based upon the information obtained from the plurality of similar polymers.

A method for analyzing a set of polymers, in which each of the polymers of the set is an individual polymer of linked units, is encompassed by the invention. The method involves the step of orienting the set of polymers parallel to one another, and detecting a polymer specific feature of the polymers.

The set of polymers are oriented parallel to one another. The polymers may be oriented by any means which is capable of causing the polymers to be positioned parallel to one another. For instance an electric field may be applied to the polymers to cause them to be oriented in a parallel form. Preferably the orientation step is in a solution free of gel.

A "polymer specific feature" as used herein is any structural feature of polymer which relates to its sequence. For instance a polymer specific feature includes but is not limited to information about the polymer such as the length of the polymer, the order of linked units in the polymer, the distance between units of the polymer, the proximity of units in the polymer, the sequence of one, some or all of the units of the polymer, and the presence of the polymer.

The step of detecting the polymer specific feature may be performed simultaneously for all of the polymers. This step encompasses the sequential detection of each of the units of all of the polymers. This can be accomplished by passing linearly each of the polymers relative to a plurality of signal generation stations, and detecting and distinguishing polymer dependent impulses generated as said polymers pass said signal generation stations.

The invention also includes a method for analyzing a set of polymers, each polymer of the set being an individual polymer of linked units. The method is performed by orienting the set of polymers in an electric field, simultaneously moving the set of polymers through defined respective channels, and detecting a polymer specific feature as the polymers are moved through the channels. The step of simultaneously moving the set of polymers through respective channels is carried out by moving one polymer per channel such that each unit passes the station individually. More than one polymer may be in the channel at a time if the polymers are positioned in tandem and only one unit interacts with one station at a time.

A "defined respective channel" as used herein is a channel in which the structure is determined before the polymer enters the channel such that the polymer will follow a defined path as it passes through the channel. Channels such as those found in a gel matrix are not defined respective channels.

The methods of the invention may also be used to detect resonance energy transfer or quenching between two interactive partners capable of such transfer or quenching. As used herein resonance energy transfer (RET) is the transfer of photonic energy between two compounds with overlapping emission and absorption spectra. Fluorescence resonance energy transfer (FRET) is the transfer of photonic energy between fluorophores. The two interactive partners are any compounds which are capable of energy transfer or quenching i.e., light emissive compounds or quenchers.

The method is performed by bringing the two partners in close enough proximity to permit such transfer or quenching, applying an agent to one of said partners, the agent selected from the group consisting of electromagnetic radiation, a quenching source and a fluorescence excitation source, shielding fluorescence resonance energy transfer and quenching occurring from electromagnetic radiation emission and interaction between the partners with a material shield, and detecting the emitted electromagnetic radiation.

As used herein a "material shield" is any material which prevents or limits energy transfer or quenching. Such materials include but are not limited to conductive materials, high index materials, and light impermeable materials. In a preferred embodiment the material shield is a conductive material shield. As used herein a "conductive material shield" is a material which is at least conductive enough to prevent energy transfer between donor and acceptor sources.

Each of the above methods of the invention are useful for at least various aspects of sequencing polymers. Also all of the methods can be used with the various labeling schemes described with respect to the method of analyzing polymers.

The methods of the invention can be accomplished using any device which produces a specific detectable signal for an individual unit of a polymer. One type of device which enables this type of analysis is one which promotes linear transfer of a polymer past an interaction station or a signal generation station. According to one aspect of the invention, an article of manufacture which is useful for performing the methods of the invention is provided. The article of manufacture includes a wall material having a surface defining a channel, an agent selected from the group consisting of an electromagnetic radiation source, a quenching source, a luminescent film layer, and a fluorescence excitation source, attached to the wall material adjacent to the channel, wherein the agent is close enough to the channel and is present in an amount sufficient to detectably interact with a partner compound selected from the group consisting of a light emissive compound and a quencher passing through the channel.

A "wall material" as used herein is a solid or semi-solid barrier of any dimensions which is capable of supporting at least one channel. A semi-solid material is a self supporting material and may be for instance a gel material such as a polyacrylamide gel. For instance the wall material may be composed of a single support material which may be conducting or non-conducting, light permeable or light impermeable, clear or unclear. In some instances the agent is embedded within the wall material. In these instances the wall material can be solely or partially made of a non-conducting layer, a light permeable layer or a clear layer to allow the agent to be exposed to the channel formed in the wall material to allow signal generation. When the wall material is only partially made from these materials the remaining wall material may be made from a conducting, light impermeable or unclear layer, which prevent signal generation. In some cases the wall material is made up of layers of different materials. For instance, the wall material may be made of a single conducting layer and a single non-conducting layer. Alternatively the wall material may be made of a single non-conducting layer surrounded by two conducing layers. Multiple layers and various combinations of materials are encompassed by the wall material of the invention.

As used herein a "luminescent film layer" is a film which is naturally luminescent or made luminescent by some means of excitation or illumination, e.g., electrooptic thin films and high index films illuminated by internal reflection.

A "conductive material" as used herein is a material which is at least conductive enough to prevent energy transfer between a donor and an acceptor.

A "nonconductive material" as used herein is a material which conducts less than that amount that would allow energy transfer between a donor and an acceptor.

A "light permeable material" as used herein is a material which is permeable to light of a wavelength produced by the specific electromagnetic radiation, quenching source, or the fluorescence excitation source being used.

A "light impermeable material" as used herein is a material which is impermeable to light of a wavelength produced by the specific electromagnetic radiation, quenching source, or the fluorescence excitation source being used.

A "channel" as used herein is a passageway through a medium through which a polymer can pass. The channel can have any dimensions as long as a polymer is capable of passing through it. For instance the channel may be an unbranched straight cylindrical channel or it may be a branched network of interconnected winding channels. Preferably the channel is a straight nanochannel or a microchannel. A "nanochannel" as used herein is a channel having dimensions on the order of nanometers. The average diameter of a nanochannel is between 1 nm and 999 µm. A "microchannel" as used herein is a channel having dimensions on the order of micrometers. The average diameter of a microchannel is between 1 µm and 1 mm. Preferred specifications and dimensions of channels useful according to the invention are set forth in detail below. In a preferred embodiment, the channel is fixed in the wall.

An agent is attached to the wall material in such a manner that it will detectably interact with a partner compound by undergoing energy transfer or quenching with the partner light emissive compound which is passing through the channel of the wall material. In order to interact with the partner compound the agent can be positioned in close proximity to the channel. For example, the agent may be attached to the inside of the channel, attached to the external surface of the wall material, attached to a concentrated region of the external surface of the wall material surrounding the rim of the channel, embedded within the wall material, or embedded in the form of a concentric ring in the wall material surrounding the channel. Optionally the agent may cover the entire surface of the wall material or may be embedded throughout the entire wall material. In order to improve signal generation when the agent is not localized, a mask may be used to cover some areas of the wall material such that only localized regions of agent are exposed. A "mask" as used herein is an object which has openings of any size or shape. More than one agent may be attached to the wall material in order to produce different signals when the agents are exposed to the partner agent.

The agent may be attached to the surface of the wall material by any means of performing attachment known in the art. Examples of methods for conjugating biomaterials are presented in Hermanson, G. T., *Bioconjugate Techniques*, Academic Press, Inc., San Diego, 1996, which is hereby incorporated by reference.

When the agent is attached to the surface of the wall material it may be attached directly to the wall material or it may be attached via a linker. A "linker" as used herein with respect to the attachment of the agent is a molecule that tethers a light emitting compound or a quenching compound to the wall material. Linkers are well known in the art. Commonly used linkers include alkanes of various lengths.

The agent is attached to the wall material in an amount sufficient to detectably interact with a partner light emissive compound. As used herein a "partner light emissive compound" is a light emissive compound as defined above but which specifically interacts with and undergoes energy transfer or quenching when positioned in close proximity to the agent. The amount of partner light emissive compound and the amount of agent required will depend on the type of agent and light emissive compound used.

Another example of an article of manufacture of the invention is a wall material having a surface defining a plurality of channels and a station attached to a discrete region of the wall material adjacent to at least one of the channels, wherein the station is close enough to the channel and is present in an amount sufficient to cause a signal to arise from a detectable physical change in a polymer of linked units passing through the channel or in the station as the polymer is exposed to the station. A "discrete region" of the wall material adjacent to at least one of the channels is a local area which is surrounded by wall material not having a station. The area surrounding the discrete region does not interact with the unit to produce the same characteristic signal produced by the interaction of the unit with the station. The discrete region is positioned in or near the channel such that the station at the dictreet region is exposed to the unit as it traverses the channel.

An additional article of manufacture of the invention is a wall material having a surface defining a channel and a plurality of stations each attached to a discrete region of the wall material adjacent to the channel, wherein the stations are close enough to the channel and are present in an amount sufficient to cause a signal to arise from a detectable physical change in a polymer of linked units passing through the channel or in the station as the polymer is exposed to the station.

As used herein a "plurality of stations" is at least two stations. Preferably a plurality of stations is at least three stations. In another preferred embodiment a plurality of stations is at least five stations.

In a preferred embodiment the article of manufacture is a nanochannel plate. The following description of an optimal design of a nanochannel plate having fluorophores embedded within the plate is provided for illustrative purposes only. The example describes methods for optimizing several aspects of the article of manufacture. The description is in no way limiting of the article of manufacture claimed herein.

Figure 4:
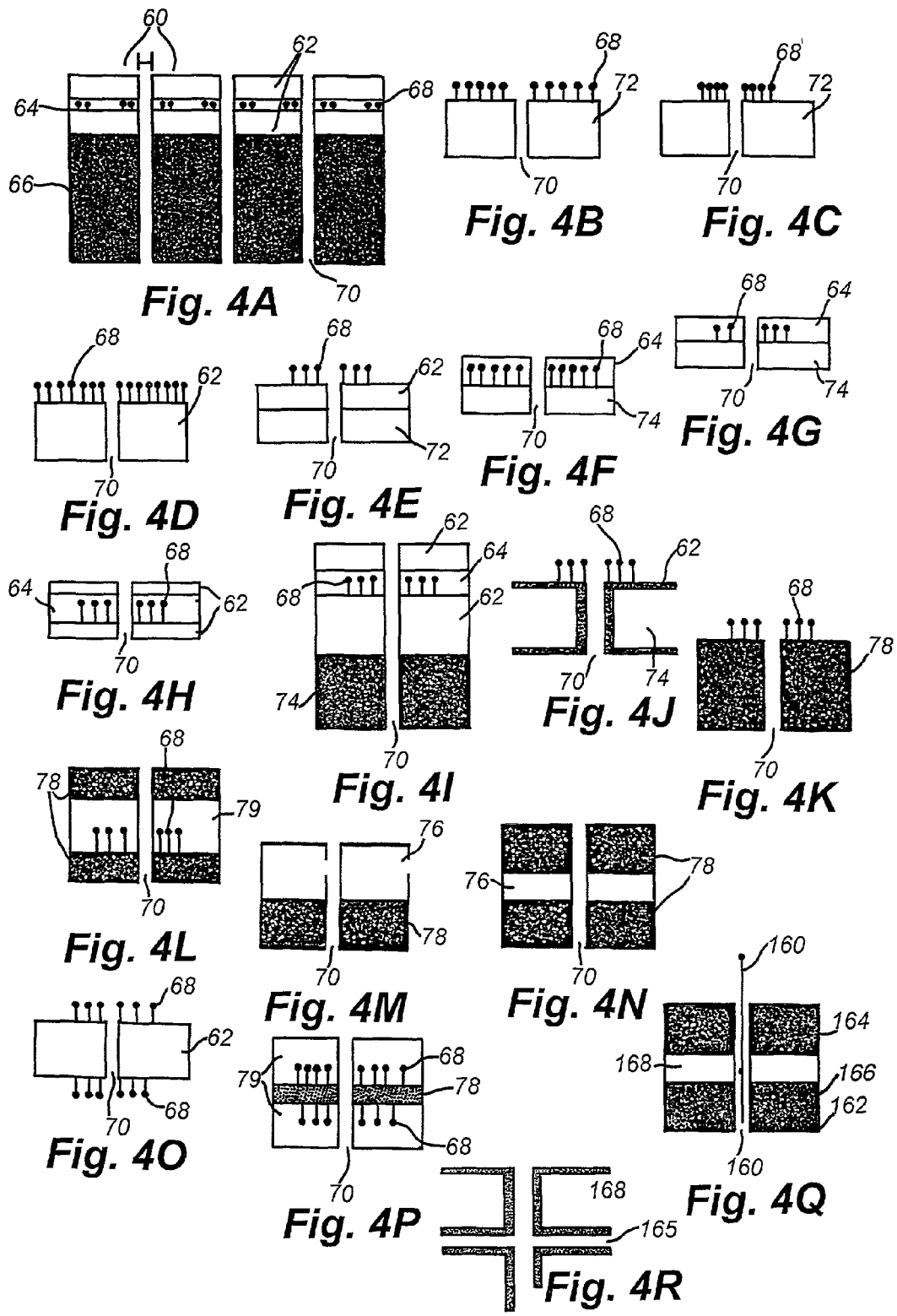
FIG. 4 is a schematic depicting various potential constructions of a nanochannel plate.

Several examples of nanochannel plates are presented in FIG. 4. FIG. 4A shows a nanochannel plate (60) having layers of conducting material (62) and non-conducting material (64). The channel (70) has a diameter that is sufficient to encompass the passage of double-stranded, labeled DNA in a linear fashion. In this example donor fluorophores (68) are embedded in the clear non-conducting material in a concentric ring around each channel. The remaining portion of the nanochannel plate is made up of a light impermeable material (66).

FIGS. 4B, C, D, E, and K show a nanochannel plate having fluorophores (68) attached to the surface of the wall material surrounding the opening produced by the channel (70). As shown in FIGS. 4B and 4D the fluorophores may cover the entire surface of the wall material. The fluorophores may also be concentrated around the channel opening as shown in FIGS. 4C, E, and K rather than covering the entire surface. Additionally, the wall material supporting the fluorophores may be a conducting layer (62) such as that shown in FIGS. 4D and E, the wall material may be a light impermeable layer (78) as shown in FIG. 4K or the wall material may be a support layer (72) as shown in FIGS. 4B and C. A support layer may be any type of wall material including but not limited to conducting, non-conducting, clear, light permeable, and light impermeable.

FIGS. 4F, G, H, I, and L show a nanochannel plate having fluorophores (68) embedded in the wall material surrounding the channel (70). Again the fluorophores may extend across the entire wall material (shown in FIG. 4F) or may be concentrated around the channel as shown in FIGS. 4G, H, and I. In the embodiments shown in FIGS. 4F, G, H, I, and L the fluorophores are embedded in a layer of non-conducting material (62) or of a clear material (74) or of a light permeable material (79). The layer having the fluorophores embedded within it may form the surface of the wall material as shown in FIGS. 4F and G or may be sandwiched between other layers. For instance the non-conducting layer (64) in FIGS. 4H and I is sandwiched between two conducting layers (62). The light permeable layer (79) of FIG. 4L is sandwiched between two light impermeable layers (78). In some cases the layers shown form the entire wall material. In other cases the layers maybe adjacent to or sandwiched between supporting layers as shown in FIG. 4I.

FIG. 4J shows a nanochannel plate having fluorophores (68) attached to the surface of the wall material surrounding the opening formed by the channel (70). The material surrounding all of the exposed surfaces of the wall material, including the surface within the channel is a conducting material.

FIGS. 4M and N show a nanochannel plate having a luminescent thin film (76) positioned within the wall material surrounding at least a portion of the channel (70). The luminescent thin film either forms the surface of the wall material and is adjacent to a light impermeable layer (78) as shown in FIG. 4M or may be sandwiched between two light impermeable layers (78) as shown in FIG. 4N.

FIGS. 4O and P show a nanochannel plate having two layers of fluorophores (68) either embedded in the wall material or attached to the surface of the wall material. In FIG. 4O the fluorophore layers (68) are attached to the surface of a conducting material (62) on either side of the wall material and surrounding the openings formed by the channel. In FIG. 4P the fluorophore layers (68) are embedded in two light permeable layers (79) which sandwich a light impermeable layer (78).

A preferred method of the invention involves the analysis of radiolabeled polymers as discussed above. Preparation of radiolabeled polymers such as DNA (for example, with $^{32}P$ or $^{3}H$) is known in the art. The following description represents one of the many possible embodiments of analyzing radiolabeled polymers according to the methods of the invention (FIG. 4Q and R). A radiolabeled nucleic acid molecule (160) is analyzed with a single fabricated multilayered nanochannel (162). The nanochannel is the diameter of the labeled nucleic acid molecule and is constructed to yield a defined region of detection. The exemplary nanochannel plates shown in FIG. 4Q and R are a heterogeneous multilayered structure consisting of two radiation impermeable layers such as lead or Lucite films (164, 166) and a film of lower density material (or scintillation layer) (168) (i.e., conventional polymers, polymethylmethacrylate, polystryrene, Teflon, etc.). The lead films in FIG. 4Q sandwich the layer of lower density material and are of such thickness as to prevent passage of radiation. The lower density material permits passage of radiation, thereby creating a defined region of radiation detection. As the radiolabel on the DNA passes through the defined region of detection, nuclear radiation is emitted, some of which will pass through the defined region of radiation detection. FIG. 4R shows a nanochannel plate having low density material (168) surrounding the opening formed by the channel. The material surrounding all of the exposed surfaces of the wall material including the surface within the channel is a radiation impermeable layer (165).

Figure 5:
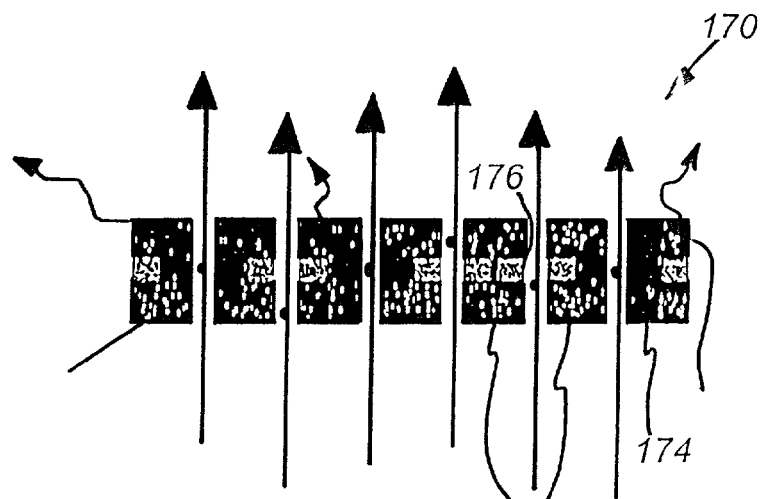
FIG. 5 is a schematic depicting a nanochannel plate for analyzing a radioactive polymer.

In a related embodiment of analysis of radiolabeled nucleotides (FIG. 5), a detection system based on scintillation counting and multiple nanochannels is presented. A nanochannel array (170) is fabricated as shown in FIG. 5. Multiple multilayered channels (172) exist for parallel amplification of data output. Each individual channel consists of two nuclear radiation shielding layers (174) which shield nuclear radiation, and a scintillation layer (176) which is fluorescently excited with exposure to nuclear radiation. The individual channels are separated from each other by a nuclear radiation shielding material. The nuclear radiation is prevented from reaching the fluorescent detection system by overlaying with optical quality Lucite (or any other transparent material which prevents the passage of nuclear radiation). This allows only the fluorescent signal to reach the detection system.

Each of the above described nanochannels is only an example. It is, therefore, anticipated that each of the limitations described with respect to these embodiments involving any one element or combinations of elements can be included in each nanochannel. Preparation of films having multiple layers of differing material have been described in the art, e.g., U.S. Pat. No. 5,462,467, Ferreira et. al., *Thin Solid Films* 244:806-809 (1994).

Figure 6:
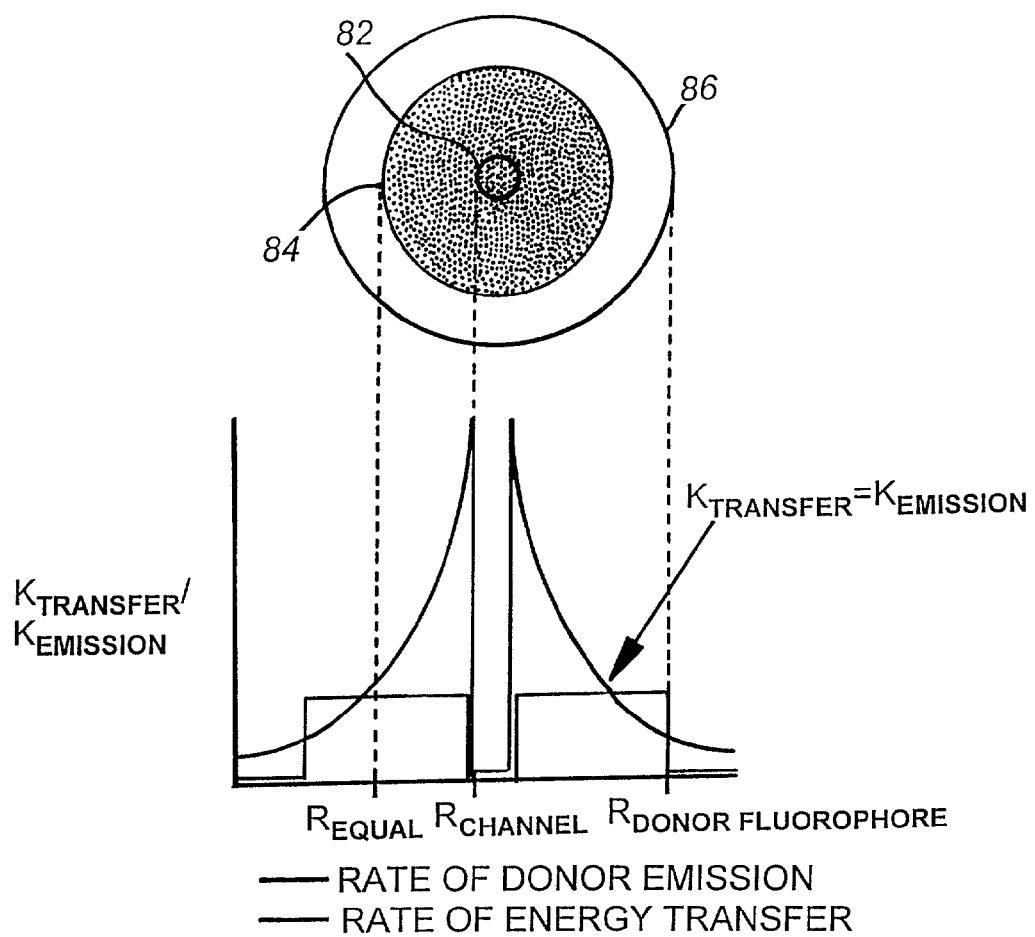
FIG. 6 is a schematic of a cross section of a nanochannel with a concentric ring of donor fluorophores and a graph showing donor emission and energy transfer on the corresponding nanochannel.

In the example provided donor fluorophores are concentrated in a concentric ring around each channel in order to optimize the donor intensity. Intuitively, a concentric ring is preferred because the range of energy transfer is limited in part by a radial Förster distance. Examining one channel in detail will illustrate the marked changes in donor intensities that can occur for the concentric ring configuration. FIG. 6 shows a single channel (82) having the concentric ring configuration. The outermost concentric ring (86) marks the edge of the donor fluorophores situated around the channel. The middle concentric area (84) denotes the region where the rate of energy transfer from the donor to the acceptor is greater than the rate of emission of the donor fluorophores.

The rationale for embedding the donor fluorophores in a solid medium is best understood by examining the mechanisms of photobleaching and quenching. The factors that may diminish a fluorescent signal include: photobleaching, temperature quenching, energy transfer quenching, collisional quenching, excited state reactions, and solvent effects. These mechanisms are similar in that they all arise from either collisional or bimolecular events. A solid medium is a physical barrier to these undesired molecular processes and is a means of isolation of the donor fluorophores. For example, the mechanism of photobleaching is due to a reaction between an excited fluorophore and oxygen to form a non-fluorescent product (Menter et al., 1978; Menter et al. 1979; Giloh and Sedat, 1982). A solid medium, especially one manufactured in an oxygen-free environment, prevents oxygen from reaching the embedded fluorophores, eliminating possible oxidative reactions (Garland and Moore, 1979; Rost, 1990). In order to understand the effect of a solid medium further, a brief summary of the other quenching effects is presented. Temperature quenching is a decrease in fluorescence as temperature increases. The degree of temperature dependence depends on the compound; it is usually about 1% change in quenching per degree Celsius (Guilbault, 1973). The effect is believed to be due to increased molecular motion and increased frequency of collisions, resulting in increased probability of transition to the ground state before fluorescence can occur. Collisional quenching is a broad category consisting of many possible mechanisms involving direct contact between a fluorophore and another molecule (Lakowicz, 1983). Excited state reactions involve the reactive excited state of a fluorophore in a reaction with nearby solvent molecules and constitutes a subset of collisional quenching (Porter, 1967; Zweig, 1973). Solvent effects consists of solvent-fluorophore collisions and interactions, including effects of hydrogen bonding, acid-base chemistry, and charge transfer interactions (Lakowicz, 1983). Energy transfer quenching is due to the effects of impurities on fluorophores via undesired FRET. From this short listing of photobleaching and quenching mechanisms, it is clear that molecular interactions with fluorophores are the main causes of diminished fluorophore emissions. A solid media thus eliminates these undesired molecular interactions, collisions, and reactions by isolating the fluorophores and creating a physical barrier that prevents the entry of undesired quenching molecules.

The equation defining energy transfer should be examined in order to determine the effect of a solid medium on energy transfer. The equation that needs to be considered describes the Förster distance (Selvin, 1995; Cantor and Schimmel, 1980; Wu and Brand, 1994; Clegg et al., 1995; Fairclough and Cantor, 1978):

$$R_o = \frac{\sqrt[6]{8.79 \times 10^{-5} J \phi_D \kappa^2}}{n^4}$$

J is the normalized spectral overlap of the donor emission and acceptor absorption, $\phi_D$ is the quantum efficiency (or quantum yield) for donor emission in the absence of acceptor ($\phi_D$ is the number of photons emitted divided by number of photons absorbed), n is the index of refraction, and $\kappa^2$ is the geometric factor related to the relative angle of the two transition dipoles. Embedding the donor fluorophore in a solid medium raises n, the index of refraction. In solvent systems, n is taken to be around 1.35 (Selvin, 1995), slightly higher than the value for water (1.33). Some typical values for solid media are 1.46 for fused quartz, 1.52 for crown glass, and 1.66 for dense flint glass. A ratio of the $R_o$'s for a solid medium and a solvent system can be used to determine the magnitude of the effect of changing the index of refraction:

$$\frac{R_o}{R_o'} = \left(\frac{n'}{n}\right)^{23}$$

where the primed values are the ones for the solid medium and the unprimed ones are for a solvent system. Assuming n'=1.5, the ratio becomes 0.93. The Förster distance thus only changes by 7%, a value that can be easily corrected for by using donor-acceptor pairs that have a higher original $R_o$.

Referring again to FIG. 6, conceptually, without presenting equations, the rate of energy transfer ($k_{transfer}$) from the center of the channel falls off with increasing distance from the center (FIG. 6). It is also known that the rate of donor emission ($k_{emit}$) is uniform over the complete area of donor fluorophores in the absence of acceptors (FIG. 6). The area closest to the channel, and thus to the acceptor, is quenched completely. At all areas less than $R_{equal}$, the donor fluorophore is quenched completely because $k_{transfer}$ is greater than $k_{emit}$. At areas greater than the $R_{equal}$, the rate of donor emission is greater than the rate of energy transfer so quenching is incomplete.

If the concentric ring of donor fluorophores has a radius equal to $R_{equal}$, then a hundred percent intensity change can occur for the donor fluorophores. This means that upon the exit of an acceptor labeled nucleotide through the channel, the acceptor is detected with perfect efficiency. Recalling that confidence intervals are related to the SNR of the system, the minimum signal to noise ratio needed to generate a 99.9% confidence interval for such a change is calculated to be 6:1. The SNRs for the detection systems proposed are greater than 600:1.

A quantitative explanation is presented at this time to calculate $R_{equal}$. The equations for the rates of donor emission and energy transfer are presented. The rate of donor emission ($k_{emit}$) is as follows:

$$k_{emit} = \frac{I \xi \rho N}{h \nu}$$

where I is the intensity of light incident upon the donor fluorophores, e is the molar extinction coefficient of the donor fluorophore, r is constant for fluorescence emission ($3.8 \times 10^{-21}$ mol cm$^3$/L), N is the number of donor fluorophores, h is Planck's constant ($6.6261 \times 10^{-34}$ J s), and $\nu$ is the frequency of excitation light.

The rate of energy transfer ($k_{transfer}$) from many donors to one acceptors is derived from the original Förster rate equation (Förster, 1965) for one donor and one acceptor. The original equation is given as:

$$k = \frac{1}{\tau_D}\left(\frac{R_o}{r}\right)^6$$

where k is the rate of energy transfer from one donor to one acceptor, $R_o$ is the Förster distance, $\tau$ is the fluorescence lifetime of the donor, and r is the distance from the donor to the acceptor. The derivation of a multi-donor system is straightforward and follows from the discussion of the multi-donor system described above.

There are two limitations in the amount of energy transferred for a multi-donor system. First, there is the saturation limit imposed by the lifetime of the acceptor. The acceptor is only able to be excited whenever it is in the ground singlet state. For an acceptor with a lifetime of 1 ns, the upper limit is $1 \times 10^9$ excitation events/second. This large saturation level is hardly a concern given the low rate of excitation for a single fluorophore (25,000 excitation events/second). The second limitation is the probability of simultaneous de-excitation of donor fluorophores. As calculated above only a very small number of simultaneous de-excitation events can occur. Since the acceptor is not saturated with excitation events resulting from energy transfer and the probability of simultaneous donor de-excitation is small, the rate of energy transfer for a multi-donor system is directly proportional to the number of donor fluorophores (N):

$$k_{transfer} = \frac{N}{\tau_D}\left(\frac{R_o}{r}\right)^6$$

With this equation, the radius at which $k_{transfer}$ is equal to $k_{emit}$ ($R_{equal}$) is found by equating the two rate equations and solving for r.
Solve for r.

$$k_{emit} = K_{transfer} \Rightarrow \frac{I\xi\rho N}{hv} = \frac{N}{\tau_D}\left(\frac{R_o}{r}\right)^6$$

$$r = R_{equal} = \frac{R_o}{\sqrt[6]{\tau_D I\xi\rho/hv}}$$

A numerical value for $R_{equal}$ can be calculated. Table 3 lists the values for the variables and the reason the particular value is chosen.

TABLE 3

| variable | value | reason |
|---|---|---|
| $R_o$ | 60 Å | range for Förster transfer is 20 Å-100 Å |
| $\tau_D$ | $1 \times 10^{-9}$ s/photon | fluorescent lifetimes range from 1 ns-20 ns |
| h | $6.6261 \times 10^{-34}$ J s | Planck's constant |
| v | $6.1224 \times 10^{14} \times s^{-1}$ | $c = v\lambda$; $\lambda = 490$ nm (excitation of fluorescein) |
| I | 30 W/cm$^2$ | intensity of 2 W laser is given by P/A. A = beam area (r = 2 mm). Intensity of laser is 64 W/cm$^2$ |
| $\epsilon$ | 91,000 1/M cm | molar extinction coefficient for fluorescein |
| $\rho$ | $3.8 \times 10 - 21$ M cm$^3$ | constant for fluorescence emission of fluorescein |
| $R_{equal}$ | 350 Å | from above equation |

$R_{equal}$ is calculated to be 350 Å, within an order of magnitude of the Förster distance. This means that a concentric ring of fluorophore around a channel with a radius equal to 350 Å will give rise to a hundred percent change in signal intensity upon the passage of an acceptor label. In practice, having such a large donor intensity decrease is unnecessary from both the standpoint of signal detection and the need to resolve adjacent bases. For example, with a SNR of 600:1, only a 0.50% intensity change will give rise to a 99.9% confidence interval. Resolution between adjacent bases is possible by looking at further decreases in the donor emission when there are two acceptors instead of one in the donor layer. If one acceptor already decreases the donor emission to zero, then an additional acceptor will not be detected because the donor emission cannot decrease further. This aspect is discussed in detail below. An example of a method for constructing a concentric ring of donor fluorophores around each channel by using a photolabile protecting group and light diffraction is also provided below.

Nanochannels having a channel diameter size of at least 1 nm are commercially obtainable in the form of polycarbonate filters from Poretics, Inc. and can be made on order by Corning Separations, Inc. There are several methods that can be used to create nanochannels of the desired diameter.

One method for preparing a nanochannel plate is by a track-etch procedure which produces cylindrical pores of uniform diameter in a membrane material. Microporous and nanoporous polymeric membranes having pore diameters on the order of 10 nm and with pore densities approaching $10^9$ pores per square centimeter can be prepared by the track-etch method (R. L. Fleischer, P. B. Price, R. M. Walker, *Nuclear Tracks in Solids* (Univ. of California Press, Berkeley, Calif. (1975)). The manufacture of pores via track-etch is a two step process. In the first step, thin polycarbonate (or other polymeric material) film is exposed to collimated, charged particles in a nuclear reactor. As these particles pass through the polycarbonate material, they leave sensitized tracks. The density of the tracks is controlled by varying the amount of time the film is in the reactor. In the second step, the tracks left by the particles are preferentially etched, or dissolved, into uniform, cylindrical channels. The diameters of the perforations can be controlled by the residence time of the etchant on the film. Many examples of methods for forming track etched membranes have been described in the art, e.g. European patent Application No. 83305268.1, Publication No. 0109147, to Varian Associates, Inc., U.S. Pat. Nos. 3,303,085; 3,662,178; 3,713,921; 3,802,972; 3,852,134, 4,956,219, 5,462,467, 5,564,959 and 5,449,917, each of which is incorporated herein by reference.

The commercially available membranes are generally prepared from polycarbonates or polyesters; however, a number of other materials are amenable to the track-etch process (Id.). For instance, other polymeric materials include but are not limited to polystyrenes, aromatic polyesters, polyolefins, including polyethylene, polyethylene terephthalate, polypropylene, vinyl plastics such as polyvinyl difluoride (PVDF), and cellulose esters such as cellulose nitrate, cellulose butyrate and cellulose acetate. If the nanochannel plate of the invention is prepared by a track-etch technique it may be formed from any material capable of being track etched can be used to form the track etched membrane.

Devices for performing bombardment of materials with high energy particles are well known in research and industry. The particles used to form the tracks may be generated by a charged particle accelerator, such as an electrostatic accelerator (e.g., a Van de Graaff accelerator or Tandem accelerator), a linear accelerator or a cyclic accelerator such as a cyclotron or any other means known in the art.

Once the damaged track is formed in the film the channels or pores are formed by selectively etching the film with a gas or liquid. The residence time of the etchant determines the size of the channels. The track etched film is exposed to the etchant for sufficient time to generate channels that are sized to match the desired application, which varies depending on the type of polymer being analyzed and the type of analysis. The channel diameter can be measured using a scanning electron microscopy (SEM) according to methods disclosed in *Basic Principles of Membrane Technology*, M. Mulder, Klumer Academic, 1991.

A second method of creating nanochannels of defined diameter is to use a combination of track-etching and surface coating. A polycarbonate membrane of a diameter greater than the desired nanochannel device is coated with a thin film of material with a defined thickness. The resulting structure is a polycarbonate membrane surface coated to the desired diameter. The first layer of thin film that is added to the nanochannel plate is a conducting layer. A conducting layer helps to resolve adjacent bases (which is discussed below in more detail).

Thin layers of conducting polymers are added to the polycarbonate membrane through solvent deposition. Solvent deposition of conducting polymers have been described (Cheung et al., 1994; Fereira et al., 1994; Fereira and Rubner, 1995; Fou and Rubner, 1995). The following is excerpted from Fou and Rubner, 1995:

We describe the solution chemistry and methodologies needed to utilize the layer-by-layer processing technique described . . . to manipulate conducting polymers such as polypyrrole and polyaniline into multilayer thin films with angstrom-level control over both film thickness and film architecture. Ultrathin films with conductivities over 300 S/cm can be made. The process involves the spontaneous adsorption of monolayers of electrically conductive polymers onto substrates from dilute solutions. Subsequent multilayer thin films are created by alternate deposition with soluble polyanions. The thickness of the thin films can be precisely controlled to the angstrom level and can range between 5 Å and greater than 1000 Å. The conductive polymers used are polypyrrole and polyaniline because these can be made extremely conductive (300 S/cm) for ultrathin layers (~50 Å).

The advantage of using a solvent deposition method to create the desired nanochannels is two-fold. First, nanochannels of any particular diameter can be created with precision and accuracy. Second, since the first layer of the nanochannel plate is a conducting layer, it is only convenient to add it. An additional advantage, though not significant, is that addition of a thick layer of conducting material can lower the peak-to-valley distance of the polycarbonate surface, creating a more uniform surface.

Another method for preparing a nanochannel device of the invention is through the production of arrays of carbon nanotubes. Iijima demonstrated the production of multiple concentric cylindrical shells of hexagonally bonded carbon atoms which can serve as catalytic surfaces to confine species in a 1-dimensional space. Iijima, *Nature,* 354:56 (1991), see also U.S. Pat. No. 4,424,054.

Li, W. Z., et. al., has also reported a method for producing large areas of highly ordered, isolated long carbon nanotubes. The method is based on a chemical vapor deposition which utilizes mesoporous silica containing iron nanoparticles embedded in the pores rather than carbon black and graphite or silica covered with transition metal nanoparticles. The following method is disclosed in Li, W. Z. et al.:

Mesoporous silica containing iron nanoparticles were prepared by sol-gel process from tetraethoxysilane (TEOS) hydrolysis in iron nitrate aqueous solution. Analytically pure TEOS (10 ml) was mixed with 10.4 ml of analytically pure ethyl alcohol and 0.1 M iron nitrate aqueous solution (11.4 ml) by magnetic stirring for ~30 min. A few drops of concentrated hydrogen fluoride (0.2 ml) were then added, and the mixture was stirred for 15 min. After gelation of the mixture, the gel was dried for 1 week at 60° C. to remove the excess water and other solvents. The gel was then calcined 10 hours at 450° C. at $10^{-2}$ torr. A silica network with relatively uniform pores was obtained with iron oxide nanoparticles embedded in the pores. The iron oxide nanoparticles were then reduced at 550° C. in 180 torr of flowing 9% $H_2/N_2$ (110 $cm^3$/min) for 5 hours to obtain iron nanoparticles, which have a high catalytic activity. Subsequently, a mixture of 9% acetylene in nitrogen was introduced into the chamber at a flow rate of 110 $cm^3$/min, and carbon nanotubes were formed on the substrate by deposition of carbon atoms obtained from decomposition of acetylene at 700° C. The samples were examined by a scanning electron microscope (SEM) (S-4200, Hitachi) before and after carbon deposition, and energy-dispersive x-ray spectra (EDX) were recorded by a SiLi detector attached to the SEM. To prepare a transmission electron microscope (TEM) specimen, the sample was ground in a mortar and suspended in ethanol; a drop was then placed on a holey carbon copper grid and examined in a JEM 200-cx microscope to characterize the carbon nanotubes.

Additionally, nanochannels may be prepared from anodic porous alumina which is a packed array of columnar hexagonal cells with central, cylindrical, uniformly sized holes typically ranging from 4 to 200 nm in diameter. Membranes of this type are prepared electrochemically from Aluminum metal (A. Despic and V. P. Parkhutik, in *Modern Aspects of Electrochemistry,* J. O. Bockris, R. E. White, B. E. Conway, Eds. (Plenum, New York, 1989), vol. 20, chap. 6.). Pore densities as high as $10^{11}$ pores per square centimeter have been achieved (D. AlMawiawi, N. Coombs, M. Moskovits, *J. Appl. Phys.* 70, 4421 (1991)). Membranes having pore diameters as small as 5 nm have been prepared using this method (and it is believed that even smaller pores can be prepared). Martin, C. R., *Science,* 266:1961 (1994).

Matsuda and Fukuda have described a modification of porous alumina membranes. The membranes which are a highly ordered metal (platinum and gold) nanohole array are prepared using a two-step replication of the honeycomb structure of anodic porous alumina. Preparation of the negative porous structure of porous alumina followed by the formation of the positive structure with metal results in a geometrical structure identical to that of anodic porous alumina. The method, therefore allows the preparation of the hole array of anodic porous alumina with desired materials other than alumina. Matsuda and Fukuda, Science, 268:1466 (1995). Matsuda and Fukuda's procedure is summarized below.

Anodic alumina was produced using a long period anodization of alumina on a substrate at 40 V which results in a minimum number of defects and dislocations, followed by removal of the aluminum substrate and the bottom part of the porous layer with saturated $HgCl_2$. The material was then dipped in 5% (by weight) phosphoric acid solution at 30° C. to adjust the pore diameter. A thin metal layer was deposited on the bottom of anodic porous alumina by vacuum deposition in order to create a catalyst or electrode for the subsequent metal-plating process. Generally the same metal as that used to create the scaffold is used for the evaporation. Metal methacrylate monomer containing a polymerization initiator such as 5% (by weight) benzoyl peroxide was injected into the holes under vacuum conditions and was polymerized by ultraviolet irradiation. The alumina layer was then removed with NaOH to produce a negative porous alumina-type structure of poly(methyl methacrylate) (PMMA). A positive structure was formed from the PMMA mold by electroless deposition of platinum as follows. The negative type of PMMA was dipped into the electroless plating solution, causing metal deposition to start at the bottom part of the cylindrical structure and the metal to gradually fill the cavity of the PMMA to the top of the negative type of PMMA. Alternatively a gold (Au) hole array was prepared using electrochemical deposition of Au into the microcavity of the PMMA under constant conditions. The porous metal was obtained by dissolving the PMMA with acetone.

Other nanoporous materials which have been described in the art include a nanochannel array glass with pore densities as high as $3 \times 10^{10}$ pores per square centimeter (R. J. Tonucci, B. L. Justus, A. J. Campillo, C. E. Ford, *Science* 258, 783 (1992) and Pearson and Tonucci, *Science,* 270: 68 (1995)). Douglas et al. have shown that the nanoscopic pores in a protein derived from a bacterium can be used to transfer an image of these pores to an underlying substrate (Douglas, et. Al., *Science* 257: 642 (1992)). Finally, Ozin has discussed a wide variety of nanoporous solids that can be used as template materials (Ozin, G. *Adv. Mater.* 4:612 (1992)). Nishizawa et. al., describe the production of metal nanotubule membranes having radii as small as 0.8 nm (Nishizawa et. al., *Science* 268:700 (1995), describing nanotubules formed by plating gold onto the walls of pores in a commercially available polycarbonate filtration membrane (Poretics) containing cylindrical nanopores of uniform radius (25 nm, $6 \times 10^8$ pores per square centimeter) running through the complete thickness (6 μm) of the membrane. "The thickness of the Au layers deposited on the pore walls can be controlled by varying the plating time. As a result, the inside radius of the Au nanotubules can be varied at will [as determined from measurements of gas (He) flux across the tubule-containing membrane.]" Berggren et. al., have demonstrated techniques for nanolithography using self-assembled monolayers and a beam of neutral inert gas. Berggren et. al., *Science* 269: 1255-1257 (1995).

La Silva et al., describe a technique for fabricating simple metal structures with a scanning tunneling microscope (STM) which have dimensions of 10's to 100's of nanometers and are partially electrically isolated from their environment. The method is performed by depositing a very thin metal film on an insulating substrate, and using the tip to machine gaps through the film where lateral electrical insulation is desired. (Journal of Vacuum Science & Technology B, (1993) 11:1992-1999).

The wall material may be constructed in a manner which is optimal for resolving adjacent units of the polymer. Since the purpose of the wall material is to provide an environment which is conducive to generating a signal, the materials used to prepare the wall material may be selected to aid in this process. For instance, the wall material surrounding the agent if the agent is embedded in the wall material preferably is a non-conducting or light permeable material. At least two other mechanisms for optimizing the wall material in an apparatus having fluorophores embedded in the wall surrounding the channel, in order to resolve adjacent labeled bases include the use of thin conducting layers and controlling the radii of donor fluorophores around each channel.

Conducting layers prevent Förster energy transfer through electrical shielding. FIG. 6 demonstrates a configuration of the conducting layers relative to the non-conducting layer which contain the donor fluorophores. The conducting "sandwich" creates a defined region where energy transfer can occur and this helps to optimize base resolution. Förster energy transfer arises because of an electrical dipole-dipole interaction between a donor and acceptor. The rationale for the use of conducting layers when the signal generated is dependnet on FRET is that FRET is electric field-dependent and thus placing an electric shield between the donor and acceptor will prevent energy transfer. It is necessary to understand fully the basis of energy transfer. Incident excitation light creates an electric field in the donor because the light induces transitions in the donor, or causes electrons in the donor to oscillate (Selvin, 1995). This creates an induced, electric dipole moment in the donor, which in turn, creates its own electric field. Energy transfer arises when an acceptor is placed in the donor's electric field. As a consequence, there are induced transitions in the acceptor which create an induced dipole moment, $p_A$. The size of the dipole moment is related to the size of the donor electric field: $p_A = \alpha_A E_D$, where $\alpha_A$ is the polarizability of the acceptor. The amount of energy absorbed by the acceptor is $p_A E_D = \alpha_A E_D^2$, which translates into the $1/R^6$ dependence of the rate of energy transfer.

The theory of electrical shielding is found in most introductory physics books. Purcell, 1985 provides a clear explanation. The potential function inside the box, ψ (x, y, z), must satisfy Laplace's equation, $\nabla^2 \psi = 0$. Given the knowledge of conductors, the boundary of the conductor is an equipotential, meaning that $\psi = \psi_o$ a constant function everywhere on the surface of the conductor. An obvious solution to Laplace's equation is $\psi = \psi_o$ throughout the volume. According to the uniqueness theorem, there can only be one solution, meaning the answer is ψ=a constant. The electric field of a constant potential function is zero because E=–grad ψ. The electric field is thus zero everywhere inside the box.

Figure 7:
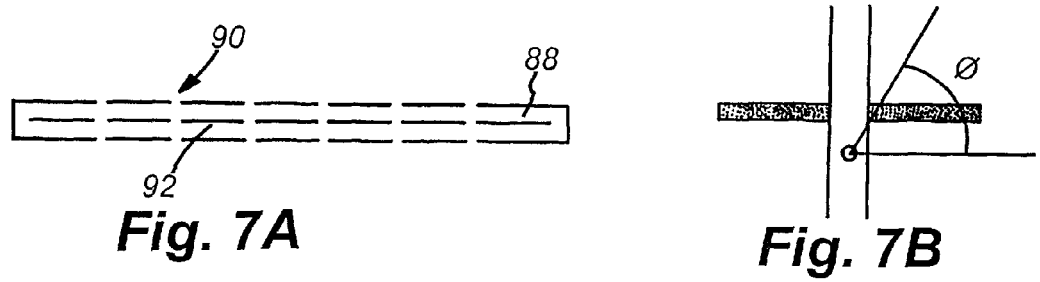
FIG. 7 shows a model of a nanochannel plate having multiple nanochannels with a layer of donor fluorophores within the plate.

The model of a box with an open hole can be applied to a nanochannel plate because essentially a nanochannel plate is a conducting box with many "holes". Consider the FIGS. 7A and 7B. FIG. 7A shows a complete nanochannel plate having nanchannels (90). The layer of donor fluorophores (88) is enclosed by the conducting "box." In this manner, there cannot be energy transfer to the donor fluorophores from outside the box because of electrical shielding (92). Recall that the basis of energy transfer is electric. At the boundary condition of the nanochannel, which is the outer surface of the nanochannel plate, $\psi = \psi_o$, an equipotential surface. A logical solution to Laplace's equation is that everywhere inside the boundary condition that, ψ=constant. From the uniqueness theorem, this is the only possible answer and thus everywhere inside the conducting nanochannel "box," E=0 because E=ψ–grad. The conclusion is that acceptor fluorophores cannot undergo energy transfer from outside the box. Even inside a nanochannel, as shown in FIG. 7B, energy transfer is limited geometrically. At any position where the acceptor molecule is not in the plane of the donor fluorophores, the amount of energy transfer is limited. In FIG. 7B, the amount of donor fluorophores that cannot undergo energy transfer is enclosed by an angle of θ, which for all purposes is very large unless the acceptor fluorophore is directly in the plane of the donor fluorophores, which is the desired configuration.

Figure 8:
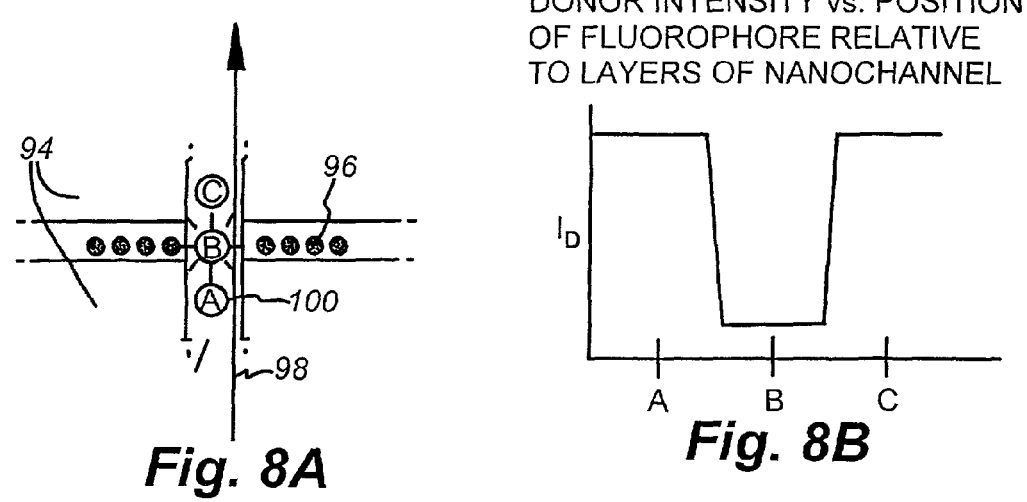
FIGS. 8A and B are schematics demonstrating signal generation upon passage of an acceptor label through the nanochannel.
FIG. 8B graphically illustrates the sharp changes in donor intensity as an acceptor label moves from positions A to C.

The consequence of the conductive layers is that a sharp signal is created upon the passage of a labeled nucleotide through the nanochannel. FIG. 8A and FIG. 8B demonstrate signal generation upon passage of an acceptor label through the nanochannel. FIG. 8A shows an enlarged view of one nanochannel (98). Only part of the conducting layers (94) is shown. The light impermeable polycarbonate layer is not shown. An acceptor label (100) on a strand of DNA moves through the nanochannel from bottom to top, starting at position A and moving to position C. FRET can only occur at position B because the conducting layers shield any interaction of the donor fluorophores (96) with the acceptor at positions A and C. FIG. 8B graphically illustrates the sharp changes in donor intensity as an acceptor label moves from positions A to C. The middle region on the graph denotes the level of the donor fluorophores. The outer regions on the graph denote the level of the conducting layer. At the interface of the conducting and donor fluorophore layers, there are dramatic changes in donor intensity due to electrical shielding.

It is clear that resolution between adjacent bases can be resolved with conducting layers. By creating a conducting "sandwich" where the thickness the donor fluorophores is less than the helical rise of B-DNA (3.4 Å), the desired resolution can be achieved. Thin films of this thickness can be constructed easily with plasma, solution, chemical vapor, or ion beam deposition methods (Spohr, 1990; Valiev, 1992; Konuma, 1992; Pauleau, 1995; Bruno et al., 1995; Dash, 1975; Stuart, 1983; Morosanu, 1990) However, it is not desirable to use a donor fluorophore film less than 3.4 Å, as will be explained under the next heading. In brief, donor fluorophores embedded in a thicker layer allows the measurement of instantaneous rate of movement of DNA. By measuring the time a labeled nucleotide spends in the thick layer and knowing the dimensions of the layer, the rate of DNA movement is known, which is important for determining distances between labeled nucleotides.

Another example of a method for precisely resolving adjacent labeled bases is to control the radii of the donor fluorophores around each nanochannel. The amount of energy transferred for two acceptor labels in the presence of a concentric ring of donor fluorophores is greater than the energy transferred for one acceptor label. Detection of the difference in energy transferred for one and two acceptors allows the resolution of adjacent bases. In order for the donor fluorophores to be able to interact with more than one acceptor, the thickness of the donor fluorophores has to be greater than the helical pitch of DNA. Furthermore, the radii of the donor fluorophores must be greater than $R_{equal}$ for one acceptor (see FIG. 6). A radii greater than $R_{equal}$ for one acceptor allows for further decreases in donor intensity in the presence of more than one acceptor. A radii at $R_{equal}$ means that upon that passage of one acceptor, the donor intensity decrease is equal to 100%. In this case, passage of two adjacent acceptors gives the same detected signal as one acceptor.

Figure 9:
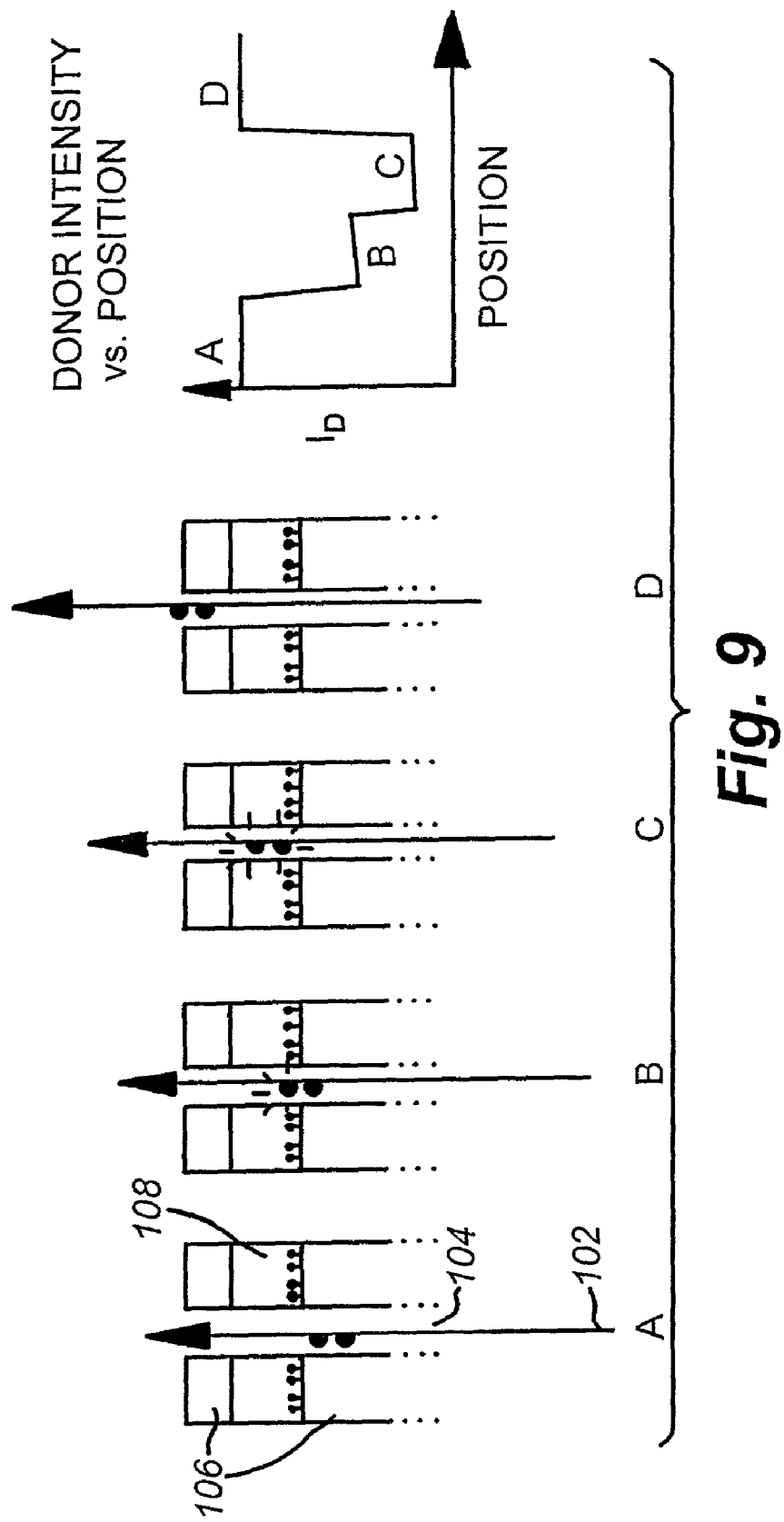
FIG. 9 schematically and graphically demonstrates the passage of a two-base labeled strand of DNA through a nanochannel with the proper thickness and radii of donor fluorophores sandwiched between conducting material.

FIG. 9 schematically demonstrates the passage of a two-base labeled strand of DNA (102) through a nanochannel (104) with the proper thickness and radii of donor fluorophores (108) sandwiched between conducting material (106). The positions labeled "A" through "D" correspond to the labels on the graph shown at the right of the illustrations. Initially, the acceptor labels on the DNA are at position A. Energy transfer is not possible at this position so donor intensity remains at a maximum. Further movement of the DNA allows one acceptor to undergo energy transfer with the donor fluorophores (B) and a sharp decrease in the donor intensity occurs. At position C, two fluorophores can undergo energy transfer yielding a further decrease in the donor intensity. Finally, the two acceptor labels exit the region of donor fluorophores, energy transfer is not longer possible, and the donor intensity returns to a maximum (D).

Figure 10:
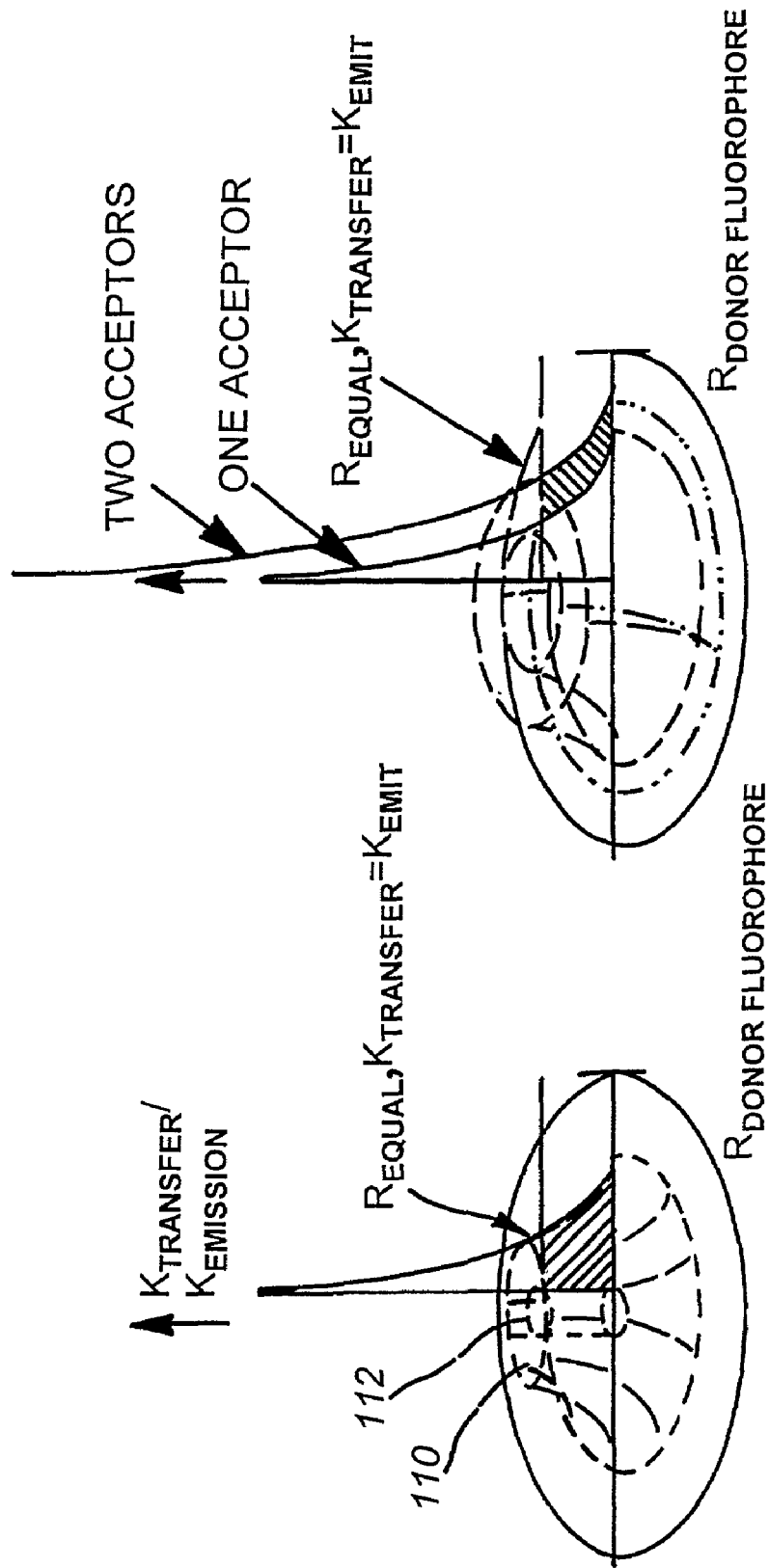
FIG. 10 is a volume graph visually demonstrating the change in donor emission in the presence of one and two acceptors.

The change in donor emission in the presence of one and two acceptors can be visually demonstrated without mathematical quantitation. FIG. 10A illustrates the amount of change as volumes. The illustrations show the amount of energy transfer as a solid volume (110). The original donor intensity is represented as the volume in the shape of a disc (112). FIG. 10B shows the change for one acceptor. The right illustration is for two acceptors. The decay curves represent the rate of energy transfer with respect to radial distance as given by Förster's equation. The decay curve for two acceptors is roughly double that of one acceptor. The rates of donor emission and energy transfer are expressed in units of 1/s nm². Integration of the rate of donor emission decrease over the surface area of energy transfer yields the net decrease in donor emission. This is represented as the shaded area under each decay curve integrated over $2\pi$. Knowing the original donor emission (shaded rectangular area integrated over $2\pi$), the percent decrease in donor emission can be found.

Mathematically, the changes can be easily calculated. In both cases, the change is equal to the striped area (FIG. 10) integrated over $2\pi$. To calculate, the rates of donor emission and energy transfer have to be expressed in the appropriate units of 1/s nm². To do so, the density of the donor fluorophores, given as N/A, is to be used in the rate equations, where $N_D$ is the number of fluorophores and A is the area which is occupied by the donor fluorophores. Accordingly, the rate of emission is given as:

$$k_{emit} = \frac{I\xi\rho N_D}{h\nu A}$$

The rate of energy transfer becomes:

$$k_{transfer} = \frac{N_D N_A}{\tau_D A}\left(\frac{R_o}{r}\right)^6$$

Where $N_A$ is the number of acceptors that can undergo energy transfer with the donors. The general equation for the striped areas integrated over $2\pi$ follows:

$$\pi(R_{equal}^2 - R_{channel}^2)K_{emit} + \int_o^{2\pi R\ donor}\int_{R\ equal} k_{transfer} rdrd\theta$$

For the present calculations, $R_{donor}$=55 nm, $N_D$=1000. The donor fluorophore density ($N_D$/A) becomes 0.11 fluorophores/nm². This value is not unreasonable because the size of the area of the largest possible fluorophore is 1 nm². This means that the density is at least an order of magnitude lower than the highest possible fluorophore density.

In order to solve the general equation, recall that $R_{equal}$ can be solved by setting $k_{emit}=k_{transfer}$, resulting in the following:

$$R_{equal} = \frac{R_o}{\sqrt[6]{\tau_D I\xi\rho/N_A h\nu}}$$

It is also important to know the original donor emission ($E_o$), given as:

$$E_o = k_{emit}\pi(R_{donor}^2 - R_{channel}^2)$$

Using the values from table 3 and from above, it is possible to tabulate donor emission values for different numbers of acceptors that are in the position to undergo energy transfer (table 4). Values for $N_A$=1-5, 11-12 are calculated as examples. It is expected that the value of the first donor emission decrease be the greatest. Subsequent decreases become progessively smaller. When $R_{equal}$ approaches $R_{donor}$, it is expected that actual (not percent) change approaches zero. This is so because essentially the donor molecules are almost completely quenched.

The percent changes and the signal-to-noise ratios determine the detection capability, not the absolute numerical changes in donor emission. As expected, the SNR decreases as the number of acceptors increase because there is greater donor quenching. Otherwise stated, the donor emission becomes smaller. This decrease in SNR is compensated by increasing percent changes from $N_A$=5 to 12. The confidence is calculated by using the SNR and the percent change. For example, the confidence for detecting the change from one to two acceptors uses the SNR for one acceptor and the percent change from one to two acceptors. In this case, there is a 95% confidence for detecting a 0.483% change. Since the percent change is high, 29.1%, the signal change from one to two acceptors is detected with a 100% confidence. The calculations from above demonstrate that multiple adjacent acceptors can be detected with high efficiency.

TABLE 4

| $N_A$ | donor emission (photons/s) | % change from previous | SNR (80% full well capacity at $E_O$, $N_A = 0$ | confidence |
|---|---|---|---|---|
| 0 | 2.5572 × 10$^7$ | — | 632:1 | ~100% |
| 1 | 1.0943 × 10$^7$ | 57.2% | 413:1 | "" |
| 2 | 7.7510 × 10$^6$ | 29.1% | 348:1 | "" |
| 3 | 5.7650 × 10$^6$ | 25.6% | 300:1 | "" |
| 4 | 4.3560 × 10$^6$ | 24.4% | 261:1 | "" |
| 5 | 3.2440 × 10$^6$ | 25.5% | 225:1 | "" |
| " | " | " | " | " |
| 11 | 3.8200 × 10$^5$ | — | 77:1 | "" |
| 12 | 2.1200 × 10$^5$ | 44.5% | 58:1 | "" |

An assumption made in the above calculations is that the donor emission remains ant during the passage of one fluorophore through the donor fluorophore layer. Recall the donor fluorophore layer may consist of a monolayer of fluorophores embedded in a non-conducting medium. The range of energy transfer for an acceptor close to the exit of the nanochannel is less than the range upon initial entry into the channel. This change is in fact significant, as shown mathematically below. Taking into account the change yields higher signal-to-noise ratios and greater changes in donor intensity for additional acceptors. This means that the values in table 4 which show very efficient signal generation/detection already are actually even slightly higher.

The change in donor emission upon passage of an acceptor through the donor fluorophore layer is determined by calculation in the following formulas. It is expected that the amount of energy transfer decreases as an acceptor passes through the donor layer due to a smaller effective energy transfer range. The consequence of this decrease is that the donor emission is greater than in the previous calculations. A higher donor emission means a higher SNR. Suppose an acceptor has entered the donor layer a small distance. A short time later, another acceptor enters the donor layer. The presence of an additional acceptor yields a decrease in the donor emission. The percentage change is large. In fact, it is larger than the previous calculations. The combination of higher SNRs and greater percentage changes mean that detection efficiencies are greater than those previously estimated. Complex patterns of labeling, such as labeling every several nucleotides, can be distinguished using this system.

The equation of donor emission when the acceptor is on the same plane as the donor fluorophores is given as:

$$k_{emit}\pi(R_{donor}^2 - R_{channel}^2) - [k_{emit}\pi(R_{equal}^2 - R_{channel}^2) + \int_0^{2\pi R_{donor}} \int_{R_{equal}} k_{transfer} r dr d\theta]$$

Recall the equations for $k_{emit}$ and $k_{transfer}$:

$$k_{emit} = \frac{I\xi\rho N_D}{h\nu A}$$

$$k_{transfer} = \frac{N_D}{\tau_D A}\left(\frac{R_o}{r}\right)^6$$

Express the original donor emission function in terms of the radial distance (x) and distance of acceptor from donor layer (d) with the following substitutions:

$$dr = \frac{x}{\sqrt{x^2 + d^2}} dx$$

$$r = \sqrt{x^2 + d^2}$$

The resulting equation, together with the substitution of the equation for $k_{transfer}$ yields:

$$k_{emit}\pi(R_{donor}^2 - R_{channel}^2) - \left[k_{emit}\pi(x_{equal}^2 - R_{channel}^2) + \left(2\pi\frac{N_D R_o^6}{\tau_D A}\right)\int_{x_{equal}}^{R_{donor}}\left(\frac{x}{x^2 + d^2}\right)dx\right.$$

Let $u = x^2 + d^2$. It follows that $dx = du/dx$.

$$k_{emit}\pi(R_{donor}^2 - R_{channel}^2) - \left[k_{emit}\pi(x_{equal}^2 - R_{channel}^2) + 2\pi\frac{N_D\pi R_o^6}{\tau_D A}\int_{U-x_{equal}^2+d^2}^{U-R_{donor}^2+d^2}\left(\frac{1}{2u^3}\right)du\right]$$

$$k_{emit}\pi(R_{donor}^2 - R_{channel}^2) - \left[k_{emit}\pi(x_{equal}^2 - R_{channel}^2) + \left(2\pi\frac{N_D R_o^6}{\tau_D A}\right)\left(\frac{1}{4(x_{equal}^2 + d^2)^2} - \frac{1}{4(R_{donor}^2 + d^2)^2}\right)\right]$$

Substitute x equal = $\sqrt{R_{equal}^2 - d^2}$ and the resulting emission function becomes:

$$E(d) = k_{emit}\pi(R_{donor}^2 - R_{channel}^2) - \left[k_{emit}\pi(R_{equal}^2 - d^2 - R_{channel}^2) + \left(2\pi\frac{N_D R_o^6}{\tau_D A}\right)\left(\frac{1}{4R_{equal}^4} - \frac{1}{4(R_{donor}^2 + d^2)^2}\right)\right]$$

The resuling donor emission function can be plotted versus distance.

| Distance | Donor Emission (photons/s) | % Change from Original |
|---|---|---|
| 0 | 1.09425 × 10$^7$ | — |
| 20 Å | 1.09740 × 10$^7$ | 0.023% |
| 40 Å | 1.0692 × 10$^7$ | 1.158% |
| 60 Å | 1.12278 × 10$^7$ | 2.607% |
| 80 Å | 1.14501 × 10$^7$ | 4.638% |
| 100 Å | 1.17365 × 10$^7$ | 7.256% |

$$E_2(d) = k_{emit}\pi(R_{donor}^2 - R_{channel}^2) - \left[k_{emit}\pi(x_{equal}^2 - R_{channel}^2) + \left(2\pi\frac{N_D R_o^6}{\tau_{DA}}\right)\left(\frac{1}{4(R_{equal}^2 + d^2)^2} - \frac{1}{4(R_{donor}^2 + d^2)^2}\right) + \left(2\pi\frac{N_D R_o^6}{\tau_{DA}}\right)\left(\frac{1}{4R_{equal}^4} - \frac{1}{4R_{donor}^4}\right)\right]$$

In order to find solutions to the above equation, $R_{equal}$ needs to be found by equating $k_{emit}$ to the sum of energy transfer of the two acceptors. Solving for $R_{equal}$ in the below equality is done by computer:

$$k_{emit} = k_{transfer(1)} + k_{transfer(2)} \Rightarrow \frac{I\xi\rho N_D}{h\nu} =$$

$$\frac{N_D}{\tau_D}\left(\frac{R_o}{R_{equal}}\right)^6 + \left(\frac{N_D}{\tau_D}\right)\frac{R_o^6}{(R_{equal}^2 + d^2)^3}$$

The percent change in donor emission from one to two acceptors is tabulated.

| Distance (d) | $R_{equal}$ 2 ac-ceptos | $E_2(d)$ | $E_1(d)$ | % change | SNR |
|---|---|---|---|---|---|
| 0Å | 39.28 | $7.7510 \times 10^8$ | $1.0943 \times 10^7$ | 29.10% | 348.0:1 |
| 20Å | 39.21 | $7.7661 \times 10^8$ | $1.0974 \times 10^7$ | 29.24% | 348.3:1 |
| 40Å | 39.11 | $7.8102 \times 10^8$ | $1.1069 \times 10^7$ | 29.44% | 349.3:1 |
| 60Å | 39.01 | $7.8815 \times 10^8$ | $1.1228 \times 10^7$ | 29.80% | 350.9:1 |
| 80Å | 38.82 | $7.9790 \times 10^8$ | $1.1450 \times 10^7$ | 30.31% | 353.1:1 |
| 100Å | 38.610 | $8.0962 \times 10^8$ | $1.1737 \times 10^7$ | 31.01% | 355.7:1 |

$$\% \text{ change} = \frac{E_1(d) - E_2(d)}{E_1(d)} \times 100$$

Therefore base resolution down to individual bases can be achieved. A corollary to the base resolution argument is that the time spent in the donor layer by an individual acceptor can be determined. This translates into information about instantaneous rates of DNA movement.

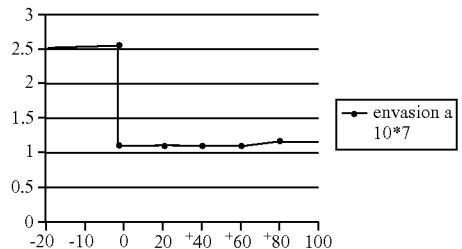

In order to achieve optimal linear crossing of a polymer across a channel it is important to consider the channel diameter as well as the method used to direct the linear crossing of the polymer e.g., an electric field. The diameter of the channels should correspond well with that of the labeled polymer. The theory for linear crossing is that the diameter of the channels correspond well with that of the polymer. For example the ring-like sliding clamps of DNA polymerases have internal diameters that correspond well with the diameter of double-stranded DNA and are successful at achieving linear crossing of a DNA molecule. Many kilobases of DNA can be threaded through the sliding clamps. Several references also have demonstrated that linear crossing of DNA through channels occurs when the diameter of the channels corresponds well with that of the diameter of the DNA. (Bustamante, 1991; Gurrieri et al., 1990; Matsumoto et al., 1981).

Single-stranded DNA, as used in the experiment, has a diameter of ~1.6-nm. A channel having an internal diameter of approximately 1.7-3 nm is sufficient to allow linear crossing of a single strand DNA molecule. The diameters of the channel and the DNA need not match exactly but it is preferred that they be similar. For double-stranded DNA which has a diameter of 3.4-nm, channel sizes between 3.5-nm and 4.5-nm are sufficient to allow linear crossing.

As discussed earlier many methods may be used to move the polymer linearly across the channel and past the interaction station or signal generation station. A preferred method according to the invention utilizes an electric field. An electric field can be used to pull a polymer through a channel because the polymer becomes stretched and aligned in the direction of the applied field as has previously been demonstrated in several studies (Bustamante, 1991; Gurrieri et al., 1990; Matsumoto et al., 1981). The most related experiments regarding linear crossing of polymers through channels arise from experiments in which polymeric molecules are pulled through protein channels with electric fields as described in Kasianowicz et al., 1996 and Bezrukov et al., 1994, each of which is hereby incorporated by reference. A brief description of these experiments is presented below in order to illustrate one method for enabling linear crossing of polymers.

In a study entitled, "Characterization of individual polynucleotide molecules using a membrane channel," Kasianowicz et al., 1996 demonstrate the linear crossing of DNA molecules through protein channels in a lipid bilayer with an electric field (also described in PCT Published Patent Application WO 96/29593). An excerpt of the abstract follows.

We show that an electric field can drive single-stranded RNA and DNA molecules through a 2.6-nm diameter ion channel in a lipid bilayer membrane. Because the channel diameter can accommodate only a single strand of RNA or DNA, each polymer traverses the membrane as an extended chain that partially blocks the channel.

The assay is performed using *Staphylococcus aureus*-hemolysin as the membrane channel. It has a diameter of 2.6-nm and can remain open for extended periods of time, allowing continuous ionic current to flow across a lipid bilayer. The hypothesis is that while a DNA molecule traverses a channel, there should be blockage in the ionic flow. Using single channel recordings, the blockage time is recorded. The length of blockage time corresponds to the length of the single-stranded DNA molecule passing through the channel if linear crossing occurs. Initially a potential of −120 mV was applied across the membrane, causing a current flow. When single-stranded DNA was added, two consecutive conductance blockades of 300 µs and 1300 µs, respectively occurred.

The data supports two hypotheses: 1) the length of blockage time (denoted as "lifetime") is directly proportional to the length of the DNA and 2) greater applied voltage shortens the blockage time for a given length of DNA., indicating that linear crossing indeed occurred. As a control, it was demonstrated that double-stranded DNA do not cross the protein channels.

Bezrukov et al., 1994 have done similar studies with alamethicin pores in a paper entitled, "Counting polymers moving through a single ion channel." Alamethicin pores have internal diameters of 2 nm. The duration of the conductance blocks were proportional to the length of the polymer pulled through the pore, supporting the hypothesis for linear crossing. The results from Kasianowicz et al., 1996 and Bezrukov et al., 1994 demonstrate that an electric field can drive DNA across a protein pore channel in a linear fashion.

Figure 11:
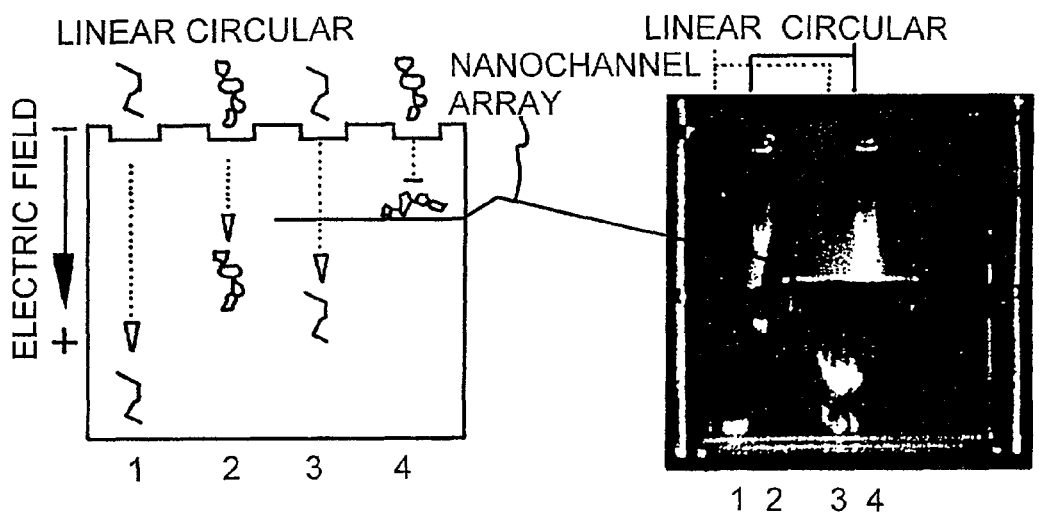
FIG. 11 shows the results of an experiment demonstrating that DNA can pass through fabricated nanochannels.

An experiment was performed to demonstrate according to the invention that DNA can pass though fabricated nanochannels. The results of the experiment are shown in FIG. 11. DNA in various forms was exposed to nanochannels to determine if it could pass through. Only double stranded linear DNA of 50 kb could pass through an array of 4 nm nanochannels. Folded DNA as modeled by a circular plasmid of the same size, cannot pass through the array. Lanes 1 and 2 are the controls. Circular DNA migrates slower than linear DNA as expected. Lanes 3 and 4 demonstrate that only linear DNA can pass through the nanochannel array. Since folded DNA which has a solvation diameter of approximately 5 nm, cannot pass through the array, the only means by which the linear DNA passes through the plate is in a linear fashion.

Using the system described above by Kasianowicz et al., a randomly labeled polymer, such as DNA can be analyzed by passing the polymer through the channel and making unit specific measurements. A channel can be prepared as a protein pore in a lipid membrane such as that described in Kasianowicz et al., and also in PCT published patent application WO/96/29593. Briefly, the S. aureus protein α-hemolysin is added to the cys side of a lipid bilayer. Lipid bilayers can be formed from, for example, diphytanoyl phosphatidylcholine by layering the solution on 0.2 mm holes in a Teflon film separating two compartments containing buffer solution. After the hemolysin is added, voltage can be applied across the bilayer and varied from 0 mV to 140 mV. DNA which is randomly labeled is added to the buffer on the cys side of the protein. A voltage is applied which causes the labeled DNA to traverse from this cys to the trans side of the channel, which has a positive charge. As each unit passes through the channel, a change in conductance as a result of the blockage of the channel occurs. The change in conductance is dependent upon the size, shape and charge of the unit passing through the channel. If the unit is labeled, the conductance change will reflect the properties of the label. In this manner, labeled unit can be identified. This method can be used to identify a particular unit or to identify specific order of units or distance between units or simply the number of units which are labeled.

Retrograde movement of the DNA is unlikely because of differences in frictional coefficients for inside the nanochannel and outside. The predicted van der Walls interaction between the solvated labeled DNA and the inside of the nanochannel creates a higher frictional resistance for the portion of the DNA located inside the nanochannel than that located in free solution. This is evidenced by the slower migration of DNA in the presence of a nanochannel plate (compare lanes 1 and 3 in FIG. 6). The differential in frictional resistance is likely to create a ratchet mechanism in the direct of the desired DNA movement.

Another method for moving a polymer linearly past an interaction station or a signal generation station involves the use of a molecular motor. A molecular motor is a device which physically interacts with the polymer and pulls the polymer past the station. Molecular motors include but are not limited to DNA polymerases and helicases. DNA polymerases have been demonstrated to function as efficient molecular motors. Preferably the internal diameters of the regions of the polymerase which clamp onto the DNA is similar to that of double stranded DNA. Furthermore, large amounts of DNA can be able to be threaded through the clamp in a linear fashion.

The overall structure of the β-subunit of DNA polymerase III holoenzyme is 80 Å in diameter with an internal diameter of ~35 Å. In comparison, a full turn of duplex B-form DNA is ~34 Å. The beta subunit fits around the DNA, in a mechanism referred to as a sliding clamp mechanism, to mediate the processive motion of the holoenzyme during DNA replication. It is well understood that the b-subunit encircles DNA during replication to confer processivity to the holoenzyme (Bloom et al., 1996; Fu et al., 1996; Griep, 1995; Herendeen and Kelly, 1996; Naktinis et al., 1996; Paz-Elizur et al., 1996; Skaliter et al., 1996). Because the sliding clamp is the mechanism of processivity for a polymerase, it necessarily means that large amounts of DNA are threaded through the clamp in a linear fashion. Several kilobases are threaded through the clamp at one time (Kornberg and Baker, 1991).

Methods for preparing the wall material of the invention are also encompassed by the invention. One method for preparing a wall material according to the invention includes the step of covalently bonding the agent to a plurality of discrete locations of a wall material. The agent is bonded to discrete locations on the wall material which are close enough to an interaction station, such that when an individual unit of a polymer, which is interactive with the agent to produce a signal, is positioned at the interaction station, the agent interacts with the individual unit to produce the signal. The discrete locations may be on the surface of the wall material or may be within the wall material such that the agent is embedded in the wall material.

Another method is for attaching a chemical substance selectively at a rim of a channel through a wall material that is opaque. An "opaque" material as used herein is a material which is light impermeable at a selected wavelength.

The wall material is provided with photoprotective chemical groups attached at the rim of the channel through the wall material. Light is then applied to the photoprotective chemical groups to dephotoprotect the chemical groups, and a chemical substance is attached to the dephotoprotected chemical groups.

A "photoprotective chemical compound" as used herein is a light sensitive compound which is capable of becoming chemically reactive when exposed to light. When light is applied to the photoprotective chemical groups the groups become dephotoprotected and are susceptible to interactions with chemical substances such as light emitting compounds and quenching compounds.

Localized regions of agent can still be prepared even if the photoprotective chemical group covers the entire surface of the wall. The light may selectively be applied to regions of the wall on which it is desirable to have the agent localized. For instance the light may be applied only to the region of the wall surrounding the channel openings so that only those regions are dephotoprotected. When the agent is added it will only attach to the wall around the regions surrounding the channel openings.

Additionally a method for preparing a wall material having localized areas of light emission on a surface of the wall material is provided. A light emissive compound is applied to the surface to produce at least localized areas of light emission on the surface. The light emissive compound may be added directly to the surface of the wall material or it may be attached indirectly to the surface through a photoprotective chemical group which has been attached to the surface and dephotoprotected by light.

A "localized area of light emission" as used herein is a region of concentrated light emissive compound on the surface of the wall material which defines a target region around a rim of a channel through the wall material for detecting light emission. The localized area can be produced in several ways. Firstly, the light emissive compound may be attached directly to the wall surface only around the rim of the channel. Secondly, the light emissive compound may be attached to a photoprotective chemical group which has been attached selectively to localized areas around the rim of the channels. Alternatively the photoprotective chemical groups may be added to the entire surface or to random regions of the surface of the wall material but only select regions are dephotoprotected by light to create localized regions to which the light emissive compound can be attached. Both the photoprotective chemical groups and the light emissive compound can be added to the entire surface or to random regions of the surface of the wall material when a mask is used to create localized regions of light emission. A mask having openings may be positioned over the wall surface such that the openings in the mask expose localized regions of the wall surface specifically around the openings of the channels.

A wall material having localized areas of light emission on a surface of the wall material may also be prepared by first applying a light emissive compound to the surface to produce at least localized areas of light emission on the surface and then by creating a channel in the wall material wherein a rim of the channel forms a target region within the localized areas of light emission.

An non-limiting example of a method for constructing an article of manufacture having a concentric ring of donor fluorophores around each channel is provided to demonstrate a preferred method of the invention. The method is achieved by the use of photolabile protecting groups and light diffraction. A light impermeable polycarbonate porous medium is coated on one side with a dense layer of covalent linkers. The linkers are protected by photolabile protecting groups. Light is transmitted through the back side of the light impermeable polycarbonate. Since the wavelength of the deprotecting light source (400-500 nm) is much greater than the size of the channels (5 nm), each channel acts as a point source of light. The intensity of transmitted light is greatest closest to the channel. Accordingly, only those groups close to the channels are deprotected. Deprotected groups are free to react with donor fluorophores in subsequent chemical reactions to generate concentric rings.

The radius of the concentric ring of deprotection is controlled through understanding the diffractive nature of light. The long wavelength of light and the small size of the channels set up a situation of very strong diffraction where diffracted angles are greater than 90°. Light does not pass through the light impermeable polycarbonate surface, but rather is forced to undergo diffraction through the channels. According to Huygen's principle, each channel acts as a secondary point source of light, spherically radiating. Huygen's principle states that all points on a wavefront can be considered as point sources for the production of spherical secondary wavelets. After a time t the new position of the wavefront will be that surface of tangency to these secondary wavelets. A direct consequence of Huygen's principle is the generation of secondary point sources at the exit ends of the channels. A further consequence is that the intensity of excitation light decreases with increasing distance from the center of each channel.

The amount of light exiting the channel and the resulting spherical distribution of light intensity can be calculated. The power of light exiting the channel is given as the cross-sectional area of the channel multiplied by the intensity of the incident light ($I_o$).

$$P = I_o \pi R_{channel}^2$$

Upon exit of the channel, the light becomes a spherically radiating point source. In this particular case, the light source is restricted to radiate to half a sphere (a surface area of $4\pi r^2/2$). The new intensities ($I(r)$) as a function of the radial distance from the center of the channel is given as the power of light exiting the channels divided by the surface area of radiation at a given distance (r).

$$I = \frac{P}{A} = \frac{I_o R_{channel}^2}{2r}$$

For a 60 W light source 1 cm away from the back side of the light impermeable polycarbonate, the intensity decreases from 4.77 W/cm² to 0.43 W/cm² at a distance 35 nm ($R_{equal}$) from the center of the channel, corresponding to a 91% intensity change. From the above equation, the radius of light around each channel can be precisely controlled by the intensity of the light source.

Photosensitive protecting groups have been described in great detail (Pillai, 1980). Depending on the type of covalent linker (amine, hydroxyl, carboxylic acid, ketone, sulfhydryl, etc.), the corresponding photosensitive protecting group is available. For example, amino groups can be protected with nitroveratryloxycarbonyl (NVOC), 2-nitrobenzyloxycarbonyl, and α-substituted 2-nitrobenzyloxycarbonyl groups. The latter two can also be used in the protection of carboxylic acids and hydroxyl groups. Photolytic deblocking of 2-nitrobenzyloxycarbonyl derivatives is straightforward, requiring only a 350 nm lamp and ethanol. The time of deprotection is controlled from 1 to 24 hours.

The invention also encompasses an apparatus for detecting a signal. The apparatus provides a support for the article of manufacture and a sensor for detecting the signals generated by the interaction which occurs as the polymer traverses the interaction station. The apparatus includes a housing with a buffer chamber, a wall defining a portion of the buffer chamber, and having a plurality of openings for aligning polymers, and a sensor fixed relative to the housing, the sensor distinguishing the signals emitted at each opening from the signals emitted at the other of the openings to generate opening dependent sensor signals.

An "opening dependent sensor signal" is a signal which arises at an opening in the wall material as a result of an interaction between a polymer and the station.

The wall within the housing defines at least one and preferably two buffer chambers. A "buffer chamber" as used herein is area which is capable of supporting a liquid medium. The two buffer chambers may be in fluid communications with one another.

The wall has a plurality of openings formed by channels within the wall. A "plurality of openings" within the wall means at least two openings formed by at least two channels. Preferably a plurality of openings is at least 50 openings.

A "sensor" as used herein is a device which responds to a physical stimulus and transmits a resulting impulse in the form of a signal. Sensors include but are not limited to optical sensors, temperature sensors, pressure sensors, auditory sensors, magnetic sensors, electrical, mechanical, radioactive and motion sensors. Preferably the sensor is an optical sensor. As used herein an "optical sensor" is a device which detects and converts input electromagnetic radiation signals an impulse. The impulse can be measured and stored as data. Optical sensors are well known in the art and include microscopes. The sensor is fixed relative to the housing such that the sensor is capable of detecting signals generated at the interaction station. It is not necessary that the sensor be secured or attached directly to the housing.

A microprocessor as used herein is a device for collecting and storing sensor signals. In general a microprocessor is a chip containing several electronic components such as ROM, RAM, registers, and I/O controls. Conventional microprocessors are well known in the electronics arts.

Figure 12:
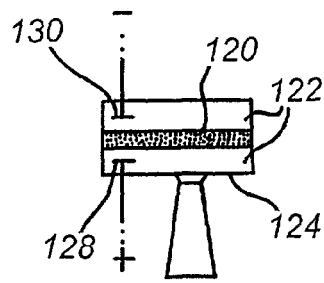
FIG. 12 shows an apparatus constructed to hold a nanochannel (or microchannel) plate which is capable of generating an electric field.

An example of an apparatus constructed to hold a nanochannel (or microchannel) plate (120) which is capable of generating an electric field is presented in FIG. 12. The electric field, created by electrodes (128, 130), is used to draw the DNA through the nanochannels. The exemplary nanochannel plate is immersed in a slightly viscous buffer solution which helps to slow the transit of the polymer through the nanochannel, so as to allow for a longer signal collection time per base. In addition, on either side of the plate are electrodes (128, 130) immersed in the buffer solution. The ensemble of nanochannel plate, buffer compartments (122), and electrodes are contained in an optical quality glass chamber suitable for image analysis and are positioned adjacent to a 60×1.4NA oil objective (126).

As discussed above the use of an electric field to cause the polymer to move linearly through a channel is preferred. The use of an electric field is suitable because the stretched, linear orientation of a polymer in an electric field is favorable for linear crossing of nanochannels. Furthermore, the rate of polymer movement can be controlled by voltage. Lastly, an electric field does not adversely affect FRET.

Light microscopy (Bustamante, 1991; Gurrieri et al., 1990; Matsumoto et al., 1981, Rampino and Chrambach, 1990; Schwartz and Koval, 1989; Smith et al., 1989), linear dichroism (LD) (Akerman et al., 1990; Akerman et al., 1985, Moore et al., 1986), fluorescence-detected LD (Holzwarth et al., 1987), and linear birefringence (Sturm and Weill, 1989; Chu et al., 1990) can be used to study the instantaneous changes in shape of DNA molecules undergoing gel electrophoresis. In these studies DNA is shown to be strongly oriented and stretched.

Guirrieri et al., 1990 has demonstrated linear and stretched conformation of DNA molecules in an electric field. In each of the cases, the DNA molecule is clearly aligned in the direction of the applied electric field. The method used to visualize the DNA molecules combines fluorescent DNA labeling and use of an image intensifier-video camera system (Bustamante, 1991; Houseal et al., 1989; Morikawa and Yanagida, 1981; Matsumoto et al., 1989; Yanagida et al., 1983). The DNA molecules shown are T2 molecules which are 164 kbp long.

The orientation of DNA in an electric field has been well studied with linear dichroism and electric dichroism (Ding et al., 1972; Yamaoka and Charney, 1973; Colson et al., 1974; Hogan et al., 1978; Priore and Allen, 1979; Yamaoka and Matsuda, 1981; Wu et al., 1981). In fact, the first studies done on DNA orientation have been performed with these two techniques. DNA was first studied in solution and then subsequently in electrophoretic gels. Studies both in solution and in gels yield similar results in that the DNA molecules are indeed oriented in the direction of the electric field.

Native DNA exhibits a negative UV linear dichroism (LD) as a result of the preferential orientation of the nucleotide bases nearly perpendicular to the field. The orientation of DNA has been attributed to the presence of either a permanent or an induced dipole moment. For example, Ding et al., 1972 describe their observation of DNA in a Tris-cacodylate buffer diluted in ethanol to give 80% v/v ethanol.

LD data from single electric pulse of 9 V/cm. Duration of pulse is indicated by the horizontal bar. At steady-state, the plateau of the $LD^r$ reads close to −1.5, which means that the DNA is oriented in the direction of the electric field (Akerman et al., 1990).

Akerman et al., 1990 have performed LD studies on pulsed-field gel electrophoresis and similar results are obtained as in solution. Akerman provides a plot of $LD^r$ versus time. $LD^r$ represents orientation in the electric field. A value of −1.5 means that the DNA molecule is oriented in the electric field. A horizontal bar on the x-axis denotes the duration of the electric pulse. The DNA is in 1% agarose. A short time after the beginning of the pulse, the curve plateaus at a $LD^r$ close to −1.5, meaning that the DNA is oriented a short time after the beginning of the pulse. When the pulse is turned off, the DNA no longer orients itself in the field and the $LD^r$ curve no longer remains at −1.5.

The rationale for DNA orientation in electric fields is based on either a permanent or induced dipole moment in DNA. Recall that dipoles align themselves in the direction of electric fields to minimize torque. Hogan et al., 1978 have proposed a rationale for the induction of a dipole moment in DNA that relates to anisotropic ion flow:

In order to explain the dependence of the dichroism on the electric field, the ionic strength of the medium, and the length of the macromolecule, we propose a new model in which anisotropic ion flow produces an asymmetric ion atmosphere around the polyelectrolyte, resulting in an orienting torque. The conclusion from the discussion on DNA alignment in electric fields is that DNA molecules and other polymers align themselves in the direction of electric fields whether in an electrophoretic gel or in solution. Solution studies were performed before electrophoretic studies. The implications of DNA alignment in an electric field further support the fact that DNA molecules and other polymers can be driven across nanochannels in a linear fashion. The unfolded orientation of the DNA is also important in the linear crossing of DNA molecules. As described above DNA and other polymeric molecules can be driven through protein channels in a linear fashion with an electric field. The data described herein rationalize this further and give a theoretical basis to why DNA molecules can behave in such a fashion. Given that DNA has been shown to pass through protein pores in a linear fashion and that DNA molecules align themselves in the direction of electric fields, linear crossing of DNA through nanochannels can be achieved.

The rate at which a polymer moves is also important because the duration of energy transfer is important. The longer an acceptor remains in the donor fluorophore layer, the greater the signal generated. Millisecond integration times allow for unequivocal signal detection. Since the layer of donor fluorophore is roughly 40 Å, the rate of polymer movement that is needed can be approximated as 40 Å/10 ms, or 4000 Å/s. In nanochannel FRET sequencing, the proposed rate is achieved by controlling either the voltage of the applied electric field or the frictional coefficient of the polymer molecule.

The rate of DNA movement can be determined given the equation that defines the movement of a DNA strand in an electric field (Tinoco et al., 1995):

$$u = \frac{ZeE}{f}$$

where Z is the (unitless) numbers of charges, e=1.6022×10$^{-19}$ coulombs, E is the electric field in colts per m, and f is the frictional coefficient in kg/s. The velocity of motion this depends on the magnitude of the electric field E, the net charge of the molecule, and the size and shape of the molecule as characterized by its frictional coefficient, f. The net charge on the molecule is designated by Ze. The frictional coefficient can be determined from the following equation (Tinoco et al., 1995):

$$f = kf_o = k(6\pi\eta r)$$

where h is the viscosity coefficient, r is the radius for a sphere having the same volume as the DNA, k is a shape factor (which for a strand of DNA is about 1.7), and $f_o$ is the frictional coefficient for a sphere having the same volume as the DNA.

Rationally, it can be seen that either the frictional coefficient or the magnitude of the electric field can be used to control the rate of polymer movement. For different voltages in a given system, there are different polymer migration rates. In a similar fashion, larger molecules or molecules in more viscous media have slower molecular mobility. From examples in gel electrophoresis, calculations of the effects of electric field strength, polymer size, and frictional coefficient are possible. It is important to understand a viscous medium can achieve the same desired effects on the frictional coefficient as a gel. Since the frictional coefficient is inversely proportional to the electrophoretic rate, doubling viscosity decreases electrophoretic rate by two-fold.

Electrophoresis in viscous solvents has been performed by a number of groups (Chang and Yeung, 1995; Bello et al., 1994; Jumppanen and Riekkoloa, 1995; Sahota and Khaledi, 1994; Klenchin et al., 1991; Harris and Kell, 1985; Korchemnaya et al., 1978). Sahota and Khaledi, 1994 demonstrate electrophoresis in formamide, which has a viscosity of 3.3 cP at 25° C., triple that of water (0.89 cP, 25° C.). Electrophoresis in formamide is more favorable than in water because formamide has a higher dielectric constant than water and can solubilize many supporting electrolytes. It is commonly used in mixtures with water in electrophoretic buffers. Mixed glycerol solutions, N-methyl-2-pyrrolidone, acetic acid, and N-methyl formamide have also been used (Korchemnaya et al., 1978). A large range of viscosities are possible, ranging from 1 cP to as high as 25 cP (Bellow et al., 1994). The actual viscosity of the solution needed depends on the frictional coefficient of polymer molecules in nanochannels. The net frictional coefficient thus depends on viscosity and also the frictional effects of the nanochannels on the polymer. From the small bore of the nanochannel, there are frictional effects from solvent trapping between the walls of the nanochannels and the labeled polymer. The magnitude of these solvent trapping effects is similar to those arising from gel electrophoresis. As a result, only a slightly viscous solution may enhance the desired rate of polymer movement.

For a given electric field, the electrophoretic mobility for different sized molecules can be determined by knowing the relationship between molecular weight and distance migrated, given as:

$$\log M = a - bx$$

where M is the molecular weight of the nucleic acid and x is the distance migrated (proportional to mobility). a and b are constants for a given electric field.

To summarize, the rate of polymer movement in an electric field can be controlled by the electric field, frictional coefficient, and molecular size. Desired values for the rate of polymer movement are readily achievable.

There are no adverse effects of an electric field on FRET. Since energy transfer is related to short range electrical dipole interactions, the presence of an outside electric field may negatively affect the ability of donor-acceptor pairs to undergo FRET. The presence of an external electric field has no adverse effects on FRET as seen from recent studies performed with FRET primers and gel-based automated DNA sequencing (Glazer and Mathies, 1997; Hung et al., 1996; Ju et al., 1996a; Ju et al., 1996b; Marra et al., 1996; Wang et al., 1996; Wang et al., 1995). FRET primers are used in the labeling of sequencing reaction products because of the large Stoke's shift and thus greater fluorophore discrimination. In these experiments, the FRET labeled DNA fragments are run on a gel and concurrently, in the presence of the electric field, the fragments are detected with a CCD camera and laser. Either a four-color capillary electrophoresis system or Applied Biosystems 373A sequencer is used. These experiments demonstrate that energy transfer occurs in the presence of a strong electric field.

Figure 13:
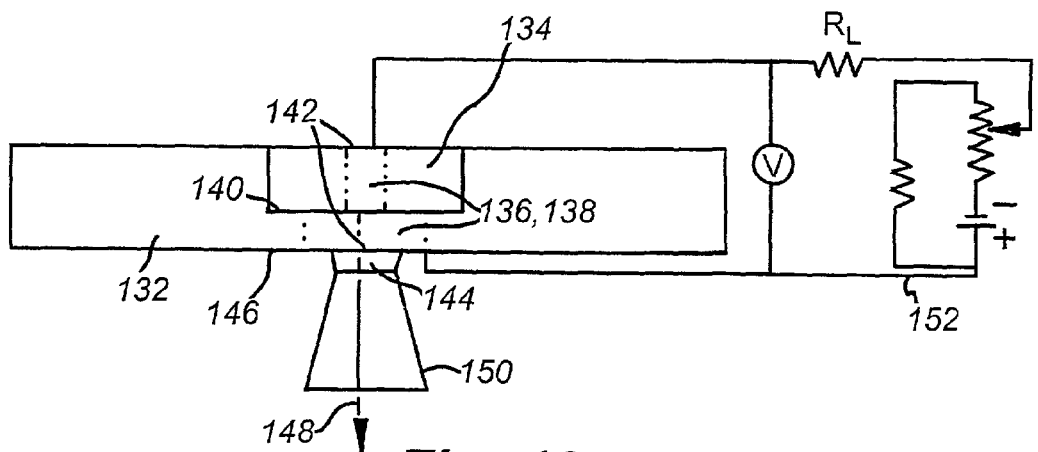
FIG. 13 depicts a nanochannel apparatus which consists of two fused Pyrex cells that hold the nanochannel plate, an upper and lower buffer region, electrodes, an immersion objective and a voltage supply.

An exemplary design of a nanochannel apparatus is shown in FIG. 13, which consists of two fused Pyrex cells (132, 134) that hold the nanochannel plate (140). The upper (136) and lower (138) buffer regions are contained in the smaller (134) and larger (132) Pyrex cells, respectively. The buffer regions are sealed off with glass coverslips (146) that have been modified with indium tin oxide (ITO). Indium tin oxide is a clear conductor which functions in this system as electrodes (142). The electrodes lead to a variable voltage supply (152) consisting of a load resistance $R_L$ (one to several G, to approach a constant current system) and a rheostat-controlled voltage from a voltage source. A voltmeter is connected in parallel. Under the glass coverslip an oil (144) coated immersion objective (150) is positioned to detect fluorescence signals (148).

The polymer is loaded into the upper buffer region and the electric field is used to drive the polymer to the lower chamber. The buffer has the desired viscosity and electrolytic properties. Epiillumination and signal collection are possible through the same 60×, 1.4 NA oil immersion objective. The dimensions of the apparatus are similar to that of a conventional microscope slide (75 mm×25 mm) for ease of mounting. The gap between the nanochannel plate and the glass coverslip is 0.4 mm. A thin coverslip with a thickness of 0.1 mm is shown. These dimensions are preferred because long working distance objectives are available. For instance, the $CFI_{60}$ system from Nikon has 60×, 1.4 NA objectives that can examine specimens over 0.6 mm thick.

A temperature control block is used to prevent Joule heating and thermal fluctuations. The block can surround the nanochannel apparatus and has inlet/outlet ports for coolant flow. The block is hollow to allow uniform temperature control of the nanochannel apparatus. There are inlet/outlet ports on either side of the apparatus that allow the recycling of the coolant through the hollow chamber.

Several groups have used specialized apparatuses for fluorescence microscopy observations of electrophoresis (Rampino and Chrambach, 1991; Matsumoto et al., 1981; Smith et al., 1989; Bustamante, 1991; Gurrieri et al., 1990; Schwartz and Koval, 1989; Smith et al., 1990). The apparatus used by Smith et al., 1990 for the observation of DNA molecules undergoing pulsed-field gel electrophoresis is described:

A 20-µl drop of molten agarose was placed between two microscope coverslips (24 mm×24 mm) and allowed to cool for 10 minutes. This sandwich arrangement was placed on top of a regular microscope slide and sealed at the four corners with fingernail polish.

The slide had been previously prepared with four copper electrodes fixed on it with epoxy adhesive. This apparatus was then refrigerated at about 5° C. for 30 minutes. Molten agarose was dropped over the electrodes to complete the electrical connection, and TBE buffer (0.5×) was occasionally added to keep it wet.

Rampino and Chrambach, 1991 describe a more complex apparatus that has larger buffer regions, platinum strip electrodes, and a region for coolant flow. The entire apparatus is mountable on the microscope stage. The actual gel itself is sandwiched between two glass coverslips and placed in the center of the apparatus, in contact with buffer blocks on either side. The design allows for a homogenous electric field and temperature control. In contrast to the apparatus described above, the Rampino and Chrambach apparatus is designed for standard and not pulsed-field gel electrophoresis.

Briefly, a description of how the apparatus (shown in FIG. 13) of the invention functions in relation to polymer is described below. A polymer such as DNA is labeled (intrinsically or extrinsically) by the methods of the invention or any other method known in the art. The labeled DNA is placed in a buffer solution, which is preferably slightly viscous. The buffer is added to the upper buffer chamber 136. An electric field is created using the electrodes and the DNA is caused to enter the nanochannels of the nanochannel plate (140) in a linear manner. As the labeled DNA emerges from the other side of the nanochannel plate the label is caused to interact with an agent or the environment surrounding the channel to produce a signal or polymer dependent impulse which is detected by the detection device. The detected signal or polymer dependent impulse is stored and processed to reveal structural information about the polymer.

A final aspect of the invention encompasses a method for preparing nucleic acids for use according to the methods of the invention as well as for any other use in which it is desirable to utilize randomly labeled nucleic acids. The method involves the steps of contacting a dividing cell with a nucleotide analog, isolating from the cell nucleic acids that have incorporated the nucleotide analog, and modifying the nucleic acid with incorporated nucleotide analog by labeling the incorporated nucleotide analog. A "nucleotide analog" as used herein is a molecule which can be substituted for A, T, G or C but which has a modified structure. Nucleotide analogs include for example but are not limited to a brominated analog, 2,4-dithiouracil, 2,4-Diselenouracil, hypoxanthine, mercaptopurine, 2-aminopurine, and selenopurine. The incorporated nucleotide analog may be labeled with an agent selected from the group consisting of a light emitting compound, a quenching source and a fluorescence excitation source.

A dividing cell is "contacted" with a nucleotide analog by any means known in the art for incorporating nucleotides into living cells. For instance the nucleotide analog may be added to the cell culture medium and taken up by the cell naturally. In order to optimize the uptake of the nucleotide analog the dividing cell may be growth arrested using conventional means prior to adding the nucleotide analog to the medium and then the arrest removed to allow the cells to reenter the cell division cycle once the nucleotide analog is added to the medium. The nucleic acids having the incorporated nucleotide analog may then be isolated after the cells have reentered and completed at least one cell division cycle.

An example of a method for incorporating a nucleotide analog into DNA is provided in Bick and Davidson, *Proc. Nat. Acad. Sci.*, 71:2082-2086 (1974). Bick and Davidson grew the BrdU-dependent cell line, B4, in a basic growth medium of Dulbecco's modified Eagle's medium supplemented with 10% fetal-calf serum (E medium) containing 0.1 mM BrdU. 100-mm Falcon plastic tissue culture dishes were inoculated with $10^6$ B4 cells in E medium containing 0.1 mM hypoxanthine, 0.4 μM aminopterin, and 10 μM BrdU (E-HAB medium) and the cells were passaged three times at high density ($5\times10^5$ cells per 100-mm dish) in E-HAB medium over six weeks. The cells were then plated at low density (1000 cells per 6-mm dish) in E-HAB medium and three weeks later, approximately 10 large colonies were observed in each dish. The cells from one dish were harvested and maintained as a new cell line called HAB. Because of the expected photosensitivity of BrdU-containing cells, the HAB cells were at all times protected from environmental lighting.

After 100 cell generations in E-HAB medium, an aliquot of HAB cells was transferred back to E medium. A new subline of cells, called HAB-E, was isolated and maintained in E medium.

Bick and Davidson grew the cell in the media (described above) to which was added $H_3^{32}PO_4$ (New England Nuclear Corp.) at an activity of 2 μCi/ml. After 2-3 population doublings the cells were harvested and DNA was isolated as described in Davidson and Bick (*Proc. Nat. Acad. Sci.*, 70:138-142 (1973)) except that after the first phenol extraction, DNA preparations were routinely treated with RNase A at a concentration of 50 μg/ml for 60 min at 37°. After a second phenol extraction, the DNA was extensively dialyzed against 10 mM Tris-HCl, 10 mM pH 7.6, 1 mM EDTA, and then finally dialyzed against 10 mM Tris-HCl pH 7.6, 1 mM EDTA. Other methods for isolating DNA are well known in the art. See e.g., Sambrook. et al., *Molecular Cloning: A Laboratory Manual,* 2nd edition, Cold Spring Harbor Laboratory Press, 1989).

The method of the invention for preparing nucleic acids is referred to hereinafter as in vitro base specific labeling (IBSA). IBSA involves the culture of cells derived from a subject in the presence of nucleotide analogs. The nucleotide analogs are either capable of subsequent chemical modifications, have a high molar extinction coefficient in the donor emission wavelengths, or have linkers for the attachment of acceptor labels. The most important analogs are the ones which contain functional groups that do not interfere with base pairing during DNA replication. The 8-substituted purines, 5-substituted pyrimidines, and 6-substituted pyrimidines satisfy this criteria.

Figure 14:
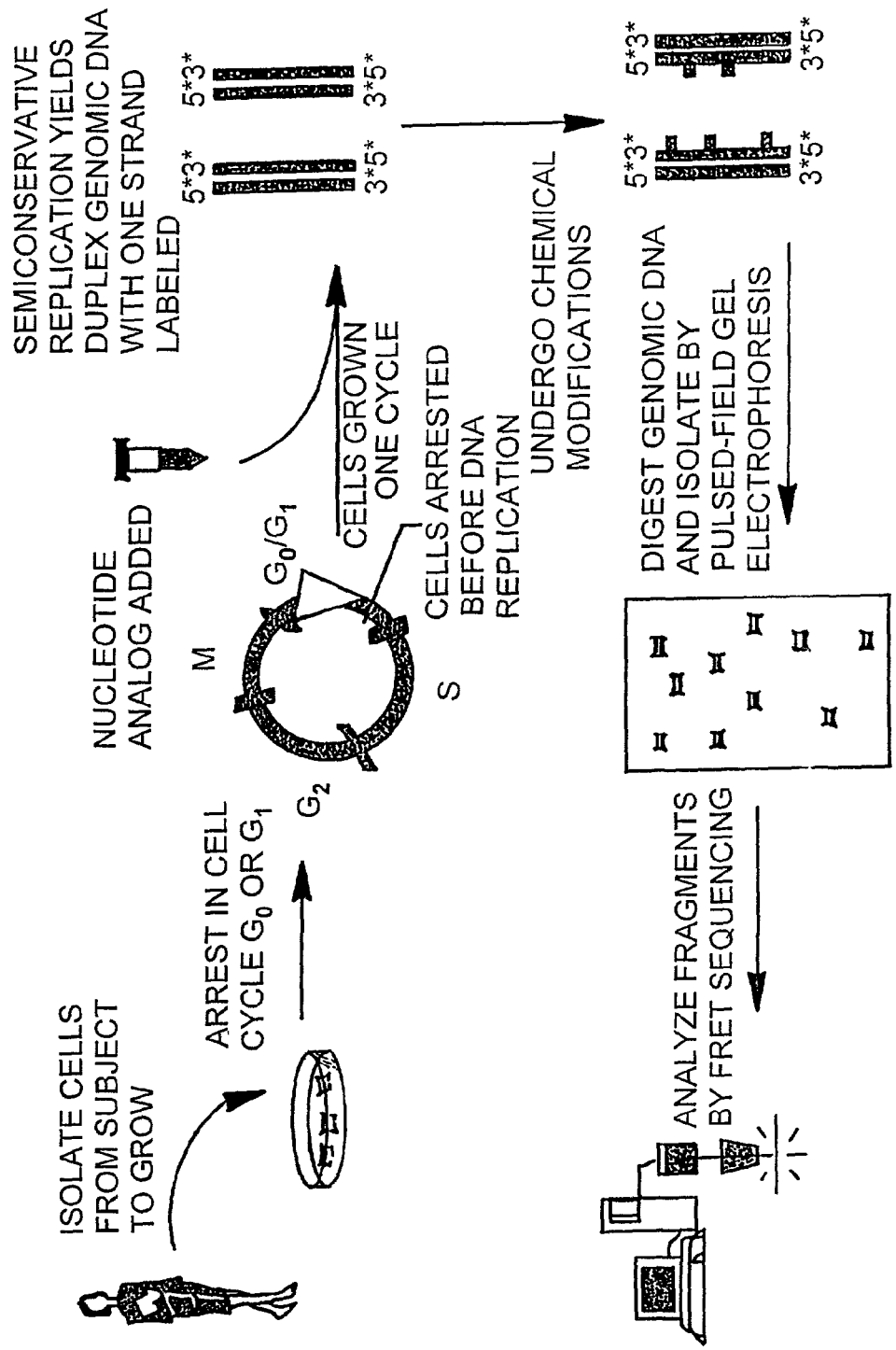
FIG. 14 is a schematic diagram of in vitro base specific (IBSA) labeling

A non-limiting example of an IBSA scheme is set forth in detail below. The method is outlined in FIG. 14 and covers the steps from initial DNA isolation to genomic labeling and to final sequence analysis. Cells are isolated from the subject and then grown. At a time when there are enough cells to provide adequate genetic material, the cells are arrested in the cell cycle. The arrest can occur at any point in the cycle as long as it does not interrupt the S phase. Nucleotide analogs that can be easily chemically derivitized, such as 8-bromo-2'-deoxypurines and 5-bromo-2'-deoxypyrimidines, are added to the growth medium. The cells are then grown for one cycle and the genomic DNA from the cells are isolated. The resulting DNA is a chimera of labeled and unlabeled DNA, a product of semiconservative replication. The advantage in having the DNA with only one strand labeled is so that the resultant duplex DNA can be used in a sequencing method of the invention.

The genomic DNA is broken down into sizes of approximately 100 kb. The genomic DNA is chemically labeled and end-labeled at this point. The advantage of culturing cells in brominated analogs is that such a modification activates the bases for further modification, the addition of acceptor labels to the bases. For a human genome, there are approximately thirty thousand fragments. The fragments are analyzed simultaneously by the sequencing methods of the invention. Fragments of similar size and potential sequences are grouped together and population analyses are performed to generate DNA sequence information. Sequencing of a genome can be completed in approximately six hours. The time from isolation of a subject's cell to the end of sequencing is approximately one week. The following paragraphs describe each individual step in detail.

The first step to the outlined scheme is cell culture and cell cycle arrest. The purpose of the cell cycle arrest is to generate a synchronous population of cells which can undergo DNA replication at the same time to ensure all the resultant DNA will be a chimera of labeled and unlabeled DNA. There are many methods to synchronize cells including methods which arrest cells at either M or S phase. Only an M phase block would produce the desired genomic chimeras. Examples of metaphase inhibitors include nitrous oxide under pressure, vinblastine (Marcus & Robbins, 1963), and colcemid. Colcemid blocks cells in metaphase but can be reversed by washing (Mitchison, 1971; Kato & Yoshida, 1970; Stubblefield, 1968). Cells are grown for a few hours in colcemid, resulting in a synchronous culture (Wunderlich & Peyk, 1969). Nitrous oxide under pressure (Rao, 1968) is advantageous in that it can be easily removed. Removal of the block and addition of the desired brominated base analog allows for a synchronous entrance into S phase.

The nucleotide analogs which can be used include but are not limited to 8-bromo-2'-deoxyadenosine, 8-bromo-2'-deoxyguanosine, 5-bromo-2'-deoxycytidine, and 5-bromo-2'-deoxyuridine. These brominated nucleotide analogs are activated for coupling to nucleophiles (Traincard et al., 1983; Sakamoto et al., 1987; Keller et al., 1988; Hermanson, 1996). Coupling of amine-containing acceptor labels and fluorophores to the base analogs is done at ambient temperatures (35° C.). The final positions of the acceptor labels are such that the base-pairing of the labeled fragment is not affected.

Brominated nucleotide analogs are commercially available (Sigma Corp., Fluka Inc., Fisher Scientific, Inc.) or can be prepared by reaction with brominating reagents. Hermanson, 1996 outlines a protocol for bromination of DNA at thymines, cytidines, and guanosines using N-bromosuccinimide (NBS). Adenine residues are prepared from other methods which do not require NBS. For an example, 8-bromo-2'-deoxyadenosine and 8-bromo-2'-deoxyguanosine can be synthesized by reaction of the native base with bromine water (Ikehara et al., 1969a; Ueda et al., 1974; Faerber & Scheit, 1971; Kochetkov et al., 1968). Bromination at the eighth position of the purines can also achieved via the nucleotide morpholidate (Lang et al., 1968; Ikehara et al., 1969b). The solvent condition for bromination is especially important. Bromination of 2'-deoxyadenosine does not take place in dimethylformamide at 0° C., but if the reaction is conducted at 50-60° C. in glacial acetic acid, 8-bromo-2'-deoxyadenosine is formed relatively easily (Guéron et al., 1967; Rahn et al., 1965).

Brominated and other base analogs have been demonstrated to be efficiently incorporated into genomic DNA during cell culture (Balzarini et al., 1984). A particular example is the incorporation of 5-bromo-2'-deoxyuridine into cells used for flow cytometry. 5-bromo-2'-deoxyuridine is incorporated into newly synthesized DNA in the place of thymidine (Crissman et al., 1990; Poot & Hoehn, 1990; Böhmer, 1990; Gaines et al., 1996; Nicolas et al., 1990). The percentage of substitution of base analog can be very high as according to Bick and Davidson, 1974 in their paper discussed above and titled, "Total Substitution of Bromodeoxyuridine for Thymidine in the DNA of a Bromodeoxyuridine-Dependent Cell Line. The following is a paragraph from this paper:

To obtain total substitution, BrdU-dependent cells were exoposed to culture medium containing aminopterin, a powerful inhibitor of thymidine biosynthesis, and BrdU in the absence of added thymidine . . . We report here the isolation of a cell line in which at least 99.8% of the thymidine in the nuclear DNA has been replaced by BrdU.

In the current proposed random one-base labeling scheme, percentages as high as 99.8% substitution are not necessary but such data gives insight into possibilities of cellular incorporation of base analogs. Other brominated base analogs can be similarly incorporated into mammalian cells with ease (Stewart et al., 1968). A few examples of non-bromine base analogs that have been incorporated in this manner include 2-aminopurine (Glickman, 1985), 5-propynyloxy-2'-deoxyuridine, and 5-ethynyl-2'-deoxyuridine (Balzarini et al., 1984).

After generation of the appropriately brominated DNA chimeras through cell culture, the chimeric genomic DNA is prepared for analysis by performing several steps, including an optional step of chromosome sorting. 100 kb DNA fragments can be generated from the partial digestion of flow sorted chromosomes. The optional flow sorting step has been covered in detail by many manuals and textbooks (de Jong et al., 1989; Fawcett et al., 1994) and will not be discussed in detail. In brief, the cells are arrested in metaphase by the addition of colcemid. Several million of the cultured cells are gently lysed to release the metaphase chromosomes into a suspension buffer in which they are stained with one or more fluorescent dyes. The target chromosomes are then identified by their pattern of fluorescence emission, using either a single fluorophore in a one laser system, or two fluorophores in a two laser detection system. The sorted chromosomes are then prepared and partially digested as according to protocols described by Glover and Hames, 1995 in DNA Cloning 3. Sizes on the order of 100 kb are obtained.

Fluorophore labeling of the brominated DNA can be done either before or after partial digestion. The base bromination activates the bases for nucleophilic displacement. Many different fluorophores with amine/hydrazine groups can be used including the popular dyes fluorescein, coumarin, eosin, rhodamine, and Texas Red (Molecular Probes, Oreg.). These have absorptions and emissions in the visible region. The amine group on these fluorophores attack the 8 position of the purines and the 5 position of the pyrimidines, undergoing a nucleophilic displacement reaction. The experimental protocol for the displacement reaction is described by Hermanson, 1996. A modified outline of the labeling scheme described is given below.

Protocol for Labeling Brominated DNA

1. Dissolve a hydrazine or amine-coupled fluorophore in water at a concentration of 80-100 mM.
2. Add 25 μl of the fluorophore solution to a bromine-activated DNA solution.
3. React for 1 h at 50° C.
4. Purify by ethanol precipitation. Add 20 μl of 4 M LiCl and 500 μl of ethanol (chilled to −20° C.). Mix well.
5. Store at −20° C. for 30 min, then separate the precipitated DNA by centrifugation at 12,000 g.
6. Remove the supernatant and wash the pellet with 70% and 100% ethanol, centrifuging after each wash.

Redissolve the labeled DNA pellet in water and store at −20° C.

From the genomic partial digestion, approximately thirty thousand 100 kb fragments are created. The fragments are end-labeled either with terminal transferase or through ligation to short labeled polynucleotides. The fluorescent labels incorporated by end-labeling are uniquely identified either by different spectral absorbances or a specific sequence of labels (as in the ligation scheme). After end-labeling, the prepared DNA is subject to nanochannel FRET sequencing as described above. The data is sorted by fragment 'size and potential sequence. Through population analysis, the DNA sequence is generated.

Figure 15:
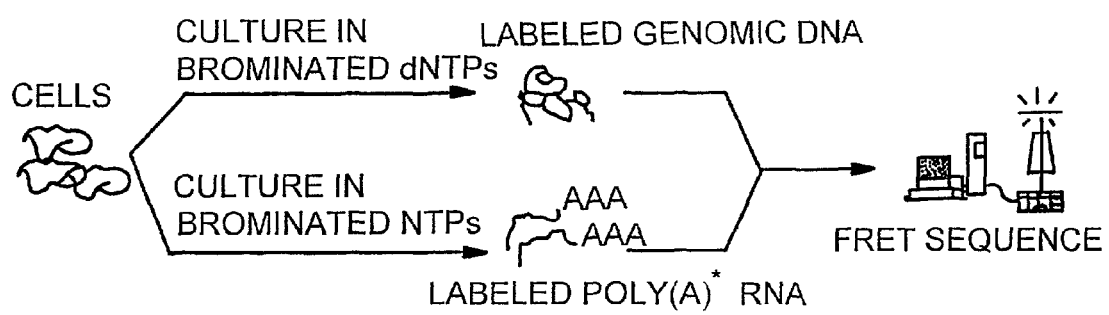
FIG. 15 shows the general scheme for deciphering DNA sequence from IBSA labeling.

FIG. 15 presents the general scheme for deciphering DNA sequence from IBSA labeling. A sample of genomic DNA has two of its bases labeled (in this case A and C). The end-labeled and internally labeled DNA fragments are analyzed by FRET sequencing. The resulting data is sorted by fragment size and potential sequence. Potential sequence is defined as the pattern of sequence-specific FRET signals generated for a particular fragment of DNA. A potential sequence does not give sequence information, but rather allows DNA molecules to be uniquely identified. Population analyses are performed to determine all the positions of the A's and C's on each of the fragments. Complementary strands are paired. The process of determining base position is repeated for only one of the bases (A). Comparison of the resulting data for one labeled base and two labeled bases generates the DNA sequence.

Hundred kilobase fragments are not always desired for sequencing. Expression mapping and single gene sequencing require much shorter labeled fragments. The generation of shorter labeled fragments can be achieved by nick translation, primer extension, and the polymerase chain reaction (PCR). In addition, smaller fragments can also be analyzed by a modification of the Sanger reaction and the use of terminal transferases. With enzymatic methods, large nucleotide analogs can often be incorporated (Hermanson, 1996).

In primer extension, modified nucleoside triphosphates are added to a DNA template using a defined amount of the desired primer. The form of polymerase used is the Klenow fragment, which lacks the 5'-3' exonuclease activity of intact $E.$ $coli$ DNA polymerase I (Kessler et al., 1990; Feinberg and Vogelstein, 1983, 1984). Equivalent enzymes are the Sequenase 2.0 and T7 polymerases. This method is a simple method of preparing internally labeled target DNA. Using the method, synthesis of large internally labeled DNA fragments with lengths greater than 10 kilobases have been synthesized with one of the nucleotides replaced by a modified base. A brief summary of the protocol involves using Sequenase 2.0 (Amersham). The annealing reaction consists of 1 µl primer (0.5 pmol/µl), 2 µl Sequenase buffer (5×), 5 µg plasmid DNA, and 10 µl sterile distilled water. After incubation in a 65° C. waterbath for 2 minutes, annealing is allowed to occur at 30° C. for 30 minutes. The actual reaction mixture consists of 10 µl of annealing reaction (primer-template), 1 µl dithiothreitol (0.1 M), 1 µM of each dNTP, 0.1 µM of a fluorophore dNTP, and 0.025 U/µl of Sequenase. After mixing, the reaction is allowed to proceed at room temperature for 15 minutes.

Using primer extension, Ambrose et al. (1993) and Harding and Keller (1992) have demonstrated the synthesis of large fluorescent DNA molecules. In their experiments, complete replacement of one pyrimidine with a fluorophore analog was achieved in DNA longer than 7 kb. Fluorescent DNA between 5 to 7 kb in length, in which two pyrimidines are completely labeled, have also been reported by the same authors. Large fragments using other unusual base analogs such as 7-(2-oxoethyl)guanine, 2'-amino-2'-deoxycytidine, 8-oxopurine, and N-4-aminodeoxycytidine have been synthesized as well (Barbin et al., 1985; Purmal et al., 1994; Aurup et al., 1994; Negishi et al., 1988).

Nick translation takes advantage of the ability of $Escherichia$ $coli$ DNA polymerase I to combine the sequential addition of nucleotide residues to the 3'-hydroxyl terminus of a nick [generated by pancreatic deoxyribonuclease (Dnase) I] with the elimination of nucleotides from the adjacent 5'-phosphoryl terminus (Meinkoth & Wahl, 1987; Rigby et al., 1977; Langer et al., 1981; Höltke et al., 1990). Many modified bases have been incorporated by nick translation (Meffert and Dose, 1988; Gebeyehu et al., 1987; Gillam and Tener, 1986). DNA polymerase I causes breaks to be filled as rapidly as they are formed, incorporating the desired nucleotides into the original strands. Since a quantity of labeled nucleoside triphosphates are present during the reaction, the labels get incorporated and the parent strands are modified. Nick translation involves a mixture of the double-stranded DNA target, 1 µl of DNAse I at a concentration of 2 ng/ml, 1 µl each of three types of unmodified deoxynucleoside triphosphates (dNTPs at 100 µM concentration), 1 µl of a labeled dNTP (at 300 µM), 32 µl water, and 1 µl of DNA polymerase containing 5-10 units of activity. Reaction proceeds for 1 h at 15° C. Reaction is quenched by 4 µl of 0.25 M EDTA, 2 µl of 10 mg/ml tRNA, and 150 µl of 10 mM Tris, pH 7.5. Labeled DNA is purified by ethanol precipitation (Bethesda Research Laboratories, New England Nuclear, and Amersham).

Direct PCR labeling not only incorporates the desired label into the target DNA, but also amplifies the amount of labeled DNA (Saiki et al., 1985, 1988). PCR uses the heat-stable forms of DNA polymerase, most commonly, the Taq polymerase from $Thermus$ $aquaticus$. Taq polymerase has the capability to incorporate labels into growing DNA copies with each cycle of PCR. In this manner, DNA fragments up to 3 kb can be labeled. Wiemann et al., 1995 describe the method of internally labeling PCR products with fluorescein-15-dATP, a protocol that can be applied to other fluorophores. The reaction mixture for PCR incorporation of fluorophores consists of 1 µM of each primer, 200 µM of each DNTP, 10 µM of a fluorophore-dNTP, and 0.025 U/µl of Taq polymerase (Perkin-Elmer, Norwalk, Conn.). The reaction buffer consists of 10 mM Tris-HCl, pH 8.3, 50 mM KCl, 1.5 mM $MgCl_2$, and 0.01% (wt/vol) gelatin. PCR is performed using thirty cycles.

Sequencing reactions generated by the Sanger method can also be analyzed with the aid of enzymatic labeling. Each chain-terminated fragment is labeled with a 5' and 3' fluorophore. The 5' fluorophore is incorporated as part of the primer and the 3' end-label is added by terminal transferase. Terminal transferase labeling was originally developed using radiolabeled nucleoside triphosphates (Roychoudhury et al., 1979; Tu and Cohen, 1980). The technique was later applied to non-radioactive nucleotide analogs (Kumar et al., 1988). The technique involves addition of the target DNA to (a) 20 µl of 0.5 M potassium cacodylate, 5 mM $CoCl_2$, 1 mM DTT, pH 7, (b) 100 µM of a modified deoxynucleoside triphosphate, 4 µl of 5 mM dCTP, and 100 µl of water. Terminal transferase is added to a final concentration of 50 units in the reaction mixture and reacted for 45 minutes at 37° C. (Hermanson, 1996).

A post-labeling procedure can be used as well. In this method, a base analog with a linker arm for attaching a fluorophore is initially incorporated into the DNA using the methods described above. Subsequent attachment of fluorophores to the linker arms is possible using covalent linking techniques such as those described by Waggoner (1995). Jett et al. (1995) has demonstrated the full length synthesis of M13 DNA (7250 bp) with complete incorporation of one of the following: 5-(3-aminopropynyl)-dCTP, 5-(3-aminoallyl)-dCTP, or 5-(3-aminoallyl)-dUTP. Covalent fluorophore attachment to the linkers was also shown. The advantage of this technique is that the label need not consist of individual fluorescent molecules, but could be larger molecules with greater number of dyes. Such examples include phycobiliproteins, dye-filled beads, tagged proteins, or chains of fluorescent tags.

Each of the foregoing patents, patent applications and references is herein incorporated by reference in its entirety. Having described the presently preferred embodiments in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

1. Akerman, B., Jonsson, M., Moore, D., and Schellman, J. 1990. Conformational dynamics of DNA during gel electrophoresis studied by linear dichroism spectroscopy. In *Electrophoresis of Large DNA Molecules* (Lai, E. and Birren, B. W., Eds). Cold Spring Harbor Laboratory Press, New York.
2. Akerman, B. Jonsson, M., and Nordén. 1985. Electrophoretic orientation of DNA detected by linear dichroism spectroscopy. *J. Chem Soc. D. Chem. Commun.* 422.
3. Alkens, R. 1992. Properties of low-light level slow-scan detectors in *Fluorescent and Luminescent Probes for Biological Activity*. Mason, W. T. (Ed.) Harcourt Brace & Company, Cambridge, England.
4. Allen, M. J., Balooch, M., Subbrah, S., Tench, R. J., Sickhaus, W., and Balhorn, R. 1991. *Scanning Microsc.* 5:625.
5. Ambrose, W. P., Goodwin, P. M., Jett, J. H., Johnson, M. E., Martin, J. C., Marrone, B. L, Schecker, J. A., wilkerson, C. W., and Keller, R. A. 1993. Application of single molecule detection to DNA sequencing and sizing. *Ber. Bunsenges. Phys: Chem.* 97:1535-1542.
6. Andersson-Engels, S., Johannson, J., and Svanberg, S. 1990. Multicolor fluorescence imaging systems for tissue diagnostics. *Proc. SPIE—Bioimag. Two-Dimens. Spectrosc.* 1205:179-89.
7. Aurup, H., Tuschl, T., Benseler, F., Ludwig, J., and Eckstein, F. 1994. Oligonucleotide duplexes containing 2'-amino-2'-deoxycytidines: thermal stability and chemical reactivity. *Nucleic Acids Res.* 22:20-4.
8. Arts, E., Kuiken, J., Jager, S., and Hoekstra, D. 1993. Fusion of artificial membranes with mammalian spermatozoa. Specific involvement of the equatorial segment after acrosome reaction. *Eur. J. Biochem.* 217:1001-9.
9. Bains, W. 1991. Hybridization methods for DNA sequencing. *Genomics,* 11:294-301.
10. Bains, W. 1997. Hybridization for sequencing of DNA: In *Molcular Biology and Biotechnology*, R. A. Meyers, Ed. VCH Publishers, New York.
11. Balzarini, J., De Clercq, E., Ayusawa, D., and Seno, T. 1984. Thymidylate synthetase-deficient mouse FM3A mammary carcinoma cell line as a tool for studying the thymidine salvage pathway and the incorporation of thymidine analogues into host cell DNA. *Biochem. J.* 217245-52.
12. Barbin, A., Laib, R. J., and Bartsch, H. 1985. Lack of miscoding properties of 7-(2-oxoethyl)guanine, the major vinyl chloride-DNA adduct. *Cancer Res.* 452440-4.
13. Bello, M. S., de Besi, R., Rezzonico, R., Righetti, P. G., and Casiraghi, E. 1994. Electroosmosis of polymer solutions in fused silica capillaries. *Electrophoresis* 15:623-6.
14. Bezrukov, S. M. Vodyanoy, I., and Parsegian, V. A. 1994. Counting polymers moving through a single ion channel. *Nature.* 370:279.
15. Bick, M. D. and Davisdon, R. L. 1974. Total substitution of bromodeoxyuridine for thymidine in the DNA of a bromodeoxyuridine-dependent cell line. *Proc. Nat. Acad. Sci. USA* 71:2082-2086.
16. Bignold, L. P. 1987. A novel polycarbonate (Nuclepore) rembrane demonstrates chemotaxis, unaffected by cherokinesis, of polymorphonuclear leukocytes in the Boyden chamber. *J. of Immunological Methods.* 105:275-280.
17. Bloom, L. B., Turner, J., Kelman, Z, Beechem, J. M., O'Donnell, M., and Goodman, M. F. 1996. Dynamics of loading the beta sliding clamp of DNA polymerase III onto DNA. *J. Biol. Chem* 271:30699-708.
18. Böck, G., Hilchenbach, M., Schauenstein, K. and Wick, G. 1985. Photometric analysis of antifading reagents for immunofluorescence with laser and conventional illumination sources. *J. of Histochemistry and Cytochemistry* 33:699-705.
19. Böhmer, R. 1990. Cell division analysis using bromodeoxyuridine-induced suppression of Hoechst 33258 fluorescence. *Methods in Cell Bology* 18:173-84.
20. Bruno, G., Capezzuto, P., and Madan, A. 1995. *Plasma deposition of amorphous silicon-based materials*. Academic Press, Boston.
21. Bustamante, C. 1991. Direct observation and manipulation of single DNA molecules using fluorescence microscopy. *Annu. Rev. Biophys. Biophys. Chem.* 20:415-46.
22. Buurman, E. P., Sanders, R., Draaijer, A. Van Veen; J. J. F., Houpt, P. M., and Levine, Y. K. 1992. Fluorescence lifetime imaging using a confocal laser scanning microscope. *Scanning* 14:155-59.
23. Cantor, C. R., Mirzabekov. A., and Southern, E. 1992. Report on the sequencing by hybridization workshop. *Genomics.* 13:1378-1383.
24. Castro, A. and Shera, E. B. 1995. Single-molecule electrophoresis. *Anal. Chem.* 67:3181-3186.
25. Chang, H. T. and Yeung, E. S. 1995. Dynamic control to improve the separation performance in capillary electrophoresis. *Electrophoresis.* 16:2069-73.
26. Chen, D. and Dovichi, N. J. 1996. Single-molecule detection in capillary electrophoresis: molecular shot noise as a fundamental limit to chemical analysis. *Anal Chem.* 68:690-696.
27. Chu, G. Vollrath, D., and Davis, R. W. 1986. Separation of large DNA molecules by contour-clamped homogeneous electric fields. *Science* 234:1582.
28. Church, G. M. and Kieffer-Higgins, S. 1988. Multiplex DNA sequencing. *Science* 240:185-88.
29. Clark, I., MacManus, J. P., Banville, D.; and Szabo, A. G. 1993. A study of sensitized lanthanide luminescence in an engineered calcium-binding protein. *Anal. Biochem.* 210:1-6.
30. Clegg, R. M., Feddersen, B., Gratton, E., and Jovin, T. M. 1991. Time-resolved imaging microscopy. *Proc. SPIE—Int. Soc. Opt Eng.* 1640:448-460.
31. Clegg, R. M. 1992. Fluorescence resonance energy transfer and nucleic acids. *Methods in Enzymology.* 211:353-379.
32. Clegg, R. M., Murchie, A. I. H., Zechel, A., and Lilley, D. M. J. 1993. Observing the helical geometry of double-stranded DNA In solution by fluorescence resonance energy transfer. *Proc. Natl. Acad. Sci. USA.* 90:2994-98.
33. Clegg, R. M. 1995. Fluorescence resonance energy transfer. *Curr. Opin. Biotech.* 6:103-110.
34. Colson, P., Houssler, C. and Fredericq, E. 1974. *Biochim. Biophys. Acta* 340:244-61.
35. Crain, P. F. 1990. *Mass Spectrom. Rev.* 9:505-54.
36. Crissnan, H. A. and Steinkamp, J. A. 1990. Detection of bromodeoxyuridine-labeled cells by differential fluorescence analysis of DNA fluorochromes. *Methods in Cell Biology* 33:199-206.

37. Cundall, R. B. and Dale, R. E. (1983). *Time-Resolved Fluorescence Spectroscopy in Biochemistry and Biology*. Plenum, New York.
38. Dash, J. G. 1975. *Films on solid surfaces: the physics and chemistry of physical adsorption*. Academic Press, New York.
39. Davis, L, Fairfield, F., Hammond, M., Harger, C., Jett, J., and Keller, R. 1992. Rapid DNA sequencing based on single-molecule detection. *Los Alamos Science.* 20:280-6.
40. Davis, L. M., Fairfield, F. R., Harger, C. A., Jett, J. H., Keller, R. A., Hahn, J. H. Krakowski, L. A., Marrone, B. L, Martin, J. C., Nutter, H. L., Ratliff, R. L., Shera, E. B., Simpson, D. J. and Soper, S. A. 1991. *Genet. Anal. Tech. Appl.* 8:1-7.
41. de Jong, P. J., Yokobata, K., Chen, C., Lohman, F., Pederson, L., McNinch, J. et al. 1989. *Cytogenet. Cell Genet.* 51:985.
42. Ding, D. W., Rill, R. and Van Holde, K. E. 1972. *Biopolymers* 11:2109-2124.
43. Dozier, J. 1988 HIRIS—The high resolution imaging spectrometer.: *Proc. SPIE—Recent Adv. Sensors, Radiometry Data Process. Remote Sens.* 924:10-22.
44. Drmanac, R., Labat, I., Brukner, I., and Crkvenjakov, R. 1989. Sequencing of megabase plus DNA by hybridization: theory of the method. *Genomics* 4:114-128.
45. Drmanac, R., Drmanac, S., Jarvis, J., and Labat, I. 1994. Sequencing by hybridization. In *Automated DNA Sequencing and Analysis Techniques*, J. Craig Ventor, Ed. Academic Press, London.
46. Eigen, M. and Rigler, R. 1994. Sorting single molecules: applications to diagnostics and evolutionary biotechnology. *Proc. Natl. Acad. Sci. USA.* 91:5740-7.
47. el-Deiry, W. S., et al., 1993. WAFl, a potential mediator of p53 tumor suppression. *Cell* 75:817-825.
48. Faerber, P. and Scheit, K. H. 1971. *Chem. Ber.* 104:456-460.
49. Fairclough, R. H., and Cantor, C. H. 1978. The use of singlet-singlet energy transfer to study macromolecular assemblies. *Methods in Enzym.* 347-79.
50. Fan, F. F. and Bard, A. J. 1995. Electrochemical detection of single molecules. *Science* 267:871-4.
51. Fawcett, J. J., Longmire, J. L, Martin, J. C., Deaven, L. L., and Cram, L. S. 1994. Large-scale chromosome sorting. *Methods in Cell Biology* 42:319-331.
52. Feinberg, A. P., and Vogelsteln, B. 1983. A technique for radiolabeling DNA restriction endonuclease fragments to high specific activity. *Anal. Biochem.* 132:6-13.
53. Feinberg, A. P. and Vogelstcin, B. 1984. A technique for radiolabeling DNA restriction endonuclease fragments to high specific activity. (Addendum). *Anal. Biochem.* 137:266-7.
54. Ferreira, M. and Rubner, M. F. 1995. Molecular-level processing of conjugated polymers. 1. layer-by-layer manipulation of conjugated polymers. *ACS* 28:7107-7114.
55. Ferrell, T., Allison, D., Thundat, T., and Warmack, R. 1997. Scanning tunneling microscopy in sequencing of DNA. In *Molecular Biology and Biotechnology*, R. A. Meyers, Ed. VCH Publishers, New York
56. Förster, T. 1965. In *Modem Quantum Chemistry*, Vol. III (Sinanoglu, O., Ed.), pp. 93-137, Academic Press, New York.
57. Fou, A. C. and Rubner, M. F. 1995. Molecular-level processing of conjugated polymers. 2. layer-by-layer processing of in-situ polymerized p-type doped conducting polymers. *ACS* 28:7115-7120.
58. Franklin, A. L. and Filion, W. G. 1985. A new technique for retarding fading of fluorescence: DPX-BME. *Stain Technology* 60:125-35.
59. Frey, M. W., Sowers, L. C., Millar, D. P., and Benkovic, S. J. 1995. The nucleotide analog 2-aminopurine as a spectroscopic probe of nucleotide incorporation by the Klenow fragment of *Escherichla coli* polymerase I and bacteriophage T4 DNA polymerase.
60. Fu, T. J., Sanders, G. M., O'Donnell, M., and Geiduschek, E. P. 1996. Dynamics of DNA-tracking by two sliding-clamp proteins. *EMBO J.* 15:4414-22.
61. Gadella, T. W. J., Jovin, T. M., and Clegg, R. M. 1993. Fluorescence lifetime imaging microscopy (FLIM): spatial resolution of microstructures on the nanosecond time scale. *Biophysical Chemistry.* 48:221-239.
62. Gains, H., Andersson, L, and Biberfeld, G. 1996. A new method for measuring lymphocyte proliferation at the singlecell level in whole blood cultures by flow cytometry. *J. of Immunological Meth.* 195:63-72.
63. Garini, Y., Katzir, N., Cabib, D., and Buckwald, R. A. 1996. Spectral bio-imaging. In *Fluorescence Imaging Spectroscopy and Microscopy* (Wang, X. -F. and Herman, B., Eds.), John Wiley & Sons, New York.
64. Garland, P. B. and Moore, C. H. 1979. Phosphorescence of protein-bound eosin and erythrosin: a possible probe for measurements of slow rotational motion. *Biochem. J.* 183, 561-572.
65. Gawrisch, K, Han, K. H., Yang, J. S., Bergelson, L. D., and Ferretti, J. A. 1993. Interaction of peptide fragment 828-848 of the envelope glycoprotein of human immunodeficiency virus type I with lipid bilayers. *Biochemistry* 32:31 12-18.
66. Gebeychu, G. Rao, P. Y., SooChan, P., Simrs, D. A., and Klevan, L. 1987. Novel biotinylated nucleotide-analogs for labeling and colorimetric detection of DNA. *Nucleic Acids Res.* 15:4513-34.
67. Gibson, T. J., Coulson, A. R., Sulston, J. E., and Little. R. F. R. 1987a. *Gene.* 53:275.
68. Gibson, T. J., Rosenthal, A., and Waterson, R. H. 1987b. *Gene* 53:283.
69. Gill, D. 1979. Inhibition of fading in fluorescence in microscopy of fixed cells. *Experientia* 35:400-1.
70. Gillam, I. C. and Tener, G. M. 1986. N4-(6-aminohexyl) cytidine and -deoxycytidine nucleotides can be used to label DNA. *Anal Biochem.* 157:199-207.
71. Giloh, H. and Sedat, J. W. 1982. Fluorescence microscopy; reduced photobleaching of rhodamine and fluorescein protein conjugates by n-propyl gallate. *Science* 217:1252-1255.
72. Glazer, A. N. and Mathies, R. A. 1997. Energy-transfer fluorescent reagents for DNA analyses. *Current Opinion in Biotechnology* 8:94-102.
73. Glickman, B. W. 1985. *Basic Life Sciences.* 31:353-79.
74. Glover, D. M. and Harnes, B. D. 1995. *DNA Cloning* 3. IRL Press, New York.
75. Goodwin, P. M., Ambrose, W. P., Martin, J. C., and Keller, R. A. 1995. Spatial dependence of the optical collection efficiency in flow cytometry. *Cytometry.* 21:133-144.
76. Gratton, E. and Llmkema, M. 1983. A continuously variable frequency cross-correlation phase fluorometer with picosecond resolution. *Biophys. J.* 44:315-325.
77. Griep, M. A. 1995. Fluorescence recovery assay: a continuous assay for processive DNA polymerases applied specifically to DNA polymerase III holoenzyme. *Anal Biochem.* 232:180-9.

78. Guédron, M., Eisinger, J., and Shulman, R. G. 1967. *J. Chem. Phys.* 47:4077.
79. Guilbault, G. G. 1973. (ed.) *Practical fluorescence: theory, methods and techniques.* Marcel Dekker, New York.
80. Gurrieri, S. Rizzarelli, E. Beach, D. and Bustamante, C. 1990. Imaging of kinked configurations of DNA molecules undergoing orthogonal field alternating gel electrophoresis by fluorescence microscopy. *Biochemistry* 29:3396-3401.
81. Haab, B. and Mathies, R. 1995. Single molecule fluorescence burst detection of DNA fragments separated by capillary electrophoresis. *Anal. Chem.* 67:3253-60.
82. Hamada, S. and Fujilta, S. 1983. DAPI staining improved for quantitative cytofluorometry. *Histochemistry* 79:219-26.
83. Harding, J. D. and Keller, R. A. 1992. Single molecule detection as an approach to rapid DNA sequencing. *Trends Biotechnol:* 10:55-57.
84. Harris, C. M. and Kell, D. B. 1985. On the dielectrically observable consequences of the diffusional motions of lipids and proteins in membranes. 2. Experiments with microbial cells, protoplasts and membrane vesicles. *Eur. Biphysics. J.* 13:11-24.
85. Haughland. R. P. 1996. *Handbook of Fluorescent Probes and Research Chemicals.* Molecular Probes, Eugene.
86. Herendeen, D. R. and Kelly, T. J. 1996. DNA polymerase III: running rings around the fork. *Cell.* 84:5-8.
87. Herman, B., Wang, X. F., Periasamy, A., Kwon, S., Gordon, G., and Wodnicki, P. Fluorescence lifetime imaging in cell biology. *Proceedings of Optical Diagnostics of Living Cells and Biofluids* 2678:88-97.
88. Hogan, M., Dattagupta, N. and Crothers, D. M. 1978. *Proc. Natl. Acad. Sci. USA* 75:195-199.
89. Höltke, H. -J., Seibl, R., Burg, J., Möhlegger, K., and Kessler, C. 1990. Non-radioactive labeling and detection of nucleic acids: II. Optimization of the digoxigenin system. *Mol. Gen. Hoppe-Seyler* 371:929-938.
90. Holzwarth, A. R. 1995. Time-resolved fluorescence spectroscopy. *Methods in Enzymology.* 246:335-361.
91. Holzwarth, G., Whitconb, R. W., Platt, K. J., Crater, G. D., and McKee, C. B. 1990. Velocity of linear DNA during pulsed-field gel electrophoresis. In *Electrophoresis of Large DNA Molecules* (Lai, E. and Birren, B. W., Eds). Cold Spring Harbor Laboratory Press, New York.
92. Holzwarth, G., McKee, C. B., Steiger, S., and Crater, G. 1987. Transient orientation of linear DNA molecules during pulsed-field gel electrophoresis. *Biopolymes* 28:1043.
93. Houseal, T. W., Bustamante, C., Stump, R. F., and Maestre, M. F. 1989. *Biophys. J.* 56:507.
94. Huff, J. C., Weston, W. L. and Wanda, K. D. 1982. Enhancement of specific immunofluorescent findings with use of para-phenylenediamine mounting buffer. *J. of Investigative Dermatology* 78:449-50.
95. Hung, S. C., Ju, J., Mathies, R. A., and Glazer, A. N. 1996. Cyanine dyes with high absorption cross section as donor chromophores in energy transfer primers. *Anal. Biochem.* 243:15-27.
96. Ickhikawa, M., Iijima, T., and Matsumoto, G. 1993. Simultaneous 16, 384-site optical recording of neural activities in the brain. In *Brain Mechanisms of Perception and Memory: From Neuron to Behanvior.* T. Ono, L. R. Squire, M. E. Raichle, D. I. Perrett & M. Fukuda (eds). Oxford University Press, NY.
97. Ikehara, M., Tazawa, I., and Fukui, T. 1969a. *Chem. Pharm. Bull.* (Tokyo). 17:1019-1024.
98. Ikehara, M., Tazawa, I., and Fukui, T. 1969b. *Biochemistry* 8:736-43.
99. Iijima, T., Ichikawa, M., & Matsumoto, G. 1989 *Abstr. Soc. Neurosci.* 15:398.
100. Janesick, J. (1980-91) Informal Notes, Jet Propulsion Laboratory, California Institute of Technology, Pasedena, Calif.
101. Jett, J., Keller, R., Martin, J., Marrone, B., Moyzis, R., Ratliff, R., Seitzinger, N., Shera, E., and Stewart, C. 1989. High-speed DNA sequencing: an approach based upon fluorescence detection of single molecules. *J. of Bio. Structure & Dynamics* 7:301-9.
102. Jett et al. 1995. U.S. Pat. No. 5,405,747.
103. Johnson, G. D., Davidson, R. S., McNamee, K. C., Russell, G., Goodwin, D. & Holborow, E. J. 1982. Fading of immunofluorescence during microscopy: a study of the phenomenon and its remedy. *J. of Immunological Methods* 55:231-242.
104. Johnson, G. D. and Nogueira Araujo, G. M. de C. 1981. A simple method of reducing the fading of Immunofluorescence during microscopy. *J. of Immunological Methods* 43:349-50.
105. Ju, J., Glazer, A. N., and Mathies, R. A. 1996a. Cassette labeling for facile construction of energy transfer fluorescent primers. *Nucleic Acids Res.* 24:1144-8.
106. Ju, J., Glazer, A. N., and Mathies, R. A. 1996b. Energy transfer primers: a new fluorescence labeling paradigm for DNA sequencing and analysis. *Nature Medicine.* 2:246-9.
107. Jumppanen. J. H. and Riekkola, M. L. 1995. Influence of electrolyte composition on the effective electric field strength in capillary zone electrophores. *Electrophoresis* 16:1441-4.
108. Kasianowicz, J. J., Brandin, E., Branton, D.; and Deamer, D. W. 1996. Characterization of individual polynucleotide molecules using a membrane channel. *Proc. Natl. Acad. Sci. USA.* 93:13770-3.
109. Kato, H. and Yoshida, T. H. 1970. Nondisjunction of chromosomes in a synchronized cell population initiated by reversal of colcemid inhibition. *Expl. cell.* 60:459-64.
110. Keough, T., Baker, T. R., Dobson, R. L. M., Lacey, M. P. Riley, T., Hasseltield, J., and Hesselberth, P. E. 1993. *Rapid Commun. Mass Spectrom.* 7:195-200.
111. Klnjo, M. and Rigler, R. Ultrasensitive hybridization analysis using fluorescence correlation spectroscopy. *Nucleic Acids Research.* 23:1795-1799.
112. Kirk, W. R., Wessels, W. S., and Prendergast, F. G. 1993. Lanthanide-dependent perturbations of luminescence in indolylethylenediaminetetraacetic acid-lanthanide chelate. *J. Phys. Chem.* 97:10326-10340.
113. Klenchin, V. A., Sukharev, S. I., Serov, S. M., Chernomordik, L. V., and Chizmadzhev, YuA. 1991. Electrically induced DNA uptake by cells is a fast process involving DNA electrophoresis. *Biophysical J.* 60:804-11.
114. Kochetkov, N. K, Budowsky, and Shibaev, V. N. *Proc. Nucl. Acid Chem.,* 1:500-2.
115. Konuma, M. 1992. *Film Deposition by plasma techniques.* Springer-Verlag, New York.
116. Korchemnaya, E. K., Ermakov, A. N., Bochkova, L. P. 1978. *J. Anal Chem USSR (Eng. Transl.)* 33:625.
117. Kornberg, A., and Baker, T. A. 1991. *DNA Replication* W. H. Freeman, New York.

118. Lakowicz, J. R. and Szmacinski, H. 1996. Imaging applications of time-resolved fluorescence spectroscopy. In *Fluorescence Imaging Spectroscopy and Microscopy* (Wang, X. F. and Herman, B. Eds). John Wiley & Sons, New York.
119. Lakowicz, J. R. and Berndt, K. W. 1991. Lifetime-selective fluorescence imaging using an RF phase-sensitive camera. *Rev. Sci. Instru.* 62:3653.
120. Lang, R. A., Robins, R. K., and Townsend, L. B. 1968. *Synthetic Procedures in Nucleic Acid Chemistry.* 1:228. Ed, Zorbach, W. W. and Tipson, R. S. John Wiley & Sons, New York.
121. Langer, P. R., Waldrop, A. A., and Ward, D. C. 1981. Enzymatic synthesis of biotin-labeled polynucleotides: novel nucleic acid affinity probes. *Proc. Natl. Acad. Sci. U.S.A.* 78-6633-6637.
122. Lee, K. B., Matsuoka, K, Nishimura; S, and Lee, Y. C. 1995. A new approach to assay endo-type carbohydrases: bifluorescent-labeled substrates for glycoamidases and ceramide glycanases. *Anal. Biochem.* 230:31-6.
123. Lee, L. G., Connell, C. R., Woo, S. L., Cheng, R. D., McArdle, B. F., Fuller, C. W., Halloran. N. D., and Wilson, R. K. *Nucleic Acids Res.* 20:2471-2483.
124. Lee, S. P., Porter, D., Chirikjian, J. G., Knutson, J. R., and Han, M. K. 1994. A fluorometric assay for DNA cleavage reactions characterized with BamHI restriction endonuclease. *Anal. Biochem.* 220:377-383.
125. Lee, S. P., Censullo, M. L, Kim, H. G., Knutson, J. R., and Han, M. K. 1995. Characterization of endonucleolytic activity of HIV-1 integrase using a fluorogenic substrate. *Anal. Biochem.* 227:295-301.
126. Lee, Y-H, Maus, R. G., Smith, B. W. and Winefordner, J. D. 1994. Laser-induced fluorescence detection of a single molecule in a capillary. *Anal. Chem.* 66:4142-9.
127. Lewotsky, K. 1994. Hyperspectral imaging: evolution of imaging spectroretry. *SPIE OE/Rep., November:*1-3.
128. Little, D. P., Chorush, R. A., Speir, J. P., Senko, M. W., Kelleher, N. L., and McLalferty, F. W. 1994. *J. Am. Chem. Soc.* 116:4893-897.
129. Livak, K. J. 1997. Quantitation of DNA/RNA using real-time PCR detection. *PE Applied Biosystems*, Foster City, Calif.
130. Lockhart, D. J., Dong, H., Byrne, M. C., Follettie, M. T. et al., 1996. Expression monitoring by hybridization to high-density oligonucleotide arrays. *Nature Biotechn.* 14:1675-1680.
131. Loros, J. J., Denome, S. A., and Dunlap, J. C. 1989. Molecular cloning of genes under control of the circadian clock in Neurospora. *Science* 243:385-388.
132. Marcus, P. I. and Robbins, E. 1963. Viral inhibition in the metaphase-arrest cell. *Proc. Natl Acad. Sci. USA* 50:1156-64.
133. Marra, M., Weinstock, L. A., and Mardis, E. R. 1996. End sequence determination from large insert clones using energy transfer fluorescent primers. *Genome Research* 6:1118-22
134. Martin, I, Dubols, M-C., Defrise-Quertain, F., Saermark, T., Bumy, A., Brasseur, R., and Ruysschaert, J-M. 1994. Correlation between fusogenicity of synthetic modified peptides corresponding to the NH2-terminal extremity of simian immunodeficiency virus gp32 and their mode of insertion into the lipid bilayer: an infrared spectroscopy study. *J. Virol.* 68:1139-48.
135. Mason, W. T. 1992. *Fluorescent and Luminescent Probes for Biological Activity.* Harcourt Brace & Company, Cambridge, UK.
136. Matayoshi, E. D., Wang, G. T., Kraft, G. A., and Erickson, J. 1990. Novel fluorogenic substrates for assaying retroviral proteases by resonance energy transfer. *Science.* 247:954.
137. Matsumoto, B. 1993. Cell biological applications of confocal microscopy. *Methods in Cell Biology.* 38:86.
138. Matsumoto, S., Morikawa, K., and Yangida, M. 1981. Light microscopic structure of DNA in solution studied by the 4',6-diamidino-2-phenytindole staining method. *J. Mol. Biol.* 152:501-516.
139. Maurizi, M. R., Kasprzyk, P. G., and Ginsberg, A. 1986. Distances between active site probes in glutamine synthetase from *Escherichia coli* fluorescence energy transfer in free and in stacked dodecamers. *Biochem* 25:141-151.
140. Mautner, H. G. 1956. *J. Am. Chem. Soc.* 78:5293.
141. Maxam, A. M. and Gilbert, W. 1977. A new method for sequencing DNA. *Proc. Natl. Acad. Sci. USA.* 74:5604.
142. Maymon, W., and Neeck, S. P. 1988. Optical system design alternatives for the Moderate-Resolution Imaging Spectrometer Tilt (MODIS-T) for the Earth Observing System (EoS). *Proc. SPIE—Recent Adv. Sensors, Radiometry Data Process Remote Sens.* 924:10-22.
143. McGown, L. B. 1989. Fluorescence lifetime filtering. *Anal. Chem.* 61:839A-847A.
144. Meffert, R. and uose, K. 1988. Uv-induced crosslinking of proteins to plasmid pER322 containing 8-azidoadenine 2'-deoxyribonucleotides. *FEBS Lets.* 239:190-4.
145. Meertz, J., Xu, C. and Webb, W. W. 1995. Single-molecule detection by two-photon-excited fluorescence. *Optics Letters* 20:253234.
146. Meinkoth, J. and Wahl, G. M. 1987. Nick translation. *Methods in Enzymology* 152:91-94.
147. Menter, J. M., Hurst, R. E. and West, S. S. 1979. Photochemistry of heparin-acridine orange complexes in solution. *Photochemistry and Photobiology.* 27:629-33.
148. Menter, J. M., Golden, J. F. & West, S. S. 1978. Kinetics of fluorescence fading of acridine orange-heparin complexes in solution. *Photochemistry and Photobiology* 27:629-633.
149. Miki, M., O'Donoghue, S. I., and Dos Remedios, C. G. 1992. Structure of actin observed by fluorescence resonance energy transfer spectroscopy. *J. Muscle Res. Cell Motil.* 13:132.
150. Miki, M. and Iio, T. 1993. Kinetics of structural changes of reconstituted skeletal muscle thin filaments observed by fluorescence resonance energy transfer. *J. Biol. Chem.* 268:7101-7106.
151. Mitchinson, J. M. 1971. *The Biology of the Cell Cycle.* Cambridge University Press, London.
152. Moore, D. P., Schellman, J. A., and Baase, W. A. 1986. The orientation, relaxation and reptation of DNA in orthogonal field, alternately-pulsed field gel electrophoresis: a linear dichroism study." *Biopphys. J.* 49:130a.
153. Morikawa, K., and Yangida, M. 1981. *J. Biochem.* 89:693.
154. Morosanu, C. E. 1990. *Thin films by chemical vapour deposition.* Elsevier, New York.
155. Morgan, C. G., Mitchell, A. C., and Murray, J. G. 1990. Nanosecond time-resolved fluorescence microscopy: principle and practice. *Trans. R. Microsc. Soc.* (Micro '90) 463-466.

156. Nakashima, M., Yamada, S., Shiono, S., and Maeda, M. 1992. *IEEE Trans. Biomed. Engng.* 39:26-36.

157. Naktinis, V., Turner, J., O'Donnell, M. 1996. A molecular switch in a replication machine defined by an internal competition for protein rings. *Cell.* 84:127-45.

158. Negishl, K., Matsumoto, K., Bessho, T., Tada, F., and Hayatsu, H. 1988. In vitro mutagenesis by incorporation of N4-aminodcoxycytidine 5'-triphosphatc. *Nucleic Acids Symposium Series.* 19:33-6.

159. Newman, J., Swiney, J. L, Day, L. A. 1977. *J. Mol. Biol.* 110:119-46.

160. Nicolas, V., Nefussi, J. R., Collin, P., and Forest, N. 1990. Effects of acidic fibroblast growth factor and epidermal growth factor on subconfluent fetal rat calvaria cell cultures: DNA synthesis and alkaline phosphatase activitiy. *Bone and Mineral.* 8:145-56.

161. Nguyen, D. C. and Keller, R. A. Detection of single molecules of phycoerythrin in hydrodynamically focused flows by laser-induced fluorescence. *Anal. Chem.* 59:2158-2161.

162. Nie, S., Chiu, D. T., and Zare, R. N. 1994. Probing individual molecules with confocal fluorescence microscopy. *Science.* 266:1018-21.

163. Oida, T., Sato, Y., and Kusumi, A. 1993. Fluorescence lifetime imaging microscopy (filmscopy): methodology development and application to studies of endosome fusion in single cells. *Biophys. J.* 64:676-685.

164. Onrust, R., and O'Donnell, M. 1993. *J. Biol. Chem.* 268:11766-72.

165. Pap, E. H. W., Bastiaens, P., Borst, J. W., van den Berg, P., van Hoek, A., Snoek, G., Wirtz, K, and Visser, A. 1993. Quantitation of the interaction of protein kinase C with diacylglycerol and phosphoinostitides by time-resolved detection of resonance energy transfer. *Biochemistry* 32:13310-17.

166. Paul, W. Professor of Physics, Harvard University.

167. Pauleau, Y. 1995. *Materials and processes for surface and interface engineering*. Kluwer Academic Publishers, Boston.

168. Paz-Elizur, T., Skaliter, R., Blumenstein, S., and Uvneh, Z. 1996. Beta*, a UV-Inducible smaller form of the beta subunit sliding clamp of DNA polymerases III of *Esherichia coli*. I. Gene expression and regulation. *J. Biol. Chem.* 271:2482-90.

169. Peck, K., Stryer, L, Glazer, A. N. and Mathies, R. A. 1989. Single-molecule fluorescence detection: autocorrelation criterion and experimental realization with phycoerythrin. *Proc. Natl. Acad. Scl. USA* 86:4087-4091.

170. Periasamy, A., Siadat-Pajouh, M., Wodnick, P., Wang, X-F., and Herman, B. Time-gated fluorescence microscopy for clinical imaging. *Microscopy and analysis.* 3:334.

171. Periasamy, A. & Herman, B. 1994. Computerized fluorescence microscopic vision in the biomedical science, *J. of Computer-Assisted Microscopy* 6:1-26.

172. Picciolo, G. L. and Kaplan, D. S. 1984. Reduction of fading of fluorescent reaction product for microphotometric quantitation. *Advances in Applied Microbiology* 30:197-234.

173. Pillai, V. N. 1980. Photoremovable protecting groups in organic synthesis. *Synthesis.* 1980:1.

174. Platt, J. L. and Michael, A. F. 1983. Retardation of fading and enhancement of intensity of immunofluorescence by p-phenylenediamine. *J. of Histochemistry and Cytochemistry* 31:840-42.

175. Poot, M. and Hoehn, H. 1990. Cell cycle analysis using continuous bromodeoxyuridine labeling and Hoeschst 33258-ethidium bromide bivariate flow cytometry. *Methods in Cell Biology* 33:185-98.

176. Porter, G. (Ed.) 1967. *Reactivity of the photoexcited organic molecule*. Interscience, New York.

177. Pringsheim, P. 1963. *Fluorescence and phosphorescence*. John Wiley, New York.

178. Priore, D. R. C. and Allen. F. S. 1979. Biopolymers 18:1809-1820.

179. Purmal, A. A., Kow, Y. W., and Wallace, S. S. 1994. 5-Hydroxyprimidine deoxynucleoside triphosphates are more efficiently incorporated into DNA by exonuclease-free Klenow fragment than 8-oxopurine deoxynucleoside triphosphates. *Nucleic Acids Res.* 22:3930-5.

180. Purcell, E. M. 1985. *Electricity and Magnetism*, Vol. 2 McGraw-Hill, New York.

181. Qu, D., et al., 19996. A role for melanin-concentrating hormone in the central regulation of feeding behaviour. *Nature* 380:243-247.

182. Rahn, R. O., Schulman, R. G., and Longworth, J. W. 1965. *Proc. Natl. Acad. Sci. USA* 53:893.

183. Rampino, N. J. and Chrambach, A. 1990. Apparatus for gel electrophoresis with continuous monitoring of individual DNA molecules by video epifluorescence microscopy. *Anal. Biochem.* 194:278-283.

184. Rao, P. N. 1968. Mitotic synchrony in mammalian cells treated with nitrous oxide at high pressures. *Science* 160:774-6.

185. Rigby, P. W. J., Dieckmann, M., Rhodes, C., and Berg, P. 1977. Labeling deoxyribonucleic acid to high specific activity in vitro by nick translation with DNA polymerase I. *J. Mol. Biol.* 113:237-51.

186. Reddick, R. C., Warmack, R. J., and Ferrell, T. L. 1989. *Phys. Rev. B* 39:767-770.

187. Rodgers, M. A. J. and Firey, P. A. 1985. *Photochem. Photobiol.* 42:613.

188. Ronaghi, M., Karamohamed, S., Pettersson, B., Uhlén, M., and Nyrén, P. 1996. Real-time DNA sequencing using detection of pyrophosphate release. *Anal. Biochem.* 242:84-89.

189. Ross, P. D. and Scruggs, L. 1964. *Biopolymers.* 2:231-6.

190. Rost, F. W. D. 1991. *Quantitative Fluorescence Microscopy*. Cambridge University Press, Cambridge.

191. Roychoudhury, R., Tu, C. -P-D., and Wu, R. 1979. Influence of nucleotide sequence adjacent to duplex DNA termini on 3'-terminal labeling by terminal transferase. *Nucleic Acids Res.* 6:1323-1333.

192. Saha, A. K., Kross, K., Kloszewski, E. D., Upson, D. A., Toner, J. L, Snow, R. A., Black, C. D. V., and Desai, V. C. 1993. Timresolved fluorescence of a new europium chelate complex: demonstration of highly sensitive detection ot protein and DNA samples. *J. Am. Chem. Soc.* 115:11032-33.

193. Sahota, R. S. and Khaledi, M. G. 1994. Nonaqueous capillary electrophoresis. *Anal. Chem.* 66:1141-6.

194. Saiki, R. K., Scharf, S., Faloona, F., Mullis, K. B., Horn, G. T., Erlich, H. A., and Amheim, N. 1985. Enzymatic amplification of beta-globin genomic sequences and restriction site analysis for diagnosis of sickle cell anemia. *Science* 230:1350-1354.

195. Saiki, R. K., Gelfand, D. H., Stoffel, S., Scharf, S. J., Higuchi, R., Horn, G. T., Mullis, K. B., and Erlich, H. A. 1988. Primer-directed enzymatic amplification of DNA with a thermostable DNA polymerase. *Science* 239:487-91.

196. Sanger, F., Nicklen, A., and Coulson, A. R. 1977. DNA sequencing with chain-terminating inhibitors. *Proc. Natl. Acad. Sci. USA.* 74:5463-7.

197. Sase, I., Miyata, H., Corrie, J., Cralk, J, and Kinosita, Jr., K. K. 1995. Real time imaging of single fluorophores on moving actin with an epifluorescence microscope. *Biophys. J.* 69:323-8.

198. Scheit, K. H. 1980. *Nucleotide Analogs: Synthesis and Biological Function*. John Wiley & Sons, New York.

199. Schellman, J. A., and Jensen, H. P. 1987. Optical spectroscopy of oriented molecules. *Chem. Rev.* 87:1359.

200. Schott, J. R. 1989. Remote sensing of the Earth: A synoptic view. *Phys Today September:*72-79.

201. Schwartz, D. C. and Koval, M. 1989. Conformational dynamics of individual DNA molecules during gel electrophoresis. *Nature* 338:520-522.

202. Selvin, P. R., Rana, T. M., and Hearst, J. E. 1994. Luminescence resonance energy transfer. *J. Am. Chem. Soc.* 116:6029-30.

203. Selvin, P. R. 1995. Fluorescence resonance energy transfer. *Methods in Enzymology.* 246:300-334.

204. Shera, E. B., Seitzinger, N. K., Davis, L. M., Keller, R. A., and Soper, S. A. 1990. Detection of single fluorescent molecules. *Chem. Phys. Letts.* 174:553-57.

205. Shlkmus, M. L., Guaglianone, P., and Herman, T. M. 1986. Synthesis and characterization of blotin-labeled nucleotide analogs. *DNA.* 5:247-55.

206. Skaliter, R., Bergstein, M., and Livneh, Z 1996. Beta*, a UV-inducible shorter form of the beta subunit of DNA polymerase III of *Escherichia coli*. II. Overproduction, purification, and activity as a polymerase processivity clamp. *J. Biol. Chem.* 271:2491-6.

207. Skoog, D. A., West, D. M., and Holler, F. J. 1992. *Analytical Chemistry*. Saunders College Publishing, New York.

208. Smirnov, I. P., Roskey, M. T., Juhasz, P., Takach, E. J., Martin, S. A., and Half, L. A. 1996. Sequencing oligonucleotides by exonuclease digestion and delayed extraction matrix-assisted laser desorption ionization time-of-flight mass spectrometry. *Anal Biochem.* 238:19-25.

209. Smith, D. P., Shleh, B. H., and Zuker, C. S. 1990. Isolation and structure of an arrestin gene from Drosophila. *Proc. Natl. Acad. Sci. USA* 87:1003-1007.

210. Smith, S. B., Burrieri, S., and Bustamante, C. 1990. Fluorescence microsocpyand computer simulations of DNA molecules in conventional and pulsed-field gel. electrophoresis. In *Electrophoresis of Large DNA Molecules* (Lai, E. and Birren, B. W., Eds). Cold Spring Harbor Laboratory Press, New York.

211. Smith, S. B., Aldridge, P. K., and Callis, J. B. 1989. Observation of individual DNA molecules undergoing gel electrophoresis. *Science* 243:203-206.

212. Smith, L. M., Sanders, J. Z. Kaiser, R. J., Hughes, P., Dodd, C., Connell, C. R., Heiner, C., Kent, S. B., and Hood, L. E. 1986. Fluorescence detection in automated DNA sequence analysis. *Nature.* 321:674-9.

213. Sober, H. A. Ed. 1970. *Handbook of Biochomistry*, 2nd ed. The Chemical Rubber Co., Cleveland.

214. Soper, S. A., Davis, L. M. and Shera. E. B. 1992. Single molecule spectroscopy in solution. *Los Alamos Science* 20:286-96.

215. Spatz, W. B. and Grabig, S. 1983. Reduced fading of fast blue fluorescence in the brain of the guinea-pig by treatment with sodium-nitroprusside. *Neuroscience Letters* 38:1-4.

216. Spohr, R. 1990. *Ion tracks and microtechnology: principles and appilcations* Vieweg, Braunschweig.

217. Steinberg, I. Z. 1971. *Annu. Rev. Biochem.* 40:83.

218. Steiner, R. F. and Weinryb, I. 1971. *Excited States of Proteins and Nucleic Acids*. Plenum Press, New York.

219. Stewart, J. E., Hahn, G. M., Parker, V., and Bagshaw, M. A. 1968. Chinese hamster cell monolayer cell cultures. *Exp. Cell Res.* 49:293-299.

220. Stuart, R: V. 1983. *Vacuum technology, thin films, and sputtering: an introduction*. Academic Press. New York.

221. Stryer, L. 1978. *Annual Review of Biochem.* 47:819.

222. Stubblefield, E. 1968. Synchronization methods for mammalian cell cultures. In *Methods in Cell Physiology*. Ed. by D. M. Prescott. 3:25-43. Academic Press, New York.

223. Sturm, J. and Weill, G. 1989. Direct observation of DNA chain orientation and relaxation by electric birefringence: implications for the mechanism of separation during pulsed-field gel electrophoresis. *Phys. Rev. Lett.* 62:1484.

224. Taliani, M., Bianchi, E., Narjes, F., Fossatelli, M., Urbani, A., Steinküler, C., De Francesco, R., and Pessi, A. 1996. A continuous assay of hepatitis C virus protease based on resonance energy transfer dipeptide substrates. *Anan. Biochem.* 240:60-7.

225. Taylor, D. L. and Salmon, E. D. 1989. *Methods in Cell Biol.* 29:207-37

226. Taylor, D. L, Reidler, J., Spudich, J. A., and Stryer, L 1981. Detection of actin assembly by fluorescence energy transfer. *J. Cell Biol.* 89:363.

227. ter Beest, M. and Hoekstra, D. 1993. Interaction of myelin basic protein with artificial membranes. Parameters governing binding, aggregation and dissociation. *Eur. J. Biochem.* 211:689-96.

228. Theil, E. 1997. Automation in genome research. In *Molecular Biology and Biotechnology*, R. A. Meyers, Ed. VCH Publishers, New York.

229. Thomas, R. S., Shimkunas, A. R., and Manger, P. E. 1992. Sub-nanosecond intensifier gating using heavy and mesh cathode underlays. *Proc. Int. Congr. High Speed Photo. Photon 19th*. 1984.

230. Tian, R. and Rodgers, M. A. J. (1991). Time-resolved fluorescence microscopy. In *New Techniques in Optical Microscopy and Spectrophotometry* (R. J. Cherry, Ed.), pp. 312-351. CRC Press, Boca Raton, Fla.

231. Tinoco, I., Sauer, K., and Wang, J. C. 1995. *Physical Chemistry* Prentice Hall, Englewood Cliffs.

232. Tu, C. -P-D., and Cohen, S. 1980 3'-End labeling of DNA with [$\alpha$-$^{32}$P] cordycepin-5'-triphosphate. *Gene* 10:177-83.

233. Uchiyama, H. Hirano, K., Kashiwasake-Jibu, M., and Taira, K. 1996. Detection of undegraded oligonucleotides in vivo by fluorescence resonance energy transfer. *J. Biol. Chem.* 271:380-84.

234. Udenfriend, S. 1962. *Fluorescence assay in biology and medicine*. Academic Press, New York and London.

235. Ueda, T., Miura, K., Imazawa, K., and Odajima, K. 1974. *Chem. Pharm. Bull.* (Tokyo). 22:2377-2382.

236. Valiev, K. A. 1992. *The physics of submicron lithography*. Plenum Press, New York.

237. Valnes, K. and Brandtzaeg, P. 1985. Retardation of immunofluorescence fading during microscopy. *J. of Histochemistry and Cytochemistry* 33:755-761.

238. van Huist, N. F., Moers, M. H. P., Noordman, O. F. J., Tack, R. G., Segerink, F. B., and Böger, B. 1993. *Appl. Phys. Lett.* 62:461

239. van de Ven, M., and Gratton, E. 1992. Time-resolved fluorescence lifetime imaging. In *Optical Microscopy: Emerging Methods and Applications* (B. Herman, and J. J. Lemaster, Eds.), 373-402. Academic Press, San Diego.

240. Vaughan, W. M. and Weber, G. 1970. Oxygen quenching of pyrenebutyric acid fluorescence in water. A dynamic probe of the microenvironment. *Biochemistry* 9:464-473.

241. Waggoner, A. 1995. Covalent labeling of proteins and nucleic acids with fluorophores. *Methods in Enzymology* 246:362-373.

242. Wang et al., 1995. Discovery of adrenomedullin in rat ischemic cortex and evidence for its role in exacerbating focal brain ischemic damage. *Proc. Natl. Acad. Sci. USA* 87:1003-1007.

243. Wang, S. Y. 1976. *Photochemistry and Photobiology of Nucleic Acids*. Academic Press, New York.

244. Wang, X. F., Periasamy, A., Wodnicki, P., Gordon, G. W., and Herman, B. 1996. Time-resolved fluorescence lifetime imaging microscopy: Instrumentation and biomedication applications. In *Fluorescence Imaging Spectroscopy and Microscopy* (Wang, X. F. and Herman, B. Ed). John Wiley & Sons, Inc., New York.

245. Wang, X. F., Periasamy, A., Wodnicki, P., Gordon, G. W., and Herman, B. 1996. Time-resolved fluorescence lifetime imaging microscopy: instrumentation and biomedical applications. *Chemical Analysis* 137:313-350.

246. Wang, X. F., Kitajima, S., Uchida, T., Coleman, D. M., and Minami, S. 1990. Time-resolved fluorescence microscopy using multichannel photon counting. *Appl. Spectrosc.* 44:25.

247. Wang, Y., Wallin, J. M., Ju, J., Sensabaugh, G. F., and Mathies, R. A. 1996. High-resolution capillary array electrophoretic sizing of multiplexed short tandem repeat loci using energy-transfer fluorescent primers. *Electrophoresis.* 17:1485-90.

248. Wang, Y., Ju, J., Carpenter, B. A., Atherton, J. M., Sensabaugh, G. F., and Mathies, R. A. 1995. Rapid sizing of short tandem repeat alleles using capillary array electrophoresis and energy-transfer fluorescent primers. *Anal. Chem.* 67:1197-203.

249. Ward, D. C. and Reich, E. 1969. Fluorescence studies of nucleotides and polynucleotides. 244:1228-1237.

250. Weimann, S., Rupp, T., Zimmermann, J., Voss, H., Schwager, C., and Ansorge, W. 1995. Primer design for automated DNA sequencing utilizing T7 DNA polymerase and internal labeling with fluorescein-15-dATP. *BioTechniques* 18:688-97.

251. Wilkinson, J. Q., Lanahan, M. B., Conner, T. W., and Klee, H. J. 1995. Identification of mRNAs with enhanced expression in ripening strawberry fruit using polymerase chain reaction differential display. *Plant Mol. Biol.* 27:1097-1108.

252. Wittwer, C. T. Herman, M. G., Moss, A. A., and Rasmussen, R. P. 1997. Continuous fluorescence monitoring of rapid cycle DNA amplification. *Biotechniques.* 22:130-1, 134-8.

253. Wooley, A. T. and Mathies, R. A. 1995. Ultra-high-speed DNA sequencing using capillary electrophoresis chips. *Anal. Chem* 67:3676-3680.

254. Woronicz, J. D., Calnan, B.; Ngo, V., and Winoto, A. 1994. Requirement for the orphan steroid receptor Nur77 in apoptosis of T-cell hybridomas. *Nature* 367: 277-281.

255. Wu, H. M., Dattagupta, N. and Crothers, D. M. 1981. *Proc. Natl. Acad. Sci. USA* 78:6808-6811.

256. Wu, P. G. and Brand, L. 1994. Resonance energy transfer: methods and applications. *Anal. Biochem.* 218: 1-13.

257. Wunderlich, F. and Peyk, D. 1969. Antimritotic agents and macronuclear division of ciliates. II. Endogeneous recovery from colchicine and colcemid-a new method of synchronization in *Tetrahymena pyriformis* GL *Expl. Cell Res.* 57:142-4.

258. Yanagida, M., Hiraoka, Y., and Katsura, I. 1983. *Cold Spring Harbor Symp. Biol.* 47:177-87.

259. Yamaoka, K. and Matsuda, K 1981. *Macromolecules* 14:595-601.

260. Yamaoka, K. and Charney, E. 1973. *Macromolecules* 6:66-76.

261. Vane, G., Chrien, T. G., Reimer, J. H., Green, R. O., and Conel, J. E. 1988. Comparison of laboratory calibrations of the Airborne Visible/infrared imaging Spectrometer (AVIRIS) at he beginning and end of the first flight season. *Proc. SPIE—Recent Adv. Sensors, Radiometry Data Process. Remote Sens.* 924:168-178.

262. Zweig, A. 1973. Photochemical generation of stable fluorescent compounds (photofluorescence). *Pure and Applied Chemistry* 33:389-410.

The invention claimed is:

1. A method comprising:
    providing a nucleic acid, labeled with a unit specific marker, and
    detecting, while the nucleic acid is moved relative to electromagnetic radiation by a tethered polymerase, at least one FRET-independent fluorescent signal emitted from the unit specific marker.

2. A method for detecting a unit specific marker bound to a nucleic acid comprising
    moving a nucleic acid relative to electromagnetic radiation using a tethered polymerase,
    exposing a fluorescently labeled unit specific marker bound to the nucleic acid to electromagnetic radiation, and
    detecting an electromagnetic radiation signal from the fluorescently labeled unit specific marker in the absence of fluorescence resonance energy transfer.

3. The method of claim 1, wherein the electromagnetic radiation is transported through a waveguide.

4. The method of claim 2, wherein the electromagnetic radiation is transported through a waveguide.

5. The method of claim 1, further including storing signatures of signals.

6. The method of claim 5, wherein the electromagnetic radiation is transported through a waveguide.

* * * * *

SEQUENCE LISTING

<160> NUMBER OF SEQ ID NOS: 5

<210> SEQ ID NO 1
<211> LENGTH: 16
<212> TYPE: DNA
<213> ORGANISM: Artificial Sequence
<220> FEATURE:
<221> NAME/KEY: misc_feature
<223> OTHER INFORMATION: Synthetic Oligonucleotide

<400> SEQUENCE: 1
acgtacgtac gtacgt            16

<210> SEQ ID NO 2
<211> LENGTH: 9
<212> TYPE: DNA
<213> ORGANISM: Artificial Sequence
<220> FEATURE:

```
<221> NAME/KEY: misc_feature
<223> OTHER INFORMATION: Synthetic Oligonucleotide

<400> SEQUENCE: 2 aggcaaacg                                                                      9

<210> SEQ ID NO 3
<211> LENGTH: 10
<212> TYPE: DNA
<213> ORGANISM: Artificial Sequence
<220> FEATURE:
<221> NAME/KEY: misc_feature
<223> OTHER INFORMATION: Synthetic Oligonucleotide

<400> SEQUENCE: 3
agtgcaaacg                                                                    10

<210> SEQ ID NO 4
<211> LENGTH: 19
<212> TYPE: DNA
<213> ORGANISM: Artificial Sequence
<220> FEATURE:
<221> NAME/KEY: misc_feature
<223> OTHER INFORMATION: Synthetic Oligonucleotide

<400> SEQUENCE: 4
tgcatgaact cggcgcaag                                                          19

<210> SEQ ID NO 5
<211> LENGTH: 19
<212> TYPE: DNA
<213> ORGANISM: Artificial Sequence
<220> FEATURE:
<221> NAME/KEY: misc_feature
<223> OTHER INFORMATION: Synthetic Oligonucleotide

<400> SEQUENCE: 5
acgtacttga gccgcgttc                                                          19
```